United States Patent [19]

Meyer et al.

[11] Patent Number: 5,597,823
[45] Date of Patent: Jan. 28, 1997

[54] TRICYCLIC SUBSTITUTED HEXAHYDROBENZ [E]ISOINDOLE ALPHA-1 ADRENERGIC ANTAGONISTS

[75] Inventors: Michael D. Meyer, Lake Villa; Robert J. Altenbach, Chicago; Fatima Z. Basha, Lake Forest; William A. Carroll, Evanston; Irene Drizin, Wadsworth; Steven W. Elmore, Libertyville; James F. Kerwin, Jr., Grayslake; Suzanne A. Lebold, Chicago; Edmund L. Lee, Lake Zurich; Kevin B. Sippy, Lindenhurst; Karin R. Tietje, Mundelein; Michael D. Wendt, North Chicago, all of Ill.

[73] Assignee: Abbott Laboratories, Abbott Park, Ill.

[21] Appl. No.: 463,528

[22] Filed: Jun. 5, 1995

Related U.S. Application Data

[63] Continuation-in-part of Ser. No. 379,414, Jan. 27, 1995, abandoned.

[51] Int. Cl.[6] ............ A61K 31/505; C07D 495/04; C07D 495/14; C07D 487/04
[52] U.S. Cl. ............ 514/250; 514/252; 514/267; 544/145; 544/163; 544/234; 544/249; 544/250; 544/251; 544/278; 544/350; 544/409; 546/114; 546/115; 546/118; 546/286; 548/427; 549/57; 549/236
[58] Field of Search ............ 544/234, 249, 544/250, 251; 514/250, 252, 267

[56] References Cited

U.S. PATENT DOCUMENTS 5,049,564 9/1991 DeBernardis et al. ............ 514/290

Primary Examiner—Emily Bernhardt
Attorney, Agent, or Firm—Gregory W. Steele; Jerry F. Janssen

[57] ABSTRACT

The present invention relates to a compound of the formula

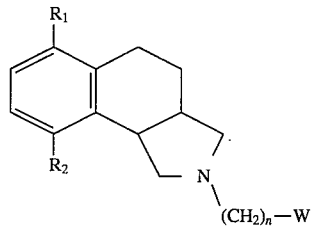

and the pharmaceutically acceptable salts thereof wherein W is a tricyclic heterocyclic ring system; which is an α-1 adrenergic antagonist and is useful in the treatment of BPH; also disclosed are α-1 antagonist compositions and a method for antagonizing α-1 receptors and treating BPH.

17 Claims, No Drawings

TRICYCLIC SUBSTITUTED HEXAHYDROBENZ [E]ISOINDOLE ALPHA-1 ADRENERGIC ANTAGONISTS

CROSS-REFERENCE TO RELATED APPLICATIONS

This application is a continuation-in-part of application Ser. No. 08/379,414 filed Jan. 27, 1995, now abandoned.

TECHNICAL FIELD

The present invention relates to novel organic compounds and compositions which are alpha-1 ($\alpha$-1) adrenoreceptor antagonists, processes for making such compounds, synthetic intermediates employed in these processes, and a method for inhibiting alpha-1 receptors and treating benign prostatic hyperplasia (BPH), also called benign prostatic hypertrophy.

BACKGROUND OF THE INVENTION

Adrenergic neurons play a major role in the innervation of heart, blood vessel and smooth muscle tissue. Compounds capable of interacting with adrenoceptor sites within adrenergic nerves can initiate a variety of physiological responses, including vasoconstfiction, vasodilation, and increased or decreased heart rate (chronotropic), contractility (inotropic) and metabolic activity. In the past, various adrenergic compounds have been employed to affect these and other physiological responses. However, many adrenergic compounds do not possess significant selectivity to enable desirable interactions with adrenergic receptor sites. That is, these adrenergic compounds do not demonstrate a high degree of specificity for differing receptor types within adrenergic neurons in order to obtain a desired physiological response separate from other possible, and perhaps less desirable, responses of the system.

Benign prostatic hyperplasia (BPH) is a condition which develops in middle-aged and elderly males and refers to the benign overgrowth of the stromal and epithelial elements of the prostate associated with aging. Symptoms of BPH include increased frequency of urination, nocturia, a weak urine stream and hesitancy or delay in starting the urine flow. Chrome consequences of BPH can include hypertrophy of bladder smooth muscle, a decompensated bladder and an increased incidence of urinary tract infection.

Typically, BPH begins at an age in the mid-fifties and is the most common cause of urinary tract problems of men of this age. BPH is apparently rare in men prior to age 40, but at age 60, approximately 50% of men have histological evidence of BPH. The prevalence of BPH continues to increase with age until, at age 80, approximately 80% of men have pathological evidence of BPH.

Although prostatic hyperplasia is a common finding in older men, the presence of urinary symptoms is the essential feature that distinguishes simple anatomic enlargement of the prostate from prostatism, which is the clinical syndrome whereby the patient experiences significant obstruction of urinary flow. It is not uncommon in older men to have a palpably enlarged prostate without showing the symptoms of prostatism. From the patient's perspective, however, the incidence and progression of urinary symptoms are more important than the mere presence of an enlarged prostate.

The discovery in the 1970's (M. Caine, et al., Brit. J. Urol., 47:193–202 (1975)) of large numbers of alpha-adrenergic receptors in the smooth muscle of the prostatic capsule and bladder neck led to the conclusion that there is both a static and a dynamic component to bladder outlet obstruction associated with BPH. The static component derives from the progressive hyperplasia of the prostate with aging, leading to urethral narrowing which causes symptoms of urinary obstruction. Superimposed on this essentially mechanical problem is the variable degree of smooth muscle contraction controlled by the sympatheic nervous system and which is affected by by factors such as stress, cold and sympathomimetic drugs. It is this dynamic component which explains the often rapid fluctuations in symptoms observed in patients with prostatism.

The currently most effective treatment for BPH is the surgical procedure of transurethral resection of the prostate (TURP) Since it removes the obstructing tissue (C. Chapple, Br. Med. Journal 304:1198–1199 (1992)) it is a treatment which is directed to the static and dynamic components of BPH. However, this surgical treatment is associated with rates of mortality (1%) and adverse event (incontinence 2–4%, infection 5–10%, and impotence 5–10%). A noninvasive alternative treatment would thus be highly desirable.

The incidental clinical observation that urinary incontinence developed in women during antihypertensive treatment with prazosin (T. Thien, K. P. Delacre, F. M. J. Debruyne, R. A. P. Koene, Br. Med. Journal, 622–623 (1978)) and the experimental work of Caine (op cit.) contributed to the recognition of the potential role of selective $\alpha$-1 adrenoceptor blockade in diseases of the lower urinary tract. Subsequent studies by several groups have documented the functional role of $\alpha$-1 adrenoceptors relative to $\alpha$-2 adrenoceptors in the stromal compartment of the prostate, thereby providing a putative molecular basis for the use of specific $\alpha$-1 adrenoceptor blockers in the non-surgical management of BPH (C. R. Chapple, M. L. Aubry, S. James, M. Greengrass, G. Burnstock, R. T. Turner-Warwick, Br. J. Urol. 63: 487–496 (1989)). Clinical efficacy of $\alpha$-1 antagonists in BPH has been demonstrated with several nonselective $\alpha$-1 blockers, including terazosin (Hytrin™), prazosin, and doxazosin. Treatment periods as short as two to four weeks with $\alpha$-1 adrenoceptor blockers have shown objective improvements in the mean and maximum urinary flow rates (14–96% ) with subjective improvements in patients' symptom scores (R. A. Janknegt, C. R. Chapple, Eur. Urol. 24: 319–326 (1993)). Longer term studies with terazosin, indoramin, prazosin, and doxazosin have similarly demonstrated significant improvements in urinary flow rates and subjective symptom scores (R. A. Janknegt, op. cit., H. Lepor, G. Knapp-Maloney, J. Urol. 145: 263A (1991), W. Chow, D. Hahn, D. Sandhu, Br. J. Urol. 65: 36–38 (1990) and C. R. Chapple, T. J. Christmas, E. J. G. Milroy, Urol. Int. 45: 47–55 (1990)). However, these agents possess similar dose limiting side effects: hypotension, dizziness, and muscle fatigue. Them thus exists a need for a "uroselective" $\alpha$-1 antagonist with reduced side effect liabilities.

SUMMARY OF THE INVENTION

In its principle embodiment, the present invention provides certain hexahydro-[1H]-benz[e]isoindole compounds which are selective $\alpha$-1 antagonists useful in the treatment of BPH.

The compounds of this invention have the structure

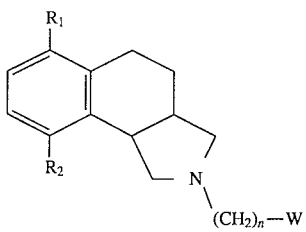

or a pharmaceutically acceptable salt thereof; where n is an integer from 2 to 6, inclusive.

The substituent groups $R_1$ and $R_2$ are independently selected from the group consisting of hydrogen, alkoxy, hydroxy, alkyl, halo, carboxy, and alkoxycarbonyl.

The group W is selected from the group consisting of

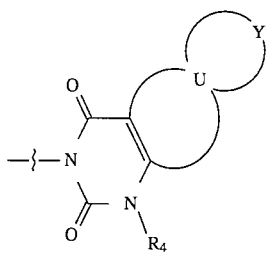

wherein $R_4$ is hydrogen or lower alkyl and

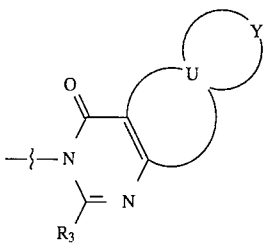

where $R_3$ is selected from the group consisting of hydrogen, lower alkyl, unsubstituted phenyl and phenyl substituted with lower alkyl.

U, taken together with the carbon atoms to which it is attached forms a ring selected from the group consisting of (a) an unsubstituted or substituted five membered ring having four carbon atoms, two double bonds and one heteroatom selected from the group consisting of —N($R_5$)—, —O— and —S— wherein R5 is hydrogen or lower alkyl and the ring substituent is selected from the group consisting of lower alkyl, phenyl, halo, cyano, nitro, carboxy, alkoxycarbonyl and alkoxy, and (b) a six-membered carbocyclic aromatic ring which is unsubstituted or substituted with a substitutent selected from the group consisting of lower alkyl, halo, cyano, nitro, carboxy, alkoxycarbonyl and alkoxy.

Y, is attached to two adjacent atoms of the ring U and, taken together with the two atoms of the ring U to which it is attached, forms a ring selected from the group consisting of (a) an unsubstituted or substituted five membered ring having four carbon atoms, two double bonds and one heteroatom selected from the group consisting of —N($R_5$)—, —O— and —S— wherein $R_5$ is hydrogen or lower alkyl and the ring substituent is selected from the group consisting of lower alkyl, phenyl, halo, cyano, nitro, carboxy, alkoxycarbonyl and alkoxy; (b) a six-membered carbocyclic aromatic ring which is unsubstituted or substituted with a substitutent selected from the group consisting of lower alkyl, halo, cyano, nitro, carboxy, alkoxycarbonyl, and alkoxy; and (c) an unsubstituted or substituted six membered ring having one to three double bonds and one or two nitrogen atoms, wherein the ring substituent is selected from the group consisting of lower alkyl, halo, cyano, nitro, carboxy, alkoxycarbonyl and alkoxy.

The present invention also relates to pharmaceutical compositions which comprise a therapeutically effective amount of a compound of claim 1 in combination with a pharmaceutically acceptable carrier.

The invention further relates to a method of antagonizing alpha-1 receptors in a host mammal in need of such treatment a therapeutically effective amount of a compound of claim 1.

DETAILED DESCRIPTION OF THE INVENTION

As used throughout this specification and the appended claims, the following terms have the meaning specified.

The terms "lower alkyl" or "alkyl" as used herein refer to straight or branched chain alkyl radicals containing from 1 to 10 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "alkoxy" as used herein refers to $R_{41}$O— wherein $R_{41}$ is a loweralkyl group, as defined above. Examples of alkoxy include, but are not limited to, methoxy, ethoxy, isopropoxy, tert-butoxy, and the like.

The term "alkoxycarbonyl" as used herein refers to an alkoxyl group as previously defined appended to the parent molecular moiety through a carbonyl group. Examples of alkoxycarbonyl include, but are not limited to methoxycarbonyl, ethoxycarbonyl, isopropoxycarbonyl and the like.

The term "six-membered carbocyclic aromatic ring" denotes a benzene ring which is fused to one or more additional rings which, in turn, may be either carbocyclic or heterocyclic.

The term "ethylenedioxy" as used herein refers to —O—$CH_2$—$CH_2$—O— which when attached to two adjacent positions on a benzene ring forms a six-membered ring.

The term "methylenedioxy" as used herein refers to —O—$CH_2$—O— which when attached to two adjacent positions on a benzene ring forms a 5-membered ring.

By "pharmaceutically acceptable salt" is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharm. Sciences,* 66: 1–19 (1977). The compounds of the present invention can be used in the form of salts derived from inorganic or organic acids. The salts can be prepared in situ during the final isolation and purification of the compounds of the invention, or separately by reacting the free base function with a suitable organic acid. These salts include but are not limited to the following: acetate, adipate, alginate, titrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Basic addition salts can be prepared in situ during the final isolation and purification of the compounds of formula (I), or separately by reacting the carboxylic acid function with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

Asymmetric centers may exist in the compounds of the present invention. The present invention comtemplates the various stereoisomers and mixtures thereof. Starting compounds of particular stereochemistry are either commercially available or are made by the methods detailed below and resolved by techniques well known in the art of organic chemistry.

Compounds falling within a particular embodiment of the invention are made clear by the following in which particular values for the groups are illustrated.

One embodiment of the present invention provides a compound of the formula

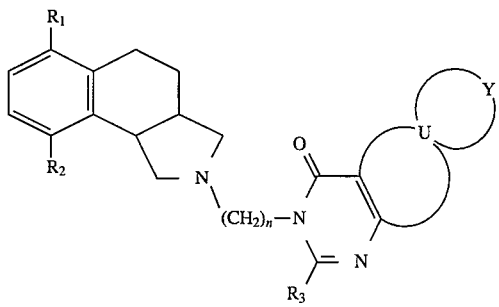
(II)

wherein $R_1$, $R_2$, n, $R_3$, U, and Y are as previously defined.

Another embodiment of the present invention provides a compound of the formula

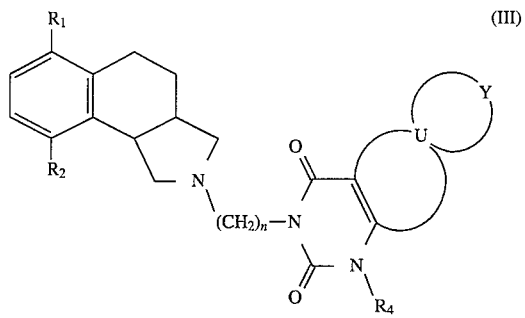
(III)

wherein $R_1$, $R_2$, n, $R_4$, U, and Y are as previously defined.

Yet another embodiment of the present invention provides a compound of formula (I) wherein W is selected from the group consisting of

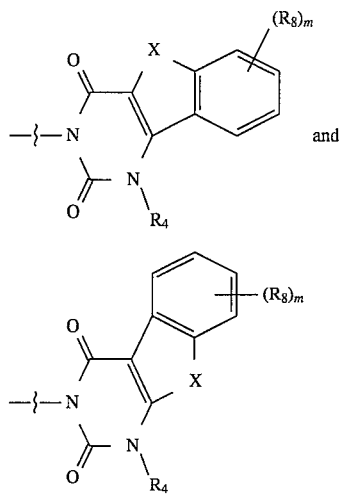

wherein X is selected from the group consisting of —N($R_5$)—, —O— and —S— wherein $R_5$ is hydrogen or lower alkyl, m is selected from 1, 2 and 3, $R_8$ at each occurence is independently selected from the group consisting of hydrogen, lower alkyl, halo, cyano, nitro, carboxy, alkoxycarbonyl, alkoxy, and, when m is two, methylenedioxy and ethylenedioxy, and $R_4$ is as previously defined.

Yet another embodiment of the present invention provides a compound of formula (I) wherein W is selected from the group consisting of

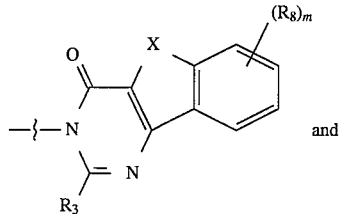

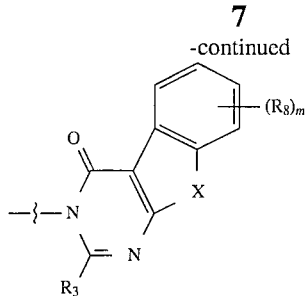

wherein X is selected from the group consisting of —N(R$_5$)—, —O— and —S— wherein R$_5$ is hydrogen or lower alkyl m is selected from 1, 2 and 3, R$_8$ at each occurence is independently selected from the group consisting of hydrogen, lower alkyl, halo, cyano, nitro, carboxy, alkoxycarbonyl, alkoxy, and, when m is two, methylenedioxy and ethylenedioxy, and R$_3$ is as previously defined.

Yet another embodiment of the present invention provides a compound of formula (I) wherein W is selected from the group consisting of

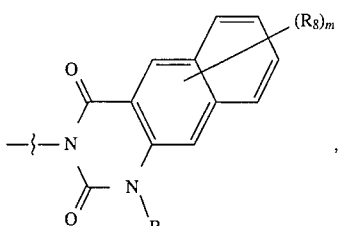

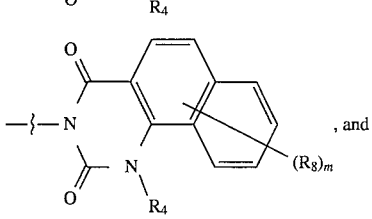

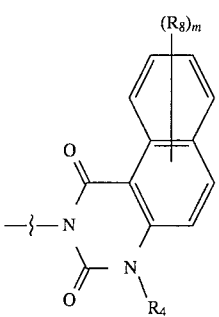

wherein m is selected from 1, 2 and 3, R$_8$ at each occurence is independently selected from the group consisting of hydrogen, lower alkyl, halo, cyano, nitro, carboxy, alkoxycarbonyl, alkoxy, and, when m is two, methylenedioxy and ethylenedioxy, and R$_4$ is a previously defined.

Yet another embodiment of the present invention provides a compound of formula (I) wherein W is selected from the group consisting of

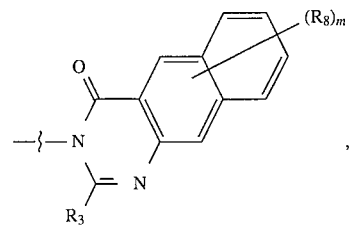

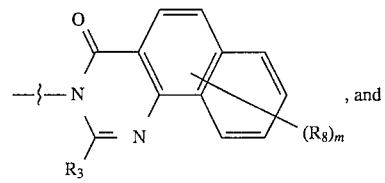

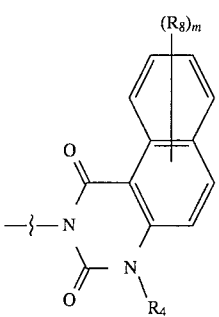

wherein m is selected from 1, 2 and 3, R$_8$ at each occurence is independently selected from the group consisting of hydrogen, lower alkyl, halo, cyano, nitro, carboxy, alkoxycarbonyl, alkoxy, and, when m is two, methylenedioxy and ethylenedioxy, and R$_3$ is as previously defined.

Yet another embodiment of the present invention provides a compound of formula (I) wherein W is selected from the group consisting of

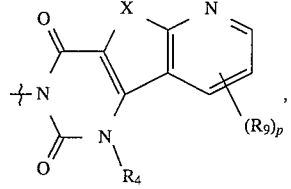

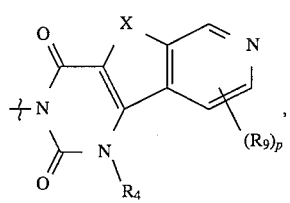

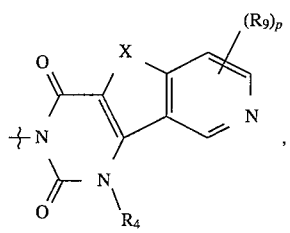

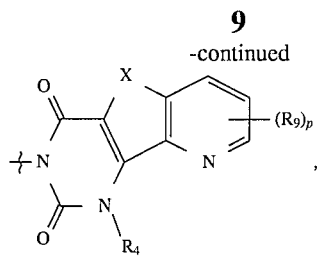

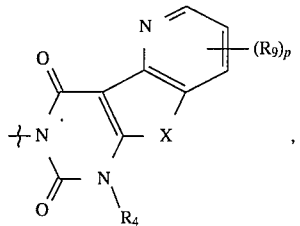

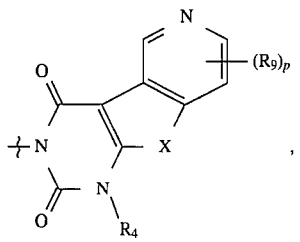

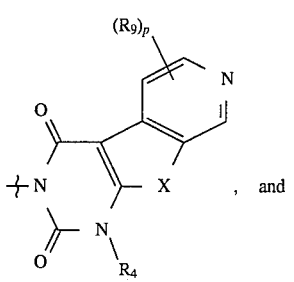

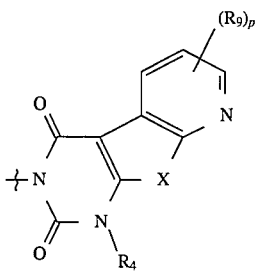, and

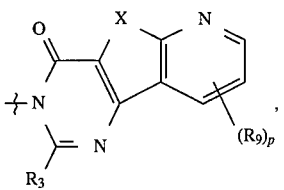

where X is selected from the group consisting of —N(R$_5$)—, —O— and —S— wherein R$_5$ is hydrogen or lower alkyl, p is selected from 1 and 2, R$_9$ at each occurence is independently selected from the group consisting of hydrogen, lower alkyl, phenyl, halo, cyano, nitro, carboxy, alkoxycarbonyl and alkoxy, and R$_4$ is as previously defined.

Yet another embodiment of the present invention provides a compound of formula (I) wherein W is selected from the group consisting of

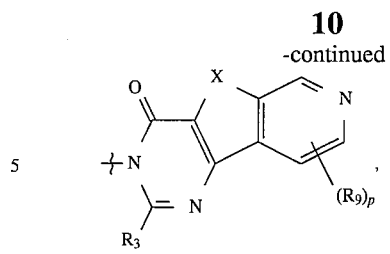

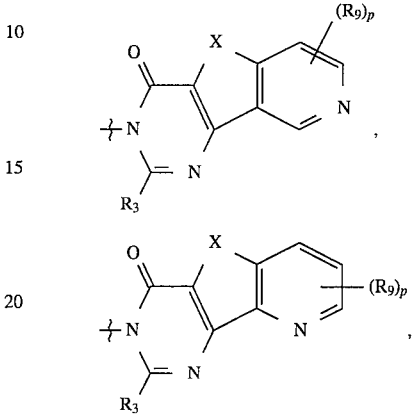, and where X is selected from the group consisting of —N(R$_5$)—, —O— and —S— wherein R$_5$ is hydrogen or lower alkyl, p is selected from 1 and 2, R$_9$ at each occurence is independently seletced from the group consisting of hydrogen, lower alkyl, phenyl, halo, cyano, nitro, carboxy, alkoxycarbonyl and alkoxy, and $R_4$ is as previously defined.
Yet another embodiment of the present invention provides a compound of formula (I) wherein W is selected from the group consisting of
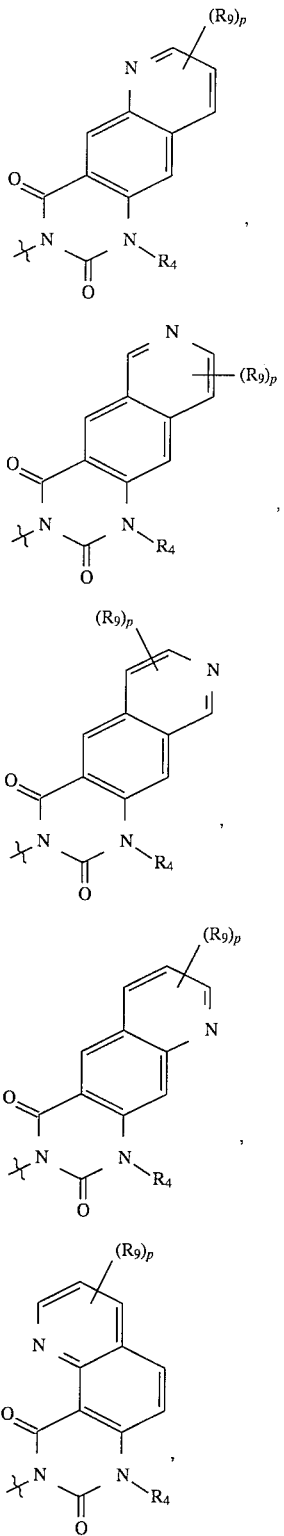
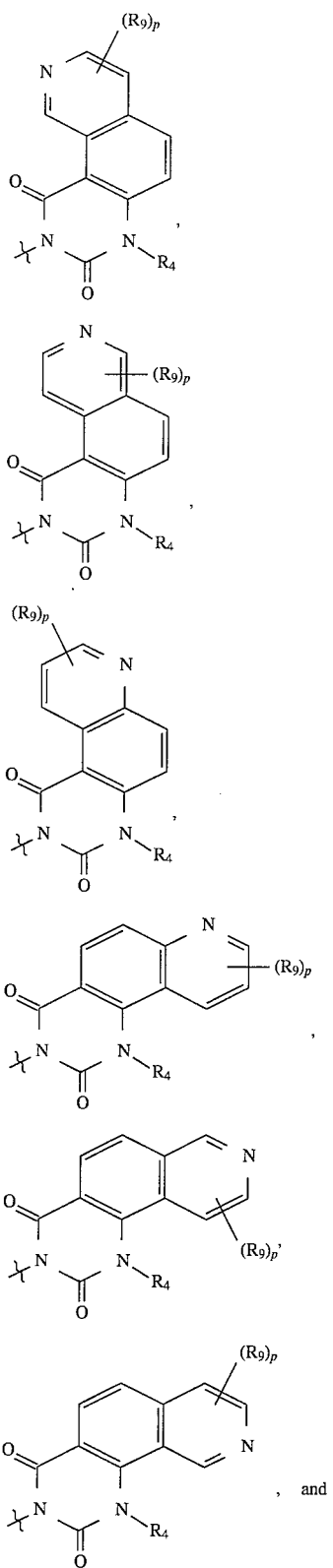
, and

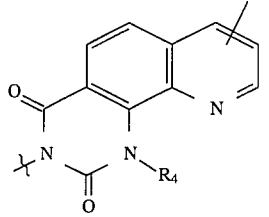
where p is selected from 1 and 2, $R_9$ at each occurrence is independent selected from the group consisting of hydrogen, lower alkyl, phenyl, halo, cyano, nitro, carboxy, alkoxycarbonyl and alkoxy, and $R_4$ is as previously defined.
Yet another embodiment of the present invention provides a compound of formula (I) wherein W is selected from the group consisting of
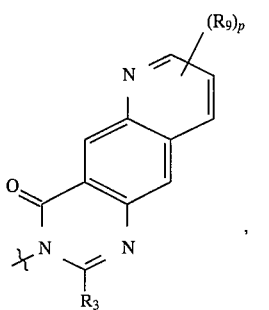
,
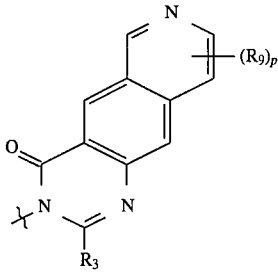
,
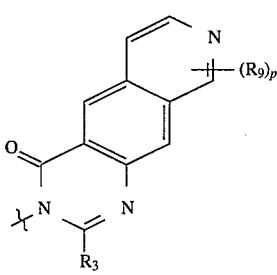
,
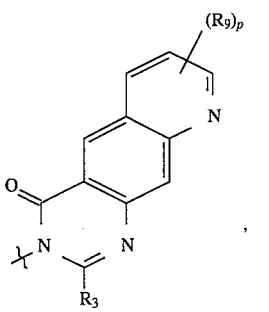
,
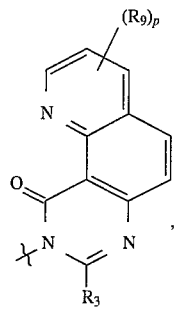
,
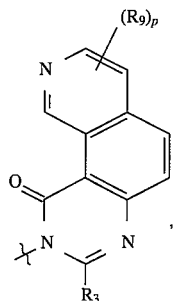
,
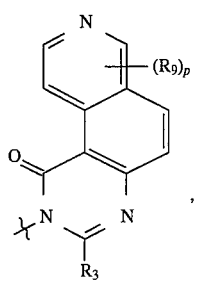
,
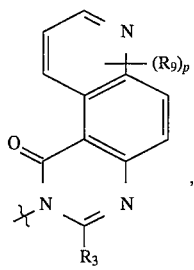
,
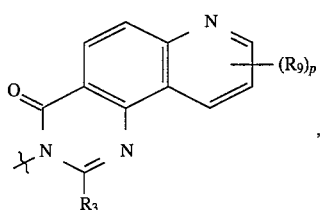
,
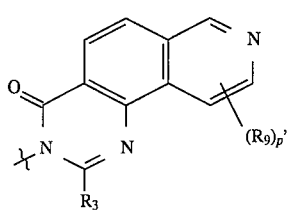
,

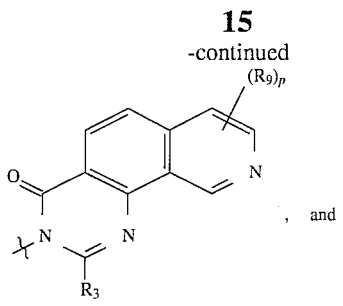
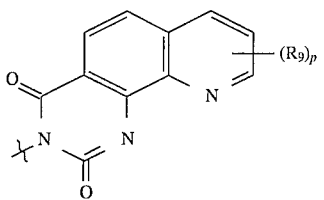
where p is selected from 1 and 2, $R_9$ at each occurrence is independently selected from the group consisting of hydrogen, lower alkyl, phenyl, halo, cyano, nitro, carboxy, alkoxycarbonyl and alkoxy, and $R_3$ is as previously defined.
Yet another embodiment of the present invention provides a compound of formula (I) wherein W is selected from the group consisting of
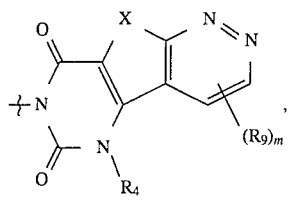
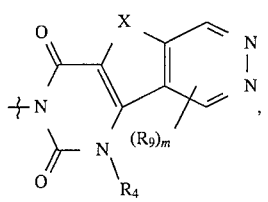
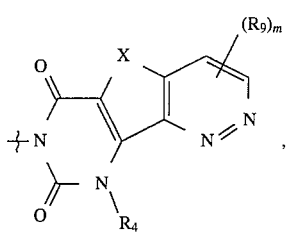
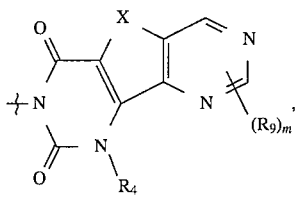
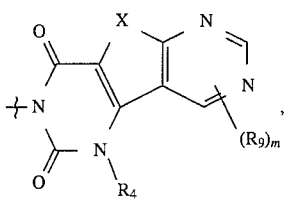
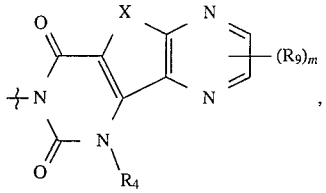
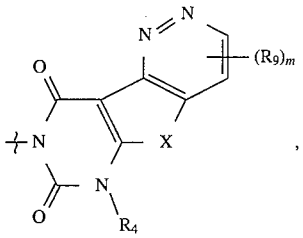
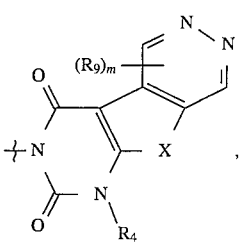
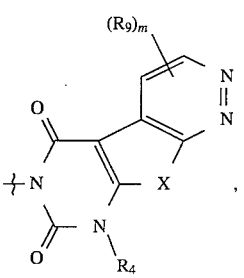
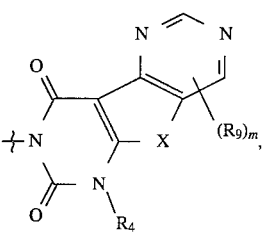
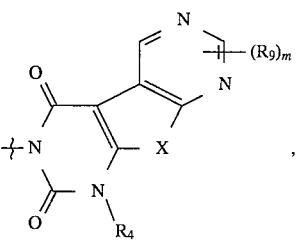
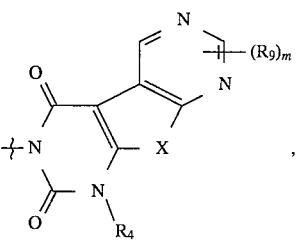, and

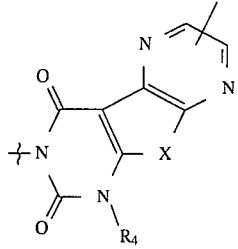

where X is selected from the group consisting of —N(R$_5$)—, —O— and —S— where R$_5$ is hydrogen or lower alkyl and m, R$_4$ and R$_9$ are as previously defined.

Yet another embodiment of the present invention provides a compound of formula (I) wherein W is selected from the group consisting of

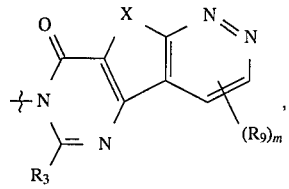

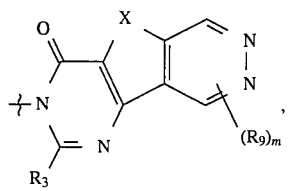

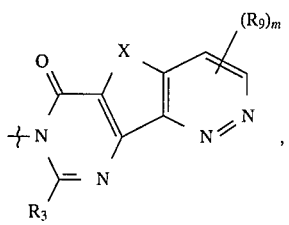

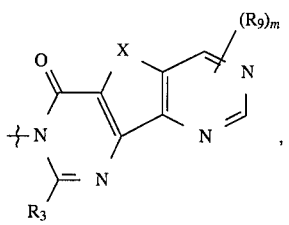

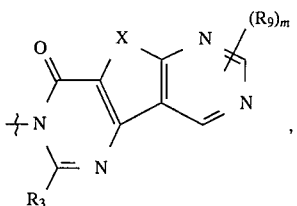

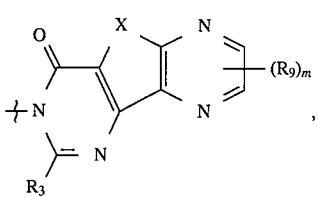

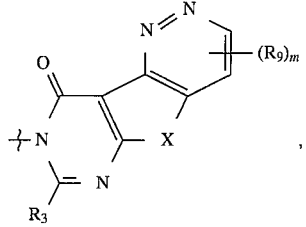

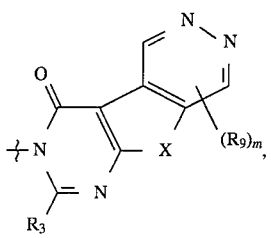

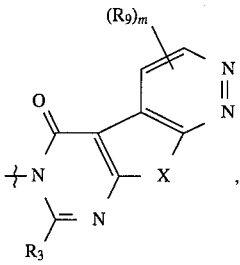

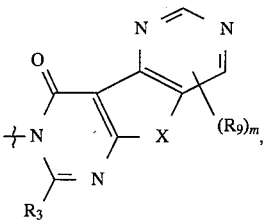

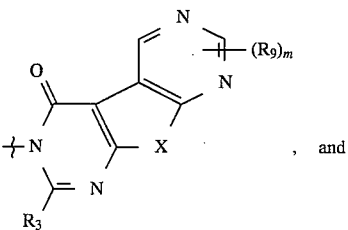, and

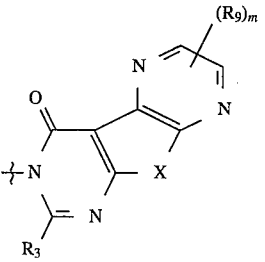

where X is selected from the group consisting of —N(R$_5$)—, —O— and —S— wherein R$_5$ is hydrogen or lower alkyl and R$_3$, m and R$_9$ are as previously defined.

Yet another embodiment of the present invention provides a compound of formula (I) wherein W is selected from the group consisting of

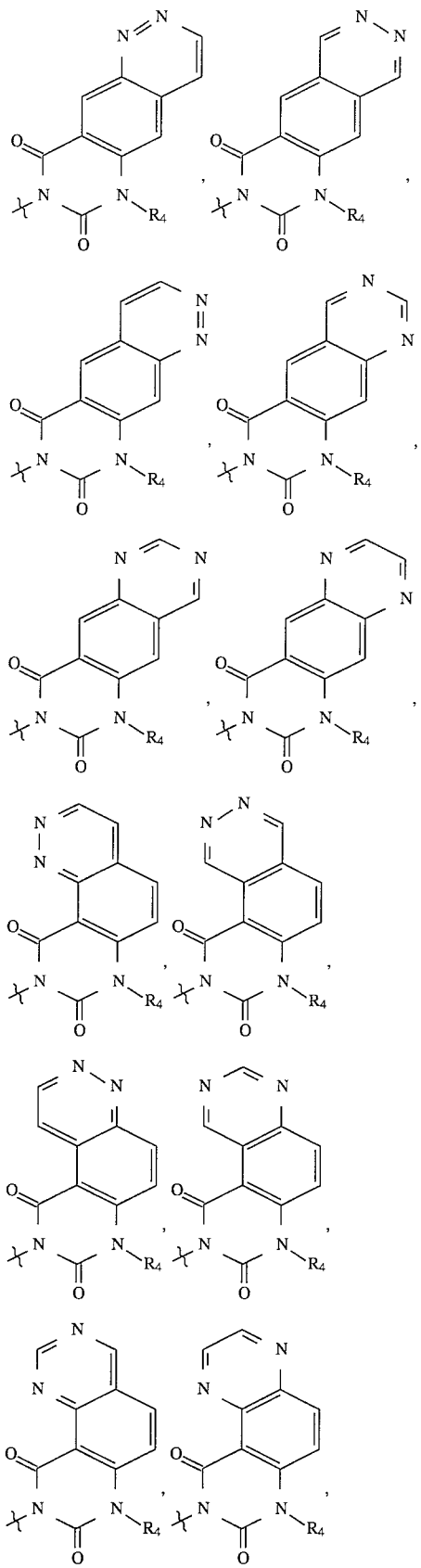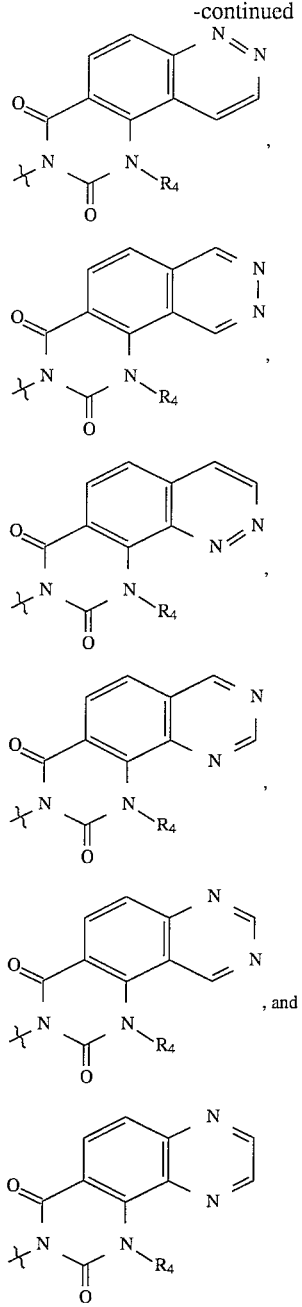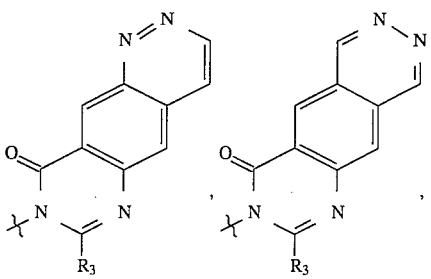
where $R_4$ is as previously defined.
Yet another embodiment of the present invention provides a compound of formula (I) wherein W is selected from the group consisting of

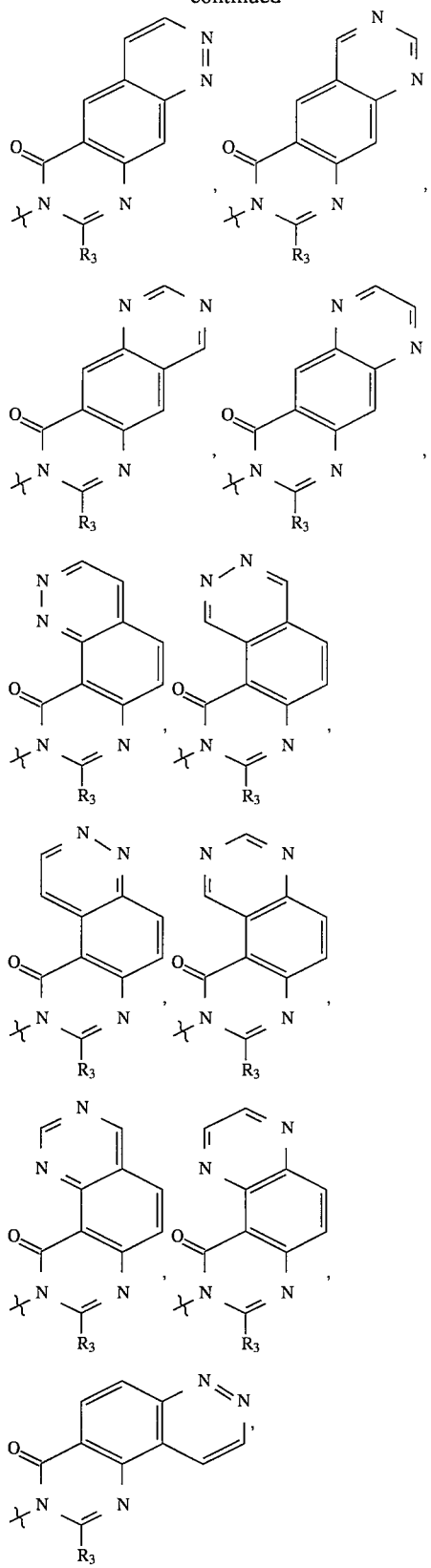

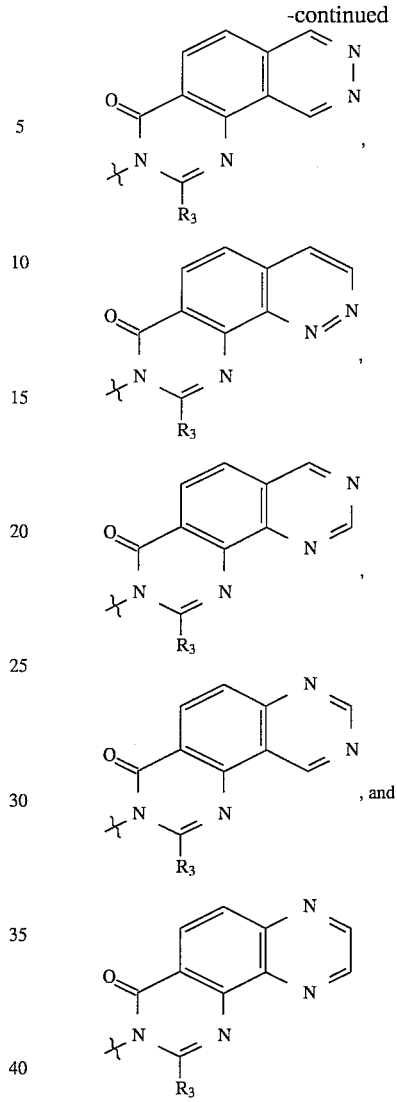

wherein $R_3$ is as previously defined.

A preferred embodiment of the present invention provides a compound of formula (I) wherein U, taken together with the carbon atoms to which it is attached forms a fused ting selelcted from the group consisting of a fused benzene, a fused thiophene, a fused furan, and a fused pyrrole ring; Y, taken together with the two carbon atoms of U to which it is attached forms a fused ring selected from the group consisting of a fused benzene ring and a fused pyridine ring; and $R_1$, $R_2$, n and $R_4$ are as previously defined.

In one particularly preferred embodiment of the present invention is a compound of formula (I) wherein one of $R_1$ and $R_2$ is alkoxy and the other one is hydrogen, n is selected from an integer from 2 to 4 and W is selected from the group consisting of

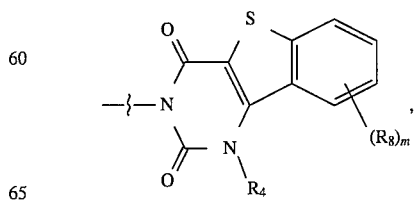

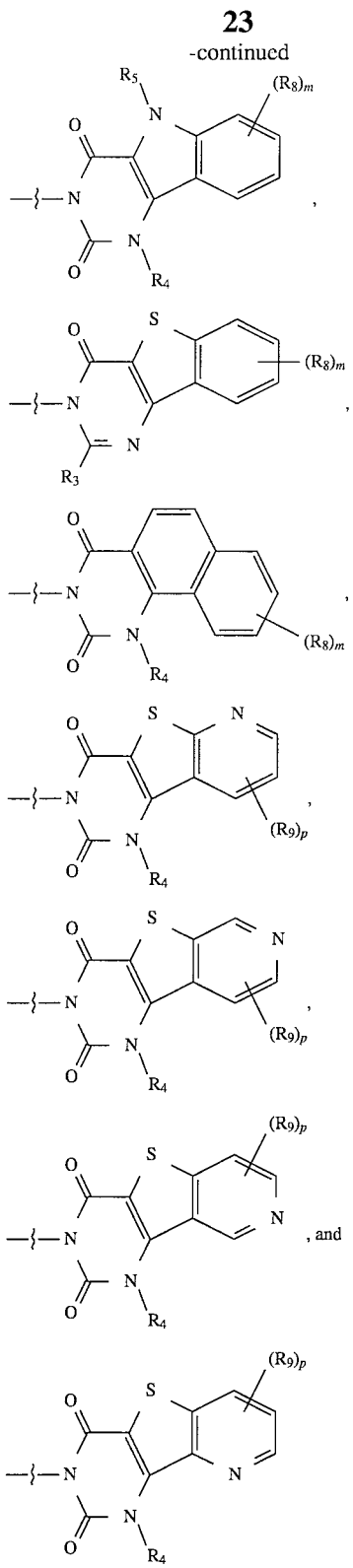

where m, p, $R_3$, $R_4$, $R_8$, and $R_9$ are as previously defined.

In another particularly preferred embodiment, the invention provides a compound selected from the group consisting of

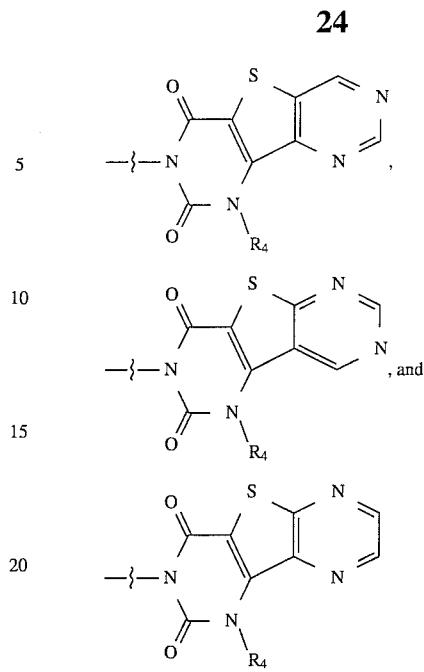

where $R_4$ is as defined above.

Representative compounds falling within the scope of the present invention include:

3-[2-(cis-6-methoxy-2,3,3a,4,5,9b-hexahydro-[1H]-benz[e]isoindol-1-yl)ethyl]-[1]-benzothieno[3,2-d]pyrimidine-2,4(1H,3H)-dione;

3-[2-(trans-9-methoxy-2,3,3a,4,5,9b-hexahydro-[1H]-benz[e]isoindol-1-yl)ethyl]-[1]-benzothieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-benzofuro[3,2-d]pyrimidine-2,4(1H,3H)-dione;

3-[3-(cis-6-methoxy-2,3,3 a,4,5,9b-hexahydro-[1H]-benz[e]isoindol-1-yl)propyl]-[1]-benzothieno[3,2-d]pyrimidine-2,4(1H,3H)-dione;

3-[2-(cis-9-methoxy-2,3,3a,4,5,9b-hexahydro-[1H]-benz[e]isoindol-1-yl)ethyl]-[1]-benzothieno[3,2-d]pyrimidine-2,4(1H,3H)-dione;

3-[3-(cis-9-methoxy-2,3,3a,4,5,9b-hexahydro-[1H]-benz[e]isoindol-1-yl)propyl]-[1]-benzothieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-[1]-5,6,7,8-tetrahydrobenzothieno[2,3-d]pyrimidine-2,4(1H,3H)-dione;

3-[2-((3aS,9bS)-cis-6-methoxy-2,3,3a,4,5,9b-hexahydro-[1H]-benz[e]isoindol-1-yl)ethyl]-[1]-benzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl-[1]-benzothieno[3,2-d]pyrimidine-2,4(1H,3H)-dione;

-[2-(trans-6-methoxy-2,3,3a,4,5,9b-hexahydro-[1 H]-benz[e]isoindol-1-yl)ethyl]-[1]-benzothieno[3,2-d]pyrimidine-2,4(1H,3H)-dione;

3-[2-(cis-6-methoxy-2,3,3a,4,5,9b- hexahydro-[1H]-benz[e]isoindol-1-yl)ethyl]- 1-methyl-[1]-benzothieno[3,2-d]pyrimidine-2,4(1H,3H)-dione;

3-[4-(cis-6-methoxy-2,3,3a,4,5,9b-hexahydro-[1H]-benz[e]isoindol-1-yl)butyl]-[1]-benzothieno[3,2-d]pyrimidine-2,4(1H,3H) -dione;

3-[2-(cis-6-methoxy-2,3,3a,4,5,9b-hexahydro-[1H]-benz[e]isoindol-1-yl)ethyl]-[1]-benzothieno[2,3-d]pyrimidine-2,4(1H,3H)-dione;

3-[2-(cis -6-methoxy-2,3,3a,4,5,9b-hexahydro-[1H]-benz[e]isoindol-1-yl)ethyl]-1H-pyrimido[5,4-b]indole-2,4(3H,5H)-dione;

3-[4-cis-9-methoxy-2,3,3a,4,5,9b-hexahydro-[1H]-benz[e]isoindol-1-yl)butyl]-[1]-benzothieno[3,2-d]pyrimidine-2,4(1H,3H)-dione;

3-[2-((3aR,9bR)-cis-9-methoxy-2,3,3a,4,5,9b-hexahydro-[1H]-benz[e]isoindol-1-yl)ethyl]-[1]-benzothieno[3,2-d]pyrimidine-2,4(1H,3H)-dione;

3-[2-(trans-6-methoxy-2,3 3a,4,5,9b-hexahydro-[1H]-benz[e]isoindol-1-yl)ethyl]1H-pyrimido[5,4-b]indole-2,4(3H,5H)-dione;

3-[2-(trans-6-methoxy-2,3 3a,4,5,9b-hexahydro-[1H]-benz[e]isoindol-1-yl)ethyl]-benzofuro[3,2-d]pyrimidine-2,4(1H,3H)-dione;

3-[2-((3aS,9bS)-cis-9-methoxy-2,3,3a,4,5,9b-hexahydro-[1H]-benz[e]isoindol-1-yl)ethyl]-[1]-benzothieno[3,2-d]pyrimidine-2,4(1H,3H)-dione;

3-[2-(cis-6-Hydroxy-2,3,3a,4,5,9b-hexahydro-[1H]-benz[e]isoindol-1-yl)ethyl]-[1]-benzothieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-benzo[g]quinazoline-2,4(1H,3H)-dione;

3-[2-(cis-6-methoxy-2,3,3a,4,5,9b-hexahydro-[1H]-benz[e]isoindol-1-yl)ethyl]-6,7,8,9-tetrahydro[1]-benzothieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]pyrido[3',2':4,5]thieno[3,2-d]pyrimidine-2,4(1H,3H)-dione;

3-[2-((3aR,9bR)-cis-9-methoxy-2,3,3a,4,5,9b-hexahydro-[1H]-benz[e]isoindol-1-yl)ethyl]-1H-pyrimido[5,4-b]indole-2,4(1H,3H)-dione;

3-[2-(cis-6-methoxy-2,3,3a,4,5,9b-hexahydro-[1H]-benz[e]isoindol-1-yl)ethyl]-benzo[h]quinazoline-2,4(1H,3H)-dione;

3-[2-((3aR,9bR)-cis-6-methoxy-2,3,3a,4,5,9b-hexahydro-[1H]-benz[e]isoindol-1-yl)ethyl]-1H-pyrimido[5,4-b]indole-2,4(1H,3H)-dione;

3-[2-(cis-6-methoxy-2,3,3a,4,5,9b-hexahydro-[1H]-benz[e]isoindol-1-yl)ethyl]-pyrido[[3',2':4,5]furo[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-benzothieno[2,3-d]pyrimidin-4(3H)-one;

3-[2-(cis-6-methoxy-2,3,3a,4,5,9b-hexahydro-[1H]-benz[e]isoindol-1-yl)ethyl]- 2-methyl-[1]-benzothieno[2,3-d]pyrimidin-4(3H)-one;

3-[2-(cis-6-methoxy-2,3,3a,4,5,9b-hexahydro-[1H]-benz[e]isoindol-1-yl)ethyl]-[1]-benzothieno[3,2-d]-1,2,3-triazine-4(3H)-one;

3-[2-(cis-6-methoxy-2,3,3a,4,5,9b-hexahydro-[1H]-benz[e]isoindol-1-yl)ethyl]-2-phenyl-[1]-benzothieno[3,2-d]-4(1H,3H)-one;

3-[2-((3aR,9bR)-cis-6-methoxy-2,3,3a,4,5,9b-hexahydro-[1H]-benz[e]isoindol-1-yl)ethyl]-pyrido[3',2':4,5]thieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-7-trifluoromethyl[1]-benzothieno[2,3-d]pyrimidine-2,4(1H,3H)-dione;

2-[2-((3aR,9bR)-cis-6-methoxy-2,3,3a,4,5,9b-hexahydro-[1H]-benz[e]isoindol-1-yl)ethyl -2H-[1]-benzothieno[3,2-e]-1,2-thiazin-3[4H]-one 1,1 dioxide;

3-[2-((3aR,9bR)-cis-6-methoxy-2,3,3a,4,5,9b- hexahydro-[1H]-benz[e]isoindol-1-yl)ethyl]-pyrido[3',2':4,5]thieno[3,2-d]pyrimidine-4(3H)-one;

3-[2-((3aR,9bR)-cis-6-methoxy-2,3,3a,4,5,9b-hexahydro-[1H]-benz[e]isoindol-1-yl)ethyl]-9-methyl[1]-benzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-pyrido[4',3':4,5]thieno[3,2-d]pyrimidine-4(1H,3H)-one;

3-[2-((3aR,9bR)-cis-6-methoxy-2,3,3a,4,5,9b-hexahydro-[1H]-benz[e]isoindol-1-yl)ethyl]-pyrido[2',3':4,5]thieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-pyrido[3',4':4,5]thieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-1-methyl-[1]-benzothieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-8-chloro-[1]-benzothieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-7,8-dimethoxy-[1]-benzothieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-1-methyl-pyrido[3',2':4,5]thieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-1-methylpyrido[3',2':4,5]pyrrolo[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-2H-[1]-benzothieno[2,3-e]-1,3-oxazine-2,4(1H,3H)-dione;

3-[2-(cis-6-methoxy-2,3,3a,4,5,9b-hexahydro-[1H]-benz[e]isoindol-1-yl)ethyl]-2H-[1]-benzothieno[2,3-e]-1,3-oxazine-4(3H)-one;

3-[2-(cis-6-methoxy-2,3,3a,4,5,9b-hexahydro-[1H]-benz[e]isoindol-1-yl)ethyl]-pyrido[3',4':4,5]thieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-pyrido[2',3':4,5]thieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-8-chloro-[1]-benzothieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-pyrido[4',3':4,5]pyrrolo[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-pyrido[3',4':4,5]pyrrolo[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-pyrido[2',3':4,5]pyrrolo[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]pyrazino[2',3':4,5]thieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-thieno[2,3-d:4,5]dipyrimidine-2,4(1H,3H)-dione;

3-[2-(cis-6-methoxy-2,3,3a,4,5,9b-hexahydro-[1H]-benz[e]isoindol-1-yl)ethyl]-thieno[3,2-d:4,5]dipyrimidine-2,4(1H,3H)-dione;

3-[2-(cis-6-methoxy-2,3,3,a,4,5,9b-hexahydro-[1H]-benz[e]isoindol-1-yl)ethyl]-pyrimido[4',5':4,5]thieno[2,3-c]pyridazine-6,8(5H,7H)-dione;

3-[2-(cis-6-methoxy-2,3,3a,4,5,9b-hexahydro-[1H]-benz[e]isoindol-1-yl)ethyl]-oxazol4,5-g]quinazoline-6,8(5H,7H)-dione;

3-[2-(cis-6-methoxy-2,3,3a,4,5,9b-hexahydro-[1H]-benz[e]isoindol-1-yl)ethyl]thiazol-[4,5-g]quinazoline-6,8(5H,7H)-dione;

3-[2-(cis-6-methoxy-2,3,3a,4,5,9b-hexahydro-[1H]-benz[e]
isoindol-1-yl)ethyl]-1H-imidazo[4,5-g]quinazoline-6,
8(5H,7H)-dione;

3-[2-((3aR,9aS)-trans-6-methoxy-2,3,3a,4,5,9b-hexahydro-
[1H]-benz[e]isoindol-1-yl)ethyl]-[1]-benzothieno[3,2-d]
pyrimidine-2,4(1H,3H)-dione;

3-[2-((3aS,9aR)-trans-6-methoxy-2,3,3a,4,5,9b-hexahydro-
[1H]-benz[e]isoindol-1-yl)ethyl]-[1]-benzothieno[3,2-d]
pyrimidine-2,4(1H,3H)-dione;

3-[2-(cis-6-Ethoxy-2,3,3a,4,5,9b-hexahydro-[1H]-benz[e]
isoindol-1-yl)ethyl]-[1]-benzothieno[3,2-d]pyrimidine-2,
4(1H;3H)-dione;

3-[2-(cis-6-Ethyl-2,3,3a,4,5,9b-hexahydro-[1H]-benz[e]
isoindol-1-yl)ethyl]-[1]-benzothieno[3,2-d]pyrimidine-2,
4(1H,3H)-dione;

3-[2-(cis-6-Bromo-2,3,3a,4,5,9b-hexahydro-[1H]-benz[e]
isoindol-1-yl)ethyl]-[1]-benzothieno[3,2-d]pyrimidine-2,
4(1H,3H)-dione;

3-[2-(cis-6-Methoxycarbonyl-2,3,3a,4,5,9b-hexahydro-
[1H]-benz[e]isoindol-1-yl)ethyl]-[1]-benzothieno[3,2-d]
pyrimidine-2,4(1H3H)-dione;

3-[2-(cis-6-methoxy-2,3,3a,4,5,9b-hexahydro-[1H]-benz[e]
isoindol-1-yl)ethyl]-1H-pyrimido[5,4-b]indole-4[3H]-
one;

3-[2-((3aS,9bS)-cis-6-methoxy-2,3,3a,4,5,9b-hexahydro-
[1H]-benz[e]isoindol-1-yl)ethyl]-pyrido[3',2':4,5]thieno
[3,2-d]pyrimidine-2,4(1H,3H)-dione;

3-[2-((3aR,9bR)-cis-6-methoxy-2,3,3a,4,5,9b-hexahydro-
[1H]-benz[e]isoindol-1-yl)ethyl]-pyrido[3',2':4,5]furo[3,
2-d]pyrimidine-2,4(1H,3H)-dione;

3-[2-((3aR,9bR)-cis-6-methoxy-2,3,3a,4,5,9b- hexahydro-
[1H]-benz[e]isoindol-1-yl)ethyl]pyrido[4',3':4,5]furo[3,
2-d]pyrimidine-2,4(1H,3H)-dione;

3-[2-(trans-6-methoxy-2,3 3a,4,5,9b-hexahydro-[1H]-benz
[e]isoindol-1-yl)ethyl]-1-methyl-[1]-benzothieno[3,2-d]
pyrimidine-2,4(1H,3H)-dione;

3-[4-(trans-9-methoxy-2,3 3a,4,5,9b-hexahydro-[1H]-benz
[e]isoindol-1-yl)butyl]-[1]-benzothieno[3,2-d]pyrimi-
dine-2,4(1H,3H)-dione;

3-[2-(trans-6-methoxy-2,3,3a,4,5,9b-hexahydro-[1H]-benz
[e]isoindol-1-yl)ethyl]pyrido[3',2':4,5]thieno[3,2-d]pyri-
midine-2,4(1H,3H)-dione;

3-[2-(trans-6-methoxy-2,3,3a,4,5,9b-hexahydro-[1H]-benz
[e]isoindol-1-yl)ethyl]-benzo[h]quinazoline-2,4(1H,3H)-
dione;

3-[2-(trans-6-methoxy-2,3,3a,4,5,9b-hexahydro-[1H]-benz
[e]isoindol-1-yl)ethyl]-pyrido[3',2':4,5]thieno[3,2-d]pyri-
midine-2,4(1H,3H)-dione;

3-[2-(trans-6-methoxy-2,3,3a,4,5,9b-hexahydro-[1H]-benz
[e]isoindol-1-yl)ethyl]-benzothieno[2,3-d]pyrimidin-
4(3H) -one;

3-[2-(trans-6-methoxy-2,3,3a,4,5,9b-hexahydro-[1H]-benz
[e]isoindol-1-yl)ethyl]-pyrido[4',3':4,5]thieno[3,2-d]pyri-
midine-2,4(1H,3H)-dione;

3-[2-(trans-6-methoxy-2,3,3a,4,5,9b-hexahydro-[1H]-ben
[e]isoindol-1-yl)ethyl]-pyrido[2',3':4,5]thieno[3,2-d]pyri-
midine-2,4(1H,3H)-dione;

3-[2-((3aR,9bR)-cis-6-methoxy-2,3,3a,4,5,9b- hexahydro-
[1H]-benz[e]isoindol-1-yl)ethyl]-[1]-7-cyano-ben-
zothieno[3,2-d]pyrimidine-2,4(1H,3H)-dione;

3-[2-((3aR,9bR)-cis-6-methoxy-2,3,3a,4,5,9b-hexahydro-
[1H]-benz[e]isoindol-1-yl)ethyl-[1]-8-cyano-benzothieno
[3,2-d]pyrimidine-2,4(1H,3H)-dione;

3-[2-((3aR,9bR)-cis-6-methoxy-2,3,3a,4,5,9b-hexahydro-
[1H]-benz[e]isoindol-1-yl)ethyl]-[1]-8-carbomethoxy-
benzothieno[3,2-d]pyrimidine-2,4(1H,3H)-dione;

3-[2-((3aR,9bR)-cis-6-methoxy-2,3,3a,4,5,9b-hexahydro-
[1H]-benz[e]isoindol-1-yl)ethyl]-[1]-8-N,N-dimethylcar-
boxamido-benzothieno[3,2-d]pyrimidine-2,4(1H,3H)-di-
one;

3-[2-((3aR,9bR)-cis-6-methoxy-2,3,3a,4,5,9b-hexahydro-
[1H]-benz[e]isoindol-1-yl)ethyl]-[1]-8-carboxamido-
benzothieno[3,2-d]pyrimidine-2,4(1H,3H)-dione;

3-[2-((3aR,9bR)-cis-6-methoxy-2,3,3a,4,5,9b-hexahydro-
[1H]-benz[e]isoindol-1-yl)ethyl]-[1]-7-nitro-benzothieno
[3,2-d]pyrimidine-2,4(1H,3H)-dione;

3-[2-((3aR,9bR)-cis-6-methoxy-2,3,3a,4,5,9b-hexahydro-
[1H]-benz[e]isoindol-1-yl)ethyl]-[1]-8-nitro-benzothieno
[3,2-d]pyrimidine-2,4(1H,3H)-dione;

3-[2-((3aR,9bR)-cis-6-methoxy-2,3,3a,4,5,9b-hexahydro-
[1H]-benz[e]isoindol-1yl)ethyl]-[1]-8-acetamido-ben-
zothieno[3,2-d]pyrimidine-2,4(1H,3H)-dione;

3-[2-((3aR,9bR)-cis-6-methoxy-2,3,3a,4,5,9b-hexahydro-
[1H]-benz[e]isoindol-1-yl)ethyl]-[1]-8-N,N-dimethy-
lamino-benzothieno[3,2-d]pyrimidine-2,4(1H,3H)-dione;

3-[2-((3aR,9bR)-cis-6-methoxy-2,3,3a,4,5,9b-hexahydro-
[1H]-benz[e]isoindol-1-yl)ethyl]-[1]-7-carboxamido-
benzothieno[3,2-d]pyrimidine-2,4(1H,3H)dione;

3-[2-((3aR,9bR)-cis-6-methoxy-2,3,3a,4,5,9b-hexahydro-
[1H]-benz[e]isoindol-1-yl)ethyl]-[1]-8-(N-methylcar-
boxamido)-benzothieno[3,2-d]pyrimidine-2,4(1H,3H)-
dione;

3-[2-((3aR,9bR)cis-6-methoxy-2,3,3a,4,5,9b-hexahydro-
[1H]-benz[e]isoindol-1-yl)ethyl]-imidazo[4,5-g]quinazo-
line-6,8(1H,5H)-dione;

3-[2-((3aR,9bR)-cis-6-methoxy-2,3,3a,4,5,9b-hexahydro-
[1H]-benz[e]isoindol-1-yl)ethyl]-[1]-9-cyano-ben-
zothieno[3,2-d]pyrimidine-2,4(1H,3H)-dione;

3-[2-((3aR,9bR)-cis-6-methoxy-2,3,3a,4,5,9b-hexahydro-
[1H]-benz[e]isoindol-1yl)ethyl]-[1]-6-cyano-benzothieno
[3,2-d]pyrimidine-2,4(1H,3H)-dione;

3-[2-((3aR,9bR)-cis-6-methoxy-2,3,3a,4,5,9b-hexahydro-
[1H]-benz[e]isoindol-1-yl))ethyl]-[1]-6-chloro-ben-
zothieno[3,2-d]pyrimidine-2,4(1H,3H)-dione;

3-[2-((3aR,9bR)-cis-6-methoxy-2,3,3a,4,5,9b-hexahydro-
[1H]-benz[e]isoindol-1yl)ethyl]-[1]-7-chloro-ben-
zothieno[3,2-d]pyrimidine-2,4(1H,3H)-dione;

3-[2-((3aR,9bR)-cis-6-methoxy-2,3,3a,4,5,9b-hexahydro-
[1H]-benz[e]isoindol-1-yl)ethyl]-[1]-8-(Nmorpholinocar-
boxamido)-benzothieno[3,2 -d]pyrimidine-2,4(1H,3H)-
dione;

3-[2-((3aR,9bR)-cis-6-methoxy-2,3,3a,4,5,9b-hexahydro-
[1H]-benz[e]isoindol-1-yl)ethyl]-[1]-8- N-methyl-aceta-
mido- benzothieno[3,2 4]pyrimidine-2,4(1H,3H)-dione;

3-[2-((3aR,9bR)-cis-6-methoxy-2,3,3a,4,5,9b-hexahydro-
[1H]-benz[e]isoindol-1-yl)ethyl]-[1]-8-(N-methoxycar-
boxamido)-benzothieno[3,2-d]pyrimidine-2,4(1H,3H)-
dione;

3-[2-((3aR,9bR)-cis-6-methoxy-2,3,3a,4,5,9b-hexahydro-
[1H]-benz[e]isoindol-1-yl)ethyl]-1-methyl-pyrido[2',3':4,
5]thieno[3,2-d]pyrimidine-2,4(1H,3H)-dione;

3-[2-((3aR,9bR)-cis-6-methoxy-2,3,3a,4,5,9b-hexahydro-
[1H]-benz[e]isoindol-1-yl)ethyl]-8-chloro-pyrido[2',3':4,
5]thieno[3,2-d]pyrimidine-2,4(1H,3H)-dione;

3-[2-((3aR,9bR)-cis-6-methoxy-2,3,3a,4,5,9b-hexahydro-
[1H]-benz[e]isoindol-1-yl)ethyl]-6-chloro-pyrido[2',3':4,
5]thieno[3,2-d]pyrimidine-2,4(1H,3H)-dione;

3-[2-((3 aR,9b R)-cis-6-methoxy-2,3,3a,4,5,9b-hexahydro-
[1H]-benz[e]isoindol-1-yl)ethyl]-8-methoxy-pyrido[2',
3':4,5]thieno[3,2-d]pyrimidine-2,4(1H,3H)-dione;

3-[2-((3aR,9bR)-cis-6-methoxy-2,3,3a,4,5,9b-hexahydro-
[1H]-benz[e]isoindol-1-yl)ethyl]-6-methoxy-pyrido[2',
3':4,5]thieno[3,2-d]pyrimidine-2,4(1H,3H)-dione;

3-[2-((3aR,9bR)-cis-6-methoxy-2,3,3a,4,5,9b-hexahydro-
[1H]-benz[e]isoindol-1-1H-pyrimido[5,4-b]indole-4(1H,
3H)-one;

3-[2-((3aR,9bR)-cis-6-methoxy-2,3,3a,4,5,9b-hexahydro-
[1H]-benz[e]isoindol-1-yl)ethyl[-[1]-8-chloro-ben-
zothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-[1]-7,8-dimethoxy-benzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-[1]-9-methyl-benzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl )ethyl]-2,3-dihydro-pyrido[3',2':4,5]thieno[3,2-d]pyrimidine-4(1H,3H)-one;

3-[2-(cis-(3aR,9bR)-6-methoxy-2,3,3a,4,5,9b-hexahydro-[1H]-benz[e]isoindol-1-yl)ethyl]-pyrazino[2',3':4,5]thieno[3,2-d]pyrimidine-4(1H,3H)-one;

3-[2-((3aR,9bR)-cis-6- methoxy-2,3,3a,4,5,9b-hexahydro-[1H]-benz[e]isoindol-1-yl)ethyl]-[1]-9-chloro-benzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-[1]-9-methoxy-benzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-[1]-8-methyl-benzothieno[3,2-d]pyrimidine-2,4(1H,3H)-dione;

3-[2-((3aS ,9bS)-cis-6-methoxy-2,3,3a,4,5,9b-hexahydro-[1H]-benz[e]isoindol-1-yl)ethyl]-pyrido[3',2':4,5]thieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-pyrido[3',2':4,5]furo[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-pyrido[2',3':4,5]furo[3,2-d]pyrimidine-2,4(1H,3H)-dione;

3-[2-((3aS,9bS)-cis-6-methoxy-2,3,3a,4,5,9b-hexahydro-[1H]-benz[e]isoindol-1-yl)ethyl]-pyrido[2',3':4,5]thieno[3,2-d]pyrimidine-2,4(1H,3H)-dione;

3-[2-((3aR,9bR)-cis-9-methoxy-2,3,3a,4,5,9b-hexahydro-[1H]-benz[e]isoindol-1-yl)butyl]-pyrido[2',3':4,5]thieno[3,2-d]pyrimidine-2,4(1H,3H)-dione;

3-[2-((3aR,9bR)-cis-9-methoxy-2,3,3a,4,5,9b-hexahydro-[1H]-benz[e]isoindol-1yl)butyl]-pyrazino[2',3':4,5]thieno[3,2-d]pyrimidine-2,4(1H,3H)-dione;

3-[2-((3aR,9bR)-cis-9-methoxy-2,3,3a,4,5,9b-hexahydro-[1H]-benz[e]isoindol-1yl)butyl]-pyrido[3',2':4,5]thieno[3,2-d]pyrimidine-2,4(1H,3H)-dione;

3-[2-((3aR,9bR)cis-6-methoxy-2,3,3a,4,5,9b-hexahydro-[1H]-benz[e]isoindol-1-yl)ethyl]-pyrido[2,3-h]quinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-pyrido[3,2-h]quinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-pyrido[3,4-h]quinazoline-2,4(1H,3H)-dione;

3-[2-(cis-(3aR,9bR)-6-methoxy-2,3,3a,4,5,9b-hexahydro-[1H]-benz[e]isoindol-1-yl)ethyl]-pyrazino[2',3':4,5]pyrrolo[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-pyrido[3',2':4,5]pyrrolo[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-pyrazino[2',3':4,5]furo[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-7-chloro-pyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-7-methoxy-pyrazino[2',3':4,5]thieno[3,2-d]pyrimidine-2,4(1H,3H) dione;

3-[2-(cis-(3aR,9bR)-6-methoxy-2,3,3a,4,5,9b-hexahydro-[1H]-benz[e]isoindol-1-yl)ethyl]-5-isopropyl-pyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-7-phenyl-pyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-7-methyl-pyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-7,8-diethyl-pyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-1-(2-methoxyethyl)-7-methyl-pyrazino[2',3':4,5]thieno[3,2d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-1-methylpyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-1-benzylpyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-pyrido[3',4':4,5]pyrrolo[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-1-ethylpyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-8-phenylpyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-7,8-diphenylpyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-1-butylpyrazino[2',3'4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-1-(2-(2-methoxyethoxy)ethyl)pyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-7,8-dimethylpyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-1-(2-methoxyethyl)pyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-1-(2-methoxyethyl)pyrido[2',3':4,5]thieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-[1]-8-methoxy-benzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1yl)ethyl]-8-hydroxypyrido[2',3':4,5]thieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl))ethyl]-8-cyanopyrido[2',3':4,5]thieno[3,2-d]pyrimidine-2,4(1H,3H)-dione;

3-[2-((3aR,9bR)-cis-6-ethoxy-2,3,3a,4,5,9b-hexahydro-[1H]-benz[e]isoindol-1-yl)ethyl]-pyrido[3',2':4,5]thieno[3,2-d]pyrimidine-2,4(1H,3H)-dione hydrochloride;

3-[2-((3aR,9bR)-cis-6-ethoxy-2,3,3a,4,5,9b-hexahydro-[1H]-benz[e]isoindol-1-yl)ethyl]-pyrido[2',3':4,5]thieno[3,2-d]pyrimidine-2,4(1H,3H)-dione;

3-[2-(cis-6,7-methylenedioxy-2,3,3a,4,5,9b-hexahydro-[1H]-benz[e]isoindol-1-yl)ethyl]-pyrido[3',2':4,5]thieno[3,2-d]pyrimidine-2,4(1H,3H)-dione;

3-[2-(cis-6,7-methylenedioxy-2,3,3a,4,5,9b-hexahydro-[1H]-benz[e]isoindol-1-yl)ethyl]-pyrido[2',3':4,5]thieno[3,2-d]pyrimidine-2,4(1H,3H)-dione;

3-[2-((3aR,9bR)-cis-6-ethyl-2,3,3a,4,5,9b-hexahydro-[1H]-benz[e]isoindol-1-yl)ethyl]-pyrido[2',3':4,5]thieno[3,2-d]pyrimidine-2,4(1H,3H)-dione; and 3-[2-((3aR,9bR)-cis-6-ethyl-2,3,3a,4,5,9b-hexahydro-[1H]-benz[e]isoindol-1-yl)ethyl]-pyrido[3',2':4,5]thieno[3,2-d]pyrimidine-2,4(1H,3H)-dione; or a pharmaceutically acceptable salt thereof.

Particularly preferred compounds of the present invention are selected from the group consisting of:

3-[2-((3aR,9bR)-cis-6-methoxy-2,3,3a,4,5,9b-hexahydro-[1H]-benz[e]isoindol-1-yl))ethyl]-[1]-benzothieno[3,2-d]pyrimidine-2,4(1H,3H)-dione;

3-[2-(trans-6-methoxy-2,3,3a,4,5,9b-hexahydro-[1H]-benz[e]isoindol-1-yl)ethyl]-[1]-benzothieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-1-methyl-[1]-benzothieno[3,2-d]pyrimidine-2,4(1H,3H)-dione;

3-[4-(cis-9-methoxy-2,3,3a,4,5,9b-hexahydro-[1H]-benz[e]isoindol-1-yl)butyl]-[1]-benzothieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-benzo[h]quinazoline-2,4(1H,3H)-dione;

3-[2-((3aR,9bR)-cis-6-methoxy-2,3,3a,4,5,9b-hexahydro-[1H]-benz[e]isoindol-1-yl)ethyl]-1H-pyrimido[5,4-b]indole-2,4(1H,3H)-dione;

3-[2-((3aR,9bR)-cis-6-methoxy-2,3 3a,4,5,9b-hexahydro-[1H]-benz[e]isoindol-1-yl)ethyl]-pyrido[3',2':4,5]thieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-pyrido[3',2':4,5]thieno[3,2-d]pyrimidine-4(3H)-one;

3-[2-((3aR,9bR)-cis-6-methoxy-2,3,3a,4,5,9b-hexahydro-[1H]-benz[e]isoindol-1-yl)ethyl]-9-methyl[1]-benzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-pyrido[4',3':4,5]thieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-1-methyl-[1]-benzothieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-pyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-thieno[2,3-d:4,5]dipyrimidine-2,4(1H,3H)-dione;

3-[2-(cis-6-methoxy-2,3,3a,4,5,9b-hexahydro-[1H]-benz[e]isoindol-1-yl)ethyl]-thieno[3,2-d:4,5]dipyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-[1]-7-cyano-benzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-[1]-8-cyano-benzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl))ethyl]-[1]-8-carboxamidobenzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-[1]-7-nitro-benzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl(ethyl]-[1]-8-nitro-benzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-[1]-8-acetamido-benzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-[1]-7-carboxamidobenzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-[1]-8-(N-methylcarboxamido)-benzothieno[3,2-d]pyrimidine-2,4(1H,3H)-dione;

3-[2-((3aR,9bR)-cis-6-methoxy-2,3 3a,4,5,9b-hexahydro-[1H]-benz[e]isoindol-1-yl)ethyl]-[1]-7-chloro-benzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-1-methyl-pyrido[2',3':4,5]thieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1yl)ethyl]-8-chloro-pyrido[2',3':4,5]thieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-6-chloro-pyrido[2',3':4,5]thieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-8-methoxy-pyrido[2',3':4,5]thieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-6-methoxy-pyrido[2',3':4,5]thieno[3,2-d]pyrimidine-2,4(1H,3H)-dione;

3-[2-((3aR,9bR)-cis-6-methoxy-2,3 ,3a,4,5,9b-hexahydro-[1H]-benz[e]isoindol-1-yl)ethyl]-[1]-8-chloro-benzothieno[3,2-d]pyrimidine-2,4(1H,3H)-dione;

3-[2-((3aR,9bR)-cis-6-methoxy-2,3 3a,4,5,9b-hexahydro-[1H]-benz[e]isoindol-1-yl)ethyl]-[1]-7,8-dimethoxy-benzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-[1]-9-methyl-benzothieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-pyrazino[2',3':4,5]thieno[3,2-d]pyrimidine-4(1H)-one;

3-[2-((3aR,9bR)-cis-6-methoxy-2,3,3a,4,5,9b-hexahydro-[1H]-benz[e]isoindol-1-yl)ethyl]-[1]-9-chloro-benzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-[1]-9-methoxy-benzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-pyrido[3',2':4,5]furo[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-pyrido[2',3':4,5]furo[3,2-d]pyrimidine-2,4(1H,3H)-dione;

3-[2-((3aR,9bR)-cis-9-methoxy-2,3,3a,4,5,9b-hexahydro-[1H]-benz[e]isoindol-1-yl)butyl]-pyrido[2',3':4,5]thieno[3,2-d]pyrimidine-2,4(1H,3H)-dione;

3-[2-((3aR,9bR)-cis-9-methoxy-2,3 3a,4,5,9b-hexahydro-[1H]-benz[e]isoindol-1-yl)butyl]-pyrazino[2',3':4,5]thieno[3,2-d]pyrimidine-2,4(1H,3H)-dione;

3-[2-((3aR,9bR)-cis-9-methoxy-2,3 3a,4,5,9b-hexahydro-[1H]-benz[e]isoindol-1-yl)butyl]-pyrido[3',2':4,5]thieno[3,2-d]pyrimidine-2,4(1H,3H)-dione;

3-[2-((3aR,9bR)cis-6-methoxy-2,3,3a,4,5,9b-hexahydro-[1H]-benz[e]isoindol-1-yl)ethyl]-pyrido[2,3-h]quinazoline-2,4(1H,3H)-dione;

3-[2-((3aR,9bR)cis-6-methoxy-2,3 3a,4,5,9b-hexahydro-[1H]-benz[e]isoindol-1-yl)ethyl]-pyrido[3,2-h]quinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-pyrido[3,4-h]quinazoline-2,4(1H,3H)-dione;

3-[2-(cis-(3aR,9bR)-6-methoxy-2,3,3a,4,5,9b-hexahydro-[1H]-benz[e]isoindol-1-yl)ethyl]-pyrido[3',2':4,5]pyrrolo[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-7-chloro-pyrazino[2'3,':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-7-methoxy-pyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-5-isopropyl-pyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-7-methyl-pyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-1-(2-methoxyethyl)-7-methyl-pyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-1-methylpyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-pyrido[3',4':4,5]pyrrolo[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-1-ethylpyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-1-(2-(2-methoxyethoxy)ethyl)pyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-7,8-dimethylpyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-1-(2-methoxyethyl)pyrazino[2',3':4,5]thieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-8-hydroxypyrido[2',3':4,5]thieno[3,2-d]pyrimidine-2,4(1H,3H)-dione; and 3-[2-((3aR,9bR)-cis-6-methoxy-2,3,3a,4,5,9b-hexahydro-[1H]-benz[e]isoindol-1-yl)ethyl]-8-cyanopyrido[2',3':4,5]thieno[3,2-d]pyrimidine-2,4(1H,3H)-dione;

or a pharmaceutically acceptable salt thereof.

Several compounds of the present invention have been evaluated for their ability to displace prazosin from its receptor.

IN VITRO BINDING ASSAYS

The compounds of the invention were evaluated for α-adrenoceptor binding affinity in vitro using [$^3$H]-prazosin as the radioligand and three cloned α-1 adrenoceptors expressed in LTK cell: α-1: α-1a(bovine), α-1b (hamster) and α-1d (rat). Additionally, binding affinity against the pharmacologically defined α-1A adrenoceptor (rat submaxillary gland) was measured.

The cDNA clones encoding the α-1 receptors (α-1a, α-1b, and α-1d) were obtained from TULCO (Triangle Universities Licensing Consortium, Research Triangle Park, N.C.) and inserted into the eukaryotic expression vector SnaB30. In this vector, expression of the receptor gene is under the transcriptional control of an SV40 early promoter. Positive drug selection is provided by a neomycin-resistance gene. Mouse fibroblast cells (LTK) were transfected with the α$_1$ expression plasmids and grown in Dulbecco's modified Eagle's medium (DMEM) containing 10% fetal calf serum and 30 μM G418. Stable G418-resistant parental lines were generated, with successful expression of receptor protein monitored using radioligand binding techniques. Stable single cell clones derived from the parental lines were screened in receptor binding assays to identify clones having high receptor density. Roller bottle cultures of the cloned lines were used to provide cell membranes for subsequent receptor binding characterization studies. A cell line containing the SnaB30 vector expressing the human erythropoietin gene served as a negative control.

For receptor binding assays, large scale membrane preparations were utilized in which 6 million cells were seeded into small (450 cm$^2$) Corning tissue culture roller bottles. 200 mL of DMEM containing 10% fetal calf serum and 300 μM G418 were added to each roller bottle. A 95% air/5% $CO_2$ gas mixture (sterile) was injected into each roller bottle prior to sealing. The bottles were then incubated at 37° C. on a roller rack for 5 days. Cells were re-fed with fresh medium after 3 days in culture.

On the fifth day of culture, growth medium was removed from cells gown in roller bottles, and the cells were washed twice with PBS (Sigma, 120 mM NaCl, 2.7 mM KCl, 10 mM $Na_2HPO_4$-$NaH_2PO_4$, pH=7:4). Cells were detached from the roller bottles by incubating for 15 minutes at 37° C. in a Tris-EDTA solution (10 mM Tris, 100 mM NaCl, 1 mM EDTA, pH=7.4). The cell suspension from each roller bottle was decanted into tared centrifuge tubes and kept on ice. An aliquot of each cell suspension was generally taken for cell counting. Cells were centrifuged at 3000×G for 5 min at 2°–4° C., washed with PBS and recentrifuged. The supernatant was decanted and the pellet weighed to determine the wet weight of cells. Cells were washed a final time in 40 vol 5 mM Tris-HCl, 5 mM EDTA, pH=7.7, and centrifuged at 40,000×G for 10 minutes. Cells were homogenized in 10 mL of 50 mM Tris-HCl, 5 mM EDTA (pH=7.4) and diluted to 40 mL/tube. Homogenates were centrifuged at 40,000×G for 10 minutes. The supernatant was decanted and the pellets rehomogenized in 50 mM Tris-HCl (pH=7.4) and centrifuged as before. The supernatant was decanted and the homogenate resuspended in 6.25 volumes (per gram wet weight) of 50 mM Tris-HCl and aliquots of the pooled homogenates frozen in liquid $N_2$ and stored at −70° C. until the time of assay. Rat submaxillary glands were used for α-1A receptors and were prepared essentially as described (Michel, A. D., Loury, D. N. and Whiting, R. L., Brit. J. Pharmacol. 98:83–889 (1989)).

Receptor binding assays for α-1 receptors were performed essentially as described by Greengrass and Bremner (Eur. J, Pharmacol. 55:323–326 (1979)). Briefly, plastic Bioblocks™ (DBM Scientific, Valencia, Calif.) were incubated at 25° C. for 50 minutes with 500 μL of membrane homogenate (diluted with an additional 96 volumes [for cloned receptors, 12 volumes for submaxillary gland] in 50 mM Tris-HCl buffer (pH=7.7 at the time of assay), 450 μL of [$^3$H]prazosin (0.2 nM final concentration, 75–85 Ci/mmole, DuPont-NEN Corp., Boston, Mass.) and 50 μL of either water (for total binding) or 10 μM phentolamine (final concentration, for nonspecific binding). Following equilibration, bound radioligand was separated from free on GF/B filters (presoaked in 0.5% polyethyleneimine) using either a Brandel or Packard cell harvester. Radioactivity was determined by standard liquid scintillation techniques. Data were analyzed as previously described (Hancock, A. A., Kyncl, J. J., Martin, Y. C. and DeBernardis, J. F., J. Receptor Res. 8:23–46 (1988)).

The results are shown in Table 1. The results show that the compounds of the invention bind to the α-1 adrenoceptor and show varying degrees of specificity for the α-1a receptor.

TABLE 1

In Vitro Data for Binding to α-1 Adrenoceptors

| Ex. No. | α-1A (Rat) (nM) | α-1b (Hamster) (nM) | α-1a (Bovine) (nM) | α-1d (Rat) (nM) |
|---|---|---|---|---|
| 1 | 0.64 | 2.569 | 0.048 | 0.372 |
| 2 | 3.372 | 2.757 | 0.152 | 2.663 |
| 3 | 2.171 | 5.392 | 0.327 | 0.685 |
| 4 | 17.061 | 14.503 | 3.068 | 7.747 |
| 5 | 5.272 | 7.821 | 0.184 | 8.672 |
| 6 | 22.466 | 17.797 | 1.132 | 16.052 |
| 7 | 11.762 | 21.799 | 1.491 | 2.283 |
| 8 | 9.027 | 14.011 | 0.941 | 6.288 |
| 9 | 0.453 | 2.547 | 0.059 | 0.965 |
| 10 | 1.078 | 3.431 | 0.056 | 0.635 |
| 11 | 0.345 | 1.774 | 0.016 | 0.662 |
| 12 | 7.426 | 9.946 | 1.401 | 4.771 |
| 13 | 27.68 | 39.849 | 2.891 | 6.031 |
| 14 | 0.792 | 2.249 | 0.171 | 0.741 |
| 15 | 0.42 | 8.816 | 0.095 | 2.731 |
| 16 | 2.569 | 3.66 | 0.077 | 3.676 |
| 17 | 1.048 | 2.173 | 0.288 | 1.18 |
| 18 | 2.099 | 5.839 | 0.304 | 1.028 |
| 19 | 61.216 | 66.602 | 4.31 | 7.948 |
| 20 | 21.971 | 22.758 | 0.922 | 4.885 |
| 21 | 2.65 | 2.176 | 0.476 | 1.356 |
| 22 | 2.366 | 5.309 | 0.471 | 1.881 |
| 23 | 1.57 | 8.743 | 0.265 | 0.779 |
| 24 | 2.303 | 3.383 | 0.363 | 1.416 |
| 25 | 0.966 | 3.11 | 0.046 | 0.79 |
| 26 | 0.479 | 1.729 | 0.124 | 0.231 |
| 27 | 6.395 | 36.165 | 1.319 | 3.01 |
| 28 | 3.35 | 13.636 | 0.464 | 3.974 |
| 29 | 9.883 | 10.929 | 0.82 | 6.797 |
| 30 | 18.016 | 7.311 | 5.32 | 4.768 |
| 31 | 0.649 | 5.433 | 0.063 | 0.568 |
| 32 | 9.274 | 23.814 |  | 6.845 |
| 33 | 1477.132 | 370.074 |  | 1455.953 |
| 34 | 0.713 | 10.318 |  | 1.474 |
| 35 | 0.533 | 6.57 |  | 0.324 |
| 36 | 0.609 | 3.079 |  | 0.305 |
| 37 | 0.087 | 2.319 |  | 0.112 |
| 38 | 0.704 | 1.028 |  | 0.187 |
| 39 | 0.721 | 12.52 | 0.101 | 2.65 |
| 40 | 0.615 | 18.42 | 0.101 | 2.44 |
| 41 | 1.62 | 15.89 | 0.365 | 3.74 |
| 42 | 0.402 | 6.202 | 0.101 | 0.738 |
| 43 | 1.646 | 14.302 | 0.243 | 0.595 |
| 44 | 4.755 | 14.305 | 0.273 | 2.843 |
| 45 | 0.278 | 1.702 | 0.253 | 0.633 |
| 46 | 0.522 | 6.337 | 0.065 | 0.509 |
| 47 | 1.21 | 8.29 | 0.127 | 1.919 |
| 48 | 0.382 | 3.981 | 0.113 | 0.403 |
| 49 | 0.255 | 1.9 | 0.111 | 0.236 |
| 50 | 1.603 | 4.32 | 0.844 | 1.786 |
| 51 | 0.428 | 1.303 | 0.065 | 0.376 |
| 52 | 0.623 | 4.413 | 0.232 | 0.677 |
| 53 | 0.249 | 0.934 | 0.144 | 0.237 |
| 54 | 3.308 | 35.827 | 1.267 | 6.602 |
| 55 | 6.349 | 26.939 | 0.713 | 2.085 |
| 56 | 98.994 | 1219.963 | 7.602 | 25.017 |
| 57 | 3.853 | 13.732 | 0.507 | 2.567 |
| 58 | 0.357 | 2.247 | 0.12 | 0.366 |
| 59 | 0.469 | 1.456 | 0.155 | 0.527 |
| 60 | 0.872 | 5.509 | 0.168 | 1.204 |
| 61 | 0.328 | 2.011 | 0.119 | 1.034 |
| 62 | 0.381 | 4.147 | 0.103 | 0.607 |
| 63 | 3.133 | 61.646 | 0.488 | 4.161 |
| 64 | 0.385 | 2.143 | 0.052 | 0.448 |
| 65 | 0.789 | 8.068 | 0.248 | 1.722 |
| 66 | 0.23 | 2.682 | 0.046 | 0.479 |
| 67 | 0.446 | 1.911 | 0.122 | 0.308 |
| 68 | 0.73 | 10.875 | 0.062 | 0.713 |
| 69 | 1.293 | 6.95 | 0.075 | 0.878 |
| 70 | 3.192 | 10.729 | 0.52 | 3.311 |
| 71 | 1.628 | 17.567 | 0.359 | 4.311 |
| 72 | 0.512 | 3.156 | 0.187 | 1.329 |
| 73 | 0.775 | 3.101 | 0.235 | 1.073 |
| 74 | 2.165 | 4.257 | 0.156 | 1.04 |
| 75 | 1.424 | 28.465 | 0.137 | 1.966 |
| 76 | 1.61 | 24.249 | 0.501 | 2.08 |
| 77 | 1.371 | 10.067 | 0.351 | 2.489 |
| 78 | 1.869 | 11.303 | 0.87 | 3.407 |
| 79 | 0.167 | 6.552 | 0.038 | 1.191 |
| 80 | 0.467 | 11.312 | 0.14 | 3.741 |
| 81 | 0.619 | 10.877 | 0.2 | 1.668 |
| 82 | 0.271 | 2.034 | 0.196 | 0.268 |
| 83 | 0.163 | 1.478 | 0.088 | 0.427 |
| 84 | 0.306 | 1.471 | 0.085 | 0.695 |
| 85 | 1.052 | 3.481 | 0.321 | 2.002 |
| 86 | 0.47 | 1.733 | 0.096 | 0.209 |
| 87 | 5.963 | 57.777 | 1.337 | 9.911 |
| 88 | 0.696 | 35.124 | 0.148 | 3.832 |
| 89 | 0.336 | 3.125 | 0.074 | 1.154 |
| 90 | 0.347 | 4.67 | 0.202 | 1.551 |
| 91 | 153.044 | 1853.68 | 19.75 | 160.441 |
| 92 | 0.495 | 13.52 | 0.133 | 2.309 |
| 93 | 6.955 | 84.679 | 1.943 | 29.436 |
| 94 | 0.318 | 9.282 | 0.14 | 1.978 |
| 95 | 0.2 | 4.678 | 0.074 | 1.603 |
| 96 | 1.876 | 6.645 | 0.25 | 2.439 |
| 97 | 0.439 | 1.762 | 0.777 | 0.089 |
| 98 | 0.335 | 5.249 | 0.119 | 1.15 |
| 99 | 3.914 | 120.453 | 0.74 | 19.837 |
| 100 | 314.108 | 10000 | 69.773 | 10000 |
| 101 | 1.376 | 5.314 | 0.197 | 2.299 |
| 102 | 0.48 | 6.529 | 0.21 | 2.376 |
| 103 | 0.392 | 13.923 | 0.137 | 3.278 |
| 104 | 0.347 | 5.641 | 0.129 | 1.383 |
| 105 | 0.651 | 2.995 | 0.302 | 1.677 |
| 107 | 1.427 | 13.75 | .324 | 1.398 |
| 108 | .712 | 7.048 | .303 | 1.052 |
| 109 | 2.406 | 12.913 | .478 | .84 |
| 111 | 3.512 | 31.179 | .797 | 11.109 |
| 112 | 2.12 | 28.09 | .486 | 9.408 |
| 113 | 1.874 | 12.978 | .237 | 4.152 |
| 114 | 2.756 | 28.873 | .559 | 3.652 |

Functional Antagonism at α-1 Adrenoceptors

Functional assays indicative of pharmacologically defined α-1 adrenoceptors were used to further characterize compounds. Inhibition of phenylephrine (PE)-induced contraction of canine prostate smooth muscle can be correlated with α-1A adrenoceptor activation. Inhibition of PE-induced contraction of rat spleen is representative of α-1B adrenoceptor antagonism and inhibition of PE-induced contraction of rat vas deferens correlates with α-1A adrenoceptor antagonism (R. P. Burt, C. R. Chapple and I. Marshall, *Br. J. Pharmacol.* 107:P324 (1992)). For each of these models, agonist dose response curves were repeated against increasing concentrations of test agent to derive a Schild plot [log ($EC_{50}$-1) against log (molarity of test agent)] to determine the $pA_2$. Data for prazosin, terazosin and doxazosin actually demonstrate a more potent effect on spleen smooth muscle by approximately an order of magnitude.

Canine prostate strips were used in vitro as previously described (Hieble, J. P., Boyce, A. J. and Caine, M., *Fed. Proc.*, 45:2609–2614 (1986)), to determine antagonist potencies against phenylephrine-induced contractions. The results are shown in Tables 2a and 2b. The results indicate that the compounds of the invention exhibit functional antagonism of α-1 receptors.

TABLE 2a

In Vitro Data for Functional Antagonism at α-1 Adrenoceptors

| Ex. No. | pA$_2$ Rat Vas Deferens [α-1A] | pA$_2$ Rat Spleen [α-1B] | pA$_2$ Dog Prostate [α-1A] |
|---|---|---|---|
| 1 | 8.37 | 7.67 | 8.74 |
| 5 | 7.86 | 6.83 | 7.79 |
| 8 | 7.76 | 7.26 | 7.63 |
| 9 | 8.71 | 7.59 | 8.63 |
| 10 | 8.51 | 7.52 | 8.37 |
| 11 | 8.55 | 7.29 | 8.57 |
| 14 | 8.57 | 7.63 | 8.23 |
| 16 | 7.98 | 7.25 | 8.54 |
| 17 | 7.97 | 7.2 | 8.29 |
| 18 | 7.86 | 7.87 | 8.37 |
| 23 | 8.29 | 6.82 | 8.97 |
| 25 | 8.66 | 6.76 | 8.27 |
| 26 | 8.56 | 8.13 | 8.63 |
| 31 | 8.65 | 7.76 | 8.78 |
| 36 | 8.6 | 8.1 | 9.71 |
| 39 | 8.33 | 7.76 | 9.16 |
| 58 | 8.36 | 7.44 | 9.09 |
| 62 | 9.14 | 7.66 | 9.24 |
| 64 | 9.1 | 7.6 | 9.63 |
| 69 | 8.6 | 7.16 | 8.25 |
| 75 | 8.23 | 7.1 | 8.04 |
| 76 | 7.6 | 7.63 | 8.74 |
| 87 | 7.74 | 7.06 | 8.67 |
| 88 | 8.96 | 7.35 | 9.35 |
| 89 | 8.93 | 8.11 | 9.03 |
| 90 | 8.84 | 7.57 | 9.05 |
| 102 | 8.44 | 7.76 | 8.96 |
| 107 | 7.7 | 7.43 | 9.22 |
| 108 | 8.47 | 7.95 | 9.03 |
| 112 | 7.92 | 7.2 | 8.18 |
| prazosin | 8.78 | 9.51 | 7.59 |
| terazosin | 8.04 | 8.6 | 7.44 |
| doxazosin | 8.69 | 9.51 | 7.59 |

TABLE 2b

In Vitro Data for Functional Antagonism at α-1 Adrenoceptors

| Ex. No. | pA$_2$ Dog Prostate [α-1A] |
|---|---|
| 2 | 7.81 |
| 3 | 8.4 |
| 6 | 6.91 |
| 7 | 7.85 |
| 12 | 7.33 |
| 13 | 7.68 |
| 15 | 7.34 |
| 19 | 6.66 |
| 20 | 7.43 |
| 21 | 7.43 |
| 22 | 8.32 |
| 24 | 8.6 |
| 27 | 8.72 |
| 28 | 7.75 |
| 29 | 7.43 |
| 30 | 7.06 |
| 32 | 7.46 |
| 33 | 6.56 |
| 34 | 9.15 |
| 35 | 8.74 |
| 37 | 9.15 |
| 38 | 9.75 |
| 40 | 9.72 |
| 41 | 9.03 |
| 42 | 9.09 |
| 43 | 8.44 |
| 44 | 8.09 |
| 45 | 9.48 |
| 46 | 9.61 |
| 47 | 8.7 |
| 48 | 8.32 |
| 49 | 7.84 |
| 50 | 7.24 |
| 53 | 9.25 |
| 54 | 8.74 |
| 55 | 8.11 |
| 56 | 7.11 |
| 57 | 7.43 |
| 58 | 9.09 |
| 61 | 9.5 |
| 62 | 9.24 |
| 63 | 8.6 |
| 64 | 9.63 |
| 65 | 8.75 |
| 66 | 9.71 |
| 67 | 8.98 |
| 68 | 7.87 |
| 69 | 8.25 |
| 70 | 8.57 |
| 71 | 9.21 |
| 72 | 8.38 |
| 73 | 8.42 |
| 74 | 8.7 |
| 75 | 8.04 |
| 76 | 8.74 |
| 77 | 9.09 |
| 78 | 7.8 |
| 79 | 8.77 |
| 80 | 8.08 |
| 82 | 9.09 |
| 83 | 8.43 |
| 84 | 8.99 |
| 87 | 8.67 |
| 88 | 9.35 |
| 89 | 9.03 |
| 90 | 9.05 |
| 91 | 6.66 |
| 92 | 9.1 |
| 95 | 9.07 |
| 96 | 7.46 |
| 97 | 9.66 |
| 98 | 9.39 |
| 99 | 7.92 |
| 100 | 6.92 |
| 101 | 7.31 |
| 102 | 8.96 |
| 103 | 9.43 |
| 104 | 9.74 |
| 105 | 8.58 |
| 107 | 9.22 |
| 108 | 9.03 |
| 109 | 8.00 |
| 111 | 8.00 |
| 112 | 8.18 |
| 113 | 8.22 |

In Vivo Determination of Intraurethral Pressure (IUP) in Canines

The intraurethral pressure (IUP) model in aged canines is an accepted model of measuring the effect of prostate smooth muscle contraction on urethral tone. Canines also have an enclosed prostate covering the urethral shaft thus providing an anatomical correlate with humans.

Beagle dogs (Marshall Farms) greater that 2 years of age and weighing between 12 and 15 kg were pre-anesthetized with thiopental sodium 15 mg/kg i.v. (Pentothal™, Abbott) and then placed used general anesthesia (isoflurane). A 7F Swan-Ganz balloon catheter (Multiflex—list no. 41224–01, Abbott) was lubricated with a water soluble jelly, inserted into the urethral orifice and advanced approximately 40 cm in male dogs (considerably less in females) until the balloon tip was placed well inside the bladder. The balloon was then inflated with 1 mL of room air and the catheter slowly withdrawn just past the first resistance that is felt at the bladder neck. Preliminary experiments in which dogs were sacrificed after such placement confirmed that this technique results in consistent positioning of the balloon within the prostatic urethra in males or the corresponding location in females. The balloon port of the catheter was connected to a Gould Shatham P23Dd pressure transducer interfaced to a computerized data acquisition system (Modular Instruments, Inc., Malvern, Pa.) for the measurement of intraurethral pressure (IUP).

Dogs were then treated with propranolol to block the β-adrenoceptor agonist effects of test agonists. Dose-response curves of the intraurethral pressor effect of epinephrine (EPI) were obtained before and after each of up to 3 increasing doses of a test antagonist (i.v.). Fifteen minutes was allowed after each antagonist dose for equilibration before the next agonist dose-response was initiated. The increase in IUP caused by a given agonist dose was allowed to return to baseline before the next dose was given. The estimated antagonist dissociation constant (in vivo pseudo $pA_2$) was determined by Schild analysis (Brune, et al., Drug Development Research (1995) in press).

The results are shown in Table 3. The results indicate that the compounds of the invention inhibit EPI induced increases in IUP.

TABLE 3

Inhibition of EPI Induced Increase in Canine IUP

| Example | Canine IUP pseudo $pA_2$ |
|---|---|
| 1 | 7.86 |
| 9 | 7.73 |
| 10 | 7.68 |
| 14 | 7.91 |
| 15 | 7.48 |
| 16 | 7.59 |
| 18 | 7.43 |
| 23 | 8.32 |
| 26 | 8.25 |
| 31 | 8.25 |
| 39 | 8.28 |
| prazosin | 7.88 |
| erazosin | 6.91 |
| doxazosin | 6.90 |

Spontaneously Hypertensive Rat (SHR) Model

The SHR model historically has been used as a predictor for the hypotensive effects of α-1 adrenoceptor antagonism. Male spontaneously hypertensive rats were anesthetized and the left femoral artery and vein catheterized for the measurement of mean arterial pressure (MAP) and drug administration respectively. The arterial catheter was connected to a Gould Statham p23ID transducer and the pressure waveform was recorded. MAP (mm Hg) and heart rate (HR, beats/min.) were determined on-line using a BUXCO Cardiovascular Analyzer. After a 30 minute predose control period, each rat was given one dose of a test antagonist i.v. and the MAP and HR were monitored for an additional 2.5 hours. The area under the hypotensive response curve up to 60 minutes post dosing ($T_{60}$ AUC) was determined using a trapezoidal rule integration of the percent change from control arterial pressure dataset. The results are shown in Table 4. The results show that the compounds of the invention are weakly hypotensive.

TABLE 4

Spontaneously Hypertensive Rat (SHR) Assay

| Example | SHR pseudo $pA_2$ |
|---|---|
| 1 | <4 |
| 2 | 5.15 |
| 5 | 4.5 |
| 8 | <4 |
| 9 | 5 |
| 10 | 5.1 |
| 11 | 5.36 |
| 16 | 5.46 |
| 23 | <4 |
| 25 | 5.5 |
| 26 | 5.9 |
| 31 | 5.9 |
| prazosin | 7.4 |
| terazosin | 6.59 |
| doxazosin | 6.74 |

Pharmaceutical Compositions

The present invention also provides pharmaceutical compositions which comprise compounds of the present invention formulated together with one or more non-toxic pharmaceutically acceptable careers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous careers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain pan of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty add esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum and release the active compound.

Compounds of the present invention can also be administered in the form of e liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 0.001 to about 100, more preferably of about 0.1 to about 5 mg of active compound per kilogram of body weight per day are administered orally to a mammalian patient. If desired, the effective daily dose may be divided into multiple doses for purposes of administration, e.g. two to four separate doses per day.

While the compounds of the invention can be administered as the sole active pharmaceutical agent, they can also be used in combination with a 5-α reductase inhibitor. A particularly preferred 5-α reductase inhibitor for use in combined therapeutic administration with the compounds of the present invention is the compound having the generic name finasteride.

Methods for preparing the compounds of the invitation are shown in Schemes I–V. In the following Schemes, $R_1$ and $R_2$ are independently hydrogen, alkoxy, hydroxy, alkyl, halo, carboxy, or alkoxycarbonyl.

Scheme I illustrates the general procedure for the preparation of the compounds of the invention. Compound 1, prepared by the procedures described in U.S. Pat. No. 4,618,683, which is incorporated herein by reference, is reacted with chloroacetonitrile under mildly basic conditions (for example. diisopropylethylamine, triethylamine and the like) to afford the cyanomethyl compound 2. The nitrile is dissolved in an inert solvent (for example, THF, ether and the like) and treated with a reducing agent (for example, lithium aluminum hydride, diborane or catalytic hydrogenation and the like) to give the ethylene diamine compound 3. The diamine is reacted with the isocyanate 4 of the aromatic compound U, prepared from the aromatic amine by treatment with phosgene or triphosgene, to give the pyrimidine dione 5.

Alternatively as shown in Scheme II, the diamine can by prepared by taking diester 6, prepared by the procedures described in U.S. Pat. No. 5,049,564, which is incorporated herein by reference, in an inert solvent (for example, THF or ether and the like) and reducing the diester with a reducing agent (for example, lithium aluminum hydride or diborane and the like) to give the diol 7. The diol is reacted with an appropriate reagent to form leaving groups (for example, LG is methanesulfonyl or toluenesulfonyl and the like) giving compound 8. Treatment of compound 8 with the appropriate diamine ($H_2N$-$(CH_2)_n$-$NH_2$ or synthon) with heating gives the pyrrolidine amine 9. Compound 9 can be further elaborated by the procedures described in Scheme I to give the final compound 10.

The compounds of the invention can also be prepared by the procedures illustrated in Scheme III. Compound 4a is reacted with a haloalkyl isocyanate (for example, 2-chloroethyl isocyanate) by the procedures described in *Eur. J. Med. Chem.* 28:499 (1993), which is incorporated herein by reference, to give haloalkyl urea 11. Compound 1, as previously described in Scheme I, is reacted with compound 11 to give the final product 5.

The preparation of chiral cis intermediates is shown in Scheme IV. Dihydronaphthylene-1-carboxylic acid 12 is esterified (for example, using diazomethane or alcohol with a trace of sulfuric acid) to give compound 13. Treatment of the α,β-unsaturated ester with lithium cyanide in DMF and acetic acid affords the cyano compound 14. The nitrile ester is hydrolyzed (for example, using KOH in ethanol/water) to give the dicarboxylic acid 15. Treatment of the diacid with acetic anhydride under reflux affords the cyclic anhydrides 16a and 16b. The anhydrides are reacted with optically active (S)-(−)-α-methylbenzylamine to give both the (3aR, 9bR)-compound 17 and the (3aS,9bS)-compound 18 as a mixture of imides separable by crystallization. Compounds 17 and 18 are reduced (for example, with diborane) to give the corresponding N-substituted pyrrolidine compounds 19 and 20. Catalytic hydrogenation affords chiral intermediates 21 and 22. These. pyrrolidines can be further elaborated by the procedures described in Schemes I and III to give the final products.

A preferred embodiment is shown in Scheme V. Compound 23 wherein R is a carboxy protecting group is reacted with 2-chloroethyl isocyanate to give urea 24. Compound 24 is reacted with compound 25 in a solvent such as DMSO in the presence of a non-nudeophilic base such as diisopropylethylamine to give the ring closed coupled product 27.

Another preferred embodiment in shown in Scheme VI. The aromatic carboxy-protected amine 28 is reacted with triphosgene to give isocyanate 29. The isocyanate is reacted with amine 30, prepared by the procedure described in Scheme I or II, to cyclize and couple in one step to give compound 31.

Scheme I

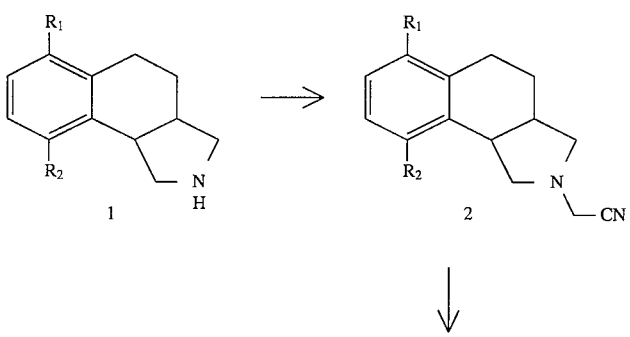

-continued
Scheme I
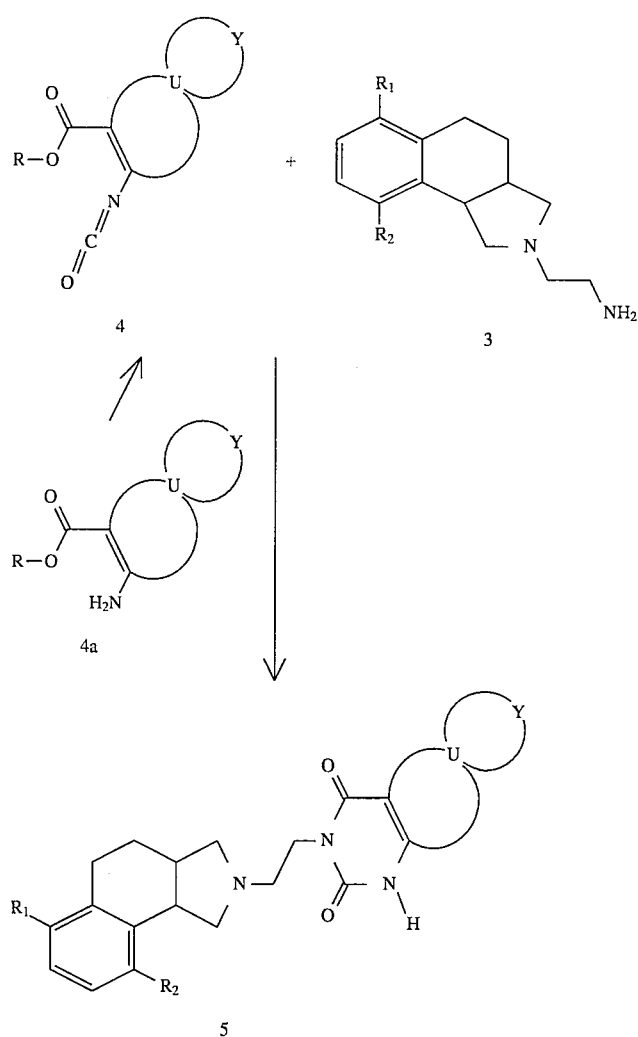
Scheme II
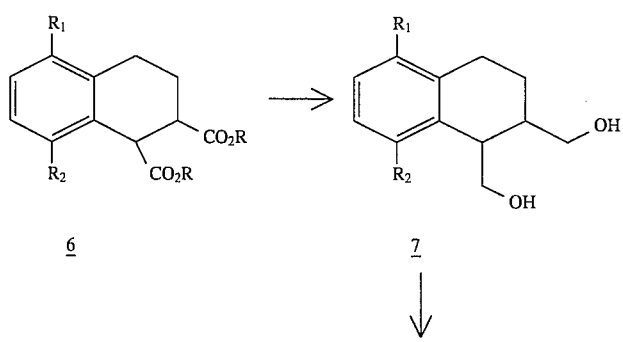

-continued
Scheme II
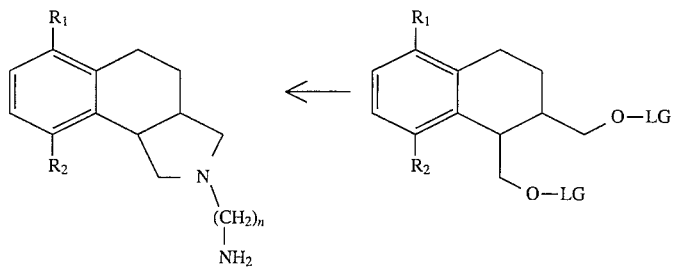
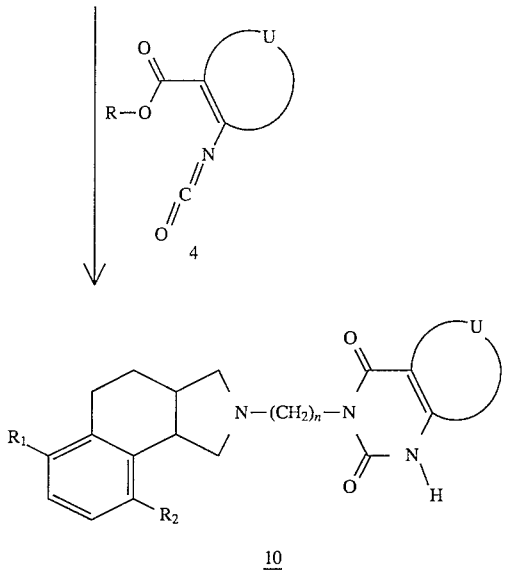
Scheme III
-continued
Scheme III
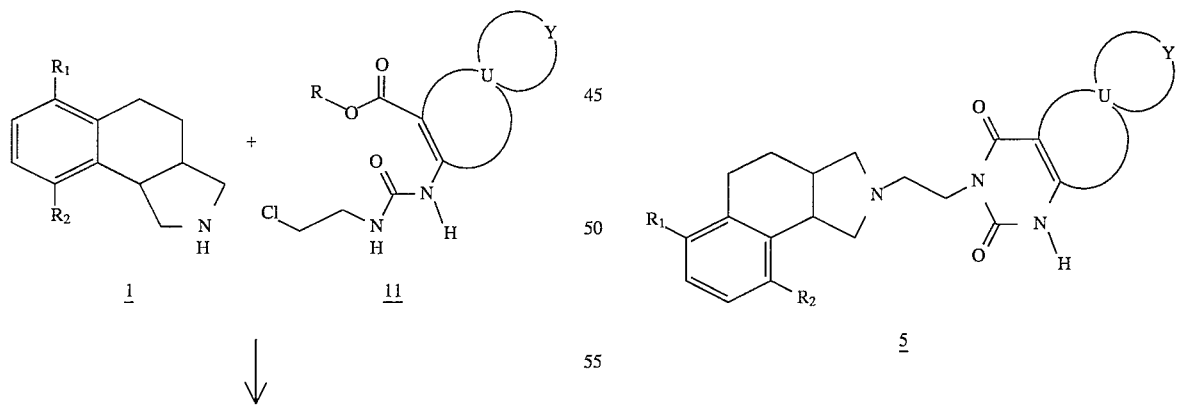

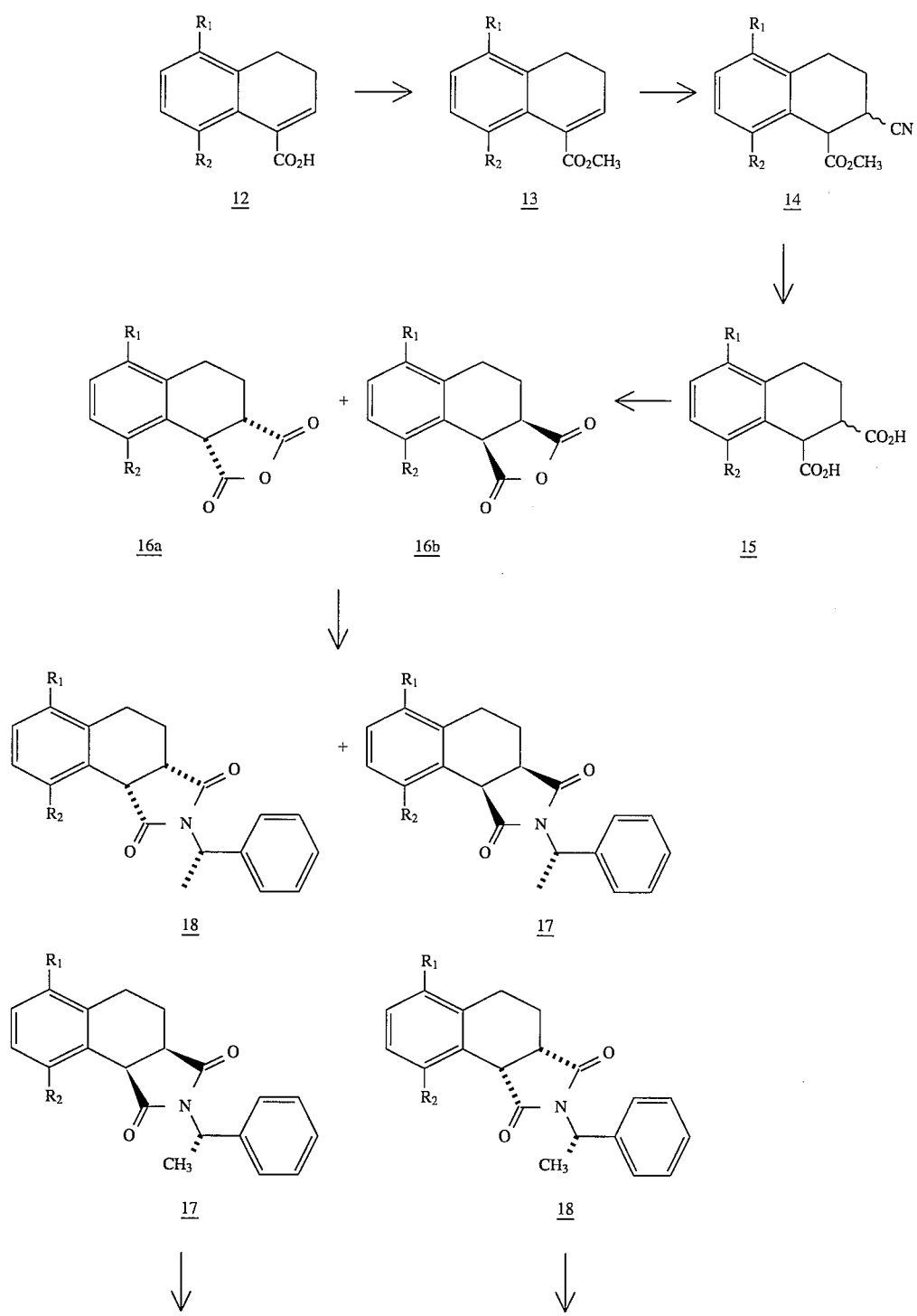
Scheme IV 5,597,823
-continued
Scheme IV
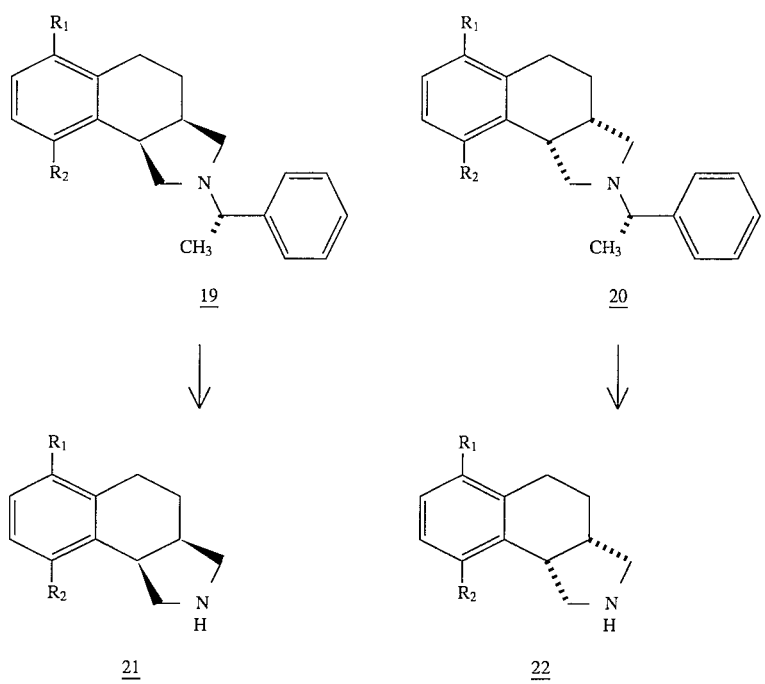
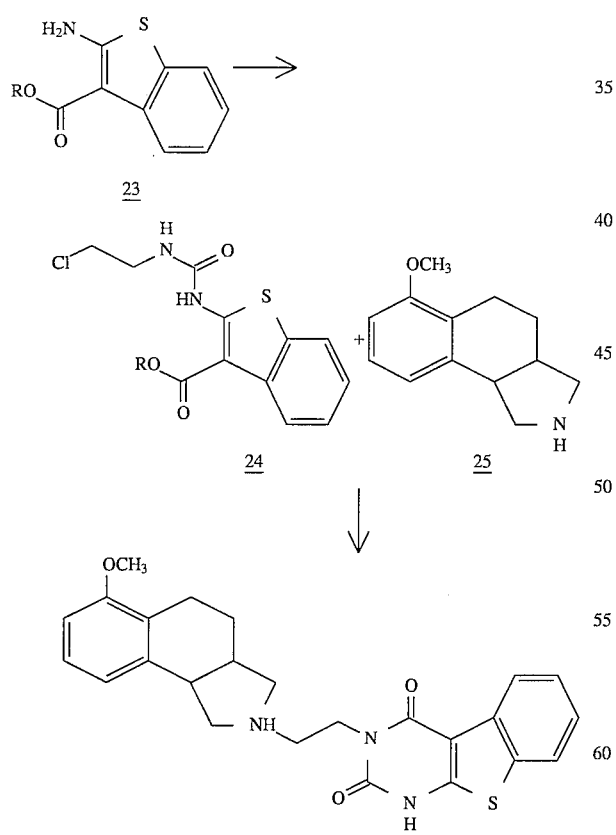
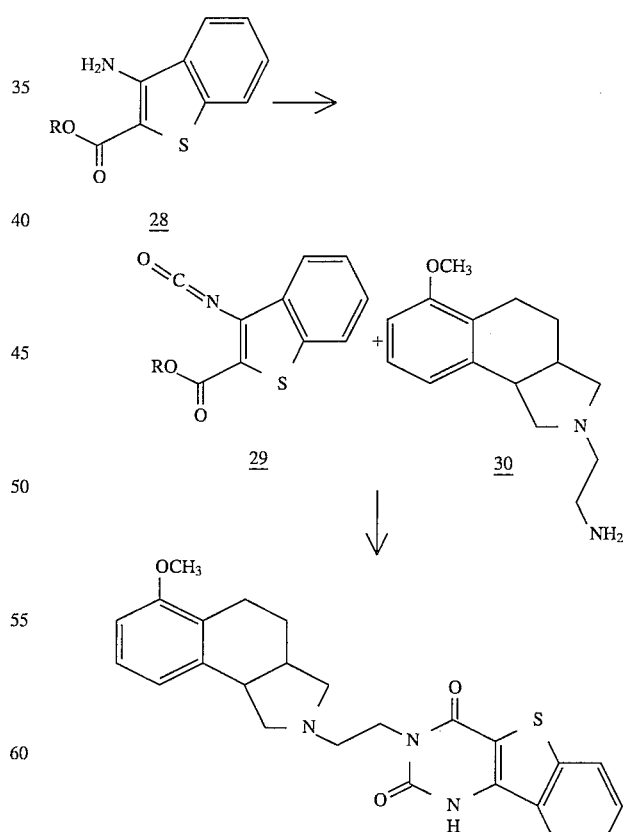

The forgoing may be better understood by reference to the following examples which are provided for illustration and not intended to limit the scope of the inventive concept.

The following abbreviations were used: BH$_3$.DMS for borane dimethylsulfide complex, DMF for dimethylformamide, DMSO for dimethylsulfoxide, Et$_3$N for triethylamine, Et$_2$O for diethyl ether, EtOAc for ethyl acetate, EtOH for ethanol, KOtBu for potassium tert-butoxide, LDA for lithium diisopropylamide, MeOH for methanol, NaOEt for sodium ethoxide, iPrOH for isopropyl alcohol and THF for tetrahydrofuran.

EXAMPLE 1

3-[2-(cis-6-Methoxy-2,3,3a,4,5,9b-hexahydro-[1H]-benz[e]isoindol-1-yl)ethyl]-[1]benzothieno[3,2-d]pyrimidine-2,4(1H,3H)-dione hydrochloride N-(2-Chloroethyl)-N'-[3-[(2-methoxycarbonyl)benzothienyl]]-urea (0.625 g, 2.00 mmol), prepared by the procedure described in *Eur. J. Med. Chem.*, 28: 499–504 (1993), cis-6-methoxy-2,3,3a,4,5,9b-hexahydro-[1H]-benz[e]isoindole (0.503 g, 2.1 mmol), prepared by the procedures described in U.S. Pat. No. 4,618,683, which is incorporated herein by reference, and diisopropylethylamine (0.35 mL, 2.0 mmol) were combined: in 1 mL DMSO and heated at 100° C. for 3 hours. The reaction was cooled and several mL of EtOH were added. The crystalline product was collected, and converted to its HCl salt and recrystallized from MeOH to yield 312 mg of the title compound as a white solid. m.p.>255° C. $^1$H NMR (300 MHz, DMSO-d$_6$) δ 1.45 (m, 1H), 1.53 (m, 1H), 2.10–2.80 (m, 6H), 3.10–3.45 (m, 4H), 3.74 (s, 3H), 4.04 (t, 2H), 6.73 (d, 2H), 7.07 (t, 1H), 7.55 (t, 1H), 7.63 (t, 3H), 8.10 (d, 1H), 8.39 (d, 1H), 12.50 (s, 1H). MS (DCI/NH3) m/e 448 (M+H)$^+$. Anal calcd for C$_{25}$H$_{26}$ClN$_3$O$_3$S·0.75 H$_2$O: C, 60.35; H, 5.41; N, 8.68. Found: C, 60.36; H, 5.43; N, 8.39.

EXAMPLE 2

3-[2-(trans-9-Methoxy-2,3,3a4,5,9b-hexahydro-[1H]-benz[e]isoindol-1-yl)ethyl]-[1]benzothieno[3,2-d]pyrimidine-2,4(1H,3H)-dione hydrochloride N-(2-Chloroethyl)-N'-[3-[(2-methoxycarbonyl)benzothienyl]]-urea (0.48 g, 1.48 mmol) and trans-9-methoxy-2,3,3a,4,5,9b-[1H]-hexahydro-benz[e]isoindole (0.30 g, 1.48 mmol), prepared by the procedures described in U.S. Pat. No. 5,049,564, which is incorporated herein by reference, were reacted by the procedures described in Example 1 to yield 0.248 g of the title compound as a white solid. m.p.>250°. $^1$H NMR (300 MHz, DMSO-d$_6$) δ 1.60 (m, 1H), 1.85–2.45 (m, 2H), 2.65–3.70 (m, 6H), 3.75 (s, 3H), 3.85 (m, 1H), 4.00 (m, 1H), 4.33 (m, 2H), 4.52 (m, 1H), 6.78 (m, 2H), 7.17 (t, 1H), 7.58 (t, 1H), 7.64 (t, 1H), 8.15 (d, 1H), 8.44 (d, 1H), 10.50 (br s, 1H), 12.68 (s, 1H). MS (DCI/NH$_3$) m/e 448 (M+H)$^+$. Anal calcd for C$_{25}$H$_{26}$ClN$_3$O$_3$S: C, 62.04; H, 5.41; N, 8.68. Found: C, 62.18; H, 5.66; N, 8.63.

EXAMPLE 3

3-[2-(cis-6-Methoxy-2,3,3a,4,5,9b-hexahydro-1H]-benz[e]isoindol-1-yl)ethyl]-benzofuro[3,2-d]pyrimidine-2,4(1H,3H)-dione hydrochloride N-(2-Chloroethyl)-N'-[3-[(2-ethoxycarbonyl)benzofuranyl]]-urea (390 mg, 1.65 mmol) and cis-6-methoxy-2,3 3a,4,5,9b-hexahydro-[1H]-benz[e]isoindole (497 mg, 1.60 mmol) were reacted by the procedures described in Example 1 to yield 0.291 g of the title compound as a white solid. m.p. 252° C. $^1$H NMR (300 MHz, CD$_3$OD) δ 1.65 (m, 1H), 1.95 (m, 1H), 2.50–3.15 (m, 6H), 3.40–3.75 (m, 3H), 3.60 (t, 2H), 3.81 (s, 3H), 4.42 (t, 2H), 6.80 (d, 1H), 6.83 (d, 1H), 7.17 (t, 1H), 7.45 (m, 1H), 7.69 (m, 2H), 7.94 (d, 1H). MS (DCI/NH$_3$) m/e 432 (M+H)$^+$. Anal calcd for C$_{25}$H$_{26}$ClN$_3$O$_5$. 0.5 H$_2$O: C, 62.95; H, 5.70; N, 8.81. Found: C, 62.84; H, 5.44; N, 8.82.

EXAMPLE 4

3-β-(cis-6-Methoxy-2,3,3a,4,5,9hexahydro-[1H]-benz[e]isoindol-1-yl)propyl-[1]benzothieno[3,2]pyrimidine-2,4(1H,3H)-dione hydrochloride N-(3-Chloropropyl)-N'-[3-[(2-methoxycarbonyl)benzothienyl]]-urea (0.613 g, 1.80 mmol) and cis-6-methoxy-2,3,3a,4,5,9b-hexahydro-[1H]-benz[e]isoindole (0.369 g, 1.82 mmol) were reacted by the procedures described in Example 1 to yield 0.100 g of the title compound as a white solid. m.p. 183°–60° C. $^1$H NMR (300 MHz, CD$_3$OD) δ 1.65 (m, 1H), 1.92 (m, 1H), 2.18 (m, 2H), 2.57 (m, 1H), 2.70–3.40 (m, 6H), 3.55–4.10 (m, 3H), 3.80 (s, 3H), 4.18 (t, 2H), 6.78 (d, 1H), 7.02 (d, 1H), 7.16 (t, 1H), 7.53 (t, 1H), 7.63 (t, 1H), 7.98 (d, 1H), 8.18 (d, 1H). MS (DCI/NH$_3$) m/e 462 (M+H)$^+$. Anal calcd for C$_{26}$H$_{28}$ClN$_3$O$_3$S: C, 62.70; H, 5.66; N, 8.43. Found: C, 62.39; H, 5.36; N, 8.46.

EXAMPLE 5

3-[2-(cis-9-Methoxy-2,3,3a,4,5,9b-hexahydro-[1H]-benz[e]isoindol-1-yl)ethyl]-[1]benzothieno[3,2-d]pyrimidine-2,4(1H,3H)-dione hydrochloride N-(2-Chloroethyl)-N'-[3-[(2-methoxycarbonyl)benzothienyl]]-urea (0.41 g, 1.25 mmol) and cis-9-methoxy-2,3,3a,4,5,9b-hexahydro-[1H]-benz[e]isoindole (0.33 g, 1.37 mmol), prepared as described in U.S. Pat. No. 5,049,564, which is incorporated herein by reference, were reacted by the procedures described in Example 1 to yield 0.170 g of the title compound as a white solid. m.p. 214°–16° C. $^1$H NMR (300 MHz, CD$_3$OD) δ 1.73 (m, 1H), 1.91 (m, 1H), 2.78 (m, 4H), 3.00–4.40 (m, 4H), 3.62 (t, 2H), 3.83 (s, 3H), 4.43 (t, 2H), 6.76 (d, 1H), 681 (d, 1H), 7.16 (t, 1H), 7.55 (t, 1H), 7.66 (t, 1H), 8.00 (d, 1H), 8.19 (d, 1H). MS (DCI/NH$_3$) m/e 448 (M+H)$^+$. Anal calcd for C$_{25}$H$_{26}$ClN$_3$O$_3$S. 0.5 H$_2$O C, 60.90; H, 5.51; N, 8.52. Found: C, 61.07; H, 5.27; N, 8.52.

EXAMPLE 6

3-[3-(cis-9-Methoxy-2,3,3a,4,5,9b-hexahydro-[1H]-benz[e]isoindol-1-yl)propyl]-[1]benzothieno[3,2-d]pyrimidine-2,4(1H,3H)-dione hydrochloride N-(3-Chloropropyl)-N'-[3-[(2-methoxycarbonyl)benzothienyl]]-urea (0.43 g, 1.25 mmol) and cis-9-methoxy-2,3,3a,4,5,9b-hexahydro-[1H]-benz[e]isoindole (0.33 g, 1.37 mmol) were reacted by the procedures described in Example 1 to yield 0.122 g of the title compound as a white solid. m.p. 203°–5° C. $^1$H NMR (300 MHz, CD$_3$OD) δ 1.73 (m, 1H), 1.91 (m, 1H), 2.18 (m, 2H), 2.87 (m, 4H), 2.95–4.15 (m, 6H), 3.84 (s, 3H), 4.18 (t, 2H), 6.76 (d, 1H), 6.81 (d, 1H), 7.15 (t, 1H), 7.54 (t, 1H), 7.63 (t, 1H), 7.98 (d, 1H), 8.18 (d, 1H). MS (DCI/NH$_3$) m/e 462 (M+H)$^+$. Anal calcd for $C_{26}H_{28}ClN_3O_3S$. 0.25 $H_2O$: C, 62.14; H, 5.71; N, 8.36. Found: C, 61.95; H, 6.01; N, 8.30.

EXAMPLE 7

3-[2-(cis-6-Methoxy-2,3,3a4,5,9b-hexahydro-[1H]-benz[e]isoindol-1-yl)ethyl]-[1]-5,6,7,8-tetrahydrobenzothieno[2,3-d]pyrimidine-2,4(1H,3H)-dione hydrochloride 2-Amino-3-carboethoxy-4,5,6,7-tetrahydrobenzothiophene (2.25 g, 10 mmol), prepared by the method of Gewald, et al., *Chem. Ber.*, 99:94 (1966), was treated with 2-chloroethyl isocyanate (0.95 ml, 11 mmol) in refluxing toluene for 3 hours, and solvent was evaporated to yield 3.5 g of the urea product. The resulting urea (0.64 g, 1.91 mmol) and cis-6-methoxy-2,3,3a,4,5,9b-hexahydro-[1H]-benz[e]isoindole (0.30 g, 1.47 mmol) were treated by the procedures described in Example 1. The resulting crude product was treated in EtOH with approximately 1 equivalent of NaOEt at reflux for 1 hour. After purification by chromatography eluting with 5:95 EtOH-EtOAc, the product (0.16 g) was converted to its HCl salt. m.p. 205°–207° C. $^1$H NMR (300 MHz, CDCl$_3$) δ 1.47–1.62 (m, 1H), 1.70–1.88 (m, 5H), 2.40–2.53 (m, 2H), 2.53–2.62 (m, 3H), 2.67–2.77 (m, 2H), 2.78–2.86 (m, 2H), 2.98–3.09 (m, 1H), 3.22–3.33 (m, 1H), 3.53 (q, 1H), 3.81 (s, 3H), 3.91 (q, 2H), 4.17–4.23 (m, 1H), 4.26–4.37 (m, 1H), 6.69 (d, 1H), 6.76 (d, 1H), 7.11 (t, 1H). MS (DCI/NH$_3$) role 452 (M+H)$^+$. Anal calcd for $C_{25}H_{29}N_3O_3S$ HCl. 0.5 $H_2O$: C, 60.49; H, 6.29; N, 8.45. Found: C, 60.20; H, 5.65; N, 8.05.

EXAMPLE 8

3-[2-((3aS,9bS)-cis-6-Methoxy-2,3,3a,4,5,9b-hexahydro-[1H]-benz[e]isoindol-1-yl)ethyl][1]benzothieno[3,2]pyrimidine-2,4(1H,3H)-dione hydrochloride

EXAMPLE 8A

5-Methoxy-3,4-dihydronaphthalene-1-carboxylic acid methyl ester

5-Methoxy-3,4-dihydronaphthalene-1-carboxylic acid (100 g, 490 mmol) was dissolved in 800 mL of methanol and 20 mL of 96% $H_2SO_4$, and heated at reflux for hours. The reaction was then cooled and evaporated under reduced pressure to a volume of 100 mL, and quenched on ice. The aqueous mixture was extracted with diethyl ether (3×100 mL), and the organic phase was washed with water, 5% aqueous NaHCO$_3$, brine, and then dried (MgSO$_4$) and evaporated to yield 101 g (94%) of the title compound as a colorless oil. $^1$H NMR (300 MHz, CDCl$_3$) δ 2.36 (m, 2H), 2.78 (t, 3H), 3.83 (s, 6H), 6.82 (d, 1H), 7.14 (t, 1H), 7.19 (t, 1H), 7.40 (t, 1H).

EXAMPLE 8B

5-Methoxy-2-cyano-1,2,3,4-tetrahydrohaphthalene-1-carboxylic acid methyl ester

A solution of 1100 mL 0.5M LiCN (550 mmol) in DMF and acetic acid (27.7 mL, 483 mmol) was prepared. The product resulting from Example 8A (101 g, 0.460 mmol) was dissolved in 100 mL DMF, and added over 15 minutes to the above solution. The reaction was stirred at 25° C. for 3.5 hours, and then poured onto ice/H$_2$O (5000 mL). The aqueous mixture was extracted with diethyl ether (3×500 mL), and the organic extracts were washed with H$_2$O and brine, dried (MgSO$_4$) and evaporated to dryness to yield 103.4 g (92%) of a light yellow oil as a mixture of cis and trans isomers of the desired product. $^1$H NMR (300 MHz, CDCl$_3$) δ 2.00–2.38 (m, 2H), 2.50–3.10 (m, 2H), 3.30–3.52 (m, 1H), 3.77 (s, 3H), 3.83 (s, 3H) 4.07 (m, 1H), 6.77 (d, 1H), 6.89 (d, 1H), 7.27 (m, 1H).

EXAMPLE 8C

5-Methoxy-1,2,3,4-tetrahydronaphthalene-1,2-dicarboxylic acid

The nitrile ester resulting from Example 8B (103 g, 422 mmol) was dissolved in 700 mL ethanol and 700 mL 45% aqueous KOH, and the reaction was heated at reflux for 10 hours. The cooled solution was diluted with 1.5 kg of ice and acidified to pH 1 with concentrated aqueous HCl. The resulting product was collected by filtration, washed with H$_2$O (3×200 mL) and dried under vacuum to yield 65.3 g (62%) of the title compound as a white solid. m.p. 200°–201° C. $^1$H NMR (300 MHz, CD$_3$OD) δ 1.85 (m, 1H), 2.27 (m, 1H), 2.65 (m, 1H), 2.85 (m, 1H), 3.10 (m, 1H), 3.80 (s, 3H), 4.05 (d, 1H), 6.79 (d, 1H), 6.92 (d, 1H), 7.11 (t, 1H).

EXAMPLE 8D

5-Methoxy-1,2,3,4-tetrahydronaphthalene-1,2-dicarboxylic anhydride

The compound resulting from Example 8C (65.3 g, 260 mmol) was dissolved in acetic anhydride (400 mL) and heated at reflux for 4 hours. The solvent was evaporated, and the resulting solid was triturated with 1:1 hexane:diethyl ether, and then collected and dried to yield 48.9 g (81%) of the title compound as a white solid. m.p. 138°–140° C. $^1$H NMR (300MHz, CDCl$_3$) δ 1.97 (m, 1H), 2.28 (m, 1H), 2.47 (m, 1H), 2.95 (m, 1H), 3.55 (m, 1H), 3.83 (s, 3H), 4.32 (d, 1H), 6.83 (d, 1H), 7.17 (d, 1H), 7.27 (t, 1H).

EXAMPLE 8E (3aR,9bR)-6-Methoxy-((S)-α-methylbenzyl)-2,3,3a,4,5,9b-[1H]-hexahydrobenz[e]isoindole-1,3-dione and (3aS,9bS)-6-Methoxy-((S)-α-methylbenzyl)-2,3,3a,4,5,9b-[1H]-hexahydrobenz[e]isoindole-1,3-dione The compound resulting from Example 8D (48.8 g, 210 mmol) was combined with (S)-(−)-α-methylbenzyl amine (28.1 g, 0.230 mmol) in xylene (200 mL), and the reaction was heated to reflux with water removal (Dean Stark trap) until the theoretical amount of water was removed. The reaction was then cooled and diluted with ethyl acetate (300 mL). The resulting solution was washed with 5% aqueous HCl, 5% aqueous NaHCO3 and brine, dried (MgSO$_4$) and evaporated to dryness. The resulting oily solid was triturated with diethyl ether, and the resulting crystalline title compound was collected (28.14 g, 81%) of the (3aR,9bR) product. m.p. 148°–150° C. $^1$H NMR (300 MHz, CDCl$_3$) δ 1.75 (d, 3H), 1.80 (m, 1H), 2.20 (m, 2H), 2.89 (m, 1H), 3.20 (m, 1H), 3.80 (s, 3H), 3.95 (d, 1H), 5.49 (q, 1H), 6.79 (d, 1H), 7.17–7.45 (m, 7H). From the mother liquor, on cooling, a second crop was collected (16.8 g, 48%) and shown to be the (3aS,9bS) product. m.p. 101°–103° C. $^1$H NMR (300 MHz, CDCl$_3$) δ 1.78 (d, 3H), 1.85 (m, 1H), 2.20 (m, 2H), 2.88 (m, 1H), 3.17 (m, 1H), 3.81 (s, 3H), 3.98 (d, 1H), 5.48 (q, 1H), 6.78 (d, 1H), 7.71–7.42 (m, 7H).

EXAMPLE 8F (3aS,9bS)-6-Methoxy-((S)-α-methylbenzyl)-2,3, 3a,4,5,9b-[1H]-hexahydrobenz[e]isoindole hydrochloride The (3aS,9bS) compound resulting from Example 8E (8.0 g, 23.8 mmol) was dissolved in THF and added over 5 minutes to a 1.0M solution of BH3 in THF. The reaction mixture was heated to reflux for 2 hours, and then cooled to 25° C. Methanol was added cautiously, and after evolution of $H_2$ ceased, the solvent was evaporated at reduced pressure. The resulting oil was dissolved in 2:1 methanol: isopropyl alcohol saturated with HCl (g), and the resalting solution was heated at reflux for 3 hours. The solvent was removed in vacuo, the resulting solid was triturated with 1:1 ethanol:diethyl ether, and the title compound (7.2 g, 88%) was collected by filtration as a white solid. $^1$H NMR (free base) (300 MHz, CDCl$_3$) δ 1.38 (d, 3H), 1.52 (m, 1H), 1.72 (m, 1H), 2.02 (t, 1H), 2.18 (dd, 1H), 2.50–2.72 (m, 3H), 2.99 (t, 1H), 3.18 (q, 1H), 3.30–3.48 (m, 2H), 3.80 (s, 3H, 6.62 (d, 1H), 6.65 (d, 1H), 7.04 (t, 1H), 7.20–7.35 (m, 5H).

EXAMPLE 8G (3aS,9bS)-6-Methoxy-2,3,3a,4,5,9b-[[1H]-hexahydrobenz[e]isoindole hydrochloride The compound resulting from Example 8F (5.7 g, 16.6 mmol) was dissolved in methanol and 10% palladium on carbon was added. The reaction was hydrogenated at 4 atmospheres of hydrogen at room temperature for 24 hours. The catalyst was removed by filtration and the solvent evaporated to yield the title compound (3.10 g, 78%) as a white solid. m.p. 222°–225° C. $^1$H NMR (300 MHz, CD$_3$OD) δ 1.60 (m, 1H), 1.93 (m, 1H), 2.54 (m, 1H), 2.67 (m, 1H), 2.93 (m, 1H) 3.09 (dd, 1H), 3.13 (dd, 1H), 3.53 (m, 1H), 3.58 (dd, 1H), 3.67 (dd, 1H), 3.80 (s, 3H), 6.78 (d, 1H), 6.81 (d, 1H), 7.16 (t, 1H). $[\alpha]D^{25}$ =22.2 (c=1.265, MeOH, free base).

EXAMPLE 8H

3-[2-((3aS,9bS)-cis-6-Methoxy-2 3 3a,4,5,9b-hexahydro-[1H! -benz[e]isoindol-1-yl)ethyl]-[1]benzothieno[3,2-d] pyrimidine-2,4(1H,3)-dione hydrochloride N-(2-Chloroethyl)-N'-[3-[(2-methoxycarbonyl)benzothienyl]]-urea (1.50 g, 4.57 mmol) and the free base of the compound resulting from Example 8G (0.450 g, 1.85 mmol) were treated by the procedures described in Example 1 to yield the title compound as a white solid. m.p.>250° C. $^1$H NMR (300 MHz, CD$_3$OD) δ 1.60–1.77 (m, 1H), 1.88–2.02 (m, 1H), 2.52–2.67 (m, 1H), 2.74–2.92 (m, 2H), 3.27–3.50 (m, 2H), 3.58–3.73 (m, 3H), 3.81 (s, 3H), 3.93–4.19 (m, 2H), 4.43 (t, 2H), 6.81 (t, 2H), 7.18 (t, 1H), 7.54 (t, 1H), 7.64 (t, 1H), 7.99 (d, 1H), 8.19 (d, 1H). MS (DCI/NH$_3$) m/e 448 (M+H)$^+$. Anal calcd for C$_{25}$H$_{25}$N$_3$O$_3$S. HCl: C, 62.04; H, 5.41; N, 8.68. Found: C, 61.96; H, 5.28; N, 8.46.

EXAMPLE 9

3-[2-((3aR,9bR)-cis-6-Methoxy-2,3,3a,4,5,9b-hexahydro-[1H]-benz[e]isoindol-1-yl)ethyl]-[1]benzothieno[3,2-d]pyrimidine-2,4(1H,3H)-dione hydrochloride

EXAMPLE 9A (3aR,9bR)-6-Methoxy-((S)-α-methylbenzyl)-2,3,3a,4,5,9b-[1H]-hexahydrobenz[e]isoindole hydrochloride The (3aR,9bR) compound resulting from Example 8E (28.0 g, 83.5 mmol) was dissolved in THF (100 mL) and added over 5 minutes to a 1.0M solution of BH$_3$ in THF. The reaction mixture was heated at reflux for 2 hours, and then cooled to 25° C. Methanol (100 mL) was added cautiously, and after evolution of $H_2$ ceased, solvent was evaporated at reduced pressure. The resulting oil was dissolved in 2:1 methanol:isopropyl alcohol saturated with HCl (g), and the resulting solution was heated at reflux for 3 hours. The solvent was removed in vacuo, the resulting solid was triturated with 1:1 ethanol:diethyl ether, and the title compound (25.8 g, 90%) was collected by filtration. m.p. 229°–23 1° C. $^1$H NMR (free base) (300 MHz, CDCl$_3$) δ 1.38 (d, 3H), 1.49 (m, 1H), 1.57 (m, 1H), 2.07 (dd, 1H), 2.15 (m, 1H), 2.40–2.72 (m, 3H), 2.97 (dd, 1H), 3.21 (q, 1H), 3.49 (m, 2H), 3.81 (s, 3H), 6.68 (d, 1H), 6.77 (d, 1H), 7.11 (t, 1H), 7.19–7.38 (m, 5H).

EXAMPLE 9B (3aR,9bR)-6-Methoxy-2,3,3a,4,5,9b-[1H]-hexahydrobenz[e]isoindole hydrochloride The compound resulting from Example 9A (25.7 g, 74.7 mmol) was dissolved in methanol (700 mL) and 10% Pd/C (5.9 g) was added. The reaction was hydrogentated at 4 atmospheres of hydrogen at room temperature for 24 hours. The catalyst was removed by filtration, and the solvent was evaporated to yield 15.9 g (89%) of the title compound as a white solid. m.p. 223°–225° C. $^1$H NMR (300 MHz, CD$_3$OD) δ 1.60 (m, 1H), 1.93 (m, 1H), 2.54 (m, 1H), 2.67 (m, 1H), 2.93 (m, 1H), 3.09 (dd, 1H), 3.13 (dd, 1H), 3.53 (m, 1H), 3.58 (dd, 1H), 3.67 (dd, 1H), 3.80 (s, 3H), 6.78 (d, 1H), 6.81 (d, 1H), 7.16 (t, 1H). $[a]D^{20}$=22.0° (c=1.39, MeOH, free base).

EXAMPLE 9C (3aR,9bR)-2-Cyanomethyl-6-methoxy-2,3,3a,4,5, 9b-[1H]-hexahydrobenz[e]isoindole The compound resulting from Example 9B (2.39 g, 10.0 mmol) was dissolved in H$_2$O, basified to pH 12 with aqueous NaOH solution and extracted 3×CH$_2$Cl$_2$. The organic extracts were dried (K$_2$CO$_3$), and evaporated to yield 1.96 g (9.64 mmol) of the free base. To the free base dissolved in CH$_3$CN (10 mL) and diisopropylethylamine (5 mL) was added 0.67 mL (10.6 mmol) of chloroacetonitrile. The reaction was heated at 70° C. for 1 hour, quenched in 5% NaHCO$_3$, and extracted with ethyl acetate (2×). The organic extracts were washed with water (2×) and brine (1×), dried (Na$_2$SO$_4$) and evaporated to yield 2.20 g of the title compound as an off white solid (90.5%). $^1$H NMR (300 MHz, CDCl$_3$) δ 1.60 (m, 2H), 1.80 (m, 1H), 2.58 (m, 3H), 2.77 (m, 1H), 3.23 (m, 2H), 3.48 (q, 1H), 3.64 (s, 2H), 3.81 (s, 3H), 6.70 (d, 1H), 6.74 (d, 1H), 7.12 (t, 1H).

EXAMPLE 9D (3aR,9bR)-2-Aminoethyl-6-methoxy-2,3,3a,4, 5,9b-[1H]-hexahydrobenz[e]isoindole LiAlH$_4$ (0.82 g, 21.5 mmol) was suspended in THF (30 mL) and cooled to 0° C. The compound resulting from Example 9C (0.80 g, 3.30 mmol) was dissolved in THF (5 mL) and added dropwise to the above LiAlH$_4$ suspension. The reaction was then stirred at room temperature for 1.5 hours, quenched by addition of H$_2$O (0.8 mL), 15% NaOH (0.8 mL) and H$_2$O (2.4 mL), filtered through celite, washing with several hot portions of THF, and the solvent evaporated to yield the title compound (0.75 g, 93%) as a colorless oil. $^1$H NMR (300 MHz, CDCl$_3$) δ 1.50 (m, 3H), 1.72 (m, 1H), 2.19 (m, 2H), 2.52 (m, 3H), 2.70 (m, 1H), 2.80 (t, 1H), 3.21 (dd, 1H), 3.28 (t, 1H, 3.40 (m, 1H), 3.80 (s, 3H), 6.67 (d, 1H), 6.75 (d, 1H), 7.11 (t, 1H).

EXAMPLE 9E

3-[2-((3aR.9bR)-cis-6- Methoxy-2,3,3a,4,5,9b-hexahydro-[1H]benz[e ]isoindol-1yl)ethyl]-[1]benzothieno[3,2- d]pyrimidine-2,4(1H,3H)-dione hydrochloride 3-Amino-2-carbomethoxy-benzothiophene (2.21 g, 10 mmol) and triphosgene (0.988 g, 3.33 mmol) were combined in 40 mL of toluene and heated at-reflux for 3 hours, and solvent was then evaporated to yield 2.45 g of the isocyanate as a white solid. The compound resulting from Example 9D (0.24 g, 1.0 mmol) and 0.260 g (1.1 mmol) of the isocyanate were combined in 10 mL of toluene and heated at reflux for 3 hours. The product was then partitioned between 5% NaHCO$_3$ and hot ethyl acetate, and the organic phase was dried (K$_2$CO$_3$) and evaporated. The resulting product was converted to its HCl salt and recrystallized from ethanol-ether to yield 0.28 g of the title compound as a white solid. m.p.>250° C. (dec.). $^1$H NMR (500 MHz, CD$_3$OD) δ 1.62–1.71 (m, 1H), 1.89–1.97 (m, 1H), 2.54–2.62 (m, 1H), 2.76–2.88 (m, 1H), 3.13–3.51 (m, 2H), 3.60 (t, 2H), 3.63–3.71 (m, 1H), 3.80 (s, 3H), 3.84–4.19 (m, 2H), 4.42 (dt, 2H), 6.80 (t, 2H), 7.16 (t, 1H), 7.53 (t, 1H), 7.63 (t, 1H), 7.98 (d, 1H), 8.18 (d, 1H). MS (DCI/NH$_3$) m/e 448 (M+H)$^+$. Anal calcd for C$_{25}$H$_{25}$N$_3$O$_3$S.HCl . H$_2$O: C, 59.81; H, 5.62; N, 8.37. Found: C, 60.12; H, 5.58; N, 8.20.

EXAMPLE 10

3-[2-(trans-6-Methoxy-2,3,3a,4,5,9b-hexahydro- [[1H]-benz[e]isoindol-1-yl)ethyl]-[1] benzothieno[3,2-d]pyrimidine-2,4(1H,3H)-dione hydrochloride N-(2-Chloroethyl)-N'-[3-[(2-methoxycarbonyl)benzothienyl]]-urea (0.40 g, 1.22 mmol) and trans -6-methoxy-2,3,3a,4,5,9b-hexahydro-[1H]-benz[e]isoindole (0.24 g, 1.2 mmol) were treated by the procedures described in Example 1 to yield the title compound as a white solid (0.064 g, 11%). mp>250° C. on a sample recrystallized from MeOH-DMF/ Et$_2$O. $^1$H NMR (300 MHz, DMSO-d$_6$) δ 12.67 (br. s, 1H), 10.27 (br. s, 1H), 8.43 (d, 1H, J=8.1 Hz), 8.13 (d, 1H, J=8.1 Hz), 7.62 (m, 2H), 7.17 (t, 1H, J=7.9 Hz), 6.88 (d, 1H, J=8,4 Hz), 6.66 (m, 1H), 4.32 (m, 3H), 4.03 (m, 1H), 3.93 (m, 1H), 3.78 (s, 3H), 3.70 (m, 2H), 2.88 (m, 1H), 2.67 (m, 2H), 2.16 (m, 2H), 1.93 (m, 1H), 1.61 (m, 1H). MS (DCI/NH$_3$) m/e 448 (M+H)$^+$. Anal. calcd for C$_{25}$H$_{26}$ClN$_3$O$_3$S . 0.25 H$_2$O: C, 61.46;H, 5.46; N, 8.60. Found: C, 61.24; H, 5.58; N, 8.48.

EXAMPLE 11

3-[2-(cis-6-Methoxy-2,3,3a,4,5,9b-hexahydro-[1H]- benz[e]isoindol-1-yl)ethyl]-1-methyl-[1] benzothieno[3,2-d]pyrimidine-2,4(1H,3H)-dione hydrochloride To the compound resulting from Example 1 as its free base (0.150 g, 0.33 mmol) dissolved in DMF (10 mL) was added 60% NaH (0.020 g, 0.50 mmol). After the evolution of H$_2$ ceased, methyl iodide (0.021 mL, 0.33 mmol) was added. After 18 hours at 25° C., the product was isolated and purified by column chromatography eluting with 100% EtOAc. Conversion of the product to its HCl salt afforded (0.029 g, 17%) of the title compound as a white solid. m.p. 230° C. $^1$H NMR (300 MHz, CD$_3$OD) δ 8.54 (d, 1H, J=0.1 Hz), 8.05 (d, 1H, J=7.7 Hz), 7.62 (m, 2H), 7.18 (t, 1H, J=8.1 Hz), 6.81 (m, 2H), 4.46 (m, 2H), 4.11 (s, 3H), 3.81 (s, 3H), 3.60 (m, 3H), 3.35 (m, 3H), 2.87 (m, 2H), 2.61 (m, 1H), 1.92 (m, 2H), 1.67 (m, 1H). MS (DCI/NH$_3$) m/e 462 (M+H)$^+$. Anal. calcd for C$_{26}$H$_{28}$ClN$_3$O$_3$S. H$_2$O: C, 60.51H, 5.85 N, 8.14. Found: C, 60.36; H, 5.56; N, 7.97.

EXAMPLE 12

3-[4-(cis-6-Methoxy-2,3,3a,4,5,9b-hexahydro-[1H]- benz[e]isoindol-1-yl)butyl]-[1]benzothieno[3,2- d]pyrimidine-2,4(1H,3H)-dione hydrochloride

EXAMPLE 12A cis-6-Methoxy-(2-(4-aminobutyl))-2,3,3a,4,5,9b- [1H]-hexahydrobenz[e]isoindole The compound resulting from Example 14B (1.89 g, 5.0 mmol) was treated by the procedures described in Example 15A to yield the title compound (1.20 g, 5%) as a colorless oil. $^1$H NMR (300 MHz, CDCl$_3$) δ 1.40–1.85 (m, 6H), 2.12 (m, 2H), 2.40–2.68 (m, 5H), 2.71 (t, 2H), 3.23–3.5 (m, 4H), 3.70 (m, 1H), (s, 3H), 6.68 (d, 1H), 6.75 (d, 1H), 7.11 (t, 1H).

EXAMPLE 12B 3-4-(cis-6-Methoxy-2,3,3a,4,5,9b-hexahydro-[1H]- benz[e]isoindol-1-yl)butyl]-[1]benzothieno [3,2-d]pyrimidine-2,4(1H,3H)-dione hydrochloride The the compound resulting from Example 12A (0.24 g, 0.87 mmol) was treated by the procedures described in Example 9E to yield the title compound (0.28 g, 67%) as a white solid. m.p. 173°–175° C. $^1$H NMR (300 MHz; DMSO-d$_6$) of the freebase δ 1.36–1.52 (m, 3H), 1.57–1.69 (m, 3H), 2.05 (t, 1H), 2.11 (dd, 1H), 2.34–2.62 (m, 5H), 3.06 (t, 1H), 3.15 (t, 1H), 3.26 (q, 1H), 3.74 (s, 3H), 3.92 (t, 2H), 6.71 (t, 2H), 7.05 (t, 1H), 7.55 (t, 1H), 7.63 (dt, 1H), 8.10 (d, 1H), 8.38 (d, 1H). MS (DCI/NH$_3$) m/e 476 (M+H)$^+$. Anal calcd for C$_{27}$H$_{29}$N$_3$O$_3$S. HCl. H$_2$O. C, 61.18; H, 6.08; N, 7.93. Found: C, 61.03; H, 5.76; N, 7.69.

EXAMPLE 13

3-[2-(cis-6-Methoxy-2,3,3a,4,5,9b-hexahydro-[1H]-benz[e]isoindol-1-yl)ethyl]-[1]benzothieno[2,3-d]pyrimidine-2,4(1H,3H)-dione hydrochloride 2-Amino-3-carboethoxybenzothiophene, prepared using the procedure described in *Chemsiche Berichte*, 101:1933 (1968), was treated with 2-chloroethylisocyanate by the procedures described in Example 1. The resulting urea (0.28 g, 1.1 mmol) and cis-6-methoxy-2,3,3a,4,5,9b-[1H]-hexahydrobenz[e]isoindole (0.22 g, 0.8 mmol) and 0.4 mL diisopropylethylamine in DMSO (1 mL) were heated at 100° C. for 1.5 hours. The reaction was quenched in $H_2O$ and extracted with ethyl acetate. The combined organic extracts were dried and concentrated in vacuo resulting in a urea ester intermediate which was treated with 0.25 mL 1.0M KOtBu in ethanol (2 mL) at reflux for 0.5 hours. After purification by column chromatography eluting with 95:5 ethyl acetate-ethanol and conversion to its HCl salt the title compound (0.15 g, 40%) was obtained as a white solid. m.p. 194°–196° C. $^1$H NMR (300 MHz, DMSO-$d_6$) δ 1.40–1.55 (m, 1H), 1.61–1.73 (m, 1H), 2.25–2.88 (m, 4H), 3.20–3.54 (m, 6H), 3.70 (s, 3H), 4.06 (t, 2H), 6.74 (d 1H), 6.76 (d, 1H), 7.10 (t, 1H), 7.3 1 (t, 1H), 7.43 (t, 1H), 7.90 (d, 1H), 8.14 (s, 1H), 8.26 (d, 1H). MS (DCI/$NH_3$) m/e 448 (M+H)$^+$. Anal calcd for $C_{25}H_{25}N_3O_3S$ HCl. $H_2O$: C, 59.81; H, 5.62; N, 8.37. Found: C, 59.10; H, 5.59; N, 8.22.

EXAMPLE 14

3-[2-(cis-6-Methoxy-2,3,3a,4,5,9b-hexahydro-[1H]-benz[e]isoindol-1-yl)ethyl]-1H-pyrimido[5,4-b]indole-2,4(3H,5H)-dione hydrochloride

EXAMPLE 14A cis-5-Methoxy-bis-(1,2-hydroxymethyl)-1,2,3,4-tetrahydronaphthalene 5-Methoxy-1,2,3,4-tetrahydronaphthalene-cis-1,2-dicarboxylic acid diethyl ester (37.0 g, 129 mmol), prepared by the procedures described in U.S. Pat. No. 5,049,564, which is incorporated herein by reference, was dissolved in THF (100 mL) and added over 15 minutes to a suspension of LiAlH$_4$ (9.20 g, 241 mmol) in THF 400 mL). The reaction was stirred at 25° C. for 18 hours and then quenched by sequential addition of 9.2 mL $H_2O$, 9.2 mL 15% aqueous KOH solution, and 29 mL $H_2O$. The reaction was filtered and the solvent evaporated at reduced pressure to yield the title compound (22.15 g, 82%) as a white solid. $^1$H NMR (300 MHz, CDCl$_3$) δ 1.70 (m, 2H), 2.04 (m, 1H), 2.53 (br s, 1H), 2.85 (m, 2H), 3.02 (br s, 1H), 3.48 (m, 1H), 3.65–3.85 (m, 4H), 3.86 (s, 3H), 6.70 (d, 1H), 6.73 (d, 1H), 7.12 (t, 1H).

EXAMPLE 14B cis-5-Methoxy-bis-(1,2-hydroxymethyl)-1,2,3,4-tetrahydronaphthalene-1,2-bis mesylate The compound resulting from Example 14A (22.2 g, 100 mmol), triethylamine (84 mL, 600 mmol) and methyene chloride (500 mL) were combined and cooled to 0° C. Methanesulfonyl chloride (23.3 mL, 300 mmol) was added over 15 minutes, and the reaction was stirred an additional 1.5 hours. The reaction was quenched in 5% aqueous NaHCO$_3$, and the organic phase was washed with one additional portion of 5% aqueous NaHCO$_3$ and brine, and then dried (MgSO$_4$) and evaportated to dryness, triturated with cold diethyl ether, and then collected by filtration to yield the title compound (33.5 g, 94%) as a white solid. $^1$H NMR (300 MHz, CDCl$_3$) δ 1.65–1.95 (m, 2H), 2.33 (m, 1H), 2.88 (m, 1H), 2.97 (s, 3H), 3.09 (s, 3H), 3.12 (m, 1H), 3.70 (m, 1H), 3.88 (s, 3H), 4.40 (m, 4H), 6.72 (d, 1H), 6.76 (d, 1H), 7.18 (t, 1H).

EXAMPLE 14C cis-6-Methoxy-(2-(2-aminoethyl))-2,3,3a,4,5,9b-[1H]-hexahydrobenz[e]isoindole The compound resulting from Example 14B was dissolved in ethylenediamine, and the reaction was heated at 65° C. for 3 hours. The reaction was quenched in 5% aqueous NaOH and extracted with CH$_2$Cl$_2$. The combined organic extracts were washed with brine, dried (K$_2$CO$_3$) and evaporated to yield the title compound as a colorless oil. $^1$H NMR (300 MHz, CDCl$_3$) δ 1.50 (m, 3H), 1.72 (m, 1H), 2.19 (m, 2H), 2.52 (m, 3H), 2.70 (m, 1H), 2.80 (t, 1H), 3.21 (dd, 1H), 3.28 (t, 1H, 3.40 (m, 1H), 3.80 (s, 3H), 6.67 (d, 1H), 6.75 (d, 1H), 7.11 (t, 1H).

EXAMPLE 14D

3-[2-(cis-6-Methoxy-2,3,3a,4,5,9b-hexahydro-[1H]-benz[e]isoindol-1-yl)ethyl]-1H-pyrimido[5,4-b]indole-2,4(3H,5)-dione hydrochloride 2-Carboethoxy-3-aminoindole, prepared by the method of Unangst, *J. Heterocyclic Chem.*, 20:495 (1983), was treated with 0.33 equivalent of triphosgene by the procedures described in Example 9E. The resulting isocyanate (0.185 g, 0.85 mmol) and the compound resulting from Example 14C (0.19 g, 0.77 mmol) were combined in toluene and heated at reflux for 5 hours. The resulting product was collected by filtration and dissolved in 15 mL of EtOH and 5 mL of THF. To this solution was added 0.58 mL 1.0M KOtBu in THF, and the mixture was heated at reflux for 45 minutes. After cooling, the product was collected by filtration and converted to its HCl salt to yield the title compound (0.12 g, 61%). m.p.>250° C. (dec.). $^1$H NMR (500 MHz, DMSO-$d_6$) δ 1.52–1.66 (m, 1H), 1.74–1.84 (m, 1H), 2.36–2.52 (m, 1H), 2.62–2.82 (m, 2H), 2.97–3.08 (m, 1H), 3.42–3.57 (m, 3H), 3.64–3.86 (m, 1H), 3.77 (s with side peak, 3H), 4.02–4.34 (m, 4H), 6.72–6.86 (m, 2H), 7.09–7.19 (m, 2H), 7.36–7.45 (m, 2H), 7.96 (t, 1H), 9.91 and 10.27 (bs a bs, 1H), 11.81 and 12.10 (d and d, 2H). MS (DCI/NH$_3$)m/e431 (M+H)$^+$. Anal s calcd for $C_{25}H_{26}N_4O_3$. HCl .0.5 $H_2O$: C, 63.22; H, 5.73; N, 11.80. Found: C, 63.45; H, 5.65; N, 11.88.

EXAMPLE 15

3-[4-(cis-9-Methoxy-2,3,3a,4,5,9b-hexahydro-1H]-benz[e]isoindol-1-yl)butyl]-[1]benzothieno[3,2-d]pyrimidine-2,4(1H,3H)-dione hydrochloride

EXAMPLE 15A cis-9-Methoxy-(2-(4-aminobutyl))-2,3,3a,4,5,9b-[1H]-hexahydrobenz[e]isoindole cis-8-Methoxy-bis-(1,2-hydroxymethyl)-1,2,3,4-tetrahydronaphthalene-1,2-bis mesylate (3.78 g, 10 mmol), prepared by the procedures described in U.S. Pat. No. 5,049,564, which is incorporated herein by reference, was dissolved in 1,4-diaminobutane (30 mL), and the reaction was heated at 65° C. for 3 hours. The reaction was quenched in 5% aqueous NaOH and extracted with $CH_2Cl_2$. The combined organic extracts were washed with brine, dried ($K_2CO_3$) and evaporated to yield the title compound (2.44 g, 89%) as a colorless oil. $^1H$ NMR (300 MHz, $CDCl_3$) δ 1.40–1.60 (m, 4H), 1.68 (q, 2H), 1.93 (t, 1H), 2.19 (dd, 1H), 2.40 (t, 2H), 2.50–2.67 (m, 3H), 2.70 (t, 2H), 3.11 (rid, 1H), 3.43 (t, 1H), 3.60 (q, 1H), 3.78 (s, 3H), 6.68 (d, 1H), 6.72 (d, 1H), 7.08 (t, 1H).

EXAMPLE 15B

3-[4-(cis-9-Methoxy-2,3,3,a,4,5,9b-hexahydro,
[1H]-benz[e]isoindol-1-yl)butyl]-[1]
benzothieno[3,2-d]pyrimidine-2,4(1H,3H)-dione
hydrochloride The compound resulting from Example 15A (0.24 g, 0.87 mmol) was treated by the procedures described in Example 9E to the yield the title compound (0.28 g, as a white solid. m.p. 186°–189° C. $^1H$ NMR (300 MHz, DMSO-$d_6$) δ 1.70 (m, 6H), 2.40–2.80 (m, 4H), 2.95 (m, 1H), 3.10–3.70 (m, 4H), 3.78 (s, 3H) 3.95 (m, 3H), 6.75 (d, 1H), 6.83 (d, 1H), 7.17 (t, 1H), 7.55 (t, 1H), 7.63 (t, 1H), 8.10 (d, 1H), 8.40 (d, 1H), 10.50 (br s, 1H), 12.54 (s, 1H). MS (DCI/$NH_3$) m/e 476 $(M+H)^+$. Anal calcd for $C_{27}H_{30}ClN_3O_3S \cdot 0.5\ H_2O$: C, 62.24; H, 6.00; N, 8.06. Found: C, 62.22; H, 6.24; N, 7.83.

EXAMPLE 16

3-[2-((3aR,9bR)-cis-9-Methoxy-2,3,3a,4,5,9b-
hexahydro-[1H]-benz[e]isoindol-1-yl)ethyl]-
[1]benzothieno[3,2-d]pyrimidine-2,4(1H,3H)-dione
hydrochloride

EXAMPLE 16A (3aR,9bR)-9-
Methoxy-((S)-α-methylbenzyl)-2,3,3a,4,5,9b-
[1H]-hexahydrobenz[e]isoindole cis-8-Methoxy-bis-(1,2-hydroxymethyl)-1,2,3,4-tetrahydronaphthalene-1,2-bis mesylate (12.08 g, 31.9 mmol), prepared using the procedures described in U.S. Pat. No. 5,049,564, which is incorporated herein by reference, was dissolved in (S)-(–)-α-methylbenzylamine (60 mL), and the reaction was heated at 70° C. for 20 hours. Excess amine was removed in vacuo, and the product was partitioned between diethyl ether and 5% aqueous NaOH solution. The organic phase was concentrated and purified by chromatography on silica gel eluting with 20% diethyl ether in hexanes to yield the title compound (3.4 g, 69%) as the first eluting product. $^1H$ NMR (300 MHz, $CDCl_3$) δ 1.37 (d, 3H), 1.61 (m, 2H), 1.93 (m, 1H), 2.12 (dd, 1H), 2.48 (m, 1H), 2.61 (m, 2H), 2.87 (dd, 1H), 3.18 (dd, 1H), 3.66 (m, 1H), 3.80 (s, 3H), 6.69 (d, 1H), 6.73 (d, 1H), 7.08 (t, 1H), 7.30 (m, 5H).

EXAMPLE 16B (3aR,9bR)-9-Methoxy-2,3,3a,4,5,9b-[1H]-
hexahydrobenz[e]isoindole hydrochloride The compound resulting from Example 16A as its HCl salt (2.2 g, 6.4 mmol) was dissolved in methanol (150 mL) and 10% Pd/C (0.44 g) was added. The reaction mixture was hydrogenated at 4 atmospheres of hydrogen for 24 hours, filtered, and the solvent evaporated. The product was recrystallized from ethanol:diethyl ether to yield the title compound (1.4 g, 91%) as a white solid. $^1H$ NMR (300 MHz, $CD_3OD$) 6 1.60 (m, 1H), 1.88 (m, 1H), 2.53 (m, 1H), 2.80 (m, 2H), 2.88 (dd, 1H), 3.60 (m, 2H), 3.82 (s, 1H), 3.93 (dd, 1H), 6.67 (d, 1H), 6.80 (d, 1H), 7.15 (t, 1H).

EXAMPLE 16C (3aR,9bR)-2-Cyanomethyl-9-methoxy-2,3,3a,4,5,9b-
[1H]-hexahydrobenz[e]isoindole The compound resulting from Example 16B (1.40 g, 5.8 mmol) was treated by the procedures described in Example 9C to yield the title compound (133 g, 95%) as a colorless oil. $^1H$ NMR (300 MHz, $CDCl_3$) δ 1.75 (q, 4H), 2.43 (t, 1H), 2.50–2.80 (m, 4H), 3.11 (m, 1H), 3.38 (t, 1H), 3.58 (q, 1H), 3.63 (s, 2H), 3.81 (s, 3 H), 6.69 (d, 1H), 6.74 (d, 1H), 7.10 (t, 1H).

EXAMPLE 16D

3-[2-((3aR,9bR)-cis-9-Methoxy,2,3,3a,4,5,9b-
hexahydro-[1H]-benz[e]isoindol-1-yl)ethyl]-
[1]benzothieno[3,2-d]pyrimidine-2,4(1H,3H)-dione
hydrochloride The compound resulting from Example 16C is reduced by the procedure described in Example 9D to give the aminoethyl compound. This compound (0.25 g, 1.02 mmol) and 2-carbomethoxy-benzothiophene-3-isocyanate (0.30 g, 1.2 mmol), prepared by the procedures described in Example 9E, were treated by the procedures described in Example 9E to yield the title compound (0.37 g, 75%) as a whim solid. m.p. 213° C. $^1H$ NMR (300 MHz, DMSO-$d_6$) δ 12.70 (hr. s, 1H), 10.00 (m, 1H), 8.43 (m, 1H), 8.14 (m, 1H), 7.63 (m, 2H), 7.16 (t, 1H, J=8.0 Hz), 6.84 (d, 1H, J=8.1 Hz), 6.76 (m, 1H), 4.28 (m, 3H), 4.02 (m, 1H), 3.78 (s, 3H), 3.54 (m, 3.11 (m, 1H), 2.85 (m, 1H), 2.51 (m, 3H), 1.74 (m, 2H). MS (DCI/$NH_3$) m/e 448 $(M+H)^+$. Anal. calcd for $C_{25}H_{26}ClN_2O_3S \cdot 1.5\ H_2O$: C, 58.75 H, 5.71 N, 8.22. Found: C, 58.60; H, 5.70; N, 8.06.

EXAMPLE 17

3-[2-(trans-6-Methoxy-2,3,3a,4,5,9b-hexahydro-[[1H]-
benz[e]isoindol-1-yl)ethyl]-1H-pyrimido[5,4-
b]indole-2,4(3H,5H)-dione hydrochloride

EXAMPLE 17A trans-2-Cyanomethyl-6-Methoxy-2,3,3a,4,5,9b-[1H]-
hexahydrobenz[e]isoindole trans-6-Methoxy-2,3,3a,4,5,9b-[1H]-hexahydrobenz[e] isoindole (1.50 g, 7.4 mmol), prepared by the procedures described in U.S. Pat. No. 4,618,683, which is incorporated herein by reference, was treated by the procedure described in Example 9C to yield the title compound (1.0 g, 56%) as a white solid. $^1H$ NMR (300 MHz, $CDCl_3$) δ 1.62 (m, 1H), 2.10 (m, 1H), 2.75 (m, 2H), 2.87–3.03 (m, 3H), 3.08 (dd, 1H), 3.40 (m, 1H), 3.72 (q, 2H), 3.82 (s, 3H), 6.58 (d, 1H), 6.72 (d, H), 7.12 (d, 1H).

EXAMPLE 17B trans-2-aminoethyl-6-Methoxy-2,3,3a,4,5,9b-[1H]-hexahydrobenz[e]isoindole dihydrochloride To the compound resulting from Example 17A (1.0 g, 4.1 mmol) dissolved in THF (10 mL) was added 1.0M BH3-THF. The reaction was heated at reflux for 16 hours, cooled to room temperature and quenched with methanol (5 mL). The solvent was removed in vacuo and the residue obtained dissolved in 2:1 methanol-isopropanol saturated with HCl (g). This mixture was heated at reflux for 2 hours, evaporated, triturated with ethyl acetate, and filtered to afford the title compound as a white solid (1.19 g, 91%). $^1$H NMR (300 MHz, CD$_3$OD) δ 1.7 (m, 1H), 2.26 (m, 2H), 2.77 (m, 1H), 2.85–3.25 (m, 4H), 3.45 (t, 2H), 3.63 (m, 2H), 3.81 (s, 3H), 4.0 (m, 2H), 6.64 (d, 1H), 6.84 (d, 1H), 7.16 (t, 1H).

EXAMPLE 17C

3-[2-(trans-6-Methoxy-2,3,3a,4,5,9b-hexahydro-[1H]-benz[e]isoindol-1-yl)ethyl]-1H-pyrimido5,4-b]indole-2,4(3H,5H)-dione hydrochloride 2-Carboethoxy-3-aminoindole, prepared by the method of Unangst, *J. 10 Heterocyclic Chem.*, 20:495 (1983 ), was treated with 0.33 equivalent triphosgene by the procedure described in Example 9E. The resulting isocyanate (0.31 g, 1.3 mmol) and the product resulting from Example 17II (0.25 g, 1.0 mmol) were combined in toluene and heated at reflux for 5 hours. The resulting product was collected by filtration and dissolved in 15 mL EtOH and 5 mL THF. To the solution was added 0.58 mL 1.0M KOtBu in THF and heated at reflux for 45 minutes. After cooling, the product was collected by filtration and converted to its HCl salt to yield the title compound (0.125 g, 47%). m.p.>270° C. $^1$H NMR (300 MHz, DMSO-d$_6$) δ 12.10 (s, 1H), 11.81 (s, 1H), 10.10 (hr. s, 1H), 7.98 (d, 1H, J-8.1 Hz), 7.41 (m, 2H), 7.15 (m, 2H), 6.88 (m, 1H), 6.65 (m, 1H), 4.33 (m, 3H), 4.04 (m, 1H), 3.95 (m, 1H), 3.78 (s, 3H), 3.60 (m, 2H), 2.85 (m, 1H), 2.64 (m, 2H), 2.15 (m, 2H), 1.92 (m, 1H), 1.60 (m, 1H). MS (DCI/NH$_3$) m/e 431 (M+H)$^+$. Anal: calcd for C$_{25}$H$_{27}$ClN$_4$O$_3$. 0.5 H$_2$O: C, 63.08; H, 5.92; N, 11.66. Found: C, 62.92; H, 5.79; N, 11.60.

EXAMPLE 18

3-[2-(trans-6-Methoxy-2,3,3a,4,5,9b-hexahydro-[[1H]-benz[e]isoindol-1-yl)ethyl]-benzofuro[3,2-d]pyrimidine-2,4(1H,3H)-dione hydrochloride 2-Carboethoxy-3-aminobenzofuran, prepared by the method of Unangst, *J. Heterocyclic Chem.*, 20:495 (1983), was treated with 0.33 equivalent triphosgene by the procedure described in Example 9E. The resulting isocyanate (0.3 19 g, 1.00 mmol) and the compound resulting from Example 19B (0.25g, 1.00 mmol) were treated by the procedure described in Example 9E to yield the title compound (0.175 g, 59%). m.p. 265° C. $^1$H NMR (300 MHz, DMSO-d$_6$) δ 12.52 (br, s, 1H), 10.35 (br, s, 1H), 8.07 (d, 1H, J=7.8 H), 7.79 (d, 1H, J=8.4 Hz), 7.67 (dt, 1H, J=7.3, 1.5 H), 7.48 (m, 1H), 7.16 (t, 1H, 7.9 Hz), 6.88 (d, 1H, J=8.1 Hz), 6.64 (m, 1H), 4.30 (m, 3H), 3.91 (m, 1H), 3.78 (s, 3H), 3.57 (m, 3H), 2.85 (m, 1H), 2.68 (m, 2H), 2.16 (m, 2H), 1.92 (m, 1H), 1.60 (m, 1H). MS (DCI/NH$_3$) m/e 432 (M+H)$^+$. Anal. calcd for C$_{25}$H$_{26}$ClN$_3$O$_4$. 0.75 H$_2$O: C, 62.36 H, 5.75 N, 8.72. Found: C, 62.36; H, 5.46; N, 8.60.

EXAMPLE 19

3-[2-((3aS,9bS)-cis-9-Methoxy-2,3,3a,4,5,9b-hexahydro-[1H-benz[e]isoindol-1-yl)ethyl][1]benzothieno[3,2-d]pyrimidine-2,4(1H,3H)-dione hydrochloride

EXAMPLE 19A (3aS,9bS)-9-Methoxy-((S)-methyl benzyl)-2,3,3a,4,5,9b-[1H]-hexahydrobenz[e]isoindole Further elution of the column chromatography described in Example 16A yielded the title compound (2.7 g, 55%) as the second eluting product. $^1$H NMR (300 MHz, CDCl$_3$) δ 1.38 (d, 3H), 1.65 (m, 2H), 2.02 (t, 1H), 2.26 (dd, 1H), 2.50–2.75 (m, 3H), 3.07–3.21 (m, 3H), 3.56 (q, 1H), 3.71 (s, 3H), 6.65 (d, 1H) (d, 1H), 7.07 (t, 1H), 7.18–7.35 (m, 5H).

EXAMPLE 19B (3aS,9bS)-9-Methoxy-2,3,3a,4,5,9b-[1H]-hexahydrobenz[e]isoindole hydrochloride The compound resulting from Example 19A was treated by the procedures described in Example 18B to yield the title compound as a white solid. $^1$H NMR (300 MHz, CD$_3$OD) δ 1.60 (m, 1H), 1.88 (m, 1H), 2.53 (m, 1H), 2.80 (m, 2H), 2.88 (dd, 1H), 3.60 (m, 2H), 3.82 (s, 1H), 3.93 (dd, 1H), 6.67 (d, 1H), 6.80 (d, 1H), 7.15 (t, 1H).

EXAMPLE 19C (3aS,9bS)-2-Cyanomethyl-9-methoxy-2,3,3a,4,5,9b-[1H]-hexahydrobenz[e]isoindole The compound resulting from Example 19B (0.65 g, 2.7 mmol) was treated by the procedures described in Example 9C to yield the title compound (036 g, 55%) as a colorless oil. $^1$H NMR (300 MHz, CDCl$_3$) δ 1.75 (q, 4H), 2.43 (t, 1H), 2.50–2.80 (m, 4H), 3.11 (m, 1H), 3.38 (t, 1H), 3.58 (q, 1H), 3.63 (s, 2H), 3.81 (s, 3H), 6.69 (d, 1H), 6.74 (d, 1H), 7.10 (t, 1H).

EXAMPLE 19D (3aS,9bS)-2-Aminoethyl-9methoxy-2,3,3a,4,5,9b-[1H]-hexahydrobenz[e]isoindole The compound resulting from Example 19C (0.36 g, 1.5 mmol) was treated by the procedures described in Example 9D to yield the title compound (0.25 g, 70%) as a colorless oil. $^1$H NMR (300 MHz, CDCl$_3$) δ 1.30 (br s, 2H), 1.70 (m, 2H), 2.06 (t, 1H), 2.28 (dd, 1H), 2.48–2.75 (m, 5H), 2.80 (t, 2H), 3.08 (dd, 1H), (t, 1H), 3.57 (q, 1H), 3.80 (s, 3H), 6.69 (d, 1H), 6.72 (d, 1H), 7.08 (t, 1H)

EXAMPLE 19E

3-[2-((3aS,9bS)-cis-9-Methoxy-2,3,3a,4,5,9b-hexahydro-[1H]-benz[e]isoindol-1-yl)ethyl]-[1]benzothieno[3,2-d]pyrimidine-2,4(1H,3H)-dione hydrochloride The compound resulting from Example 19D (0.23 g, 1.0 mmol) was treated by the procedure described in Example 9E to yield 0.27 g (70%) of the title compoud as a white solid. m.p. 213°–15° C. $^1$H NMR (300 MHz, DMSO-d$_6$) δ 1.75 (m, 2H), 2.58–2.92 (m, 4H), 3.00–3.85 (m, 4H), 3.80 (s, 3H), 3.90–4.45 (m, 4H), 6.77 (d, 1H), 6.85 (d, 1H), 7.17 (t, 1H), 7.57 (t, 1H), 7.67 (t, 1H), 8.14 (d, 1H) (d, 1H), 9.90 (br s, 1H), 12.70 (s, 1H). MS (DCI/NH$_3$) m/e 448 (M+H)$^+$. Anal calcd for C$_{25}$H$_{26}$ClN$_3$O$_3$S . 2H$_2$O: C, 57.74; H, 5.81; N, 8.08. Found: C, 57.95; H, 5.50; N, 7.98.

EXAMPLE 20

3-2-(cis-6-Hydroxy-2,3,3a,4,5,9b-hexahydro-[1H]-benz[e]isoindol-1-yl)ethyl]-[1]benzothieno[3,2-d]pyrimidine-2,4(1H,3H)-dione hydrobromide To the compound resulting from Example 1 (0.112 g, 0.25 mmol) suspended in CH$_2$Cl$_2$ (40 mL) and cooled to –70° C. was added BBr3 (0.10 mL, 1.0 mmol). The reaction was warmed to 25° C. for 3 hours, cooled to –70° C. and quenched by the addition of 2 mL of MeOH. After evaporation of the solvent, the product was recrystallized from MeOH-diethyl ether to yield the title compound (0.105 g, 85%) as a white solid. m.p.>255° C. $^1$H NMR (300 MHz, DMSO-d$_6$) δ 1.42–1.90 (m, 2H), 2.30–2.47 (m, 2H), 2.60–2.80 (m, 2H), 2.90–3.75 (m, 4H), 3.85 (m, 1H), 4.00–4.39 (m, 3H), 6.60(d, 1H), 6.68 (d, 1H), 7.00 (t, 1H), 7.62 (m, 2H), 8.15 (d, 1H), 8.22 (d, 1H), 9.40 (s, 1H), 9.65 (br s, 1H), 12.70 (s, 1H). MS (DCI/NH$_3$) m/e 434 (M+H)$^+$. Anal calcd for C$_{24}$H$_{24}$BrN$_3$O$_3$S . 0.25 H$_2$O: C, 55.54; H, 4.75; N, 8.09. Found: C, 55.25; H, 4.84; N,

EXAMPLE 21

3-[2-(cis-6-Methoxy-2,3,3a,4,5,9b-hexahydro-[1H]-benz[e]isoindol-1-yl)ethyl]-benzo[g]quinazoline-2,4(1H,3H):dione hydrochloride 2-Amino-3-carbethoxynaphthalene was treated with 0.33 equivalent triphosgene. The resulting isocyanate (0.41 g, 1.5 mmol) and the compound resulting from Example 14C (0.30 g, 1.2 mmol) were treated by the procedures described in Example 9E to yield the title compound (0.11 g, 53%) as a white solid. m.p. 258°–259° C. $^1$H NMR (300 MHz, DMSO-d$_6$) δ 8.75 (d, 1H), 8.13 (t, 1H), 7.95 (t, 1H), 7.61 (m, 2H), 7.48 (m, 1H), 7.18 (t, 1H), 6.85 (m, 1H), 6.75 (d, 1H), 4.3 (m, 2H), 4.17 (m, 1H), 4.05 (m, 1H), 3.78 (s, 3H), 3.4–3.78 (m, 5H), 3.05 (m, 1H), 2.62–2.85 (m, 2H), 1.8 (m, 1H), 1.6 (m, 1H,). MS (DCI/NH$_3$) m/e 442 (M+H)$^+$. Anal calcd for C$_{27}$H$_{27}$N$_3$O$_3$. HCl. 1.5 H$_2$O: C, 64.22; H, 6.19; N, 8.32. Found: C, 63.88; H, 6.07; N, 8.14.

EXAMPLE 22

3-[2-(cis-6-Methoxy-2,3,3a,4,5,9b-hexahydro-[1H]-benz[e]isoindol-1-yl)ethyl]-6,7,8,9-tetrahydro[1]benzothieno[3,2-d]pyrimidine-2,4(1H,3H)-dione hydrochloride 2-Amino-3-carboethoxy-4,5,6,7-tetrahydrobenzothiophene was treated with 0.33 equivalent triphosgene. The resulting isocyanate (0.28 g, 1.2 mmol) and the compound resulting from Example 14C (0.25 g, 1.0 mmol) were treated by the procedures described in Example 9E to yield the title compound (0.04 g, 8.5%) as a white solid. m.p. 188°–190° C. $^1$H NMR (300 MHz, CDCl$_3$) δ 1.53–1.66 (m, 1H), 1.79–1.94 (m, 5H), 2.48–2.63 (m, 3H), 2.69–2.85 (m, 6H), 3.22–3.69 (m, 3H), 3.82 (s, 3H), 3.97–4.16 (m, 2H), 4.33 (t, 2H), 6.73 (t, 2H), 7.14 (t, 1H), 8.18 (bs, 2H). MS (DCI/NH$_3$) m/e 452 (M+H)$^+$. Anal calcd for C$_{25}$H$_{29}$N$_3$O$_3$S. HCl. H$_2$O. C, 59.34; H, 6.37; N, 8.30. Found: C, 59.11; H, 5.98; N, 7.87.

EXAMPLE 23

3–12-(cis-6-Methoxy-2,3,3a,4,5,9b-hexahydro-[1H]-benz[e]isoindol-1-yl)ethyl]-pyrido[3',2':4,5]thieno[3,2-d]pyrimidine-2,4(1H,3H)-dione hydrochloride 3-Amino-2-carbomethoxythieno[2,3-b]pyridine, prepared by the method of Dunn and Norrie, *J. Heterocyclic Chem.*, 24: 85 (1987), was treated with 0.33 equivalent triphosgene. The resulting isocyanate (0.26 g, 1.1 mmol) and the compound resulting from Example 14C (0.25 g, 1.0 mmol) were treated by the procedures described in Example 9E to yield the title compound (0.134 g, 28%) as a white solid. m.p. 209°–212° C. $^1$H NMR (300 MHz, DMSO-d$_6$) δ 1.61 (m, 1H), 1.80 (m, 1H), 2.30–3.12 (m, 4H), 3.15–3.90 (m, 4H), 3.79 (s, 3H), 3.95–4.20 (m, 2H), 4.28 (m, 2H), 6.74 (d, 1H), 6.84 (d, 1H), 7.18 (t, 1H), 7.66 (d, 1H), 8.80 (m, 2H), 10.50 (br s, 1H), 12.83 (s, 1H). MS (DCI/NH$_3$) m/e 449 (M+H)$^+$. Anal calcd for C$_{24}$H$_{25}$ClN$_4$O$_3$S . H$_2$O: C, 57.31; H, 5.41; N, 11.14. Found: C, 57.08; H, 5.34; N, 10.81.

EXAMPLE 24

3-[2-((3aR,9bR)-cis-9-Methoxy-2,3,3a,4,5,9b-hexahydro-[1H]-benz[e]isoindol-1-yl)ethyl]-1H-pyrimido[5,4-b]indole-2,4(3H,5H)-dione hydrochloride

EXAMPLE 24A

(3aR,9bR)-2-Aminoethyl-9-methoxy-2,3,3a,4,5,9b-[1H]-hexahydrobenz[e]isoindole The compound resulting from Example 16C (1.30 g, 5.3 mmol) was treated by the procedures described in Example 9D to yield the title compound (1.21 g, 92%) as a colorless oil. $^1$H NMR (300 MHz, CDCl$_3$) δ 1.30 (br s, 2H), 1.70 (m, 2H), 2.06 (t, 1H), 2.28 (dd, 1H), 2.48–2.75 (m, 5H), 2.80 (t, 2H), 3.08 (dd, 1H), 3.38 (t, 1H), 3.57 (q, 1H), 3.80 (s, 3H), 6.69 (d, 1H), 6.72 (d, 1H), 7.08 (t, 1H).

EXAMPLE 24B

3-[2-((3aR,9bR)-cis-9-Methoxy-2,3,3a,4,5,9b-hexahydro-[1H]-benz[e]isoindol-1-yl)ethyl]-1H-pyrimido[5,4-b]indole-2,4(3H,5H)-dione hydrochloride 2-Carboethoxy-3-aminoindole, prepared by the method of Unangst, *J. Heterocyclic Chem.*, 20:495 (1983), was treated with 0.33 equivalent triphosgene by the procedures described in Example 9E. The resulting isocyanate (0.23 g, 1.0 mmol) and the compound resulting from Example 24A (0.20 g, 0.8 mmol) were treated by the procedures described in Example 9E to yield the title compound (0.07 g, 36%). m.p. 233° C. $^1$H NMR (300 MHz, DMSO-d$_6$) δ 12.12 (s, 1H), 11.83 (s, 1H), 7.97 (m, 1H), 7.42 (m, 2H), 7.15 (m, 2H), 6.83 (d, 1H, J=5.1 Hz), 6.76 (m, 1H), 4.29 (m, 3H), 4.03 (m, 1H), 3.78 (s, 3H), 3.54 (m, 3H), 3.10 (m, 2H), 2.67 (m, 3H), 1.74 (m, 2H). MS (DCI/NH$_3$) m/e 43 1 (M+H)$^+$. Anal. calcd for C$_{25}$H$_{26}$ClN$_4$O$_3$ . H$_2$O: C, 62.04 H, 5.83 N, 11.57. Found: C, 61.93; H, 5.83; N, 11.41.

EXAMPLE 25

3-[2-(cis-6-Methoxy-2,3,3a,4,5,9b-hexahydro-[1H]-benz[e]isoindol-1-yl)ethyl]-benzo[h]quinazoline-2,4(1H,3H)-dione hydrochloride 1-Amino-2-carbomethoxynaphthalene, prepared by the method of Zhang, et al., *Heterocycles*, 36: 2229 (1993), was treated with 0.33 equivalent triphosgene by the procedures described in Example 9E. The resulting isocyanate (0.27 g, 1.2 mmol) and the compound resulting from Exaple 14C (0.25 g, 1.0 mmol) were treated by the procedures described in Example 9E to yield the title compound (0.17 g, 38%) as a white solid. m.p.>250° C. (dec.). $^1$H NMR (300 MHz, DMSO-$d_6$) δ 8.9 (m, 1H), 8.04 (d, 1H), 7.95 (t, 1H), 7.64–7.81 (m, 3H), 7.18 (t, 1H), 6.71–6.9 (m, 2H), 4.22–4.41 (m, 2H), 4.0–4.22 (m, 2H), 3.78 (s, 3H), 3.38–3.72 (m, 4) 2.98–3.15 (m, 1H), 2.6–2.82 (m, 2H), 2.38–2.45 (m, 1H), 1.72–1.88 (m, 1H), 1.55–1.7 (m, 1H). MS (DCI/NH$_3$) m/e 442 (M+H)$^+$. Anal calcd for $C_{27}H_{27}N_3O_3$ · HCl · 0.5 H$_2$O: C, 66.59; H, 6.00; N, 8.63. Found: C, 66.39; H, 5.87; N, 8.57.

EXAMPLE 26

3-[2-((3aR,9bR)-cis-6-Methoxy-2,3,3a,4,5,9b-hexahydro-[1H]-benz[e]isoindol-1-yl)ethyl]-1H-pyrimido[5.4-b]indole-2,4(1H,3H)-dione hydrochloride 2-Carboethoxy-3-aminoindole, prepared by the method of Unangst, *J. Heterocyclic Chem.*, 20:495 (1983), was treated with 0.33 equivalent triphosgene by the procedures described in Example 9E. The resulting isocyanate (0.50 g, 2.4 mmol) and the compound resulting from Example 9D (0.55 g, 2.2 mmol) were treated by the procedures described in Example 9E to yield the title compound (0.60 g, 82%). m.p. 284°–287° C. (dec.). $^1$H NMR (300 MHz, DMSO-$d_6$) δ 1.53–1.68 (m, 1H), 1.74–1.86 (m, 1H), 2.35–2.54 (m, 1H), 2.61–2.79 (m, 2H), 2.94–3.09 (m, 1H), 3.42–3.49 (m, 3H), 3.63–3.88 (m, 1H), 3.78 (s (with small side peak), 3H), 4.01–4.12 (m, 1H), 4.14–4.23 (m, 1H), 4.29 (t, 2H), 6.75 (t, 1H), 6.83 (t, 1H), 7.08–7.18 (m, 1H), 7.11 (t, 1H), 7.35–7.47 (m, 2H), 7.97 (dd, 1H), 9.88 and 10.22 (bs and bs, 1H), 11.81 and 12.11 (d and d, 1H). MS (DCI/NH$_3$) m/e 431 (M+H)$^+$. Anal calcd for $C_{25}H_{26}N_4O_3$ · HCl · 1.25 H$_2$O: C, 61.35; H, 6.07; N, 11.45. Found: C, 61.26; H, 5.71; N, 11.48.

EXAMPLE 27

3-[2-(cis-6-Methoxy-2,3,3a,4,5,9b-hexahydro-[1H]-benz[e]isoindol-1-yl)ethyl]-pyrido[3',2':4,5]furo[3,2-d]pyrimidine-2,4(1H,3H)-dione hydrochloride 3-Amino-2-carbomethoxyfuro[2,3-b]pyridine, prepared by the method of Dunn and Norrie, *J. Heterocyclic Chem.*, 24:85 (1987), was treated with 0.33 equivalent triphosgene. The resulting isocyanate (0.79 g, 3.6 mmol) and the compound resulting from Example 14C (0.74 g, 3.0 mmol) were treated by the procedures described in Example 9E to yield the title compound (0.515 g, 37%) as a white solid. mp>260° C. $^1$H NMR (300 MHz, DMSO-$d_6$) 5 12.64 (br. s, 1H), 10.41 (m, 1H), 8.64 (dd, 1H, J=4.8, 1.5 Hz), 8.52 (d, 1H, J=8.1 Hz), 7.61 (dd, 1H, J=7.9, 5.0 Hz), 7.17 (t, 1H, J=7.9 Hz), 6.84 (d, 1H, J-8.0 Hz), 6.76 (d, 1H, J=8.1 Hz), 4.26 (m, 2H), 4.13 (m, 1H), 4.02 (m, 1H), 3.77 (s, 3H), 3.50 (m, 3H), 3.03 (m, 2H), 2.72 (m, 2H), 2.49 (m, 1H), 1.79 (m, 1H), 1.61 (m, 1H). MS (DCI/NH$_3$) m/e 433 (M+H)$^+$. Anal. calcd for $C_{24}H_{25}ClN_4O_4$ · 0.5 H$_2$O: C, 60.31 H, 5.48; N, 11.72. Found: C, 60.04; H, 5.49; N, 11.53.

EXAMPLE 28

3-[2-(cis-6-Methoxy-2,3,3a,4,5,9b-hexahydro-[1H]-benz[e]isoindol-1-yl)ethyl]-benzothieno[2,3-d]pyrimidin-4(3H)-one dihydrochloride

EXAMPLE 28A

Cis-6-Methoxy-2(2-chloroethyl)-2,3,3a,4,5,9b-[1H]-hexahydrobenz[e]isoindole hydrochloride To a solution of cis-6-methoxy-2,3,3a,4,5,9b-[1H]-hexahydrobenz-[e]isoindole (2.0 g, 8.3 mmol) in DMF (25 mL) was added $K_2CO_3$ (2.52 g, 18.3 mmol) and 1-bromo-2-chloroethane (0.83 mL, 10.0 mmol). The reaction mixture was stirred at room temperature for 24 hours and filtered. The filtrate was adjusted to pH 2.0 with HCl saturated EtOH followed by addition of Et$_2$O to give a white solid. The title compound was filtered and recrystallized from EtOH-Et$_2$O to give the product as a white solid (2.0 g, 79%).

EXAMPLE 28B

3-[2-(cis-6-Methoxy-2,3,3a,4,5,9b-hexahydro-[1H]-benz[e]isoindol-1-yl)ethyl]-benzothieno[2,3-d]pyrimidin-4(3H)-one dihydrochloride To benzothieno[3,2-d]pyrimidin-4(3H)-one (0.6 g, 3.0 mmol), prepared according to the method of J. R. Beck and J. A. Yahner, *J. Org. Chem.*, 2450 (1973), and the compound resulting from Example 28A (1.08 g, 3.6 mmol) in DMF (12 mL) was added dropwise a solution of KOH (0.35 g) in 2.5 mL of H$_2$O. The reaction mixture was stirred for 48 hours at room temperature, filtered and washed with H$_2$O to give a gummy solid. The solid was dissolved in methylene chloride, washed with water followed by brine solution, dried over anhydrous sodium sulfate, filtered and concentrated in vacuo to give a gummy solid. The solid was dissolved in MeOH and filtered. The methanol filtrate was concentrated to an oil and purified by flash column chromatography eluting with 10:90 EtOH-EtOAc to give a solid. The solid was dissolved in methanol, filtered and the filtrate concentrated to give a white solid. The solid was dissolved in EtOH and treated with a solution of HCl(g) dissolved in Et$_2$O to yield the title compound (0.060 g, 4%) as a solid. m.p. ~150° C. (dec.). $^1$H NMR (300 MHz, DMSO-$d_6$) δ 8.72–8.70 (d, 1H), 8.34–8.14 (dd, J=9Hz, 2H), 7.73–7.60 (m, 2H), 7.17 (t, J=8.1Hz), 6.86–6.78 (m, 2H), 4.49–4.44 (m, 2H), 4.19–4.16 (m, 1H), 4.01–3.97 (m, 1H), 3.77 (s, 3H), 3.75–3.67 (m, 3H), 3.07–298 (m, 1H), 2.77–2.60 (m, 2H), 1.82–1.77 (m, 1H), 1.64–1.56 (m, 1H). MS (DCI/NH$_3$) m/e 432 (M+H)$^+$. Anal. calcd for $C_{25}H_{27}Cl_2N_3O_2S$ · 0.5 H$_2$O: C, 57.66; H, 5.45; N, 8.06. Found: C, 57.60; H, 5.47; N, 8.22.

EXAMPLE 29

3-[2-(cis-6-Methoxy-2,3,3a,4,5,9b-hexahydro-[1H]-benz[e]isoindol-1yl)ethyl]-2-methyl-[1]benzothieno[2,3-d]pyrimidin-4(3H)-one dihydrochloride An ethanol solution (absolute, 50 mL) of cis-6-methoxy-(2-(2-aminoethyl))-2,3,3a,4,5,9b-[1H]-hexahydrobenz[e]isoindole HCl salt (0.59 g, 2.1 mmol), 2-methyl-4H-[1]

benzothieno[3,2-d][1,3]oxazin-4-one (0.5 g, 2.3 mmol), prepared by the method of Beck and Yahner, *J. Org. Chem.* 2450 (1973), and triethylamine (0.34 mL, 2.4 mmol) were refluxed for 24 hours. The reaction mixture was concentrated and the residue obtained purified by flash column chromatography eluting with 10:90 EtOH-EtOAc to give a purple colored solid. The solid was then dissolved in EtOH and treated with HCl(g) dissolved in Et$_2$O to yield the title compound (0.33 g, 30%) as a solid. m.p. 195° C. (dec) on a sample recrystallized from ethanol-ether. $^1$H NMR (300 MHz, CD$_3$OD) δ 8.33–8.32 (d, 1H), 8.04–8.01 (d, 1H), 7.69–7.56 (m, 2H), 7.21–7.15 (t, 1H), 6.85–6.80 (m, 2H), 4.65–4.61 (m, 2H), 4.37–4.22 (m, 1H), 3.82 (s, 3H), 3.77–3.61 (m, 2H), 3.22–3.06 (mm, 5H), 2.84 (s, 3H), 2.66–2.57 (m, 2H), 2.01–1.93 (m, 1H), 1.74–1.69 (m, 1H). MS (DCI/NH$_3$) m/e 4.66 (M+H)$^+$. Anal. calcd for C$_{26}$H$_{29}$Cl$_2$N$_3$O$_2$S . 0.5 H$_2$O C: 58.59; H, 5.73; N, 7.88. Found: C, 58.57; H, 5.74; N, 7.61.

EXAMPLE 30

3-[2-(cis-6- Methoxy-2 3 3a,4,5,9b-hexahydro-[1H]-benz[e]isoindol-1-yl)ethyl]-2-phenyl-[1]benzothieno[3,2-d]-4(1H,3H)-one hydrochloride An ethanol solution (absolute, 60 mL) of cis-6-methoxy-(2-(2-aminoethyl))-2,3,3a,4,5,9b-[1H]-hexahydrobenz[e]isoindole HCl salt (0.64 g, 2.3 mmol), 2-phenyl-4H-[1]benzothien[3,2-d][1,3]oxazin-4-one (0.7 g, 2.5 mmol), prepared according to the method of Beck and Yahner, *J. Org. Chem.*, 2450 (1973), and triethylamine (0.32 mL, 2.3 mmol) was refluxed for 24 hours. The reaction mixture was concentrated under reduced pressure, and the resulting residue was purified by flash column chromatagraphy eluting with 60:. 40 hexane-ethyl acetate to give a white solid. The solid was dissolved in EtOH and treated with a solution of HCl(g) in Et$_2$O to yield the title compound (0.25 g, 20%) as a solid. m.p. 165° C. (dec) (recrystallized from EtOH/Et$_2$O). $^1$H NMR (300MHz, DMSO) δ 8.22 (t, J=9 Hz, 2H), 7.77–7.60 (m, 7H), 7.16 (t, J=7.8Hz, 1H), 6.83–6.81 (dd, 1H), 6.69–6.67 (d, 1H), 4.40–4.24 (m, 2H), 3.77 (s, 3H), 3.47–3.24 (m, 3H), 2.78–2.27 (m, 7H), 1.76–1.68 (m, 1H), 1.54–1.48 (m, 1H). MS (DCI/NH$_3$) m/e 508 (M+H)$^+$. Anal. calcd for C$_{31}$H$_{30}$ClN$_3$O$_2$S . 0.75 H$_2$O: C, 65.17; H, 5.61; N, 7.355. Found: C, 65.08; H, 5.55; N, 7.72.

EXAMPLE 31

3,2-((3aR,9bR)-cis-6-Methoxy-2,3,3a,4,5,9b-hexahydro-[1H]-benz[e]isoindol-1-yl))ethyl]-pyrido[3',2':4,5]thieno[3,2-d]pyrimidine-2,4(1H,3H)-dione hydrochloride 3-Amino-2-carbomethoxythieno[2,3-b]pyridine, prepared by the method of Dunn and Norrie, *J. Heterocyclic Chem.*, 24:85 (1987), was treated with 0.33 equivalent triphosgene. The resulting isocyanate (0.86 g, 3.6 mmol) and the compound resulting from Example 9D (0.75 g, 3.0 mmol) were treated by the procedure described in Example 9E to yield the title compound (0.68 g, 47%) as a white solid. m.p. 23 1° C. (dec). $^1$H NMR (300 MHz, DMSO-d$_6$) δ 12.83 (m, 1H), 10.46 (br. s, 1H), 8.82 (m, 2H), 7.67 (m, 1H), 7.17 (t, 1H, J=7.9 Hz), 6.80 (m, 2H), 4.29 (m, 3H), 4.16 (m, 1H), 4.03 (m, 1H), 3.78 (s, 3H), 3.53 (m, 2H), 3.04 (m, 2H), 2.70 (m, 2H), 2.44 (m, 1H), 1.80 (m, 1H), 1.63 (m, 1H). MS (DCI/NH$_3$) m/e 449 (M+H)$^+$. Anal. calcd for C$_{24}$H$_{25}$ClN$_4$O$_3$S . 0.5 H$_2$O: C, 58.35; H, 5.30; N, 11.34. Found: C, 58.14; H, 5.27; N, 11.28.

EXAMPLE 32

3-[2-((3aR,9bR)-cis76-Methoxy-2,3,3a,4,5,9b-hexahydro-[1-benz[e]isoindol-1-yl)ethyl]-7-trifluoromethyl[1]benzothieno[23-d]pyrimidine-2,4(1H,3H)-dione hydrochloride 6-Trifluoromethyl-3-amino-2-ethoxycarbonylbenzothiophene was prepared from 4-trifluoromethyl-2-nitrobenzonitrile and ethylthioglycolate using the procedure of J. R. Beck *J. Org. Chem.*, 3224 (1972). 6-Trifluoromethyl-3-amino-2-ethoxycarbonylbenzothiophene (0.556 g, 1.49 mmol) was reacted with triphosgene (0.19 g, 0.64 mmol) by the procedure described in Example 9E. The resulting isocyanate was reacted with the compound resulting from Example 14C (1.24 mmol), in the prescence of Et$_3$N (1.2 equiv., 0.21 mL) in PhCH$_3$ (10 mL) at reflux for 18 hours. The reaction mixture was cooled to room temperature, filtered and the solid collected partitioned between EtOAc and NaHCO$_3$ solution. The aqueous phase was extracted with EtOAc (2×). The combined organic extracts were washed with brine, dried over Na$_2$SO$_4$ and evaporated. The resulting free base was dissolved in EtOH/EtOAc, and ethanolic HCl was added. This solution was allowed to cool and triturated with Et$_2$O to yield the title compound (0.292 g, 43%). m.p.>270° C. [α]$_D$=+30.6°(c=0.54, EtOH). $^1$H NMR (300 MHz, DMSO-d$_6$) δ 12.82 (br. s, 1H), 8.70 (s, 1H), 8.63 (d, J=8.8 Hz, 1H), 7.93 (d, J-8.1 Hz, 1H), 7.17 (t, J=7.9 Hz, 1H), 6.84 (br. d, J=8.1 Hz, 1H), 6.75 (br. d,J=8.1 Hz, 1H), 4.29 (m, 2H), 4.17 (m, 1H), 4.04 (m, 1H), 3.77 (s, 3H), 3.52 (m, 3H), 3.04 (m, 2H), 2.70 (m, 2H), 2.43 (m, 1H), 1.78 (m, 1H), 1.59 (m, 1H). MS (DCI/NH$_3$) m/e 516 (M+H)$^+$. Anal. calcd for C$_{26}$H$_{25}$F$_3$ClN$_3$O$_3$S . 0.3 HCl: C, 55.47; H, 4.53; N, 7.46. Found: C, 55.36; H, 4.42; N, 7.39.

EXAMPLE 33

3-[2-((3aR,9bR)-cis-6-Methoxy-2,3,3a,4,5,9b-hexahydro-[1H]-benz[e]isoindol-1-yl)ethyl]-1-methyl-[1]benzothieno[3,2-d]pyrimidine-2,4(1H,3H)-dione hydrochloride

EXAMPLE 33A

3-(N-Methyamino)-2-carboethoxy-benzothiophene

3-Amino-2-carboethoxy-benzothiophene (1.11 g, 5 mmol) was reacted with formic acetic anhydride followed by reduction by BH3.DMS, using the procedure described by Krishmanurthy in *Tetrahedron Lett*, 23:33 15–8 (1982), to yield 0.59 g of the title compound as a light yellow solid. $^1$H NMR (300 MHz, CDCl$_3$) δ 1.39 (t, 3H), 3.41 (d, 3H), 4.33 (q, 2H), 7.28 (t, 1H), 7.41 (t, 1H), 7.53 (br s, 1H) (d, 1H), 8.18 (d, 1H).

EXAMPLE 33B

N-(2-Chloroethyl)-N'-Methyl-N'-(3-(2-carboethoxy-benzthienyl)-urea

The compound resulting from Example 33A (0.55 g, 2.34 mmol) was combined with 2-chloroethylisocyanate (0.25 mL, 2.92 mmol) in toluene (10 mL) and heated at 90° C. for 24 hours. Evaporation of the solvent and purification by column chromatography yielded 0.54 g (68%) of the title compound as a white solid. $^1$H NMR (300 MHz, CDCl$_3$) δ

1.40 (t, 3H), 3.39 (s, 3H), 3.40 (m, 1H), 3.55 (t, 2H), 3.62 (m, 1H), 4.40 (m, 2H), 4.63 (br s, 1H), 7.42-(m, 2H), 7.77 (d, 1H), 7.87 (d, 1H).

EXAMPLE 33C

3-[2-((3aR,9bR)-cis-6-Methoxy-2,3,3a,4,5,9b-hexahydro-[1H]-benz[e]isoindol-1-yl)ethyl]-1-methyl-[1]benzothieno[3,2-d]pyrimidine-2,4(1H,3H)-dione hydrochloride (3aR,9bR)-6-Methoxy-2,3,3a,4,5,9b-[1H]-hexahydrobenz[e]isoindole (0.305 g, 1.50 mmol) and the compound resulting from Example 33B (0.50 g, 1.47 mmol) were combined in 2 mL CH$_3$CN and 1.3 mL diisopropylethylamine and heated at reflux for 72 hours. The reaction was diluted with water (5 mL) and the product collected by filtration. The free base was converted to its HCl salt and recrystallized from methanol to afford 0.375 g of the title compound as a white solid. m.p.>250° C. $^1$H NMR (300 MHz, DMSO-d$_6$) δ 1.60 (m, 1H), 1.80 (m, 1H), 2.30–3.10 (m, 5H), 3.79 (s, 3H), 3.97 (s, 3H), 3.20–3.90 (m, 4H), 4.14 (m, 1H), 4.32 (m, 2H), 6.75, (m, 1H), 6.82 (m, 1H), 7.17 (t, 1H), 7.58 (t, 1H), 7.65 (t, 1H), 8.18 (d, 1H), 2.53 (d, 1H), 10.5 (br s, 1H). MS (DCI/NH$_3$) m/e 462 (M+H)$^+$. Analysis calcd for C$_{26}$H$_{27}$N$_3$O$_3$S . HCl . 1.25 H$_2$O: C, 59.99; H, 5.90; N, 8.07. Found: C, 59.92; H, 5.65; N, 8.18.

EXAMPLE 34

3-[2-((3aR,9bR)-cis-6-Methoxy-2,3,3a,4,5,9b-hexahydro-[1H]-benz[e]isoindol-1-yl) ethyl]-pyrido[3',2':4,5]thieno[3,2:d] pyrimidine-4(3H)-one dihydrochloride

EXAMPLE 34A

2-Carboxyethyl-3-(N,N-dimethyl-N'-formamidinyl)thieno[2,3-b]pyridine

The title compound was prepared by the method of Gupton J. T., Miller J. F., Bryant R. D. Maloney P. R., and Foster B. S., *Tetrahedron* 43(8): 1747–1752 (1987) from 2-carboxethyl-3-aminothieno[2,3-b]pyridine.

EXAMPLE 34B

3-[2-((3aR,9bR)-cis-6-Methoxy-2,3,3a,4,5,9b-hexahydro[1H]-benz[e]isoindol-1yl)ethyl]-pyrido[3',2':4,5]thieno[2-d]pyrimidine-4(1H,3H)-one dihydrochloride The compound resulting from Example 34A (680 mg, 2.45 mmol) and (3aR,9bR)-2-aminoethyl-6-methoxy-2,3,3a,4,5,9b-[1H]-hexahydrobenz[e]isoindole (484 mg, 1.96 mmol) were refluxed in a solution of 1,4-dioxane (10 mL) and p-toluenesulfonic acid monohydrate (300 mg, 1.60 mmol) for 4 hours. The volatiles were removed under reduced pressure to give a crude product as white solid. Chromatography on silica eluting with 3% EtOH in EtOAc afforded the product as a free base. The free base was dissolved in methylene chloride and treated with HCl(g) in Et$_2$O to yield the title compound (690 mg, 76%) as a white solid. m.p. 182°–184° C. (on a sample recrystallized from EtOH-Et$_2$O). $^1$H NMR (300 MHz, CD$_3$OD) δ 1.58 (m,1H), 1.75 (m, 1H), 2.42 (m, 1H), 2.55 (m, 2H), 2.72 (m, 1H), 2.90 (m, 2H), 3.25 (m, 2H), 3.40 (m, 1H), 3.82 (s, 3H), 4.12 (m, 2H), 4.25 (m, 2H), 6.70 (t, J=9 Hz, 2H), 7.10 (t, J=9 Hz, 1H), 7.50 (dd, J=6 Hz, 1H), 8.20 (s, 1H), J=Hz), 8.80 (dd, J=3Hz, 1H). MS (DCI/NH$_3$) m/e 433 (M+H)$^+$. Anal calcd for C$_{24}$H$_{26}$N$_4$O$_2$SCl$_2$ . 0.5 HCl: C, 55.04; H, 5.10; N, 10.70. Found: C, 55.41; H, 5.00; N, 10.30.

EXAMPLE 35

3-2-((3aR,9bR)-cis-6-Methoxy-2,3,3a,4,5,9b-hexahydro-[1H]-benz[e]isoindol-1-yl)ethyl]-9-methyl[1]benzothieno[3,2-d] pyrimidine-2,4(1H,3H)-dione hydrochloride 4- Methyl -3 -amino- 2-caroboethoxy benzothiophene, prepared from 6- nitro-o-toluonitrile and ethylthioglycolate by the method of J. R. Beck, *J. Org. Chem.*, 3224 (1972), (0.505 g, 2.15 mmol) and triphosgene (0.234 g, 0.79 mmol) in toluene were reacted at reflux to give the isocyanate. The resulting isocyanate was reacted with (3aR,9bR)-2-aminoethyl-6-methoxy-2,3,3a,4,5,9b-[1H]-hexahydrobenz[e] isoindole (1.65 mmol), in the presence of Et$_3$N (1.2 equiv, 0.28 mL) in toluene (15 mL) at reflux for 18 hours. The reaction mixture was cooled to room temperature and the solid collected by filtration. The solid was dissolved in warm CH$_2$Cl$_2$ and the solution washed with saturated aqueous NaHCO$_3$ (1×). The aqueous wash was backed extracted with CH$_2$Cl$_2$ (1×). The combined organic extracts were washed with brine (1×), dried (Na$_2$SO$_4$) and evaporated. The free base was dissolved in EtOH-EtOAc and ethanolic HCl added. The solution was allowed to cool and triturated with Et$_2$O to yield the title compound (0.525 g, 64%) as a white solid. m.p. 270° C. $^1$H NMR (300 MHz, DMSO-d$_6$) δ 7.94 (d, 1H, J=8.1 Hz), 7.51 (dd, 1H, J=8.1, 7.4 Hz), 7.30 (d, 1H, J=0.0 Hz), 7.17 (dd, 1H, J=8.1, 7.7 Hz), 6.84 (d, 1H J=8.5 Hz), 6.77 (m, 1H), 4.27 (m, 2H), 4.18 (m, 1H), 4.05 (m, 1H), 3.77 (s, 3H) 3.52 (m, 3H), 3.08 (m, 2H), 2.87 (s, 3H), 2.72 (m, 2H), 2.42 (m, 1H), 1.83 (m, 1H), 1.59 (m, 1H). MS (DCI/NH$_3$) m/e 462 (M+H)$^+$. Anal. calcd for C$_{26}$H$_{28}$ClN$_3$O$_3$S . 0.2 HCl: C, 61.80; H, 5.63; N, 8.32. Found: C, 61.74; H, 5.69; N, 8.17

EXAMPLE 36

3-[2-((3aR,9bR)-cis-6-Methoxy-2,3,3a,4,5,9b-hexahydro-[1H]-benz[e]isoindol-1-yl)ethyl]-pyrido[4',3':4,5]thieno[3,2-]pyrimidine-2,4(1H,3H)-dione dihydrochloride 3-Amino-2-carbomethoxythieno[2,3-c]pyridine (0.61 g, 2.9 mmol), prepared by the procedure described in *J. Heterocyclic Chem.*, 24:85 (1987), and Et$_3$N (0.88 mL, 6.3 mmol) were taken up in anhydrous methylene chloride under nitrogen and cooled to −78° C. Phosgene (1.5 mL of a 1.93M solution in toluene, 2.9 mmol) was added, and the reaction was stirred at −78° C. for 45 minutes and room temperature for 1.5 hours. (3aR,9bR)-2-Aminoethyl-6-methoxy-2,3,3a,4,5,9b-[1H]hexahydrobenz[e]isoindole (0.60 g, 2.4 mmol) in methylene chloride was added, and the reaction mixture was stirred for 2 hours. The reaction mixture was partitioned between 1M NaOH and CH$_2$Cl$_2$. The methylene chloride layer was dried over magnesium sulfate, filtered, and concentrated in vacuo. The residue obtained was taken up in THF and treated with 1M KO-t-Bu in THF. The reaction was stirred for 1 hour at room temperature, concentrated under reduced pressure and chromatographed on silica gel eluting with 5% EtOH in CH$_2$Cl$_2$ saturated with NH$_3$ increasing the EtOH concentration to 10% to provide 1.01 g (92%). The product was converted to its HCl salt and recrystallized from EtOH-Et$_2$O. m.p. 226°–229° C. 1H NMR (300 MHz, CDCl$_3$) of the free base δ 1.48–1.62 (m, 1H), 170–1.83 (m, 1H), 2.45 (d, 3H), 2.52–2.75 (m, 3H), 2.88–2.99 (m, 1H), 3.03–3.13 (m, 1H), 3.40–3.63 (m, 3H), 3.78 (s, 3H), 4.31–4.47 (m, 2H), 6.64 (d, 1H), 6.69 (d, 1H), 7.03 (t 1H), 8.01 (d, 1H), 8.60 (d, 1H), 9.19 (s, 1H). MS (DCI/NH$_3$) m/e 449 (M+H)$^+$. Anal calcd for C$_{24}$H$_{24}$N$_4$O$_3$S . 2 HCl . 0.5 H$_2$O: C, 54.34; H, 5.13; N, 10.56. Found: C, 54.56; H, 5.21; N, 10.51.

EXAMPLE 37

3-[2-(3aR,9bR)-cis-6-Methoxy-2,3,3a,4,5,9b-hexahydro-[1H]-benz[e]isoindol-1-yl)ethyl]-pyrido[2',3':4,5]thieno[3,2-d]pyrimidine-2,4(1H,3H)-dione dihydrochloride Following the procedure described in Example 36, 3-amino-2-carbomethoxythieno[3,2-b]pyridine (0.51 g, 2.4 mmol), prepared by the procedure described in *J. Heterocyclic Chem.*, 24:85 (1987), Et$_3$N (0.74 mL, 5.3 mmol), phosgene (1.3 mL 1.93M solution in toluene, 2.4 mmol), and (3aR,9bR)-2-aminoethyl-6-methoxy-2,3,3a,4,5,9b-[1H]-hexahydrobenz[e]isoindole (0.50 g, 2.0 mmol) provided 0.68 g (75 %) of the desired product which was convened to the HCl salt. m.p. 256°–257° C. $^1$H NMR (300 MHz, DMSO-d$_6$) δ 1.53–1.68 (m, 1H), 1.73–1.86 (m, 1H), 2.60–3.10 (m, 4H), 3.64–3.83 (m, 4H), 3.77 (s, 3H), 3.83–4.35 (m, 4H), 6.73–6.87 (m, 2H), 7.17 (t, 1H), 7.65–7.71 (m, 1H), 8.66,8.70 (m, 1H), 8.84–8.88 (m, 1H), 10.30 and 10.64 (bs and bs, 1H), 12.79 (s, 1H). MS (DCI/NH$_3$) m/e 449 (M+H)$^+$. Anal calcd for C$_{24}$H$_{24}$N$_4$O$_3$S . 2 HCl: C, 55.28; H, 5.03; N, 10.74. Found: C, 55.92; H, 4.93; N, 10.74.

EXAMPLE 38

3-[2-((3aR,9bR)-cis-6-Methoxy-2,3,3a,4,5,9b-hexahydro-[1H]-benz[e]isoindol-1-yl)ethyl]1-pyrido[3',4':4,5]thieno[3,2-d]pyrimidine-2,4(1H,3H)-dione dihydrochloride Following the procedure described in Example 36 and using THF in place of CH$_2$Cl$_2$ as the solvent, 3-amino-2-carbomethoxythieno[3,2-c]pyridine (0.51 g, 2.4 mmol), prepared by the procedure described in *J. Heterocyclic Chem.*, 24:85 (1987), Et$_3$N (0.74 mL, 5.3 mmol), phosgene (1.3 mL 1.93M solution in toluene, 2.4 mmol), and (3aR,9bR)-2-aminoethyl-6-methoxy-2,3,3a,4,5,9b-[1H]-hexahydrobenz[e]isoindole (0.50 g, 2.0 mmol) provided 0.68 g (75 %) of the desired product which was converted to its HCl salt. m.p. 261°–262° C. $^1$H NMR (300 MHz, CDCl$_3$) of the free base δ 1.48–1.63 (m, 1H), 1.70–1.83 (m, 1H), 2.44–2.76 (m, 5H), 2.93–3.05 (m, 1H), 3.09–3.21 (m, 1H), 3.41–3.55 (m, 1H), 3.59–3.71 (m, 2H), 3.79 (s, 3H), 4.29–4.45 (m, 2H), 6.62 (d, 1H), 6.70 (d, 1H), 7.01 (t, 1H), 7.76 (d, 1H), 8.62 (d, 1H), 9.45 (s, 1H). MS (DCI/NH$_3$) m/e 449 (M+H)$^+$. Anal calcd for C$_{24}$H$_{24}$N$_4$O$_3$S . 2 HCl: C, 55.28; H, 5.03; N, 10.74. Found: C, 55.36; H, 5.04; N, 10.69.

EXAMPLE 39

3-[2-(cis-(3aR,9bR)-6-Methoxy-2,3,3a,4,5,9b-hexahydro-[1H]-benz[e]isoindol-1-yl)ethyl]-pyrazino[2',3':4,5]thieno[3,2-d]pyrimidine-2,4(1H,3H)-dione Ethyl 3-aminothieno[2,3-b]pyrazine-2-carboxylate (1.56 g, 6.99 mmol) prepared by the method of Schneller and Clough, J. Het. Chem., 12:513 (1975), was treated with 2.07 g (6.99 mmol) triphosgene in 100 ml refluxing 1:1 toluene:THF mixture for 13 hours. The solvent was removed in vacuo and the resulting solid isocyanate treated With 1.7.1 g (6.94 mmol) of the compound resulting from Example 9D and 1.48 g (14.58 mmol) triethylamine in 100 ml refluxing 1:1 toluene:THF mixture for 3 hours. The reaction mixture was concentrated to a yellow solid and purified by column chromatography on silica gel eluting first with18:1:1 ethyl acetate:formic acid:water then 9: 1:1 ethyl acetate:formic acid:water to yeild 2.51 g (73%) of the title compound as the formic acid salt. This was converted to the HCl salt by treatment with an excess of HCl in methanol to give a tan solid, mp 293°–295° C. $^1$H NMR (300 MHz, DMSO-d$_6$) δ 1.62 (m, 1H), 1.80 (m, 1H), 2.30–2.87 (m, 3H), 3.02 (m, 1H), 3.30–3.90 (m, 4H), 3.78 (s, 3H), 4.02 (m, 1H), 4.14 (m, 1H), 4.30 (m, 2H), 6.74 (d, 1H), 6.85 (d, 1H), 7.17 (t, 1H), 8.91 (d, 1H), 8.99 (d, 1H), 13.01 (s, 1H). MS (DCI/NH$_3$) m/e 450 (M+H)$^+$. Analysis calc'd. for C$_{23}$H$_{25}$N$_5$O$_3$S-2HCl: C, 52.88; H, 4.82; N, 13.40; Found: C, 52.75; H, 4.99; N,13.27.

EXAMPLE 40

3-[2-(cis-(3aR,9bR)-6-Methoxy-2,3,3a,4,5,9b-hexahydro-[1H]-benz[e]isoindol-1-yl)ethyl]-thieno[2,3-d:4,5]dipyrimidine-2,4(1H,3H)-dione

EXAMPLE 40A

Ethyl 3-aminothieno[2,3-d]pyrimidine-2-carboxylate

A 75 ml dimethylformamide solution of 2-chloro-3-cyanopyrimidine (5.60 g, 40.1 mmol), prepared by the method of Bredcrick, et al., Chem. Ber., 98:3883 (1965), was treated sequentially with 5.30 g (44.2 mmol) ethyl thioglycolate and 3.00 g (44.2 mmol) sodium ethoxide at room temperature. After 4 hours, the reaction mixture was diluted with water and chloroform and the layers separated. The aqueous layer was extracted several times with chloroform and the combined organic layers washed with water, brine and dried over sodium sulfate. Concentration gave a redbrown oil that was purified by column chromatography on silica gel eluting first with 2:1 hexanes:ethyl acetate then 1:1 hexanes:ethyl acetate to give 4.26 g (48%) of the title compound as a yellow solid, mp 138°–140° C. $^1$H NMR (300 MHz, CDCl$_3$) δ 1.42 (t, 3H), 4.39 (q, 2H), 6.08 (br s, 2H), 9.05 (s, 1H), 9.17 (s, 1H). MS (DCI/NH$_3$) m/e 224 (M+H)$^+$, 241 (M+NH$_4$)$^+$.

EXAMPLE 40B

3-[2-(cis--(3aR,9bR)-6-Methoxy-2,3,3a,4,5,9b-hexahydro-[1H]-benz[e]isoindol-1-yl)ethyl]-thieno[2,3-d:4,5]dipyrimidine-2,4(1H,3H)-dione The product resulting from Example 40A (0.400 g, 1.79 mmol) was treated with 0.532 g (1.79 mmol) triphosgene according to the procedure described in Example 39. The resulting isocyanate was then treated with the compound resulting from Example 9D (0.420 g, 1.70 mmol) and 0.543 g (5.37 mmol) triethylamine according to the procedure described in Example 40 to yield 0.360 g (43%) of the title compound as its formic acid salt. This was convened to the HCl salt by treatment with an excess of methanolic HCl, mp 243°–246° C. $^1$H NMR (300 MHz, DMSO-d$_6$) δ 1.45 (m, 1H), 1.63 (m, 1H), 2.10–2.34 (m, 2H), 2.36–2.78 (m, 5H), 3.12–3.38 (m, 3H), 3.74 (s, 3H), 4.03 (t, 2H), 6.73 (d, 1H), 7.08 (t, 1H), 9.24 (s, 9.52 (s, 1H). MS (DCI/NH$_3$) m/e 450 (M+H)$^+$. Analysis calc'd. for C$_{23}$H$_{23}$N$_5$O$_3$S-2HCl-H$_2$O: C, 51.11; H, 5.04; N, 12.96; Found: C, 50.82; H, 4.70; N 12.75.

EXAMPLE 41

3-[2-(Cis-6-Methoxy-2,3,3a,4,5,9b-hexahydro-[1H]-benz[e]isoindol-1-yl)ethyl]-thieno[3,2-d:4,5]dipyrimidine-2,4(1H,3H)-dione

EXAMPLE 41A

Ethyl 3-aminothieno[3,2-d]pyrimidine-2-carboxylate

5-Bromo-4-cyanopyrimidine (2.10 g, 11.4 mmol), prepared by the method of Yamanaka, et al., Chem. Pharm. Bull., 35:3119 (1987), was treated with 1.38 g (11.5 mmol) ethyl thioglycolate and 1.21 g (11.4 g) sodium carbonate in 36 ml of refluxing ethanol. After 3 hours, the reaction mixture was cooled to room temperature, quenched with water and concentrated. The residue was purified by column chromatography on silica gel eluting first with 4:1 then 1:1 hexanes: ethyl acetate to give 1.10 g (43%) of the title compound, mp 139°–141° C. $^1$H NMR (300 MHz, CDCl$_3$) δ 1.42 (t, 3H), 4.41 (q, 2H), 6.17 (br s, 2H), 9.19 (s, 1H), 9.20 (s, 1H). MS (DCI/NH$_3$) m/e 224 (M+H)$^+$, 241 (M+NH$_4$)$^+$.

EXAMPLE 41B

3-[2-(cis-6-Methoxy-2,3,3a,4,5,9b-hexahydro-[1H]-benz[e]isoindol-1-yl)ethyl]-thieno1 3,2-d:4,5]dipyrimidinc-2,4(1H3H)-dione The product resulting from Example 41A (0.400 g, 1.79 mmol) was treated with 0.584 g (1.97 mmol) triphosgene according to the procedure described in Example 39. The resulting isocyanate was further treated with the compound resulting from Example 9D (0.384 g, 1.56 mmol) and 0.332 g (3.28 mmol) triethylamine according to the procedure described in Example 39 to yield 0.399 g (52%) of the title compound as its formic acid salt. This was converted to its HCl salt by treatment with an excess of methanolic HCl, mp 230°–235° C. $^1$H NMR (300 MHz, DMSO-d$_6$) δ 1.64 (m, 1H), 1.80 (m, 1H), 2.25–2.90 (m, 3H), 3.02 (m, 1H), 3.26–3.60 (m, 3H), 3.61–4.19 (m, 3H), 3.77 (s, 3H), 4.30 (m, 2H), 6.74 (d, 1H), 6.84 (d, 1H), 7.18 (t, 1H), 9.40 (s, 1H), 9.78 (s, 1H), 12.93 (s, 1H). MS (FAB/high resolution) calc'd m/e for (M+H)$^+$ C$_{23}$H$_{24}$N$_5$O$_3$S, 450.1600; obs'd m/e, 450.1599. Analysis calc'd. for C23H23N5O3S-3HCl-1H$_2$O: C, 47.88; H, 4.89; N, 12.14; Found: C, 47.63; H, 4.38; N 11.72.

EXAMPLE 42

3-2-((3aR,9bR)-cis-6-Methoxy-2,3,3a,4,5,9b-hexahydro-[1H]-benz[e]isoindol-1-yl)ethyl]-[1]-7-cyano-benzothien[3,2-d]pyrimidine-2,4(1H,3H)-dione hydrochloride

EXAMPLE 42A

3-Amino-2-carbomethoxy-6-cyano-benzthiophene

Nitroterephthalonitrile (5.0 g, 28.9 mmol), prepared by the method of Gorvin, U.S. Pat. No. 4,250,182, was treated with 1 equivalent methyl thioglycolate and 1 equivalent Na$_2$CO$_3$ in methanol by the prcx:edure described in Example 41A to yield the title compound (5.50 g, 82%). $^1$H NMR (300 MHz, DMSO) δ 8.50 (s, 1H), 8.32 (d, 1H), 7.80 (dd, 1H), 7.29 (br s, 2H), 3.81 (s, 3H). MS (DCI/NH$_3$) m/e 250 (M+NH$_4$)$^+$.

EXAMPLE 42B

3-[2-((3aR,9bR)-cis-6-Methoxy-2,3,3a,4,5,9b-hexahydro-[1H]-benz[e]isoindol-1-yl)ethyl]-[1]-7-cyano-benzothieno[3,2-d]pyrimidine-2,4(1H,3H)-dione hydrochloride The resulting product from Example 42A (0.465 g, 2.0 mmol) was dissolved in THF (40 mL), triphosgene was added (0.198 g, 0.667 mmol), the mixture was refluxed for 4 hours, and the solution was cooled and evaporated. The resulting isocyanate (0.51 g, 2.0 mmol) was dissolved in THF (40 mL) and the compound resulting from Example 9D (0.39 g, 1.6 mmol) was added and the mixture refluxed for 24 hours. The reaction was evaporated, and the crude product was chromatographed on SiO$_2$ using 18:1:1 EtOAc:HCOOH:water, converted to the HCl salt, and recrystallized from EtOH/ether to yield the title compound (0.28 g, 34%). $^1$H NMR (300 MHz, DMSO) δ 12.87 (d, 1H), 10.82 (s, 1H), 8.78 (s, 1H), 8.56 (d, 1H), 7.97 (d, 1H), 7.17 (t, 1H), 6.71–6.86 (m, 2H), 4.29 (m, 2H), 4.15 (m, 1H), 4.01 (m, 1H), 3.78 (s, 3H), 3.51 (m, 2H), 3.02 (m, 1H), 2.58–2.82 (m, 3H), 1.79 (m, 2H), 1.61 (m, 2H). MS (DCI/NH$_3$) m/e 473 (M+H)$^+$. Anal calcd for C$_{26}$H$_{24}$N$_4$O$_3$S.2.25HCl: C, 56.31; H, 4.77; N, 10.10. Found: C, 56.26; H, 4.38; N, 9.98.

EXAMPLE 43

3-[2-((3aR,9bR)-cis-6-Methoxy-2,3,3a,4,5,9b-hexahydro-[1H]-benz[e]isoindol-1-yl)ethyl]-[1]-8-cyano-benzothieno[3,2-d]pyrimidine-2,4(1H,3H):dione hydrochloride

EXAMPLE 43A

3-Amino-2-carbomethoxy-5-cyano-benzthiophene

4-Chloroisophthalonitrile (5.69 g, 35 mmol), prepared by the method of Markley et al, J. Med. Chem., 29: 427 (1986), was treated with 1 equivalent methyl thioglycolate and 1 equivalent Na$_2$CO$_3$ in methanol by the procedure described in Example 41A to yield the title compound (3.00 g, 37%). m.p. 248° C. $^1$H NMR (300 MHz, DMSO) δ 8.71 (s, 1H), 8.09 (d, 1H), 7.86 (dd, 1H), 7.30 (br s, 2H), 3.81 (s, 3H). MS (DCI/NH$_3$) m/e 250 (M+NH4)$^+$.

EXAMPLE 43B

3-[2-((3aR,9bR)-cis-6-Methoxy-2,3,3a,4,5,9b-hexahydro-[1H]-benz[e]isoindol-1-yl)ethyl]-[1]-8-cyano-benzothieno[3,2-d]pyrimidine-2,4(1H,3H)-dione hydrochloride The product from Example 43A was treated with 0.33 equivalent triphosgene by the procedure described in Example 42B. The restating isocyanate (0.51 g, 2.0 mmol) and the compound resulting from Example 9D (0.39 g, 1.6 mmol) were treated by the procedure dscribed in Example 42B to yield the title compound (0.68 g, 83%). $^1$H NMR (300 MHz, DMSO) δ 12.82 (d, 1H), 10.69 (s, 1H), 8.90 (d, 1H), 8.39 (d, 1H), 8.02 (d, 1H), 7.17 (t, 1H), 6.71–6.86 (m, 2H), 4.29 (m, 2H), 4.14 (m, 1H), 4.01 (m, 1H), 3.78 (s, 3H), 3.52 (m, 2H), 3.02 (m, 1H), 2.59–2.83 (m, 3H), 1.79 (m, 2H), 1.61 (m, 2H). MS (DCI/NH$_3$) m/e 473 (M+H)$^+$. Anal calcd for C$_{26}$H$_{24}$N$_4$O$_3$S.2.1HCl: C, 56.87; H, 4.79; N, 10.20. Found: C, 56.96; H, 4.58; N, 10.06.

EXAMPLE 44

3-[2-((3aR,9bR)-cis-6-Methoxy-2,3,3a,4,5,9b-hexahydro-[1H]-benz[e]isoindol-1-yl) ethyl]-[1]-8-carbomethoxy-benzothieno[3, 2-d]pyrimidine-2,4(1H,3H)-dione hydrochloride

EXAMPLE 44A

3-Cyano-4-chloro-benzoic acid

3-Amino-4-chlorobenzoic acid (18.72 g, 109.1 mmol), commercially available, was added to a mixture of water (200 mL) and 37% HCl (35 mL), and the resulting slurry was cooled to 5° C. A solution of $NaNO_2$ (8.65 g, 125 mmol) in water (70 mL) was added dropwise, and the solution stirred at 5° C for 30 min. The solution was then added to a slurry consisting of water (400 mL), CuCN (9.85 g, 109 mmol),and KCN(12.06g, 185 mmol), while maintaining the temperature at5°–10° C. The mixture was stirred at 10° C. for another 30 min, and then heated to 80° C. for 1 hour. The reaction was cooled, and the pH adjusted to ~1 by addition of concentrated HCl. The solution was extracted with 5× $CHCl_3$, and the combined extracts were rinsed with 1M HCl and brine, and dried over $MgSO_4$. The solvent was removed in vacuo, and the crude product was recrystallized from $CHCl_3$/EtOAc to yield 15.9 g (80%) of the title compound. m.p. 180° C. $^1$H NMR (300 MHz, $CDCl_3$) δ 10.55 (br s, 1H), 8.42 (d, 1H), 8.26 (dd, 1H), 7.68 (d, 1H). MS (DCI/$NH_3$) m/e 213 $(M+NH_4)^+$.

EXAMPLE 44B

Methyl-3-Cyano-4-chloro-benzoate

The product from Example 44A (4.83 g, 26.6 mmol) was dissolved in MeOAc (75 mL) and MeOH (75 mL) and stirred at room temperature, and a 2.0M solution of trimethylsilyldiazomethane ($TMSCHN_2$) in hexanes (25 mL) was added slowly. The reaction was stirred an additional 10 min, and condensed in vacuo. The residue was recrystallized from hexane/EtOAc to yield 3.19 g (61%) of the title compound. m.p. 193° C. $^1$H NMR (300 MHz, $CDCl_3$) 6 8.34 (d, 1H), 8.19 (dd, H), 7.52 (d, 1H), 3.97 (s, 3H). MS (DCI/$NH_3$) m/e 199 $(M+NH_4)^+$.

EXAMPLE 44C

3-Amino-2,5-carbomethoxy-benz[b]thiophene

The product from Example 44B (3.19 g, 16.3 mmol), was treated with 1 equivalent methyl thioglycolate and 1 equivalent $Na_2CO_3$ in methanol by the procedure described in Example 41A to yield the title compound (2.78 g, 64%). m.p. 93° C. $^1$H NMR (300 MHz, DMSO) δ 8.88 (d, 1H), 8.03 (dd, 1H), 7.97 (d, 1H), 7.39 (br s, 2H), 3.91 (s, 3H), 3.80 (s, 3H). MS (DCI/$NH_3$) m/e 283 $(M+NH4)^+$.

EXAMPLE 44D

3-[2-((3aR,9bR)-cis-6-Methoxy-2,3,3a,4,5,9b-hexahydro-[1H]-benz[e]isoindol-1yl)ethyl]-[1]-8-carbomethoxy-benzothieno[3,2-d]pyrimidine-2,4(1H,3H)-dione hydrochloride The product from Example 44C was treated with 0.33 equivalents triphosgene by the procedure described in Example 42B. The resulting isocyanate (0.58 g, 2.0 mmol) and the compound resulting from Example 9D (0.30 g, 1.2 mmol) were treated by the procedure dscribed in Example 42B to yield the title compound (0.44 g, 68%). m.p.>300° C. $^1$H NMR (300 MHz, DMSO) δ 12.83 (d, 1H), 10.50 (s, 1H), 9.19 (d, 1H), 8.28 (d, 1H), 8.14 (d, 1H), 7.17 (t, 1H), 6.72–6.86 (m, 2H), 4.29 (m, 2H), 4.15 (m, 1H), 4.02 (m, 1H), 3.78 (s, 3H), 3.52 (m, 2H), 3.02 (m, 1H), 2.58–284 (m, 3), 1.80 (m, 2H), 1.61 (m, 2H). MS (DCI/$NH_3$) m/e 506 $(M+H)^+$. Anal calcd for $C_{27}H_{27}N_3O_5S$. 1.75HCl: C, 53.53; H, 4.95; N, 6.94. Found: C, 53.54; H, 4.56; N, 6.75.

EXAMPLE 45

3-[2-((3aR,9bR)-cis-6-Methoxy-2,3,3a,4,5,9b-hexahydro-[1H]-benz[e]isoindol-1-yl)ethyl]-[1]-8-N,N-dimethylcarboxamido-benzothieno[3,2-d]pyrimidine-2,4(1H,3H)-dione hydrochloride

EXAMPLE 45A

3-Cyano-4-chloro-N,N-dimethylbenzamide

The product from Example 44A (5.55 g, 30.5 mol) was dissolved in toluene (100 mL), oxalyl chloride (2.93 mL, 33.6 mmol) and pyridine (0.1 mL) were added, and the solution was refluxed until HCl evolution ceased (6 hours). The reaction was cooled and most of the solvent removed in vacuo. The resulting solution was poured into a stirred mixture of 40% aqueous dimethylamine (150 mL) and EtOAc (150 mL), and the reaction stirred for 10 min. The layers were separated, the aqueous layer was extracted with 2× EtOAc, and the combined organic layers were rinsed with 2× 1M HCl, and brine, and dried over $MgSO_4$. The solution was condensed, and the residue was recrystallized from EtOAc to yield 4.91 g (77%) of the title compound. m.p. 193° C. $^1$H NMR (300 MHz, $CDCl_3$) δ 8.28 (d, 1H), 7.61 (dd, 1H), 7.58 (d, H), 3.12 (br s, 2H), 3.00 (br s, 3H). MS (DCI/$NH_3$) m/e 226 $(M+NH_4)^+$.

EXAMPLE 45B

3-Amino-2-carbomethoxy-5-N,N-dimethylcarboxamido-benz[b]thiophene

The product resulting from Example 45A (3.00 g, 14.4 mmol) was treated with 1 equivalent methyl thioglycolate and 1 equivalent $Na_2CO_3$ in methanol by the procedure described in Example 41A to yield the title compound (1.55 g, 39%). m.p. 218°–220° C. $^1$H NMR (300 MHz, DMSO) δ 8.28 (d, 1H), 7.90 (dd, 1H), 7.54 (d, 1H), 7.23 (br s, 2H), 3.80 (s, 3H), 3.02 (br s, 3H), 2.98 (br s, 3H). MS (DCI/$NH_3$) m/e 296 $(M+NH_4)^+$.

EXAMPLE 45C

3-[2-((3aR,9bR)-cis-6-Methoxy-2,3,3a,4,5,9b-hexahydro-[1H]-benz[e]isoindol-1-yl)ethyl]-[1]-8-N,N-dimethylcarboxamido-benzothieno[3,2-d]pyrimidine-2,4(1H,3H)-dione hydrochloride The product resulting from Example 45B was treated with 0.33 equivalents triphosgene by the procedure described in Example 42B. The resulting isocyanate (0.547 g, 2.0 mmol) and the compound resulting from Example 9D (0.35 g, 1.42 mmol) were treated by the procedure dscribed in Example 42B to yield the title compound (0.183 g, 23%). m.p. 216°–219° C. $^1$H NMR (300 MHz, DMSO) δ12.79 (d, 1H), 10.66 (s, 1H), 8.53 (d, $^1$H), 8.20 (d, $^1$H), 7.69 (d, $^1$H), 7.17 (t, 1H), 6.72–6.87 (m, 2H), 4.29 (m, 2H), 4.15 (m, 1H), 4.02

(m, 1H), 3.78 (s, 3H), 3.55 (m, 2H), 3.04 (s, 3H), 3.02 (m, 1H), 2.92 (s, 3H), 2.60–2.85 (m, 3H), 1.80 (m, 2H), 1.62 (m, 2H). MS (DCI/NH$_3$) m/e 519 (M+H)$^+$. Anal calcd for C$_{28}$H$_{30}$N$_4$O$_4$S.2.5HCl: C, 55.15; H, 5.37; N, 9.19. Found: C, 55.50; H, 5.30; N, 8.96.

EXAMPLE 46

3-[2-((3aR,9bR)-cis-6-Methoxy-2,3,3a.4,5,9b-hexahydro-[1H]-benz[e]isoindol-1-yl)ethyl]-[1]-8-carboxamido-benzothieno[3,2-d]pyrimidine-2,4(1H,3H)-dione hydrochloride

EXAMPLE 46A

3-Cyano-4-chloro-benzamide

The product from Example 44A (5.55 g, 30.5 mmol) was treated with oxalyl chloride (2.93 mL, 33.6 mmol) by the procedure described in Example 45A. The resulting acid chloride was poured into a stirred mixture of saturated NH$_4$OH solution (150 mL) and EtOAc (150 mL), and the reaction stirred for 10 min. The layers were separated, the aqueous layer was extracted with 2x EtOAc, and the combined organic layers were rinsed with 2x 1M HCl, and brine, and dried over MgSO$_4$. The solution was condensed, and the residue was recrystallized from EtOAc to yield 3.35 g (61%) of the title compound. m.p. 193° C. $^1$H NMR (300 MHz, CDCl$_3$) δ8.12 (d, 1H), 7.98 (dd, 1H), 7.63 (d, 1H), 5.50–6.20 (br s, 2H). MS (DCI/NH$_3$) m/e 198 (M+NH$_4$)$^+$.

EXAMPLE 46B

3-Amino-2-carbomethoxy-5-carboxamido-benz[b]thiophene

The product from Example 46A (3.30 g, 18.3 mmol) was treated with 1 equivalent methyl thioglycolate and 1 equivalent Na$_2$CO$_3$ in methanol by the s procedure described in Example 41A to yield the title compound (1.08 g, 30%). m.p. 248° C. $^1$H NMR (300 MHz, DMSO) δ9.31 (d, 1H), 7.98 (dd, 1H), 7.96 (br s, 1H), 7.91 (d, 1H), 7.48 (br s, 1H), 7.21 (br s, 2H), 3.80 (s, 3H). MS (DCI/NH$_3$) m/e 268 (M+NH$_4$)$^+$.

EXAMPLE 46C

3-[2-((3aR,9bR)-cis-6-Methoxy-2,3,3a,4,5,9b-hexahydro-[1H]-benz[e]isoindol-1yl)ethyl]-[1 ]-8-carboxamido-benzothieno[3,2-d]pyrimidine-2,4(1H,3H)-dione hydrochloride The product from Example 46B was treated with 0.33 equivalents triphosgene by the procedure described in Example 42B. The resulting isocyanate (0.276 g, 1.0 s mmol) and the compound resulting from Example 9D (0.246 g, 1.0 mmol) were refluxed in THF (40 mL) for 24 hours. The reaction mixture was condensed in vacuo, taken up in EtOAc (50 mL), stirred for 1 hour, and filtered to give the free base. The compound was converted into the HCl salt with MeOH/HCl, and recrystallized from EtOH/ether to give the title compound (0.117 g, 22%). m.p. >300° C. $^1$H NMR (300 MHz, DMSO) δ12.72 (d, 1H), 11.20 (s, 1H), 9.08 (d, 1H), 8.19 (d, 1H), 8.10 (s, 1H), 8.08 (d, 1H), 7.56 (s, 1H), 7.17(t, 1H), 6.72–6.87 (m, 2H), 4.29 (m, 2H), 4.14 (m, 1H), 4.01 (m, 1H), 3.78 (s, 3H), 3.51 (m, 2H), 3.01 (m, 1H), 2.58–2.85 (m, 3H), 1.79 (m, 2H), 1.62 (m, 2H). MS (DCI/NH$_3$) m/e 491 (M+H)$^+$. Anal calcd for C$_{26}$H$_{26}$N$_4$O$_4$S.HCl.0.75H$_2$O: C, 57.77; H, 5.31; N, 10.36. Found: C, 57.85; H, 5.37; N, 10.17.

EXAMPLE 47

3-[2-((3aR,9bR)-cis-6-Methoxy-2,3,3a,4,5,9b-hexahydro-[1H]-benz[e]isoindol-1- -yl)ethyl ]-[1]-7-nitro-benzothieno[3,2-d]pyrimidine-2,4(1H,3H)-dione hydrochloride

EXAMPLE 47A 2,4-Dinitro-benzamide 2,4-Dinitrobenzoic acid (8.17 g, 38.5 mmol) was treated with oxalyl chloride (3.90 mL, 44.7 mmol). The resulting acid chloride was treated with saturated NH$_4$OH solution (200 mL) to yield the title compound (7.25 g, 89%). m.p. 202°–204° C. $^1$H NMR (300 MHz, DMSO) δ8.75 (d, 1H), 8.58 (dd, 1H), 8.48 (br s, 1H), 7.99 (br s, 1H), 7.91 (d, 1H), 5.50–6.20 (br s, 2H). MS (DCI/NH$_3$) m/e 229 (M+NH$_4$)$^+$.

EXAMPLE 47B 2,4-Dinitro-benzonitrile

The product from Example 47A (7.23 g, 34.2 mmol) in POCl$_3$ (100 mL) was heated to 95° C. for 2 hours, and the solution was condensed in vacuo. The residue was carefully taken up in EtOAc and pH 7 buffer was carefully added. The layers were separated, the aqueous layer was extracted with 2x EtOAc, and the combined organic layers were washed with brine and dried over MgSO$_4$. The solution was condensed in vacuo to yield the title compound (6.12 g, 93%). m.p. 87°–89° C. $^1$H NMR (300 MHz, CDCl$_3$) δ9.17 (d, 1H), 8.69 (dd, 1H), 8.21 (d, 1H).

EXAMPLE 47C

3-Amino-2-carbomethoxy-6-nitro-benzthiophene

The product from Example 47B (3.73 g, 19.3 mmol) was treated with 1 equivalent ethyl thioglycolate and 1 equivalent K$_2$CO$_3$ in ethanol by the procedure described in Example 41A to yield the title compound (2.35 g, 46%). m.p. 169°–170° C. $^1$H NMR (300 MHz, DMSO) δ8.90 (d, 1H), 8.37 (d, 1H), 8.20 (dd, 1H), 7.29 (br s, 2H), 4.31 (q, 2H), 1.31 (t, 3H). MS (DCI/NH$_3$) m/e 284 (M+NH$_4$)$^+$.

EXAMPLE 47D

3-[2-((3aR,9bR)-cis-6-Methoxy-2,3,3a.4,5,9b-hexahydro-[1H]-benz[e]isoindol-1-yl)ethyl]-[1]-7-nitro-benzothieno[3,2-d]pyrimidine-2,4(1H,3H)-dione hydrochloride The product from Example 47C was treated with 0.33 equivalents triphosgene by the procedure described in Example 42B. The resulting isocyanate (0.555 g, 1.9 mmol) and the compound resulting from Example 9D (0.418 g, 1.7 mmol) were treated by the procedure described in Example 42B to yield the title compound (0.525 g, 58%). m.p. 276°–278° C. $^1$H NMR (300 MHz, DMSO) δ12.79 (d, 1H), 10.96 (s, 1H), 9.21 (s, 1H), 8.62 (dd, 1H), 8.36 (m, 1H), 7.17 (t, $^1$H), 6.71–6.86 (m, 2H), 4.29 (m, 2H), 4.15 (m, 1H), 4.01 (m, 1H), 3.78 (s, 3H), 3.51 (m, 2H), 3.02 (m, 1H), 2.60–2.85 (m, 3H), 1.79 (m, 2H), 1.62 (m, 2H). MS (DCI/NH$_3$) m/e 493 (M+H)$^+$. Anal calcd for C$_{25}$H$_{24}$N$_4$O$_5$S.HCl: C, 56.76; H, 4.76; N, 10.59. Found: C, 56.47; H, 4.84; N, 10.35.

EXAMPLE 48

3-[2-((3aR,9bR)-cis-6-Methoxy-2,3,3a,4,5,9b-hexahydro-[1H]-benz[e]isoindol-1-yl)ethyl]-[1]-8-nitro-benzothieno[3,2-d]pyrimidine-2,4(1H,3H)-dione hydrochloride

EXAMPLE 48A

3-Amino-2-carbomethoxy-5-nitro-benzthiophene

2-Chloro-5-nitrobenzonitrile (25.0 g, 136.9 mmol), commercially available, was treated with 1 equivalent ethyl thioglycolate and 1 equivalent K$_2$CO$_3$ in ethanol by the procedure described in Example 41A to yield the title compound (19.68 g, 54%). m.p. 208°–210° C. $^1$H NMR(300MHz, DMSO) δ9.23 (d, 1H), 8.29 (d, 1H), 8.11 (dd, 1H), 7.45 (br s, 2H), 4.29 (q, 2H), 1.31 (t, 3H). MS (DCI/NH$_3$) m/e 284 (M+NH$_4$)$^+$.

EXAMPLE 48B

3-[2-((3aR,9bR)-cis-6-Methoxy-2,3,3a,4,5,9b-hexahydro-[1H]-benz[e]isoindol-1-yl)ethyl]-[1]-8-nitro-benzothieno[3,2-d]pyrimidine-2,4(1H,3H)-dione hydrochloride The product from Example 48A was treated with 0.33 equivalent triphosgene by the procedure described in Example 42B. The resulting isocyanate (0.555 g, 1.9 mmol) and the compound resulting from Example 9D (0.418 g, 1.7 mmol) were treated by the procedure dscribed in Example 42B to yield the title compound (0.329 g, 37%). m.p. 298°–305° C. $^1$H NMR (300 MHz, DMSO) δ12.93 (d, 1H), 10.37 (s, 1H), 9.48 (d, 1H), 8.42 (s, 2H), 7.17 (t, 1H), 6.72–6.86 (m, 2H), 4.29 (m, 2H), 4.15 (m, 1H), 4.02 (m, 1H), 3.78 (s, 3H), 3.52 (m, 2H), 3.02 (m, 1H), 2.59–2.86 (m, 3H), 1.79 (m, 2H), 1.61 (m, 2H). MS (DCI/NH$_3$) m/e 493 (M+H)$^+$. Anal calcd for C$_{25}$H$_{24}$N$_4$O$_5$S.HCl: C, 56.76; H, 4.76; N, 10.59. Found: C, 56.51; H, 4.70; N, 10.33.

EXAMPLE 49

3-[2-((3aR,9bR)-cis-6-Methoxy-2,3,3a,4,5,9b-hexahydro-[1H]-benz[e]isoindol-1-yl)ethyl]-[1]-8-acetamido-benzothieno[3,2-d]pyrimidine-2,4(1H,3H)-dione hydrochloride

EXAMPLE 49A 3,5-Diamino-2-carbomethoxy-benzthiophene

The product from Example 48A (10.4 g, 39.1 mmol) was suspended in isopropanol (200 mL) and 37% HCl (100 mL). SnCl$_2$.2H$_2$O (32.6 g, 144 6 mmol) was added, the reaction was refluxed for 2 hours, and then cooled, and concentrated. The residue was taken up in 1M NaOH (200 mL), and extracted with 4x CH$_2$Cl$_2$. The combined extracts were washed with water, dried over K$_2$CO$_3$, and condensed. The crude product was recrystallized from EtOAc/hexane to yield 5.60 g (61%) of the title compound. m.p. 128°–130° C. $^1$H NMR (300 MHz, DMSO) δ7.43 (d, 1H), 7.11 (d, 1H), 6.90 (br s, 2H), 6.88 (dd, 1H), 5.19 (br s, 2H), 4.23 (q, 2H), 1.28 (t, 3H). MS (DCI/NH$_3$) m/e 236 M$^+$.

EXAMPLE 49B

3-Amino-2-carbomethoxy-5-acetamido-benzthiophene

The product from Example 49A (5.30 g, 22.4 mmol) was dissolved in THF (40 mL) and toluene (120 mL) and diisopropylethylamine (4.69 mL, 26.9 mmol) and acetyl chloride (1.59 mL, 22.4 mmol) were sequentially added. The reaction was stirred for 20 min, poured into NaHCO$_3$ solution, and extracted with 4x CH$_2$Cl$_2$. The combined extracts were washed with NaHCO$_3$ solution, dried over MgSO$_4$, and condensed. The crude product was chromatographed on SiO$_2$ using EtOAc as eluent to yield 3.22 g (52%) of the title compound. m.p. 248° C. $^1$H NMR (300 MHz, DMSO) δ10.09 (br s, 1H), 8.34 (d, 1H), 7.73 (d, 1H), 7.50 (dd, 1H), 7.06 (br s, 2H), 4.25 (q, 2H), 2.08 (s, 3H), 1.28 (t, 3H). MS (DCI/NH$_3$) m/e 296 (M+NH$_4$)$^+$.

EXAMPLE 49C

3-[2-((3aR,9bR)-cis-6-Methoxy-2,3,3a,4,5,9b-hexahydro-[1H]-benz[e]isoindol-1-yl)ethyl ]-1-[1]-8-acetamido-benzothieno[3,2-d]pyrimidine-2,4(1H,3H)-dione hydrochloride The product resulting from Example 49B was treated with 0.33 equivalent triphosgene by the procedure described in Example 42B. The resulting isocyanate (0.578 g, 1.9 mmol) and the compound resulting from Example 9D (0.418 g, 1.7 mmol) were treated by the procedure described in Example 42B to yield the free base of the title compound, which was chromatographed on SiO$_2$ using 20% MeOH/EtOAc as eluent, taken up in a mixture of EtOAc (.50 mL) and 96% formic acid (50 mL), condensed, and then taken up in toluene (50 mL), and condensed to yield the title compound (0.292 g, 3 1%). m.p. 193°–195° C. $^1$H NMR (300 MHz, DMSO) δ10.20 (s, 1H), 8.71 (s, 1H), 8.18 (s, 2.9H), 8.00 (d, 1H), 7.61 (d, 1H), 7.19 (t, 1H), 6.73 (dd, 2H), 4.05 (t, 2H), 3.73 (s, 3H), 3.24–3.42 (m, 3H), 2.69–2.81 (m, 2H), 2.31–2.65 (m, 2H), 2.49 (t, 1H), 2.10 (s, 3H), 1.65 (m, 2H), 1.48 (m, 2H). MS (DCI/NH$_3$) m/e 505 (M+H)$^+$. Anal calcd for C$_{27}$H$_{28}$N$_4$O$_4$S.1.9HCO$_2$H: C, 58.63; H, 5.41; N, 9.46. Found: C, 58.62; H, 5.48; N, 9.37.

EXAMPLE 50

3-[2-((3aR,9bR)-cis-6-Methoxy-2,3,3a,4,5,9b-hexahydro-[1H]-benz[e]isoindol-1-yl)ethyl]-[1]-8-N,N-dimethylamino-benzothieno[3,2-d]pyrimidine-2,4(1H,3H)-dione hydrochloride

EXAMPLE 50A

3-Amino-2-carbomethoxy-5-formamido-benzthiophene

A mixture of 96% formic acid (1.69 mL, 43.1 mmol) and acetic anhydride (2.54 mL, 26.9 mmol) was heated to 70° C. for 2 hours, cooled, and added to a solution of the product from Example 49A (5.00 g, 21.16 mmol) in THF (70 mL). The reaction was stirred at room temperature for 24 hours, and filtered. The solution was condensed in vacuo, taken up in EtOAc, and filtered. The combined filtrates yielded 4.15 g (74%) of the title compound. m.p. 202°–204° C. $^1$H NMR (300 MHz, DMSO) δ10.32 (br s, 1H), 8.35 (d, 1H), 8.33 (d, 1H), 7.78 (d, 1H), 7.59 (dd, 1H), 7.11 (br s, 2H), 4.26 (q, 2H), 1.29 (t, 3H). MS (DCI/NH$_3$) m/e 282 (M+NH$_4$)$^+$.

EXAMPLE 50B

3-Amino-2-carbomethoxy-5-(N-Methyl)-formamido-benzthiophene

The product from Example 50A (1.78 g, 6.73 mmol) was added to a suspension of KOH (831 mg, 14.8 mmol) in DMSO (40 mL). Iodomethane (0.461 mL, 7.41 mmol) was then added, and the reaction was stirred for 5min, and poured into water (200 mL). The solution was extracted with 3x CH$_2$Cl$_2$, and the extracts were washed with 2x water, dried over MgSO$_4$, and condensed. The residue was chromatographed on SiO$_2$ using 20% EtOAc/CH$_2$Cl$_2$ as eluent, to yield 1.05 g (56%) of the title compound. m.p. 173°–175° C. $^1$H NMR (300 MHz, DMSO) δ8.59 (s, 1H), 8.12 (d, 1H), 7.89 (d, 1H), 7.55 (br s, 1H), 7.13 (br s, 2H), 4.27 (q, 2H), 3.43 (s, 3H), 1.30 (t, 3H). MS (DCI/NH$_3$) m/e 296 (M+NH$_4$)$^+$.

EXAMPLE 50C

3-Amino-2-carbomethoxy-5-N,N-dimethylamino-benzthiophene

The product from Example 50B (1.91 g, 6.86 mmol) was dissolved in THF (50 mL) and cooled to 0° C., and 10M BH$_3$.DMS solution (1.72 mL, 17.2 mmol) was added. The reaction was warmed to room temperature, stirred for 6 hours, and quenched by the slow addition of MeOH (8 mL). The reaction was condensed in vacuo, taken up in THF (150 mL) and TMEDA (15 mL), and stirred for 12 hours. The solution was then added to $Na_2CO_3$ solution (250 mL), and extracted with 3x EtOAc, and the extracts were washed with water, and brine, dried over $K_2CO_3$, and condensed. The crude product was chromatographed on $SiO_2$ using 20% EtOAc/hexane as eluent, to yield 0.80 g (49%) of the title compound. $^1H$ NMR (300 MHz, DMSO) δ7.58 (d, 1H), 7.40 (d, 1H), 7.10 (dd, 1H), 7.06 (br s, 2H), 4.23 (q, 2H), 2.94 (s, 6H), 1.28 (t, 3H). MS ($DCI/NH_3$) m/e 265 $(M+H)^+$.

EXAMPLE 50D

3-[2-((3aR,9bR)-cis-6-Methoxy-2,3,3a,4,5,9b-hexahydro-[1H]-benz[e]isoindol-1-yl)ethyl]-[1]-8-N,N-dimethylamino-benzothieno[3,2-d]pyrimidine-2,4(1H,3H)-dione hydrochloride The product from Example 50C was treated with 0.33 equivalent triphosgene by the procedure described in Example 42B. The resulting isocyanate (0.464 g, 1.6 mmol) and the compound resulting from Example 9D (0.37 g, 1.5 mmol) were treated by the procedure described in Example 42B to yield the free base of the title s compound, which was chromatographed on $SiO_2$ using 20% MeOH/EtOAc as eluent. The free base was converted into the HCl salt with MeOH/HCl, and recrystallized from EtOH/ether to give the title compound (0.586 g, 69%). m.p. 240°–243° C. $^1H$ NMR (300 MHz, DMSO) δ12.57 (d, 1H), 10.92 (s, 1H), 7.95 (m, 2H), 7.38 (m, 1H), 7.17 (t, 1H), 6.72–6.87 (m, 2H), 4.50 (s, 1H), 4.29 (m, 2H), 4.15 (m, 1H), 4.02 (m, 1H), 3.78 (s, 3H), 3.51 (m, 2H), 3.02 (s, 6H), 3.01 (m, 1H), 2.60–2.85 (m, 3H), 1.79 (m, 2H), 1.61 (m, 2H). MS ($DCI/NH_3$) m/e 491 $(M+H)^+$. Anal calcd for $C_{27}H_{30}N_4O_3S.3.22HCl$: C, 53.34; H, 5.51; N, 9.21. Found: C, 53.35; H, 5.43; N, 9.09.

EXAMPLE 51

3-[2-((3aR,9bR)-cis-6-Methoxy-2,3,3a,4,5,9b-hexahydro-[1H]-benz[e]isoindol-1-yl)ethyl]-[1]-7-carboxamido-benzothieno[3,2-d]pyrimidine-2,4(1H,3H)-dione hydrochloride

EXAMPLE 51A

3-Amino-2-carbomethoxy 4-carboxamido-benzthiophene

The product from Example 42A (2.46 g, 10.6 mmol) and ground KOH (7.12 g, 127 mmol) were taken up in tert-butanol (80 mL) to form a slurry, which was refluxed for 24 hours. The mixture was cooled, poured into water, and the solution adjusted to pH 3 with 37% HCl. The resulting mixture was filtered, and the crude amido acid was dissolved in DMSO (125 mL) and MeOH (75 mL) and stirred at room temperature. A 2.0M solution of trimethylsilyldiazomethane ($TMSCHN_2$) in hexanes (8 mL) was added slowly. The reaction was stirred an additional 10 min, and condensed in vacuo. The crude product was chromatographed on $SiO_2$ using EtOAc as eluent, and the residue was recrystallized from MeOH/EtOAc to yield 0.90 g (34%) of the title compound. $^1H$ NMR (300 MHz, DMSO) δ8.32 (d, 1H), 8.21 (d, 1H), 8.11 (br s, 1H), 7.88 (dd, 1H), 7.52 (br s, 1H), 7.22 (br s, 2H), 3.81 (s, 3H). MS ($DCI/NH_3$) m/e 268 $(M+NH_4)^+$.

EXAMPLE 51B

3-[2-((3aR,9bR)-cis-6-Methoxy-2,3,3a,4,5,9b-hexahydro-[1H]-benz[e]isoindol-1-yl)ethyl]-[1]-7-carboxamido-benzothieno[3,2-d]pyrimidine-2,4(1H,3H)-dione hydrochloride The product from Example 51A was treated with 0.33 equivalent triphosgene by the procedure described in Example 42B. The resulting isocyanate (0.462 g, 1.67 mmol) and the compound resulting from Example 9D (0.369 g, 1.5 mmol) were S treated by the procedure described in Example 42B to yield the free base, which was taken up in 4.0M HCl in dioxane, and triturated with EtOH to give the title compound (0.191 g, 24%). m.p. >300° C. $^1H$ NMR (300 MHz, DMSO) δ12.88 (d, 1H), 10.48 (s, 1H), 8.60 (s, 1H), 8.46 (dd, 1H), 8.20 (s, 1H), 8.02 (dd, 1H), 7.62 (s, 1H), 7.17 (t, 1H), 6.72–6.87 (m, 2H), 4.29(m, 2H), 4.16 (m, 1H), 4.02 (m, 1H), 3.78 (s, 3H), 3.51 (m, 2H), 3.02 (m, 1H), 2.60–2.85 (m, 3H), 1.79 (m, 2H), 1.61 (m, 2H). MS ($DCI/NH_3$) m/e 491 $(M+H)^+$. Anal calcd for $C_{26}H_{26}N_4O_4S.2HCl.0.72H_2O$: C, 54.17; H, 5.15; N, 9.72. Found: C, 54.26; H, 5.39; N, 9.35.

EXAMPLE 52

3-[2-((3aR,9bR)-cis-6-Methoxy-2,3,3a,4,5,9b-hexahydro-[1H]-benz[e]isoindol-1-yl )ethyl 1-[1]-8-(N-methylcarboxamido)-benzothieno[3,2-d]pyrimidine-2,4(1H,3H)-dione hydrochloride

EXAMPLE 52A

3-Cyano-4-chloro-N-methylcarboxamide

The product from Example 44A (3.81 g, 21.0 mmol) was treated with oxalyl chloride (2.09 mL, 23.1 mmol). The resulting acid chloride was poured into a stirred mixture of methylamine solution (150 mL) and EtOAc (150 mL), and the reaction stirred for 10 min. The layers were separated, the aqueous layer was extracted with 2x EtOAc, and the combined organic layers were rinsed with 2x 1M HCl, and brine, and dried over $MgSO_4$. The solution was condensed, and the residue was recrystallized from EtOAc to yield 2.53 g (62%) of the title compound. m.p. 154°–156° C. $^1H$ NMR (300 MHz, $CDCl_3$) δ8.70 (br q, 1H), 8.35 (d, 1H), 8.23 (dd, 1H), 7.98 (d, 1H), 2.80 (d, 3H). MS ($DCI/NH_3$) m/e 212 $(M+NH_4)^+$.

EXAMPLE 52B

3-Amino-2-carbomethoxy-5-(N-methyl-carboxamido)-benz[b]thiophene

The product from Example 52A (2.52 g, 12.95 mmol) was treated with 1 equivalent methyl thioglycolate and 1 equivalent $Na_2CO_3$ in methanol by the procedure described in Example 41A to yield the title compound (1.91 g, 56%). m.p. 222° C. $^1H$ NMR (300 MHz, DMSO) δ8.66 (s, 1H), 8.46 (br q, 1H), 7.91 (s, 2H), 7.34 (br s, 2H), 3.80 (s, 3H), 2.82 (d, 3H). MS ($DCI/NH_3$) m/e 282 $(M+NH_4)^+$.

EXAMPLE 52C

3-[2-((3aR,9bR)-cis-6-Methoxy-2,3,3a,4,5,9b-hexahydro-[1H]-benz[e]isoindol-1-yl)ethyl]-[1]-8-(N-methylcarboxamido)-benzothieno[2-d]pyrimidine-2,4(1H,3H)-dione hydrochloride The product from Example 52B was treated with 0.33 equivalent triphosgene by the procedure described in Example 42B. The resulting isocyanate (0.522 g, 1.8 mmol) and the compound resulting from Example 9D (0.394 g, 1.6 mmol) were treated by the procedure described in Example 42B to yield the title compound (0.368 g, 43%). m.p. >300° C. $^1H$ NMR (300 MHz, DMSO) δ12.77 (d, 1H), 10.84 (s, 1H), 9.00 (d, 1H), 8.62 (d, 1H), 8.20 (dd, 1H), 8.04 (dd, 1H), 7.18 (t, 1H), 6.72–6.87 (m, 2H), 4.29 (m, 2H), 4.15 (m, 1H), 4.01 (m, 1H), 3.79 (s, 3H), 3.52 (m, 2H), 3.02 (m, 1H), 2.84 (d, 3H), 2.61–2.89 (m, 3H), 1.79 (m, 2H), 1.62 (m, 2H). MS ($DCI/NH_3$) m/e 505 $(M+H)^+$. Anal calcd for $C_{27}H_{28}N_4O_4S.1.9HCl$: C, 56.51; H, 5.25; N, 9.76. Found: C, 56.51; H, 5.40; N, 9.64.

EXAMPLE 53

7-[2-((3aR,9bR)cis-6-Methoxy-2,3,3a,4,5,9b-hexahydro, [1H]-benz[e]isoindol-1-yl)ethyl]-imidazo[4,5-g]quinazoline-6,8(1H,5H)-dione hydrochloride 5-Amino-6-carbomethoxy-benzimidazole (Keyser and Leonard, JOC, 41, (1976), pp 3529–3532) was treated with triphosgene as described in Example 9E. The resulting isocyanate (480 mg, 1.5 mmol) and the compound resulting from Example 9D (400 mg, 1.6 mmol) were refluxed in 30 mL of toluene for 16 h and concentrated. The residue was flash chromatographed on silica (8:1:1 EtOAc/water/formic acid) and then converted to the title compound by treatment with methanolic HCl.to yield the title compound, m.p. 301°–304° C., 32% yield. $^1$H NMR (300 MHz, D6-DMSO) d 1.52–1.68 (m, 1H), 1.70–1.85 (m, 1H), 2.30–2.57 (m, 1H), 2.60–2.84 (m, 3H), 2.95–3.10 (m, 1H), 3.33–3.60 (m, 3H), 3.75 (s, 3H), 3.96–4.08 (m, 1H), 4.09–4.19 (m, 1H), 4.26 (m, 2H), 6.73 (d, 1H), 6.83 (d, 1H), 7.17 (t, 1H), 7.50 (s, 1H), 8.30 (s, 1H), 9.15 (s, 1H), 10.56 (s, 1H), 11.18 (s, 1H). MS (DCI/NH$_3$) m/e 432 (M+H)+. Anal calcd for C24H25N5O3.2HCl.H2O: C, 55.18; H, 5.60; N, 13.41. Found: C, 54.91; H, 5.26; N, 13.28.

EXAMPLE 54

3-2-((3aR,9bR)-cis-6-Methoxy-2,3,3a,4,5,9b-hexahydro-[1H]-benz[e]isoindol-1-yl)ethyl]-[1]-9-cyano-benzothieno[3,2-d]pyrimidine-2,4(1H,3H)-dione hydrochloride

EXAMPLE 54A

3-Amino-2-carbomethoxy-4-cyano-benzthiophene 2,3-Didicyanonitrobenzene (2.6 g, 15 mmol) was treated with 1 eq of methyl thioglycolate and 1 eq sodium carbonate in methanol as described in Example 41A to give the title compound in 47% yield, mp 169°–170° C. $^1$H NMR (300 MHz, D6-DMSO d 3.83 (s, 3H), 6.66 (bs, 2H), 7.68 (t, J=8 Hz, 1H), 7.97 (d, J=8 Hz, 1H), 8.30 (d, J=8 Hz, 1H). MS (DCI/NH3) m/e 250 (M+NH4)+.

EXAMPLE 54B

3-[2-((3aR,9bR)-cis-6-Methoxy-2,3,3a,4,5,9b-hexahydro-[1H],benz[e]isoindol-1-yl)ethyl]-[1]-9-cyano-benzothieno[3,2-d]pyrimidine-2,4(1H,3H)-dione hydrochloride The product from Example 54A (350 mg, 1.5 mmol) was treated with s triphosgene as in Example 9E. The resulting isocyanate (380 mg, 1.5 mmol) and the compound resulting from Example 9D (370 mg, 1.6 mmol) were refluxed in 30 mL of THF for 16 h and concentrated. The residue was flash chromatographed on silica (18:1:1 EtOAc/water/formic acid) and then converted to the title compound with methanolic HCl. 360 mg, 47% yield, m.p. 306°–308° C. $^1$H NMR (300 MHz, D6-DMSO) d 1.52–1.68 (m, 1H), 1.70–1.85 (m, 1H), 2.33–2.58 (m, 1H), 2.62–2.92 (m, 3H), 2.95–3.08 (m, 1H), 3.44–3.60 (m, 3H), 3.77 (s, 3H), 3.94–4.17 (m, 2H), 4.19–4.35 (m, 2H), 6.73 (d, 1H), 6.84 (d, 1H), 7.17 (t, 1H), 7.82 (t, 1H), 8.18 (d, 1H), 8.55(d 1H). MS (DCI/NH3) m/e 473 (M+H)+. Anal calcd for C26H24N4O3S.HCl.0.25 H2O: C, 60.81; H, 5.01; N, 10.91. Found: C, 60.90; H, 4.85; N, 10.90.

EXAMPLE 55

3-[2-((3aR,9bR)-cis-6-Methoxy-2,3,3a,4,5,9b-hexahydro-[1H]-benz[e]isoindol-1-yl)ethyl]-[1]-6-cyano-benzothieno[3,2-d]pyrimidine-2,4(1H,3H)-dione hydrochloride

EXAMPLE 55A

3-Amino-2-carbomethoxy-7-cyano-benzthiophene 2-chloro-1,3-dicyanobenzene (972 mg, 6.0 mmol) was treated with 1 eq of methyl thioglycolate and 1 eq sodium carbonate in methanol as described in Example 41A to give the title compound in 65% yield. 1H NMR (300 MHz, D6-DMSO d 3.83 (s, 3H), 7.38 (bs, 2H), 7.62 (t, J=8 Hz, 1H), 8.10 (d, J=8 Hz, 1H), 8.50 (d, J=8 Hz, 1H). MS (DCI/NH3) m/e 250 (M+NH4)+.

EXAMPLE 55B

3-[2-((3aR,9bR)-cis-6-Methoxy-2,3,3a,4,5,9b-hexahydro-[1H]-benz[e]isoindol-1s -yl)ethyl]-[1]-6-cyano-benzothieno[3,2-d]pyrimidine-2,4(1H,3H)-dione hydrochloride The product from Example 55A (350 mg, 1.5 mmol) was treated with 0.33 eq triphosgene as in Example 9E. The resulting isocyanate (380 mg, 1.5 mmol) and the compound resulting from Example 9D (370 mg, 1.5 mmol) were refluxed in 30 mL of THF for 16 h and concentrated. The residue was flash chromatographed on silica (18:1:1 EtOAc/water/formic acid) and then converted to the title compound with methanolic HCl; 540 mg, 68% yield, m.p. 265°–269° C. $^1$H NMR (300 MHz, D6-DMSO) d 1.52–1.68 (m, 1H), 1.70–1.85 (m, 1H), 2.33–2.58 (m, 1H), 2.62–2.92 (m, 3H), 2.95–3.08 (m, 1H), 3.44–3.60 (m, 3H), 3.77 (s, 3H), 3.94–4.20 (m, 2H), 4.20–4.35 (m, 2H), 6.73 (d, 1H), 6.84 (d, 1H), 7.17 (t, 1H), 7.82 (t, 1H), 8.27 (d, 1H), 8.74(d 1H) 10.55 (bs, 1H), 12.95 (s, 1H). MS (DCI/NH$_3$) m/e 473 (M+H)+. Anal calcd for C26H24N4O3S.HCl.1.0 H2O: C, 59.25; H, 5.16; N, 10.63. Found: C, 59.49; H, 4.75; N, 10.54.

EXAMPLE 56

3-[2-((3aR,9bR)-cis-6-Methoxy-2,3,3a,4,5,9b-hexahydro-[1H]-benz[e]isoindol-1-yl)ethyl]-[1]-6-chloro-benzothieno[3,2.-d]pyrimidine-2,4(1H,3H)-dione hydrochloride

EXAMPLE 56A 2,3-Dichlorobenzamide

A soln of 2,3-dichlorobenzoic acid (10.0 g, 52.4 mmol) and oxalyl chloride (7.0 g, 55 mmol) in 100 mL of toluene was refluxed for 4 h, cooled and concentrated. The resulting acid chloride was added to a mix of EtOAc and 12N ammonium hydroxide and stirred vigorously. The layers were separated and the EtOAc layer was washed with 1M HCl, brine, dried (MgSO4) and concentrated to give 9.4 g, 95% yield of the benzamide. 1H NMR (300 MHz, CDCl3) d 6.06 (bs, 2H), 7.28 (t, J=8Hz, 1H), 7.54–7.62 (m, 2H). MS (DCI/NH3) m/e 207 (M+NH4)+.

EXAMPLE 56B 2,3-Dichlorobenzonitrile

The product from Example 56A (9.4 g, 50 mmol) in 150 mL POCl$_3$ was heated for 2 h at 95° C. The soln was cooled and concentrated. The residue was partitioned between EtOAc and 10% aq potassium carbonate. The layers were separated and the EtOAc layer was washed 2×50 mls with water, with brine, dried (MgSO4) and concentrated to give a 96% yield (8.2g, m.p. 60°–61° C.) of the benzonitrile. 1H NMR (300 MHz, CDCl$_3$ 7.34 (t, J=8 Hz, 1H), 7.62 (dd, J=8,1 Hz, 1H), 7.71 (dd, J=8,1 Hz, 1H).

EXAMPLE 56C

3-Amino-2-carbomethoxy-7-chloro-benzthiophene

The product from Example 56B (1.7 g, 10 mmol) was treated with 1 eq of methyl thioglycolate and 1 eq sodium carbonate in methanol as described in Example 41A to give after chromatography (4:1 hexane/EtOAc) the title compound in 12% yield. 1H NMR (300 MHz, CDCl3) d 3.81 (s, 3H), 5.90 (bs, 2H), 7.34 (t, J=8 Hz, 1H), 7.48 (dd, J=8.1 Hz, 1H), 7.56 (dd, J=8,1 Hz, 1H). MS (DCI/NH3) m/e 259 (M+NH4)+.

EXAMPLE 56D

3-[2-((3aR,9bR)-cis-6-Methoxy-2,3,3a,4,5,9b-hexahydro-[1H]-benz[e]isoindol-1-yl)ethyl]-[1]-6-chloro-benzothieno[3,2-d]pyrimidine-2,4(1H,3H)-dione hydrochloride The product from Example 56C (300 mg, 1.25 mmol) was treated with 0.33 eq triphosgene as in Example 9E. The resulting isocyanate (300 mg, 1.12mmol) and the compound resulting from Example 9D (270 mg, 1.1 mmol)) were refluxed in 30 mL of THF for 16 h and concentrated. The residue was flash chromatographed on silica (18:1:1 EtOAc/water/formic acid) and then converted to the title compound with methanolic HCl. 320 mg of a white solid, m.p.250°–253° C., 55% yield. 1H NMR (300 MHz, D6-DMSO) d 1.52–1.68 (m, 1H), 1.70–1.85 (m, 1H), 2.33–2.58 (m, 1H), 2.62–2.86 (m, 3H), 2.95–3.08 (m, 1H), 3.44–3.60 (m, 3H), 3.77 (s, 3H), 3.94–4.20 (m, 2H), 4.20–4.35 (m, 2H), 6.73 (d, 1H), 6.84 (d, 1H), 7.17 (t, 1H), 7.63 (t, 1H), 7.81 (d, 1H), 8.42 (d, 1H), 10.82 (s, 1H), 12.81 (s, 1H). MS (DCI/NH3) m/e 482 (M+H)+. Anal calcd for C25H24N3O3SCl.HCl.0.75 H2O: C, 56.42; H, 5.02; N, 7.90. Found: C, 56.20; H, 4.62; N, 7.94.

EXAMPLE 57

3-[2-((3aR,9bR)-cis-6-Methoxy-2,3,3a,4,5,9b-hexahydro-[1H]-benz[e]isoindol-1-yl)ethyl]-[1]-7-chloro-benzothieno[3,2-d]pyrimidine-2,4(1H,3H)-dione hydrochloride

EXAMPLE 57A

3-Amino-2-carbomethoxy-6-chloro-benzthiophene 2-nitro-4-chlorobenzonitrile (1.94 g, 10.6 mmol) was treated with 1 eq of ethyl thioglycolate and 1 eq potassium carbonate in EtOH as described in Example 41A to give after chromatography (4:1 hexane/EtOAc) the title compound in 31% yield. 1H NMR (300 MHz, CDCl3) d 1.38 (t, J=7 Hz, 3H), 4.36 (q, J=7 Hz, 2H), 5.85 (bs, 2H), 7.33 (dd, J=9,2 Hz, 1H), 7.54 (d, J=9 Hz; 1H), 7.1 (d, J=2 Hz, 1H). MS (DCI/NH3) m/e 256 (M+H)+.

EXAMPLE 57B

3-[2-((3aR,9bR)-cis-6-Methoxy-2,3,3a,4,5,9b-hexahydro-[1H]-benz[e]isoindol-1-yl)ethyl]-[1]-7-chloro-benzothieno[3,2-d]pyrimidine-2,4(1H,3H)-dione hydrochloride The product from Example 57A (300 mg, 1.18 mmol) was treated with 0.33 eq triphosgene as in Example 9E. The resulting isocyanate (300 mg, 1.12mmol) and the compound resulting from Example 9D (270 mg, 1.1 mmol)) were refluxed in 30 mL of THF for 16 h and concentrated. The residue was triturated with EtOAc and filtered to give the free base which upon treatment with methanolic HCl gave the title compound in 52% yield (300 mg), m.p. 278°–280° C. ¹H NMR (300 MHz, D6-DMSO) d 1.52–1.68 (m, 1H), 1.70–1.85 (m, 1H), 2.33–2.58 (m, 1H), 2.62–2.86 (m, 3H), 2.95–3.08 (m, 1H), 3.44–3.60 (m, 3H), 3.77 (s, 3H), 3.94–4.20 (m, 2H), 4.20–4.35 (m, 2H), 6.73 (d, 1H), 6.84 (d, 1H), 7.17 (t, 1H), 7.62 (d, 1H), 8.33 (s, 1H), 8.41 (d, 1H), 10.72 (s, 1H), 12.74 (s, 1H). MS (DCI/NH3) m/e 482 (M+H)+. Anal calcd for C25H24N3O3SCl.HCl.0.5 H2O: C, 56.93; H, 4.97; N, 7.97. Found: C, 57.07; H, 5.08; N, 7.76.

EXAMPLE 58

3-[2-((3aR,9bR)-cis-6-Methoxy-2,3,3a,4,5,9b-hexahydro-[1H]-benz[e]isoindol-1-yl)ethyl]-[1]-8-(Nmorpholinocarboxamido)-benzothieno[3,2-d]pyrimidine-2,4(1H,3H)-dione hydrochloride

EXAMPLE 58A

3-Cyano-4-Chloro-N-morpholinobenzamide 3-cyano-4-chlorobenzoic acid (2.0 g, 11.3 mmol) was treated with oxalyl chloride. The resulting acid cloride 2.3 g, 11.3 mmol) was treated with 2.2 g (24 mmol) of morpholine in methylene chloride to give after chromatography (1:1 hexane/EtOAc) the title compound in 78% yield (2.2 g). 1H NMR (300 MHz, D6-DMSO) d 3.47–3.70 (m, 8H), 7.76 (rid, J=9,2 Hz, 1H), 7.84 (d, J=9 Hz, 1H), 8.06 (d, J=2 Hz, 1H). MS (DCI/NH3) m/e 268 (M+NH4)+.

EXAMPLE 58B

3-Amino-2-carbomethoxy-5-(N-morpholinocarboxamido)-benzthiophene

The product from Example 58A (2.1 g, 8.4 mmol) was treated with 1 eq of methyl thioglycolate and 1 eq sodium carbonate in MeOH as described in Example 41A to give after chromatography (7:3 hexane/EtOAc) the title compound in 52% yield, 1.4 g. 1H NMR (300 MHz, CDCl3) d 3.47–3.85 (m, 8H), 3.90 (s, 3H), 5.95 (bs, 2H), 7.45 (dd, J=9,2 Hz, 1H), 7.75 (d, J=9 Hz, 1H), 7.77 (d, J=2 Hz, 1H). MS (DCI/NH3) m/e 338 (M+NH4)+.

EXAMPLE 58C

3-[2-((3aR,9bR)-cis-6-Methoxy-2,3,3a,4,5,9b-hexahydro-[1H]-benz[e]isoindol-1-yl)ethyl]-[1]-8-(Nmorpholinocarboxamido)-benzothieno[3,2-d]pyrimidine-2,4(1H,3H)-dione hydrochloride The product from Example 58B (320 mg, 1.0 mmol) was treated with 0.33 eq triphosgene as in Example 9E. The resulting isocyanate (1.0 mmol) and the compound resulting from Example 9D (250 mg, 1.0 mmol)) were refluxed in 30 mL of THF for 16 h and concentrated. The residue was triturated with EtOAc and filtered to give the free base which upon treatment with methanolic HCl gave the title compound in 20% yield (120 mg), m.p. 222°–228° C. ¹H NMR (300 MHz, D6-DMSO) d 1.52–1.68 (m, 1H), 1.70–1.85 (m, 1H), 2.33–2.58 (m, 1H), 2.62–2.86 (m, 3H), 2.95–3.08 (m, 1H), 3.24–3.72 (m, 11H), 3.77 (s, 3H), 3.94–4.20 (m, 2H), 4.20–4.35 (m, 2H), 6.73 (d, 1H), 6.84 (d, 1H), 7.17 (t, 1H), 7.68 (d, 1H), 8.21 (d, 1H), 8.50 (s, 1H), 10.48 (s, 1H), 12.69 (s, 1H). MS (DCI/NH3) m/e 561 (M+H)+. Anal calcd for C30H32N4O5S.HCl.1.0 H2O: C, 58.58; H, 5.73; N, 9.11. Found: C, 58.45; H, 5.64; N, 8.88.

EXAMPLE 59

3-[2-((3aR,9bR)-cis-6-Methoxy-2,3,3a,4,5,9b-hexahydro-[1H]-benz[e]isoindol-1-[1]-8-N-methyl-acetamido-benzothieno[3,2-d]pyrimidine-2,4(1H,3H)-dione hydrochloride

EXAMPLE 59A

3-Amino-2-carbomethoxy-5-(N-Methyl)-acetamido-benzthiophene

The product from Example 49B (556 mg, 2.0 mmol) was treated with MeI (2.0 mmol) and powdered KOH (4 mmol) in 3 ml of DMSO at 25° C. for 15 min. The mixture was poured into 20 mL of ice water and extracted 3x 25 mL with EtOAc. The extracts were combined, dried (MgSO4) and concentrated. Flash chromatography (4:1 methylene chloride/EtOAc ) gave 250 mg (48% yield) of the title compound. 1H NMR (300 MHz, CDCl$_3$) d 1.40 (t, J=7 Hz, 3H), 1.89 (s, 3H), 3.32 (s, 3H), 4.37 (q, J=7 Hz, 2H), 5.87 (bs, 2H), 7.29 (dd, J=9,2 Hz, 1H), 7.46 (d, J=2 Hz, 1H), 7.78 (d, J=9 Hz, 1H). MS (DCI/NH3) m/e 3 10 (M+NH4)+.

EXAMPLE 59B

3-[2-((3aR,9bR)-cis-6-Methoxy-2,3,3a,4,5,9b-hexahydro-[1H]-benz[e]isoindol-1-yl)ethyl]-[1]-8-N-methyl-acetamido-benzothieno[3,2 -d]pyrimidine-2,4(1H,3H)-dione hydrochloride The product from Example 59A (280 mg, 0.96 mmol) was converted to the isocyanate as desribed previously and combined with the product of Example 9D as described previously. Chromatography (15:1:1 EtOAc/water/formic acid) gave 300 mg (54% yield)of the title compound as the formic acid salt, m.p. 158°–164° C. $^1$H NMR (300 MHz, D6-DMSO) d 1.38–1.50 (m, 1H), 1.58–1.70 (m, 1H), 1.72–1.95 (m, 3H), 2.10–2.28 (m, 2H), 2.37–2.50 (m, 2H), 2.53–2.72, m, 4H), 3.15–3.32(m, 6H), 3.72 (s, 3H), 4.03 (t, 2H), 6.72 (d, 2H), 7.08 (t, 1H), 7.62 (dd, 1H), 8.14 (d, 1H), 8.30 (d, 1H), 8.31 (s, 1H). MS (DCI/NH3) m/e 519 (M+H)+. Anal calcd for C28H30N4O$_5$S.HCO2H.0.5 H2O: C, 60.72; H, 5.80; N, 9.77. Found: C, 60.43; H, 5.76; N, 9.72.

EXAMPLE 60

3-[2-((3aR,9bR)-cis-6-Methoxy-2,3,3a,4,5,9b-hexahydro-[1H]-benz[e]isoindol-1-yl)ethyl]-[1]-8-(N-methoxycarboxamido)-benzothieno[3,2-d]pyrimidine-2,4(1H,3H)-dione hydrochloride

EXAMPLE 60A

3-Cyano4-chloro-N-methoxybenzamide

The product from Example 44A was converted into the acid chloride as described in Example 45A and treated with methoxylamine to give the title compound in 78% yield. 1H NMR (300 MHz, D6-DMSO) d 3.70 (s, 3H), 7.90 (d, J=9 Hz, 1H), 8.50 (dd, J=9,2 Hz, 1H), 8.28 (d, J=2 Hz, 1H), 12.03 (s, 1H).

EXAMPLE 60B

3-Amino-2-carbomethoxy-5-(N-methoxycarboxamido)-benzthiophene

The product from Example 60A was treated with methyl thioglycolate and sodium carbonate in MeOH as described previously to give a 15% yield of the title compound. 1H NMR (300 MHz, D6-DMSO) d 3.73 (s, 3H), 3.80 (s, 3H), 7.28 (bs, 2H), 7.78 (dd, J=9,2 Hz, 1H), 7.92 (d, J=9 Hz, 1H), 8.61 (d, J=2 Hz, 1H), 11.78 (s, 1H).

EXAMPLE 60C

3-[2-((3aR,9bR)-cis-6-Methoxy-2,3,3a,4,5,9b-hexahydro-[1H]-benz[e]isoindol-1-yl)ethyl]-[1]-8-(N-methoxycarboxamido)-benzothieno[3,2-d]pyrimidine-2,4(1H,3H)-dione hydrochloride The product from Example 60B (370mg, 1.32 mmol) was convened to the isocyanate as desribed in Example 42B and combined with the product of Example 9D as described previously. The residue was triturated with EtOAc and filtered to give the free base which upon treatment with HCl in dioxane gave the title compound in yield, m.p. 235°–240° C. $^1$H NMR (300 MHz, D6-DMSO) d 1.52–1.68 (m, 1H), 1.70–1.85 (m, 1H), 2.33–2.58 (m, 1H), 2.62–2.86 (m, 3H), 2.95–3.08 (m, 1H), 3.42–3.55 (m, 3H), 3.75 (s, 3H), 3.77 (s, 3H), 3.94–4.20 (m, 2H), 4.20–4.35 (m, 2H), 6.73 (d, 1H), 6.84 (d, 1H), 7.17 (t, 1H), 7.92 (d, 1H), 8.21 (d, 1H), 8.94 (s, 1H),10.58 (s, 1H), 11.95 (s, 1H), 12.78 (s,1H). MS (DCI/NH3) m/e 521 (M+H)+. Anal calcd for C27H28N4O5S.HCl.H2O: C, 56.39; H, 5.43 N, 9.74. Found: C, 56.68; H, 5.36; N, 9.56.

EXAMPLE 61

3-[2-((3aR,9bR)-cis-6-Methoxy-2,3,3a,4,5,9b-hexahydro-[1H]-benz[e]isoindol-1-yl)ethyl]-1-methyl-pyrido[2',3':4,5]thieno[3,2-d]pyrimidine-2,4(1H,3H)-dione dihydrochloride

EXAMPLE 61A

3-N-Methylamino-2-carbomethoxythieno[3.2-b]pyridine

To a 0° C. suspension of sodium hydride (0.13g 60% in oil, 3.3 mmol) in DMF (5 mL) under N2 was added a solution of 3-amino-2-carbomethoxythieno[3,2b]pyridine (62 g, 3.0 mmol), prepared as described in *J. Heterocyclic Chem.*, 85 (1987), dropwise. After stirring at 25° C. for 30 min the RXN was cooled to 0° C. and MeI (0.20 mL, 3.3 mmol) was added. After 1 h at 25C., the RXN was partitioned between Et2O and H2O. The Et2O layer was washed with H2O, washed with brine, dried (MgSO4), filtered, conc., and chromatographed (10:1 hex:EtOAc) to yield 460 mg (70%) of the desired product and 170 mg (24%) of the dimethylamino compound: $^1$H NMR (300 MHz, CDCl$_3$(mono-methyl compound)) δ3.65 (s, 3H), 3.89 (s, 3H), 7.30 (dd, 1H), 7.35 (bs, 1H), 8.01 (dd, 1H), 8.52 (dd, 1H); MS (DCI/NH3) m/e 223 (M+H)$^+$.

EXAMPLE 61B

3-[2-((3aR,9bR)-cis-6-Methoxy-2,3,3a,4,5,9b-hexahydro-[1H]-benz[e]isoindol-1-yl)ethyl]-1-methyl-pyrido[2',3':4,5]thieno[3,2-d]pyrimidine-2,4(1H,3H)-dione dihydrochloride The product from Example 61A (340 mg, 1.8 mmol), Et3N (0.59 mL, 4.2 mmol), and phosgene (0.8 mL of 1.93M sln in toluene) were reacted to yield the intermediate carbamoyl chloride, which was reacted with the product from Example 9D (0.40 g, 1.6 mmol) to provide 0.60 g (80%) of the desired product which was converted to the HCl salt: m.p. 254°–257°; $^1$H NMR (300 MHz, CDCl$_3$(free base)) δ1.46–1.60 (m, 1H), 1.69–1.81 (m, 1H), 2.22–2.35 (m, 2H), 2.48–2.60 (m, 2H), 2.64–2.92 (m, 3H), 3.36–3.49 (m, 3H), 3.80 (s, 3H), 4.29 (s, 3H), 4.30 (t, 2H), 6.66 (d, 1H), 6.76 (d, 1H), 7.10 (t, 1H), 7.44 (dd, 1H), 8.23 (dd, 1H), 8.78 (dd, 1H); MS (DCI/NH3) m/e 463 (M+H)+; Analysis calc'd for C25H26N4O3S.HCl: C, 60.17; H, 5.45; N, 11.23; found: C, 60.13; H, 5.61; N, 11.14.

EXAMPLE 62

3-[2-((3aR,9bR)-cis-6-Methoxy-2,3,3a,4,5,9b-hexahydro-[1H]-benz[e]isoindol-1-yl)ethyl]-8-chloro-pyrido[2',3':4,5]thieno[3,2-d]pyrimidine-2,4(1H,3H)-dione dihydrochloride

EXAMPLE 62A

3-Amino-2-carbomethoxy-5-chlorothieno[3,2-b]pyridine and 3-Amino-2-carbomethoxy-7-chlorothieno[3,2-b]pyridine To a solution of 3-chloro-2-cyanopyridine (40g, 0.29 mol) in 500 mL acetic acid added hydrogen peroxide (30%, 52 g, 0.45 mol) dropwise. After stirring at 90° C. for 18 h, the reaction is cooled to 25° C. and a solution of sodium sulfite (57 g, 0.45 mol) in H$_2$O is added dropwise. The reaction is concentrated to remove the bulk of the acetic acid and the residue is partitioned between 1M NaOH and CH$_2$Cl$_2$. The CH$_2$Cl$_2$ layer is dried (MgSO4), filtered, concentrated, and recrystallized from EtOAc to provide 23 g (51%) of 3-chloro-2-cyanopyridine-N-oxide. The N-oxide from above (12.2 g, 79 mmol) was taken up in DMF (160 mL) at 0° C. Methyl thioglycolate (7.1 mL, 79 mmol) was added followed by sodium methoxide (8.5 g, 160 mmol) in portions. The RXN was stirred for 1 h. The RXN was poured onto ice and the resulting solid was collected by filtration, washed with water, dissolved in CH$_2$Cl$_2$, dried (MgSO$_4$), filtered, concentrated, and recrystallized from EtOAc. 10.6 g (60%) of 3-amino-2-carbomethoxythieno[3,2-b]pyridine-4-oxide was obtained. The pyridine-N-oxide (10.6 g, 47 mmol) is mixed with phosphorous oxychloride (100 mL). The RXN is heated to 80° C. for 30 min. The RXN is concentrated and partitioned between CH$_2$Cl$_2$ and NaHCO$_3$ sln. The CH$_2$Cl$_2$ layer is dried (MgSO$_4$), filtered, conc, and chromatographed (5:1 hex:EtOAc). 8.3g (73%) of the 5-chloro and 2.0 g (18%) of the 7-chloro product were obtained: $^1$H NMR (300 MHz, CDCl$_3$(5-chloro)) δ3.92 (s, 3H), 6.15 (bs, 2H), 7.37 (d, 1H), 7.99 (d, 1H); MS (DCI/NH3) m/e 243 (M+H)$^+$. $^1$H NMR (300 MHz, CDCl$_3$(7-chloro)) δ3.93 (s, 3H), 6.20 (bs, 2H), 7.41 (d, 1H), 8.54 (db, 1H); MS (DCI/NH3) m/e 243 (M+H)$^+$.

EXAMPLE 62B

3-[2-((3aR,9bR)-cis-6-Methoxy-2,3,3a,4,5,9b-hexahydro-[1H]-benz[e]isoindol-1-yl)ethyl]-8-chloro-pyrido[2',3':4,5]thieno[3,2-d]pyrimidine-2,4(1H,3H)-dione dihydrochloride 3-Amino-2-carbomethoxy-5-chlorothieno[3,2-b]pyridine, prepared as described in Example 62A (540 mg, 2.2 mmol), Et$_3$N (0.74 mL, 5.3 mmol), phosgene (1.2 mL of 1.93M sln in toluene), and the product from Example 9D (0.50 g, 2.0 mmol) were reacted as described in Example 42B to provide 0.61 g (62%) of the desired product which was converted to the HCl salt: m.p. 129°–131°; $^1$H NMR (300 MHz, CDCl$_3$(free base)) δ1.59–1.74 (m, 1H), 1.89–2.01 (m, 1H), 2.52–2.65 (m, 1H), 2.73–2.91 (m, 3H), 2.91–3.05 (m, 1H), 3.32–3.53 (m, 1H), 3.73–3.88 (m, 1H), 3.82 (s, 3H), 3.88–4.13 (m, 1H), 4.26–4.39 (m, 1H), 4.51–4.66 (m, 1H), 4.66–4.86 (m, 2H), 6.69 (d, 1H), 6.78 (d, 1H), 7.10 (t, 1H), 7.36 (d, 1H), 7.87 (d, 1H); MS (DCI/NH3) m/e 483 (M+H)+; Analysis calc'd for C$_{24}$H$_{23}$ClN$_4$O$_3$S.HCl.(H$_2$O)$_{0.25}$: C, 55.02; H, 4.71; N, 10.69; found: C, 54.90; H, 4.46; N, 10.42.

EXAMPLE 63

3-[2-((3aR,9bR)-cis-6-Methoxy-2,3,3a,4,5,9b-hexahydro-[1H]-benz[e]isoindol-1-yl)ethyl]-6-chloro-pyrido[2',3':4,5]thieno[3,2-d]pyrimidine-2,4(1H,3H)-dione dihydrochloride Following the procedure described in Example 62B, 3-amino-2-carbomethoxy-7-chlorothieno[3,2-b]pyridine, prepared as described in Example 62A (540 mg, 2.2 mmol), Et$_3$N (0.71 mL, 5.1 mmol), phosgene (1.2 mL of 1.93M solution in toluene), and the product from Example 9D (0.50 g, 2.0 mmol) were reacted to provide 0.46 g (43%) of the title compound, which was converted to the HCl salt: m.p. >255°; $^1$H NMR (300 MHz, CDCl$_3$(free base)) δ1.54–1.70 (m, 1H), 1.84–1.96 (m, 1H), 2.48–2.61 (m, 1H), 2.65–2.92 (m, 4H), 3.35–3.50 (m, 1H), 3.70–3.87 (m, 2H), 3.80 (s, 3H), 4.31–4.42 (m, 1H), 4.45–4.63 (m, 3H), 6.68 (d, 1H), 6.77 (d, 1H), 7.10 (t, 1H), 7.42 (d, 1H), 8.58 (bd, 1H); MS (DCI/NH3) m/e 483 (M+H)+; Analysis calc'd for C$_{24}$H$_{23}$ClN$_4$O$_3$S.HCl: C, 55.49; H, 4.66; N, 10.79; found: C, 55.44; H, 4.52; N, 10.55.

EXAMPLE 64

3-[2-((3aR,9bR)-cis-6-Methoxy-2,3,3a,4,5,9b-hexahydro-[1H]-benz[e]isoindol-1-yl)ethyl]-8-methoxy-pyrido[2',3':4,5]thieno[3,2-d]pyrimidine-2,4(1H,3H)-dione dihydrochloride

EXAMPLE 64A

3-Amino-2-carbomethoxy-5-methoxythieno[3,2-b]pyridine

A solution of 3-amino-2-carbomethoxy-5-chlorothieno[3,2-b]pyridine, prepared as described in Example 62A (5g, 21 mmol) and sodium methoxide (4.5 g, 82 mmol) in MeOH (150 mL) were refluxed for 18 h. The reaction was concentrated and partitioned between EtOAc and NaHCO$_3$ solution. The EtOAc layer was dried (MgSO$_4$), filtered, concentrated, and chromatographed (5:1 hex: EtOAc) to yield 2.5 g of the title compound: $^1$H NMR (300 MHz, CDCl$_3$) δ3.80 (s, 3H), 4.02 (s, 3H), 6.05 (bs, 2H), 6.89 (d, 1H), 7.88 (d, 1H); MS (DCI/NH3) m/e 239 (M+H)$^+$.

EXAMPLE 64B

3-[2-((3aR,9bR)-cis-6-Methoxy-2,3,3a,4,5,9b-hexahydro-[1H]-benz[e]isoindol-1-yl)ethyl ]-8-methoxy-pyrido[2',3':4,5]thieno[3,2-d]pyrimidine-2,4(1H,3H)-dione dihydrochloride Following the procedure described in Example 62B, the product from Example 64A (530 mg, 2.2 mmol), Et$_3$N (0.71 mL, 5.1 mmol), phosgene (1.2 mL of 1.93M solution in toluene), and the product from Example 9D (50 g, 2.0 mmol) provided 0.91 g (94%) of the title compound which was converted to the HCl salt: m.p. 128°–130°; $^1$H NMR (300 MHz, CDCl$_3$(free base)) δ1.46–1.59 (m, 1H), 1.69–1.81 (m, 1H), 2.24–2.34 (m, 2H), 2.48–2.60 (m, 2H), 2.64–2.94 (m, 3H), 3.36–3.52 (m, 3H), 3.80 (s, 3H), 4.04 (s, 3H), 4.26 (t, 2H), 6.67 (d, 1H), 6.75 (d, 1H), 6.98 (d, 1H), 7.09 (t, 1H), 8.02 (d, 1H); MS (DCI/NH3) m/e 479 (M+H)+; Analysis calc'd for C$_{25}$H$_{26}$N$_4$O$_4$S.HCl: C, 58.30; H, 5.28; N, 10.88; found: C, 57.91; H, 5.20; N, 10.68.

EXAMPLE 65

3-[2-((3aR,9bR)-cis-6-Methoxy-2,3,3a,4,5,9b-hexahydro-[1H]-benz[e]isoindol-1-yl)ethyl]-6-methoxy-pyrido[2',3':4,5]thieno[3,2-d]pyrimidine-2,4(1H,3H)-dione dihydrochloride

EXAMPLE 65A

3-Amino-2-carbomethoxy-7-methoxythieno[3,2-b]pyridine

Following the procedure described in Example 64A, 3-amino-2-carbomethoxy-7-chlorothieno[3,2-b]pyridine prepared as described in Example 62A 0 (2.0 g, 8.2 mmol) provided 1.1 g (56%) of the title compound after chromatography with 1:1 hex:EtOAc.: $^1$H NMR (300 MHz, CDCl$_3$) δ3.92 (s, 3H), 4.05 (s, 3H), 6.18 (bs, 2H), 6.81 (d, 2H), 8.52 (d, 2H); MS (DCI/NH3) m/e 239 (M+H)$^+$.

EXAMPLE 65B

3-[2-((3aR,9bR)-cis-6-Methoxy-2,3,3a,4,5,9b-hexahydro-[1H]-benz[e]isoindol-1-yl)ethyl]-6-methoxy-pyrido[2',3':4,5]thieno[3,2-d]pyrimidine-2,4(1H,3H)-dione dihydrochloride Following the procedure described in Example 64B, the product from Example 65A (530mg, 2.2 mmol), Et$_3$N (0.71 mL, 5.1 mmol), phosgene (1.2 mL of 1.93M solution in toluene), and the the product from Example 9D (0.50 g, 2.0 mmol) provided 0.82 g (85%) of the title compound which was converted to the HCl salt: m.p. 235°–237°; 1H NMR (300 MHz, CDCl3(free base)) d 1.48–1.62 (m, 1H), 1.75–1.87 (m, 1H), 2.31–2.41 (m, 2H), 2.47–2.59 (m, 1H), 2.66–2.79 (m, 2H), 3.07–3.19 (m, 2H), 3.34–3.45 (m, 1H), 3.66 (q, 1H), 3.80 (s, 3H), 4.07 (s, 3H), 4.13 (q, 2H), 4.26–4.45 (m, 2H), 6.66 (d, 1H), 6.77 (d, 1H), 6.84 (d, 1H), 7.08 (t, 1H), 8.59 (d, 1H); MS (DCI/NH3) m/e 479 (M+H)+; Analysis calc'd for C25H26N4O4S.HCl.(H2O)0.5: C, 57.30; H, 5.39; N, 10.69; found: C, 56.93; H, 5.04; N, 10.46

EXAMPLE 66

3-2-((3aR,9bR)-cis-6-Methoxy-2,3,3a,4,5,9b-hexahydro-[1H]-benz[e]isoindol-1-yl)ethyl]-1H-pyrimido[5,4-b]indole-4(1H,3H)-one hydrochloride 2-Carboethoxy-3-(N,N'-dimethyl-N'-formamidinyl) indole was prepared from the known 2-carobethoxy-3-amino indole (Unangst, P. C. *J. Heterocyclic Chem.* 1983, 20, 495) by the method of Gupton, J. T., Miller, J. F., Bryant, R. D., Maloney, P. R., Foster, B. S. Tetrahedron, 1987, 43(8), 1747. 2-Carboethoxy-3-(N,N'-dimethyl-N'-formamidinyl) indole (0.75 g, 2.9 mmol) and the compound resulting from Example 9D (0.5 g, 2.0 mmol) were combined as in Example 34B to yield the title compound (0.45g, 46%) as a solid: mp >210° C. (MeOH/Et$_2$O); [α]$_D$+26.8° (c0.41 in MeOH); $^1$H NMR (300 MHz, D$_2$O) δ8.29 (s, 1H), 8.13–8.09 (d, 1H), 7.70–7.60 (m, 2H), 7.41–7.36 (m, 1H), 7.26 (t, J=9.0 Hz, 1H), 6.96–6.93 (d, 1H), 6.91–6.88 (d, 1H), 4.81–4.78 (m, 3H), 4.55 (t, J=6 Hz, 2H), 3.85 (s, 3H), 3.73 (t, J=6 Hz 3H) 2.90–2.70 (m, 3H) 2.55–2.65 (m, 1H), 1.89–2.0 (m, 1H), 1.63–1.70 (m, 1H); MS (DCI/NH$_3$) m/z 415 (M+H)$^+$. Anal. calcd for C$_{25}$H$_{28}$Cl$_2$N$_4$O$_2$.0.1H$_2$O: C, 61.14; H, 5.76; N, 11.40. Found: C, 61.13; H, 5.71; N, 11.27.

EXAMPLE 67

3-[2-((3aR,9bR)-cis-6-Methoxy-2,3,3a.,4,5,9b-hexahydro-[1H]-benz[e]isoindol-1-yl)ethyl]-[1]-8-chloro-benzothieno[3,2-d]pyrimidine-2,4(1H,3H)-dione hydrochloride 5-Chloro-3-amino-2-caroboethoxy benzothiophene was prepared from 3-chloro-6-nitrobenzonitrile and ethylthioglycolate utilizing the method of Beck, J. R. *J. Org. Chem.* 1972, 3224. This compound (0.52 g, 2.03 mmol) was treated in the manner described in Example 9E and the resultant isocyanate was combined with the material from Example 9D (0.417 g, 1.69 mmol) and treated as in Example 9E to yield the title compound (0.273 g, 32%) as a white solid: mp >210° C.; $^1$H NMR (300 MHz, DMSO-d$_6$) δ12.65 (m, 1H), 8.54 (m, 1H), 8.19 (m, 1H), 7.70 (m, 1H), 7.17 (m, 1H), 6.84 (m, 1H), 6.76 (m, 1H), 4.28 (m, 2H), 4.18 (m, 1H), 4.03 (m, 1H), 3.78 (s, 3H), 3.52 (m, 2H), 3.03 (m, 2H), 2.74 (m, 2H), 2.45 (m, 1H), 1.80 (m, 1H), 1.62 (m, 1H); MS (CI) m/z 482 (M+H)$^+$. Anal. calcd for C$_{25}$H$_{25}$Cl$_2$N$_3$O$_3$S.0.9 HCl: C, 54.47; H, 4.74; N, 7.62. Found: C, 54.47; H, 4.70; N, 7.49.

EXAMPLE 68

3-[2-((3aR,9bR)-cis-6-Methoxy-2,3,3a,4,5,9b-hexahydro-[1H]-benz[e]isoindol-1-yl)ethyl]-[1]-7,8-dimethoxy-benzothieno[3,2-d]pyrimidine-2,4(1H,3H)-dione hydrochloride 5,6-Dimethoxy-3-amino-2-caroboethoxy benzothiophene was prepared from 4,5-dimethoxy-2-nitro benzonitrile and ethyl thioglycolate as described in De Angelis, G. G.; Hess, H-J. E. U.S. Pat. No. 3,706,747. This compound (0.355 g, 1.33 mmol) was treated in the manner described in Example 9E and the resultant isocyanate was combined with the material from Example 9D (1.42 mmol) and treated as in Example 9E to yield the title compound (0.079 g, 10%) as a white solid: mp >220° C.; $^1$H NMR (300 MHz, DMSO-d$_6$) δ12.44 (m, 1H), 8.00 (m, 1H), 7.68 (m, 1H), 7.17 (m, 1H), 6.80 (m, 2H), 4.20 (m, 2H), 4.18 (m, 1H), 4.03 (m, 1H), 3.88 (s, 3H), 3.84 (s, 3H), 3.78 (s, 3H), 3.52 (m, 3H), 3.02 (m, 2H), 2.70 (m, 3H), 1.80 (m, 1H), 1.63 (m, 1H); MS (CI) m/z 508 (M+H)$^+$. Anal. calcd for C$_{27}$H$_{31}$Cl$_2$N$_3$O$_5$S.0.9 HCl: C, 52.87; H, 5.24; N, 6.85. Found: C, 53.00; H, 5.34; N, 6.69.

EXAMPLE 69

3-[2-((3aR,9bR)-cis-6-Methoxy-2,3,3a,4,5,9b-hexahydro-[1H]-benz[e]isoindol-1-yl)ethyl]-[1]-9-methyl-benzothieno[3,2-d]pyrimidine-2,4(1H,3H)-dione hydrochloride 4-Methyl-3-amino-2-caroboethoxy benzothiophene was prepared from 6-nitro-o-toluonitrile and ethylthioglycolate utilizing the method of Beck, J. R. *J. Org. Chem.* 1972, 3224. This compound (0.853 g, 3.86 mmol) was treated in the manner described in Example 9E and the resultant isocyanate was combined with the material from Example 9D (3.21 mmol) and treated as in Example 9E to yield the title compound (0.95 g, 59%) as a white solid: mp >270° C.; [α]$_D$ +27.6° (c 0.41 in MeOH); $^1$H NMR (300 MHz, DMSO-d$_6$) δ7.94 (m, 1H), 7.51 (m, 1H), 7.30 (m, 1H), 7.17 (m, 1H), 6.84 (m, 1H), 6.76 (m, 1H), 4.29 (m, 2H), 4.15 (m, 1H), 4.05 (m, 1H), 3.77 (s, 3H), 3.54 (m, 3H), 3.08 (m, 2H), 2.87 (s, 3H), 2.70 (m, 2H), 1.83 (m, 2H), 1.62 (m, 1H); MS (CI) m/z 462 (M+H)$^+$. Anal. calcd for C$_{26}$H$_{28}$ClN$_3$O$_3$S.0.2 HCl: C, 61.80; H, 5.63; N, 8.32. Found: C, 61.59; H, 5.66; N, 8.20.

EXAMPLE 70

3-[2-((3aR,9bR)-cis-6-Methoxy-2,3,3a,4,5,9b-hexahydro-[1H]-benz[e]isoindol-1-yl)ethyl]-2,3-dihydro-pyrido[3',2':4,5]thieno[3,2-d]pyrimidine-4(1H,3H)-one dihydrochloride To a solution of the product from Example 9D (0.50 g, 2.03 mmol) in CH$_2$Cl$_2$ (10 mL) and DMF (10 mL) was added 3-amino-thieno[2,3-b]pyridine-2-carboxylic acid (0.52 g, 2.23 mmol), EDCI (0.59 g, 3.1 mmol, HOBT, 0.47 g, 3.1 mmol), and diisopropylethylamine (0.60 mL, 3.1 mmol). The reaction was stirred at rt for 18 h. The reaction was quenched in 5% NaHCO$_3$, extracted with ethyl acetate, the organic layer was dried (MgSO$_4$), and evaporated. The resultant amide (1.1 g, 2.61 mmol) and 37% formaldehyde solution and KOH (219 mg, 3.91 mmol) in MeOH (50 ml) was allowed to reflux for 4 hours. The solution was concentrated to a white solid and chromatographed on silica gel (CHCl$_3$:MeOH:H$_4$OH/800:120:9) to give the product as a free base. This was dissolved in CH$_2$Cl$_2$ and treated with HCl/Et2O (1M) which upon evaporation gave the hydrochloride. The salt was recrystallized from EtOH/Et2O to yield the title compound (495 mg, 45%) as light yellow solid: mp 228°–230° C. (EtOH/Et$_2$O); [α]$_D$ +39.2° (c 0.60, MeOH); $^1$H NMR (300 MHz, DMSO-d$_6$) δ1.62 (m, 1H), 1.80 (m, 1H), 2.50 (m, 2H), 2.65 (m, 3H), 2.80 (m, 1H), 3.20 (m, 2H), 3.40 (m, 2H), 3.50 (m, 1H), 3.70 (m, 1H), 3.82 ( 3H), 4.30 (m, 2H), 4.70 (m, 2H), 6.75 (q, J=9 Hz, 2H), 7.10 (t, J=9 Hz, 1H), 7.30 (dd, J=6 Hz, 1H), 7.95 (dd, J=3Hz, 1H), 8.68 (dd, J=3Hz, 1H); MS (DCI/NH$_3$) m/z 435 (M+H)$^+$. Anal. calcd for C$_{24}$H$_{28}$Cl$_2$N$_3$O$_2$S.0.30 HCl: C, 55.60; H, 5.50; N, 10.81. Found: C, 55.48; H, 5.48; N, 10.51.

EXAMPLE 71

3-[2-(cis-(3.aR,9bR)-6-Methoxy-2,3 .,3a,4,5,9b-hexahydro-[1H]-benz[e]isoindol-1-yl)ethyl]-pyrazino[2',3':4,5]thieno[3,2-d]pyrimidine-4(1H,3H)-one hydrochloride 2-Carboethoxy-3-(N,N'-dimethyl-N'-formamidinyl) pyrazinothiophene was prepared from the known 2-caroethoxy-3-amino pyrazinethiophene (Schneller, S. W.; Cloush, F. W.; *J. Heterocyclic Chem.* 1975, 12, 513) by the method of Gupton, J. T.; Miller, J. F.; Bryant, R. D.; Maloney, P. R.; Foster B. S. *Tetrahedron,* 1987, 43(8), 1747. 2-Carboethoxy-3-(N,N'-dimethyl-N'-formamidinyl) pyrazinethiophene (500 mg, 1.79 mmol) and the compound resulting from Example 9D (442 mg, 1.79 mmol) were combined as in Example 34B to yield the title compound (558 mg, 67%) as a solid: mp 185°–187° C.; $[\alpha]_D$ +29.9° (c 0.61, MeOH); $^1$H NMR (300 MHz, DMSO-$d_6$) δ1.54 (m, 2H), 1.78 (m, 1H), 2.40 (m, 1H), 2.50 (m, 2H); 2.70 (m, 1H); 2.90 (m, 2H); 3.20 (m, 2H); 3.40 (m, 1H); 3.80 (s, 3H); 4.20 (m, 2H); 6.70 (t, J=9 Hz, 2H); 7.10 (t, J=9 Hz, 1H); 8.30 (s, 1H); 8.75 (d, J=3Hz, 1H); 8.82 (d, J=3Hz, 1H); MS (DCI/NH3) m/z 434 (M+H)$^+$. Anal. calcd for $C_{23}H_{24}ClN_5O_2S.0.50$ HCl: C, 56.58; H, 5.06; N, 14.34. Found: C, 56.75; H, 5.23; N, 14.06.

EXAMPLE 72

3-[2-((3aR,9bR)-cis-6-Methoxy-2,3,3a,4,5,9b-hexahydro-[1H]-benz[e]isoindol-1-yl)ethyl]-[1]-9-chloro-benzothieno[3,2-d]pyrimidine-2,4(1H,3H)-dione hydrochloride 4-Chloro-3-amino-2-caroboethoxy benzothiophene was prepared from 2,6-dichlorobenzonitrile and ethylthioglycolate as described in De Angelis, G. G.; Hess, H-J. E. U.S. Pat. No. 3,706,747. This compound (1.0 g, 4.17 mmol) was treated in the manner described in Example 9E and a portion of the resultant isocyanate (0.442 g, 1.65 mmol) was combined with the material from Example 9D (1.65 mmol) and treated as in Example 9E to yield the title compound (0.273 g, 32%) as a white solid: mp >270° C.; $[\alpha]_D$ +25.7° (c 0.51 in MeOH); $^1$H NMR (300 MHz, DMSO-$d_6$) δ8.16 (m, 1H), 7.64 (m, 2H), 7.1 (m, 1H), 6.84 (m, 1H), 6.77 (m, 1H), 4.29 (m, 2H), 4.15 (m, 1H), 4.03 (m, 1H), 3.77 (s, 3H), 3.52 (m, 3H), 3.04 (m, 2H), 238 (m, 1H), 2.70 (m, 2H), 1.81 (m, 1H), 1.61 (m, 1H); MS (CI) m/z 482 (M+$^+$. Anal. calcd for $C_{25}H_{25}Cl_2N_3O_3S, 0.2$ HCl: C, 57.11; H, 4.83; N, 7.99. Found: C, 57.09; H, 4.78; N, 7.78.

EXAMPLE 73

3-[2-((3aR,9bR)-cis-6-Methoxy-2,3,3a,4,5,9b-hexahydro-[1H]-benz[e]isoindol-1-yl)ethyl]-[1]-9-methoxy-benzothieno[3,2-d]pyrimidine-2,4(1H,3H)-dione hydrochloride 4-Methoxy-3-amino-2-caroboethoxy benzothiophene from 2-methoxy-6-chlorobenzonitrile and ethylthioglycolate utilizing the method of Schneller, S. W.; Cloush, F. W. *J. Heterocyclic Chem.* 1975, 12, 513. This compound (800 mg, 3.18 mmol) was treated in the manner described in Example 9E and the resultant isocyanate was combined with the material from Example 9D (710 mg, 2.88 mmol) and treated as in Example 9E to yield the title compound (130 mg, 10%) as a white solid; mp 193°–195° C.; [a]$_D$ +31.4° (c 0.56, MeOH); $^1$H NMR (300 MHz, MeOD) δ1.65 (m, 2H); 2.02 (m, 2H), 2.60 (m, 2H), 2.92 (m, 2H); 3.18 (m, 1H); 3.62 (m, 3H); 3.85 (s, 3H); 4.15 (s, 3H); 4.45 (m, 2H); 6.80 (m, 2H); 7.08 (m, 1H); 7.20 (m, 1H); 7.60 (m, 2H). MS (DCI/NH$_3$) m/z 478 (M+H)$^+$. Anal. calcd for $C_{26}H_{28}ClN_3O_4S.0.80$ HCl.0.10 $H_2O$: C, 57.30; H, 5.36; N, 7.71. Found: C, 57.30; H, 5.69; N, 7.50.

EXAMPLE 74

3-[2,((3aR,9bR)-cis-6-Methoxy-2,3,3a,4,5,9b-hexahydro-[1H]-benz[e]isoindol-1-yl)ethyl]-[1]-8-methyl-benzothieno[3,2-d]pyrimidine-2,4(1H,3H)-dione hydrochloride 5-Methyl-3-amino-2-caroboethoxy benzothiophene was prepared from 3-methyl-6-chlorobenzonitrile and ethylthioglycolate utilizing the method of De Angelis, G. G.; Hess, H-J. E. U.S. Pat. No. 3,706,747. This compound (1.0 g, 4.26 mmol) was treated in the manner described in Example 9E and the resultant isocyanate was combined with the material from Example 9D (350 mg, 1.45 mmol) and treated as in Example 9E to yield the title compound (340 mg, 52%) as a white solid: mp 196°–198° C.; $[\alpha]_D$ +27.8° (c0.66, MeOH); $^1$H NMR (300 MHz, MeOD) δ1.20 (m, 1H); 1.40 s (m, 2H); 2.1.(m, 1H); 2.50 (s, 3H); 2.65 (m, 2H); 3.10 (m, 2H); 3.58 (m, 2H); 3.74 (s, 3H); 3.84 (m, 2H); 4.12 (m, 2H); 6.75 (q, J=9 Hz, 2H); 7.02 (t, J=9 Hz, 1H); 7.40 (m, 1H); 7.75 (m, 1H); 7.90 (d, J=3Hz, 1H). MS (DCI/NH$_3$) m/z 462 (M+H)$^+$. Anal. calcd for $C_{26}H_{28}ClN_3O_3S.0.10$ HCl: C, 62.25; H, 5.65; N, 8.38. Found: C, 62.12; H, 5.51; N, 8.12.

EXAMPLE 75

3-[2-((3aS,9bS)-cis-6-Methoxy-2,3,3a,4,5,9b-hexahydro-[1H]-benz[e]isoindol-1-yl)ethyl]-pyrido[3',2':4,5]thieno[3,2-d]pyrimidine-2,4(1H ,3H)-dione hydrochloride

EXAMPLE 75A (3aS,9bS)-2-Cyanomethyl-6-methoxy-2,3,3a,4,5,9b-[1H]-hexahydrobenz[e]isoindole Following the procedure described in Example 9C, (3aS, 9bS)-6-Methoxy-2,3,3a,4,5,9b-[1H]-hexahydrobenz[e]isoindole hydrochloride (2.8 g, 11.7 mmol), chloroacetonitrile (0.97 g, 12.8 mmol), diisopropylamine (7.5 mL), and acetonitrile (15 mL) provided 2.48 g (88%) of the desired product after chromatography (hex:EtOAc 4:1). $^1$H NMR (300 MHz, CDCl3) δ1.60 (m, 2H), 1.80 (m, 1H), 2.58 (m, 3H), 2.77 (m, 1H), 3.23 (m, 2H), 3.48 (q, 1H), 3.64 (s, 2H), 3.81 (s, 3H), 6.70 (d, 1H), 6.74 (d, 1H), 7.12 (t, 1H).

EXAMPLE 75B (3aS,9bS)-2-Aminoethyl-6-methoxy-2,3,3a,4,5,9b-[1H]-hexahydrobenz[e]isoindole Following the procedure described in Example 9D, the product from Example 75A (1.88 g, 7.8 mmol), litium aluminum hydride (1.77 g, 46 mmol), and THF (50 mL) provided 1.9 g (99%) of the title compound. $^1$H NMR (300 MHz, CDCl3) δ1.50 (m, 3H), 1.72 (m, 1H), 2.19 (m, 2H), 2.52 (m, 3H), 2.70 (m, 1H), 2.80 (t, 1H), 3.21 (dd, 1H), 3.28 (t, 1H, 3.40 (m, 1H), 3.80 (s, 3H), 6.67 (d, 1H), 6.75 (d, 1H), 7.11 (t, 1H).

EXAMPLE 75C

3-[2-((3aS,9bS)-cis -6-Methoxy-2,3,3a,4,5,9b-hexahydro-[1H]-benz[e]isoindol-1-yl)ethyl]-pyrido[3',2':4,5]thieno[3,2-d]pyrimidine-2,4(1H ,3H)-dione hydrochloride Following the procedure described in Example 3 1, the isocyanate (0.25 g, 1.0 mmol) of 3-amino-2-carbomethoxythieno[2,3-b]pyridine, prepared by the method of Dunn and Norrie, J. Heterocyclic Chem., 24:85 (1987), the product from Example 75B (0.20 g, 0.83 mmol), triethylamine (0.10 g, 1.0 mmol), and toluene (20 mL) provided 0.32 g (86%) of the desired product which was converted to the HCl salt: m.p. 216°–218°; $^1$H NMR (300 MHz, CD$_3$OD) δ1.60–1.75 (m, 1H), 1.89–2.00 (m, 1H), 2.53–2.66 (m, 1H), 2.74–2.92

(m, 2H), 3.06–3.21 (m, 1H), 3.21–3.40 (m, 1H), 3.55–3.68 (m, 3H), 3.68–3.89 (m, 1H), 3.81 (s, 3H), 4.18–4.35 (m, 1H), 4.41–4.47 (m, 2H), 6.76–6.86 (m, 2H), 7.17 (t, 1H), 7.60 (dd, 1H), 8.57 (t, 1H), 8.79 (d, 1H); MS (DCI/NH$_3$) m/e 449 (M+H)+; Analysis calc'd for C$_{24}$H$_{24}$N$_4$O$_3$S.HCl: C, 59.43; H, 5.19; N, 11.55; found: C, 59.16; H, 5.05; N, 11.26.

EXAMPLE 76

3-[24 (3aR,9bR)-cis-6-Methoxy-2,3,3a,4,5,9b-hexahydro-[1H]-benz[e]isoindol-1-yl)ethyl]-pyrido[3',2':4,5]furo[3,2-d]pyrimidine-2,4(1H,3H)-dione hydrochloride

EXAMPLE 76A

3-Amino-2-carbomethoxyfuro[2,3-b]pyridine

2-Cyano-3-hydroxypyridine (1.2 g, 10 mmol), prepared as described in *Synthesis* 316 (1983), was aedded in portions to a 0° C. suspension of NaH (0.4 g of 60% dispersion, 10 mmol) in DMF (5 mL). After stirring for 20 min at 0° C., ethyl bromoacetate was added dropwise. The reaction was stirred for 30 min at 25° C. and was the poured into ice water. The resulting solid was collected by filtration and was washed with a small portion of water. The crude ethyl ester was taken up in EtOAc, dried (MgSO4), filted, and concentrated (1.16 g obtained). To the pyridine (1.0 g, 5.0 mmol) in THF (20 mL) was added potassium t-butoxide (0.56 g, 5.0 mmol). After stirring for 45 min, the reaction was partitioned between EtOAc and NaHCO$_3$ solution. The layers were seperated and the aqueous layer was extracted with EtOAc (2x). The combined organic layers were washed with brine, dried (MgSO$_4$), filtered, and concentrated to provide 0.76 g (76%) of the title compound: $^1$H NMR (300 MHz, CDCl3) δ1.46 (t, 3H), 4.47 (q, 2H), 5.21 (bs, 2H), 7.38 (dd, 1H), 7.76 (dd, 1H), 8.56 (dd, 1H).

EXAMPLE 76B

3-[2-((3aR,9bR)-cis-6-Methoxy-2,3,3a,4,5,9b-hexahydro-[1H]-benz[e]isoindol-1-yl)ethyl]-pyrido[3',2':4,5]furo[3,2-d]pyrimidine-2,4(1H,3H)-dione hydrochloride Following the procedure from Example 27, the isocyanate of the product from Example 76A (0.44 g, 2.0 mmol), the product from Example 9D (0.4 g, 1.6 mmol), triethylamine (0.2 g, 2.0 mmol), and toluene (15 mL) provided the intermediate urea (0.36 g, 0.75mmol). Treatment of the urea with potassium t-butoxide (0.75 mL of 1 M solution in THF) in ethanol (10 mL) and THF (3 mL) at reflux for 1 h at reflux yielded the title compound which was converted to the HCl salt: m.p. 218°–220°; $^1$H NMR (300 MHz, CD$_3$OD) δ1.60–174 (m, 1H), 1.88–2.01 (m, 1H), 2.52–2.65 (m, 1H), 2.75–2.92 (m, 2H), 3.14–3.48 (m, 2H), 3.58–3.74 (m, 3H), 3.82 (s, 3H), 3.87–4.22 (m, 2H), 4.42 (t, 2H), 6.78–6.84 (m, 2H), 7.17 (t, 1H), 7.55 (dd, 1H), 8.40 (dd, 1H), 8.61 (dd, 1H); MS (DCI/NH$_3$) m/e 433 (M+H)+; Analysis calc'd for C$_{24}$H$_{24}$N$_4$O$_4$.HCl.(H$_2$O)$_{0.5}$: C, 60.31; H, 5.48; N, 11.72; found: C, 60.36; H, 5.39; N, 11.49.

EXAMPLE 77

3-[2-((3aR,9bR)-cis-6-Methoxy-2,3,3a,4,5,9b-hexahydro-[1H]-benz[e]yl)ethyl]-pyrido[2',3':4,5]furo[3,2-d]pyrimidine-2,4(1H$_3$H)-dione hydrochloride Following the procedure described in Example 36, 3-amino-2-carbomethoxyfuro[2,3-b]pyridine (0.52 g, 2.6 mmol), the product from Example 9D (0.52 g, 2.1 mmol), triethylamine (0.59 mL, 4.2 mmol), and phosgene (1.1 mL of 1.93M sln in toluene) substituting THF for CH$_2$Cl$_2$ as the solvent provided 0.31 g (55%) of the title compound which was converted to the HCl salt: $^1$H NMR (300 MHz, DMSO-d$_6$) δ1.53–1.68 (m, 1H), 1.73–1.86 (m, 1H), 2.26–2.56 (m, 1H), 2.60–2.84 (m, 2H), 2.95–3.11 (m, 1H), 3.20–3.43 (m, 1H), 3.43–3.64 (m, 3H), 3.69–3.88 (m, 1H), 3.77 (s, 3H), 3.96–4.32 (m, 3H), 6.73–6.88 (m, 2H), 7.18 (t, 1H), 7.76–7.74 (m, 1H), 8.27–8.33 (m, 1H), 8.74–8.79 (m, 1H), 10.02 and 10.35 (bs and bs, 1H), 12.71 (bd, 1H); MS (DCI/NH$_3$) m/e 433 (M+H)+; Analysis calc'd for C$_{24}$H$_{24}$N$_4$O$_4$.HCl.(H$_2$O)0.75: C, 59.74; H, 5.53; N, 11.61; found: C, 59.76; H, 5.07; N, 11.56.

EXAMPLE 78

3-[2-((3aS,9bS)-cis-6-Methoxy-2,3,3a,4,5,9b-hexahydro-[1H]-benz[e]isoindol-1-yl)ethyl]-pyrido[2',3':4,5]thieno[3,2-d]pyrimidine-2,4(1H,3H)-dione dihydrochloride Following the procedure described in Example 31, the isocyanate (0.56 g, 2.4 mmol) of 3-amino-2-carbomethoxythieno[3,2-b]pyridine, prepared by the method of Dunn and Norrie, J. Heterocyclic Chem., 24: 85 (1987), the product from Example 75B (0.49 g, 2.0 mmol), and toluene provided 0.72 g (80%) of the title compound which was converted to the di-HCl salt: m.p. >260°; $^1$H NMR (300 MHz, CD$_3$OD) δ1.58–1.75 (m, 1H), 1.89–2.00 (m, 1H), 2.53–2.66 (m, 1H), 2.72–2.93 (m, 2H), 3.07–3.19 (m, 2H), 3.59–3.67 (m, 3H), 3.70–3.89 (m, 1H), 3.82 (s, 3H), 4.19–4.34 (m, 1H), 4.45 (t, 2H), 6.78–6.84 (m, 2H), 7.14–7.21 (m, 1H), 7.57–7.64 (m, 1H), 8.25–8.33 (m, 1H), 8.80–8.85 (m, 1H); MS (DCI/NH$_3$) m/e 449 (M+H)+; Analysis calc'd for C$_{24}$H$_{24}$N$_4$O$_3$S.(HCl)$_2$: C, 55.28; H, 5.02; N, 10.74; found: C, 55.32; H, 5.12; N, 10.65.

EXAMPLE 79

3-[2-((3aR,9bR)-cis-9-Methoxy-2,3,3a,4,5,9b-hexahydro-[1H]-benz[e]isoindol-1-yl)butyl]-pyrido[2',3':4,5]thieno[3,2-d]pyrimidine-2,4(1H,3H)-dione dihydrochloride

EXAMPLE 79A (3aR,9bR)-9-Methoxy-(2-(4-aminobutyl))-2 3 3a,4,5,9b-[1H]-hexahydrobenz[e]isoindole A suspensioin of the free base of the product from Example 16B (1.95 g, 8. 1 mmol), 4-bromobutyronitrile (0.81 mL, 8.1 mmol), and potassium carbonate (1.66 g, 12.2 mmol) in acetonitrile was stirred for 18 h at 25° C. The reaction was partitioned between cold water and EtOAc. The layers are seperated and the aqueous layer is s extracted with EtOAc (2x). The combined ethyl acetate layers were washed with brine, dried (MgSO$_4$), filtered, concentrated, and chromatographed (2% EtOH in EtOAc) to provide 1.87 g (85%) of the nitrile intermediate. A solution of the nitrile (1.8 g, 6.7 mmol) in THF was added dropwise to a stirred suspension of lithium aluminum hydride (1.52 g, 40 mmol) in THF (40 mL). After 4 h at 25° C., a Fieser workup provided 1.8 g of the title compound: $^1$H NMR (300 MHz, CDCl3) δ1.40–1.60 (m, 4H), 1.68 (q, 2H), 1.93 (t, 1H), 2.19 (dd, 1H), 2.40 (t, 2H), 2.50–2.67 (m, 3H), 2.70 (t, 2H), 3.11 (dd, 1H), 3.43 (t, 1H), 3.60 (q, 1H), 3.78 (s, 3H), 6.68 (d, 1H), 6.72 (d, 1H), 7.08 (t, 1H).: MS (DCI/NH$_3$).

EXAMPLE 79B

3-[2-((3aR,9bR)-cis-9-Methoxy-2,3,3a,4,5,9b-hexahydro-[1H]-benz[e]isoindol-1-yl)butyl]-pyrido[2',3':4,5]thieno[3,2-d]pyrimidine-2,4(1H,3H)-dione dihydrochloride Following the procedure described in Example 36, 3-amino-2-carbomethoxythieno[3,2-b]pyridine (0.36 g, 1.8 mmol), prepared by the method of Dunn and Norrie, J.

Heterocyclic Chem., 24:85 (1987), the product from Example 79A (0.40 g, 1.5 mmol), triethylamine (0.50 mL, 3.7 mmol), and phosgene (0.94 mL of 1.93M solution in toluene) substituting THF for $CH_2Cl_2$ as the solvent provided 0.12 g (17%) of the title compound which was converted to the di-HCl salt: m.p. >250°; $^1$H NMR (300 MHz, $CD_3OD$) δ1.79–1.85 (m, 6H), 2.67–2.88 (m, 3H), 3.02–3.10 (m, 1H), 3.32–3.40 (m, 1H), 3.44–3.54 (m, 1H), 3.60–3.72 (m, 2H), 3.83 (s, 3H), 3.96 (dd, 1H), 4.09–4.17 (m, 2H), 4.24 (dd, 1H), 6.74–6.84 (m, 2H), 7.13–7.20 (m, 1H), 7.60 (dd, 1H), 8.47 (dd, 1H), 8.81 (dd, 1H); MS ($DCI/NH_3$) m/e 477 (M+H)+; Analysis calc'd for $C_{26}H_{28}N_4O_3S.(HCl)_2.(NH_4Cl)_{0.5}$: C, 54.19; H, 5.59; N, 10.93; found: C, 54.35; H, 5.59; N, 10.87.

EXAMPLE 80

3-[2-((3aR,9bR)-cis-9-Methoxy-2,3,3a,4,5,9b-hexahydro-[1H]-benz[e]isoindol-1-yl)butyl]-pyrazino[2',3':4,5]thieno[3,2-d]pyrimidine-2,4(1H,3H)-dione hydrochloride Ethyl 3-aminothieno[2,3-b]pyrazine-2-carboxylate (0.43 g, 1.9 mmol) prepared by the method of Schneller and Clough, J. Het. Chem., 12: 513 (1975), triphosgene (0.13 g, 0.43 mmol), triethylamine (0.44 mL, 3.2 mmol), and toluene were stirred at 25° C. for 2 h and then heated to near reflux. Triethylamine hydrochloride was removed by filtration and the filtrate was concentrated. The residue and the product from Example 79A (0.44 g, 1.6 mmol) were taken up in a small amount of toluene. After refluxing for 18 h, the reaction was concentrated and chromatographed (10% EtOH in $CH_2Cl_2$) to provide 0.24 g (3 1%) of the title compound which was converted to the HCl salt: m.p. 185° (dec); $^1$H NMR (300 MHz, $CD_3OD$) δ1.63–1.98 (m, 6H), 2.69–2.85 (m, 3H), 3.20–3.41 (m, 4H), 3.60–3.82 (m, 2H), 3.84 (s, 3H), 4.11–4.16 (m, 3H), 6.77 (d, 1H), 6.81 (d, 1H), 7.16 (t, 1H), 8.77 (d, 1H), 8.84 (d, 1H); MS ($DCI/NH_3$) m/e 478 (M+H)+; Analysis calc'd for $C_{25}H_{27}N_5O_3S.HCl.H_2O$: C, 56.43; H, 5.68; N, 13.16; found: C, 56.00; H, 5.46; N, 12.78.

EXAMPLE 81

2S 3-[2-((3aR,9bR)-cis-9-Methoxy-2,3,3a,4,5,9b-hexahydro-[1H]-benz[e]isoindol-1-yl)butyl]-pyrido[3',2':4,5]thieno[3,2-d]pyrimidine-2,4(1H,3H)-dione hydrochloride 3-Amino-2-carbomethoxythieno[2,3-b]pyridine, prepared by the method of Dunn and Norrie, J. Heterocyclic Chem., 24:85 (1987), was treated with 0.33 equivalent triphosgene. The resulting isocyanate (0.27 g, 1.1 mmol) and the product from Example 79A (0.26 g, 0.95 mmol) were treated by the procedure described in Example 9E to yield 0.17 g (40%) of the title compound after chromatography (10% EtOH in $CH_2Cl_2$) which was converted to the HCl salt: m.p. 190°; $^1$H NMR (300 MHz, DMSO-$d_6$) δ1.60–1.80 (m, 6H), 2.56–2.80 (m, 4H), 2.90–3.01 (m, 1H), 3.12–3.29 (m, 2H), 3.32–3.58 (m, 1H), 3.73–3.87 (m, 1H), 3.79 (s, 3H), 3.91–4.08 (m, 3H), 6.75 (t, 1H), 6.83 (dd, 1H), 7.16 (t, 1H), 7.62–7.68 (m, 1H), 8.73–8.82 (m, 2H), 10.78 (bs, 1H), 12.70 (bd, 1H); MS ($DCI/NH_3$) m/e 477 (M+H)+; Analysis calc'd for $C_{26}H_{28}N_4O_3S.HCl.(H_2O)1.5$: C, 57.82; H, 5.97; N, 10.37; found: C, 57.37; H, 5.54; N, 12.28.

EXAMPLE 82

3-[2-((3aR,9bR)cis-6-Methoxy-2,3,3a,4,5,9b-hexahydro-[1H]-benz[e]isoindol-1-yl)ethyl]-pyrido[2,3-h]quinazoline-2,4(1H,3H)-dione hydrochloride 5-Amino-6-quinolinecarbonitrile(1.25g,7.39mmol), prepared by the method of Y. Tomioko, Chem. Pharm. Bull.33(4): 1360,1985 was hydrolyzed to the corresponding acid by treatment with ethanol/NaOH (1:1). The resulting acid (0.9g, 4.7mmol was treated with TMS-diazomethane in $CH_2Cl$ to yield the corresponding ester. Treatment with 0.33 equivalent of triphosgene as described in Example 9E yielded the corresponding isocyanate The resulting isocyanate (0.55g,2.4mmol) and the compound resulting from the Example 9D (0.5g,2mmol) were treated by the procedure described in Example 9E to yield after chromatography in 18:1: l(ehyl acetate:formic acid:water) the title compound (0.25g, 28%) as a free base. It was converted to HCl salt and crystalized from ethanol/ether to yield the title compound as white solid: m.p. >250°; $^1$H NMR (300 MHz, $CDCl_3$) δ9.02 (dd, 1H), 8.91 (d, 1H), 8.32 (d, 1H), 7.9 (d, 1H), 7.48 (m, 1H), 7.06 (m, 1H), 6.68 (m, 2H), 4.39 (t, 2H), 3.8 (s, 3H), 3.42 (m, 3H), 2.9 (t, 2H), 2.5–2.75 (m, 3H), 2.38 (m, 2H), 1.5–1.8 (m, 2H); MS ($DCI(NH_3)$) m/e 443(M+H); Analysis calc'd for $C_{26}H_{26}N_4O_3.2HCl$: C, 60.59; H, 5.48; N, 10.87; found: C, 60.10; H, 5.55; N, 10.55.

EXAMPLE 83

3-[2-((3aR,9bR)cis-6-Methoxy-2,3,3a,4,5,9b-hexahydro-[1H]-benz[e]isoindol-1-yl)ethyl]-pyrido[3,2-h]quinazoline-2,4(1H,3H)-dione hydrochloride Following the procedure described in Example 82, 8-amino-7-methoxycarbonylquinoline, prepared by substituting 5-nitroquinoline with 8nitroquinoline, was treated with 0.33 equiv. of triphosgene as described in Example 9E. The resulting isocyanate((0.6g,2.6mmol) and the compound from Example 9D (0.42g, 1.7mmol) were treated by the procedures described in Example 9E to yield the title compound after chromatography.(0.2g,27%): m.p. >250°; $^1$H NMR (300 MHz, $CDCl_3$) δ9.78 (s, 1H), 8.92 (dd, 1H), 8.22 (dd, 1H), 8.14 (s, 1H), 8.11 (d, 1H), 7.62 (dd, 1H), 7.58 (d, 1H), 7.12 (t, 1H), 6.78 (d, 1H), 6.71 (d, 1H), 4.45 (t, 2H), 4.0 (m, 2H), 3.82 (s, 3H), 3.61 (m, 1H), 3.26 (m, 2H), 2.72 (m, 4H), 2.57 (m, 1H), 1.88 (m, 1H), 1.6 (m, 1H); MS (DCI) m/e 443(M+H)+; Analysis calc'd for $C_{26}H_{26}N_4O_3.2HCl$: C, 60.59; H, 5.48; N, 10.87; found: C, 60.10; H, 5.55; N, 10.55.

EXAMPLE 84

3-[2-((3aR,9bR)cis-6-Methoxy-2,3,3a,4,5,9b-hexahydro-[1H]-benz[e]isoindol-1-yl)ethyl]-pyrido[3,4-h]quinazoline-2,4(1H,3H)-dione hydrochloride Following the procedure described Example 82, 5-amino-6-methoxycarbonylisoquinoline(0.35g, 1.74mmol), prepared by substituting 5-nitroquinoline with 5-nitroisoquinoline, was dissolved in 20ml of THF and treated with 1 equiv. of 1.93M solution of phosgene in toluene as described in Example 36. The resulting isocyanate was reacted with the compound resulting from Example 9D (0.42g,1.7mmol) by the procedures described in Example 36 to yield the title compound after the chromatography.(0.12g,15%): $^1$H NMR (300 MHz, CDCl3)(free base) δ9.48 (s, 1H), 8.78 (d, 1H), 8.25 (d, 1H), 8.03 (d, 1H), 7.8 (d, 1H), 7.08 (t, 1H), 6.75 (d, 1H), 6.65 (d, 1H), 4.35 (t, 2H), 3.8 (s, 3H), 3.42 (m, 3H), 2.5–2.95 (m, 5H), 2.38 (m, 2H), 1.74 (m, 1H), 1.58 (m, 1H); Analysis calc'd for $C_{26}H_{26}N_4O_3.2HCl.1.5C_2H_5OH$: C, 59.59; H, 6.38; N, 9.58; found: C, 59.11; H, 5.80; N, 9.23.

EXAMPLE 85

3-[2-(cis-(3.aR,9bR)-6-Methoxy-2,3,3a,4,5,9b-hexahydro-[1H]-benz[e]isoindol-1-yl)ethyl]-pyrazino[2',3':4,5]pyrrolo[3,2-d]pyrimidine-2,4(1H,3H)-dione hydrochloride

EXAMPLE 85A

5-Methyl-6-carboethoxy-7-amino-1H-pyrrolo[2,3-b]pyrazine

2-Chloro-3-cyanopyrazine (0.808 g, 5.79 mmol), prepared by the method of Shneller, et. al., J. Het. Chem., 12:513 (1975), was dissolved in 30 ml DMF under nitrogen and treated with sarcosine ethyl ester hydrochloride (0.978 g, 6.37 mmol) followed by $K_2CO_3$ (1.68 g, 12.16 mmol) at rt. The reaction mixture was gently refluxed for 36 h after which the cooled solution was partitioned between water and $CHCl_3$. The aqueous phase was extracted with $CHCl_3$ and the combined organics washed with water then brine and dried over $Na_2SO_4$. Concentration gave a green-black oil that was purified by chromatography on silica gel eluting with a gradient from 3:1 to 1:1 hexanes:ethyl acetate to give 0.40 g (31%) of the title compound as an orange solid. mp: 119°–121° C. $^1$H NMR (300 MHz, $CDCl_3$) δ1.47 (t, 3H), 4.01 (s, 3H), 4.46 (q, 2H), 5.65 (br s, 2H), 8.32 (d, 1H), 8.38 (d, 1H). MS ($DCI/NH_3$) m/e 220 (M+H)$^+$. Analysis calc'd. for C10H12N4O2: C, 54.54; H, 5.49; N, 25.44; Found: C, 54.29; H, 5.52; N, 25.42.

EXAMPLE 85B

3-[2-(cis-(3aR,9bR)-6-Methoxy-2,3,3a,4,5,9b-hexahydro-[1H]-benz[e]isoindol-1-yl)ethyl]-pyrazino[2',3':4,5]pyrrolo[3,2-d]pyrimidine-2,4(1H,3H)-dione hydrochloride The compound resulting from Example 85A (0.375 g, 1.70 mmol) was combined with triphosgene (0.500 g, 1.70 mmol) in 40 ml 1:1 THF:toluene under nitrogen and refluxed for 14 h. The solvent was removed and the resulting white solid isocyanate was dissolved in 40 ml 1:1 THF:toluene and treated with triethylamine (0.47 ml, 3.40 mmol) followed by a 5 ml THF solution of the compound resulting from example 9D (0.398 g, 1.62 mmol). This mixture was refluxed for 16 h, allowed to cool and then treated with 1.2 ml (1.20 mmol) of 1M KOt-Bu in THF. The reaction mixture was partitioned between water and $CHCl_3$. The aqueous phase was extracted with CHCl3 and the combined organics washed with water then brine and dried over $Na_2SO_4$. Concentration gave a yellow solid that was convened to the HCl salt which was recrystallized from boiling ethanol to give the title compound (0.225 g, 29%). mp: 300°–302° C. $^1$H NMR (300 MHz, DMSO-$d_6$) δ1.63 (m, 1H), 1.80 (m, 1H), 2.30–2.87 (m, 3H), 3.02 (m, 1H), 3.34–3.90 (m, 4H), 3.78 (s, 3H), 3.97–4.22 (m, 2H), 4.10 (s, 3H), 4.30 (m, 2H), 6.76 (d, 1H), 6.85 (d, 1H), 7.18 (t, 1H), 8.64 (s, 2H), 12.49 (s, 1H). HRFAB calc'd. for $C_{24}H_{27}N_6O_3$: 447.2145; Found: 447.2144. Analysis calc'd. for $C_{24}H_{26}N_6O_3$-HCl-0.25$H_2O$: C, 59.13; H, 5.69; N, 17.24; Found: C, 59.16; H, 5.72; N, 16.77.

EXAMPLE 86

3-[2-(cis-(3aR,9bR)-6-Methoxy-2,3,3a,4,5,9b-hexahydro-[1H]-benz[e]isoindol-1-yl)ethyl]-pyrido[3',2':4,5]pyrrolo[3,2-d]pyrimidine-2,4(1H,3H)-dione dihydrochloride

EXAMPLE 86A

1-Methyl-2-carboethoxy-3-amino-1H-pyrrole[2 3-b]pyridine

2-Chloro-3-cyanopyridine (2.00 g, 14.43 mmol) was treated with sarcosine ethyl ester hydrochloride (3.32 g, 21.65 mmol) and potassium carbonate (6.98 g, 50.52 mmol) in DMF as described in Example 85A to yield the title compound (1.04 g, 33%) as an orange solid. mp: 123°–126° C. $^1$H NMR(300MHz, $CDCl_3$) δ1.45 (t, 3H), 4.00 (s, 3H), 4.43 (q, 2H), 4.95 (br s, 2H), 6.97 (dd, 1H), 7.88 (dd, 1H), 8.46 (dd, 1H). MS ($DCI/NH_3$) m/e 220 (M+H)$^+$.

EXAMPLE 86B

3-[2-(cis-(3aR,9bR)-6-Methoxy-2,3,3a,4,5,9b-hexahydro-[1H]-benz[e]isoindol-1-yl)ethyl]-pyrido[3',2':4,5]pyrrolo[3,2-d]pyrimidine-2,4(1H,3H)-dione dihydrochloride The compound resulting from Example 86A was treated with triphosgene (0.365 g, 1.23 mmol) as described in example Example 85B. The resulting isocyanate was further treated with triethylamine (0.46 ml, 3.28 mmol) and the compound resulting from example 9D (0.385 g, 1.56 mmol) and finally with 2.0 ml 1M KOt-Bu in THF according to Example 85B to yield 0.35 g of the HCl salt as yellow solid. mp: 232°–235° C. $^1$H NMR (300 MHz, DMSO-$d_6$) δ5 1.63 (m, 1H), 1.79 (m, 1H), 2.30–2.86 (m, 3H), 3.01 (m, 1H), 3.35–3.60 (m, 3H), 3.60–3.90 (m, 1H), 3.78 (s, 3H), 3.96–4.40 (m, 4H), 4.07 (s, 3H), 6.75 (d, 1H), 6.84 (d, 1H), 7.18 (t, 1H), 7.27 (m, 1H), 8.43 (m, 1H), 8.58 (m, 1H), 12.34 (br s, 1H). HRFAB calc'd. for $C_{25}H_{28}N_5O_3$: 446.2192; Found: 446.2183. Analysis calc'd. for $C_{25}H_{27}N_5O_3$-2HCl-0.5$H_2O$: C, 56.93; H, 5.73; N, 13.28; Found: C, 57.20; H, 5.61; N, 13.22.

EXAMPLE 87

3-[2-(cis-(3aR,9bR)-6-Methoxy-2,3,3a,4,5,9b-hexahydro-[1H]-benz[e]isoindol-1-yl)ethyl]-pyrazino[2',3':4,5]furo[3,2-d]pyrimidine-2,4(1H,3H)-dione hydrochloride

EXAMPLE 87A

6-Carbomethoxy-7-amino-1H-furo[2,3-b]pyrazine

2-Chloro-3-cyanopyrazine (0.751 g, 5.38 mmol) was treated with methyl glycolate (0.533 g, 5.92 mmol) and potassium carbonate (1.12 g, 8.07 mmol) in 20 ml DMF as described in Example 85A. Column chromatograhpy on silica gel eluting with 1:1 hexanes:ethyl acetate gave the title compound (0.33 g, 32%) as a yellow solid. $^1$H NMR (300 MHz, CDCl3) δ4.02 (s, 3H), 5.29 (br s, 2H), 8.47 (d, 1H), 8.56 (d, 1H). MS ($DCI/NH_3$) m/e 194 (M+H)$^+$, 211 (M+$NH_4$)$^+$.

EXAMPLE 87B

3-[2-(Cis-(3aR,9bR)-6-Methoxy-2,3,3a,4,5,9b-hexahydro-[1H]-benz[e]isoindol-1-yl)ethyl]-pyrazino[2',3':4,5]furo[3,2-d]pyrimidine-2,4(1H,3H)-dione hydrochloride The compound resulting from Example 87A (0.32 g, 1.65 mmol) was combined with triphosgene (0.490 g, 1.65 mmol) in 40 ml 1:1 THF:toluene under nitrogen and refluxed for 14 h. The solvent was removed and the resulting white solid isocyanate was dissolved in 40 ml 1:1 THF:toluene and treated with triethylamine (0.34 ml, 2.50 mmol) followed by a 5 ml THF solution of the compound resulting from Example 9D (0.406 g, 1.65 mmol). This mixture was refluxed for 12 h, allowed to cool and filtered. The filtrate was concentrated to give a solid that was converted to its HCl salt. Trituration in boiling ethanol gave the title compound (0.258 g, 33%) as an offwhite solid. mp: 310°–312° C. $^1$H NMR (300 MHz, DMSO-$d_6$) δ1.62 (m, 1H), 1.80 (m,1H), 2.30–2.87 (m, 3H), 3.02 (m, 1H), 3.42–3.60 (m, 4H), 3.78 (s, 3H), 4.01 (m, 1H), 4.13 (m, 1H), 4.28 (m, 2H), 6.75 (d, 1H), 6.84 (d, 1H), 7.17 (t, 1H), 8.74 (d, 1H), 8.82 (d, 1H), 12.91 (br s, 1H). HRFAB calc'd. for $C_{23}H_{24}N_5O_4$: 434.1828; Found: 434.1830. Analysis calc'd. for $C_{23}H_{23}N_5O_4$-HCl-0.5$H_2O$: C, 57.68; H, 5.26; N, 14.62; Found: C, 58.01; H, 5.33; N, 14.44.

EXAMPLE 88

3-[2-(cis-(3aR,9bR)-6-Methoxy-2,3,3a,4,5,9b-hexahydro-[1H]-benz[e]isoindol-1-yl)ethyl]-7-chloro-pyrazino[2',3':4,5]thieno[3,2-d]pyrimidine-2,4(1H,3H)-dione hydrochloride

EXAMPLE 88A

2-Chloro-3-cyano-pyridne-1-oxide

2-Chloro-3-cyanopyrazine (5.00 g, 35.94 mmol) was dissolved in 35 ml concentrated $H_2SO_4$ under nitrogen and cooled to 0° C. To this was added 11.65 g (43.95 mmol) $K_2S_2O_8$ portionwise. The flask was fitted with a $CaCl_2$ drying tube, the reaction mixture allowed to warm to rt and stir for 24 h. After partitioning between $CHCl_3$ and ice water, the separated aqueous phase was extracted with $CHCl_3$. The combined organics were washed with water, saturated $NaHCO_3$, brine and dried over $MgSO_4$. Concentration gave 2.01 g (36%) of the title compound as an offwhite solid. $^1$H NMR (300 MHz, $CDCl_3$) $\delta$8.12 (d, 1H), 8.38 (d, 1H). MS (DCI/$NH_3$) m/e 173 (M+$NH_4$)+.

EXAMPLE 88B

Ethyl-3-aminothieno[2,3-b]pyrazine-2-carboxylate-7-oxide

The compound resulting from Example 88A (2.90 g, 18.64 mmol) was dissolved in 100 ml DMF under nitrogen and treated with ethyl thioglycolate (2.24 g, s 18.64 mmol). After cooling the solution to 0° C., it was treated with solid NaOEt (2.54 g, 37.29 mmol) allowed to warm to rt and then stirred for 13 h. The reaction mixture was partitioned between ethyl acetate and brine and the layers separated. After extracting the aqueous phase with ethyl acetate, the combined organics were washed With water, brine and dried over $MgSO_4$. Concentration gave a yellow solid that was purified by column chromatography on silica gel eluting with 2:1 then 1:1 hexanes:ethyl acetate to yield 3.50 g (78%) of the title compound as a yellow solid. mp: 126–127. $^1$H NMR (300 MHz, $CDCl_3$) $\delta$1.40 (t, 3H), 4.38 (q, 2H), 7.25 (br s, 2H), 8.02 (d, 1H), 8.41 (d, 1H). MS (DCI/$NH_3$) m/e 240 (M+H)$^+$, 257 (M+$NH_4$)$^+$. Analysis calc'd. for $C_9H_9N_3O_3S$: C, 45.18; H, 3.79; N, 17.%; Found: C, 44.94; H, 3.77; N, 17.47.

EXAMPLE 88C

Ethyl -3-amino-6-chloro-thieno[2,3-b]pyrazine-2-carboxylate

The compound resulting from Example 88B (0.88 g, 3.68 mmol) was dissolved in 50 ml $POCl_3$ under nitrogen and heated to 95° C. for 3 h. The reaction mixture was concentrated and partitioned between ethyl acetate and water. After extracting the aqueous phase with ethyl acetate, the combined organics were washed with water, saturated $NaHCO_3$, brine and dried over $Na_2SO_4$. Concentration gave a two component mixture that was separated by column chromatography on silica gel using a gradient elution from 10:1 to 1:1 hexanes:ethyl acetate to give 0.56 g (59%) of the title compound and 0.30 g (34%)starting material. $^1$H NMR (300 MHz, $CDCl_3$) $\delta$1.41 (t, 3H), 4.40 (q, 2H), 6.11 (br s, 2H), 8.60 (s, 1H). MS (DCI/$NH_3$) m/e 258 (M+H)$^+$, 275 (M+$NH_4$)$^+$.

EXAMPLE 88D

3-[2-(cis-(3aR,9bR)-6-Methoxy-2,3,3a,4,5,9b-hexahydro-[1H]-benz[e]isoindol-1-yl)ethyl]-7-chloro-pyrazino[2',3':4,5]thieno[3,2-d]pyrimidine-2,4(1H,3H)-dione hydrochloride The compound resulting from Example 88C (0.420 g, 1.63 mmol) was treated with triphosgene (0.484 g, 1.63 mmol) as described in Example 85B. The resulting isocyanate was treated with triethylamine (0.32 g, 3.20 mmol) and the compound resulting from Example 9D (0.394 g, 1.60 mmol) as described. Recrystallization of the HCl salt from boiling ethanol gave 0.394 g (47%) of the title compound as a yellow solid. mp: 262°–265° C. $^1$H NMR (300 MHz, DMSO-$d_6$) $\delta$1.61 (m, 1H), 1.79 (m, 1H), 2.35–2.90 (m, 3H), 3.02 (m, 1H), 3.41–3.65 (m, 4H), 3.77 (s, 3H), 4.01 (m, 1H), 4.12 (m, 1H), 4.39 (m, 2H), 6.75 (d, 1H), 6.84 (d, 1H), 7.17 (t, 1H), 9.04 (s, 1H), 13.03 (br s, 1H). MS (DCI/$NH_3$)m/e 484 (M+H)$^+$. Analysis calc'd. for C23H22N5O3SCl-HCl.0.75 $H_2O$: C, 51.74; H, 4.63; N, 13.12; Found: C, 51.73; H, 4.30; N, 12.93.

EXAMPLE 89

3-[2-(cis-(3aR,9bR)-6-Methoxy-2,3,3a,4,5,9b-hexahydro-[1H]-benz[e]isoindol-1-yl)ethyl]-7-methoxy-pyrazino [2',3':4,5]thieno[3,2-d]pyrimidine-2,4(1H,3H)-dione hydrochloride

EXAMPLE 89A

Ethyl-3-amino-6-methxoy-thieno[2,3-b]pyrazine-2-carboxylate

The compound resulting from Example 88C (0.700 g, 2.72 mmol) was dissolved in 75 ml MeOH, treated with solid NaOMe (1.47 g, 27.2 mmol) and the resulting solution refluxed for 12 h. The reaction mixture was partitioned between saturated $NH_4Cl$ and $CHCl_3$. After extracting the aqueous phase with $CHCl_3$, the combined organics were washed with water then brine and dried over $Na_2SO_4$. Concentration gave 0.500 g (77%) pure title compound as a yellow solid. mp: 181°–182° C. $^1$H NMR (300 MHz, $CDCl_3$) $\delta$3.92 (s, 3H), 4.05 (s, 3H), 6.02 (br s, 2H), 8.30 (s, 1H). MS (DCI/$NH_3$) m/e 240 (M+H)$^+$, 257 (M+$NH_4$)$^+$. Analysis calc'd. for $C_9H_9N_3O_3S$: C, 45.18; H, 3.79; N, 17.56; Found: C, 45.25; H, 3.48; N, 17.41.

EXAMPLE 89B

3-[2-(cis-(3aR,9bR)-6-Methoxy-2,3,3a,4,5,9b-hexahydro-[1H]-benz[e]isoindol-1-yl)ethyl]-7-methoxy-pyrazino[2',3':4,5]thieno[3,2-d]pyrimidine-2,4(1H,3H)-dione hydrochloride The compound resulting from Example 89A (0.400 g, 1.67 mmol) was treated with triphosgene (0.50 g, 1.67 mmol) as described in Example 85B. The resulting isocyanate was treated with triethylamine (0.25 g, 2.50 mmol) and the compound resulting from Example 9D (0.411 g, 1.67 mmol) as described. Trituration of the HCl salt in boiling ethanol gave 0.457 g (56%) of the title compound as a tan solid. mp: 243°–245° C. $^1$H NMR (300 MHz, DMSO-$d_6$) $\delta$1.63 (m, 1H), 1.80 (m, 1H), 2.42 (m, 1H), 2.58–2.86 (m, 2H), 3.02 (m, 1H), 3.37–3.91 (m, 4H), 3.79 (s, 3H), 3.91–4.20 (m, 2H), 4.10 (s, 3H), 4.30 (m, 2H), 6.75 (d, 1H), 6.84 (d, 1H), 7.17 (t, 1H), 8.56 (s, 1H), 12.77 (s, 1H). HRFAB calc'd. for $C_{24}H_{26}N_5O_4$: 480.1706; Found: 480.1710. Analysis calc'd. for $C_{24}H_{25}N_5O_4S$-HCl.0.5$H_2O$: C, 54.90; H, 5.18; N, 13.34; Found: C, 55.02; H, 5.04; N, 13.43.

EXAMPLE 90

3-[2-(cis-(3aR,9bR)-6-Methoxy-2,3,3a,4,5,9b-hexahydro-[1H]-benz[e]isoindol-1-yl)ethyl]-5-isopropyl-pyrazino[2',3':4,5]thieno[3,2d]pyrimidine-2,4(1H,3H)-dione hydrochloride

EXAMPLE 90A

Ethyl 3-(N-isopropyl)aminothieno[2,3-b]pyrazine-2-carboxylate

Ethyl 3-aminothieno[2,3-b]pyrazine-2-carboxylate (0.500 g, 2.24 mmol) was dissolved in 15 ml THF under nitrogen. The solution was cooled to −78° C and dropwise treated with 4.9 ml 0.5M KHMDS in toluene (2.46 mmol). The resulting purple reaction mixture was allowed to warm to rt, treated with 2-iodopropane (0.46 s g, 2.69 mmol) and then brought to reflux for 48h. After the addition of 1 ml EtOH, the reaction mixture was concentrated and applied directly to a silica gel column. Elution with a solvent gradient from 10:1 to 4:1 hexanes: ethyl acetate gave the title compound (0.210 g, 35%). $^1$H NMR (300 MHz, CDCl3) δ1.30 (d, 6H), 1.40 (t, 3H), 4.37 (q, 2H), 5.27 (dh, 1H), 7.42 (br d, 1H), 8.55 (d, 1H), 8.58 (d, 1H). MS (DCI/NH$_3$) m/e 266 (M+H).

EXAMPLE 90B

Ethyl 3-(N-isopropyl-N-chlorocarbamoyl)aminothieno[2,3-b]pyrazine-2-carboxylate

A CH$_2$Cl$_2$ solution of the compound resulting from Example 90A (0.200 g, 0.754 mmol) was cooled to 0° C. and sequentially treated with triethylamine (0.19 g, 1.88 mmol) and phosgene (1.20 ml of a 20% solution in toluene, 2.26 mmol). The reaction mixture was allowed to warm to rt and stir for 15 h. The reaction mixture was concentrated and applied directly to a silica gel column. Elution with a solvent gradient from 10:1 to 5:1 hexanes: ethyl acetate gave the title compound (0.206 g, 83%) as a colorless oil. $^1$H NMR (300 MHz, CDCl$_3$) δ1.23 (d, 3H), 1.39 (d, 3H), 1.46 (t, 3H), 4.50 (m, 3H), 8.71 (d, 1H), 8.83 (d, 1H). MS (DCI/NH$_3$) m/e 328 (M+H)$^+$, 345 (M+NH$_4$)$^+$.

EXAMPLE 90C

3-[2-(cis-(3aR,9bR)-6-Methoxy-2,3,3a,4,5,9b-hexahydro-[1H]-benz[e]isoindol-1-yl)ethyl]-5-isopropyl-pyrazino[2',3':4,5]thieno[3,2-d]pyrimidine-2,4(1H,3H)-dione hydrochloride The compound resulting from Example 90B (0.200 g, 0.610 mmol) was dissolved in 15 ml toluene and treated with triethylamine followed by the compound resulting from Example 9D (0.150 g, 0.610 mmOl). After refluxing for 3 h, the reaction mixture was concentrated and applied directly to a silica gel column. Elution with 18:1:1 ethyl acetate:water:formic acid gave the title compound. Conversion to the HCl salt gave 0.188 g (58%) of a tan solid. mp: 286°–288° C. $^1$H NMR (300 MHz, DMSO-d6) δ1.55–1.70 (m, 7H), 1.80 (m, 1H), 2.35–2.85 (m, 3H), 3.04 (m, 1H), 3.40–3.65 (m, 4H), 3.78 (s, 3H), 4.00 (m, 1H), 4.14 (m, 1H), 4.32 (m, 2H), 6.57 (m, 1H), 6.75 (br d, 1H), 6.84 (br d, 1H), 7.17 (t, 1H), 8.93 (m, 1H), 9.01 (m, 1H). HRFAB calc'd. for C$_{26}$H$_{30}$N$_5$O$_3$S: 492.2069; Found: 492.2079. Analysis calc'd. for C$_{26}$H$_{29}$N$_5$O$_3$S-HCl.0.25 H$_2$O: C, 58.64; H, 5.77; N, 13.15; Found: C, 58.65; H, 5.53; N, 13.05.

EXAMPLE 91

3-[2-(cis-(3aR,9bR)-6-Methoxy-2.3 .3a,4,5,9b-hexahydro-[1H]-benz[e]isoindol-1-yl)ethyl]-7-phenyl-pyrazino[2',3':4,5]thieno[3,2-d]pyrimidine-2,4(1H,3H)-dione hydrochloride

EXAMPLE 91A

3-Cyano-2-chloro-6-phenylpyrazine

3-Carboxamido-2-hydroxy-6-phenylpyrazine (7.56 g, 35.13 mmol), prepared by the method of Dick and Wood, J. Chem. Soc., xx: 1379 (1955), was suspended in triethylamine (7. 11 g, 70.26 mmol), cooled to 0° C. and dissolved in 50 ml POCl$_3$. The mixture was refluxed for 3 h before concentrating in vacuo. The resulting black oil was extracted 5×100 ml Et2O and the combined extracts treated with 250 ml cold 10% Na$_2$CO$_3$. The layers were separated and the organic phase washed with water, brine and dried over Na$_2$SO$_4$. Concentration gave the title compound (3.20 g, 42%) as a tan solid. mp: 143°–145° C. $^1$H NMR (300 MHz, CDCl$_3$) δ7.57 (m, 3H), 8.10 (m, 2H), 9.05 (s, 1H). MS (DCI/NH$_3$) m/e 233 (M+NH$_4$)$^+$.

EXAMPLE 91B

Ethyl-3-amino-6-phenyl-thieno[2,3-b]pyrazine-2-carboxylate

The compound resulting from Example 91A (1.00 g, 4.65 mmol) was treated as described in example 41A with ethyl thioglycolate (0.56 g, 4.65 mmol) and Na$_2$CO$_3$ (0.49 g, 4.65 mmol) in 20 ml EtOH. Recrystallization of the crude product from EtOH/H$_2$O gave the title compound (1.19 g, 86%) as a yellow-green solid. mp: 173°–175° C. $^1$H NMR (300 MHz, CDCl$_3$) δ1.42 (t, 3H), 4.41 (q, 2H), 6.18 (br s, 2H), 7.55 (m, 3H), 8.12 (m, 2H), 9.03 (s, 1H). MS (DCI/NH$_3$) m/e 300 (M+H)$^+$.

EXAMPLE 91C

3-[2,(cis.(3aR,9bR)-6-Methoxy-2,3,3a,4,5,9b-hexahydro-[1H]-benz[e]isoindol-1-yl)ethyl]-7-phenyl-pyrazino[2',3':4,5]thieno[3,2-d]pyrimidine-2,4(1H,3H)-dione hydrochloride The compound resulting from Example 91B (0.710 g, 2.37 mmol) was treated with triphosgene (0.700 g, 2.37 mmol) as described in Example 85B. The resulting isocyanate was treated with triethylamine (0.48 g, 4.74 mmol) and the compound resulting from Example 9D (0.550 g, 2.25 mmol) as described. Trituration of the HCl salt in boiling ethanol and filtration gave 0.435 g (33%) of the title compound as a yellow-green solid. mp: 3 10°–311° C. $^1$H NMR (300 MHz, DMSO-d$_6$) δ1.63 (m, 1H), 1.80 (m, 1H), 2.35–2.90 (m, 3H), 3.04 (m, 1H), 3.44–3.65 (m, 4H), 3.78 (s, 3H), 4.03 (m, 1H), 4.15 (m, 1H), 4.30 (m, 2H), 6.75 (d, 1H), 6.84 (d, 1H), 7.17 (t, 1H), 7.61 (m, 3H), 8.33 (m, 2H), 9.59 (s, 1H), 13.03 (br s, 1H). MS (DCI/NH$_3$) m/e 526 (M+H)$^+$. Analysis calc'd. for C$_{29}$H$_{27}$N$_5$O$_3$S-HCl: C, 61.97; H, 5.02; N, 12.46; Found: C, 61.75; H, 5.01; N, 12.29.

EXAMPLE 92

3-[2-(cis-(3aR,9bR)-6-Methoxy -2,3,3a,4,5,9b-hexahydro-[1H]-benz[e]isoindol-1-yl)ethyl]-7-methyl-pyrazino[2',3':4,5]thieno[3,2-d]pyrimidine-2,4(1H,3H)-dione hydrochloride

EXAMPLE 92A

3-Cyano-2-chloro-6-methyl-pyrazine

3-Carboxamido-2-hydroxy-6-methylpyrazine (4.09 g, 26.70 mmol), prepared by the method of Dick and Wood, J. Chem. Soc.,1379 (1955), was treated as described in Example 91A with triethylamine (5.41 g, 53.41 mmol) and 70 ml POCl$_3$ to yield the title compound (3.16 g, 77%) as a fluffy yellow solid. mp: 63°–65° C. $^1$H NMR (300 MHz, CDCl3) δ2.70 (s, 3H), 8.50 (s, 1H). MS (DCI/NH$_3$) m/e 171 (M+NH$_4$)$^+$.

EXAMPLE 92B

Ethyl-3-amino-6-methyl-thieno[2,3-b]pyrazine-2-carboxylate

The compound resulting from Example 92A (1.00 g, 6.51 mmol) was treated as described in Example 41A with ethyl thioglycolate (0.782 g, 6.51 mmol) and $Na_2CO_3$ (0.69 g, 6.51 mmol) in 20 ml EtOH. Recrystallization of the crude product from $EtOH/H_2O$ gave the title compound (1.12 g, 72%) as a bright yellow solid. mp: 121°–123° C. $^1$H NMR (300 MHz, $CDCl_3$) δ1.41 (t, 3H), 2.71 (s, 3H), 4.38 (q, 2H), 6.15 (br s, 2H), 8.45 (s, 1H). MS ($DCI/NH_3$) m/e 238 $(M+H)^+$, 255 $(M+NH_4)^+$. Analysis calc'd. for $C_{10}H_{11}N_3O_2S$: C, 50.62; H, 4.67; N, 17.71; Found: C, 50.75; H, 4.45; N, 17.70.

EXAMPLE 92C

3-[2-(cis-(3aR,9bR)-6-Methoxy-2,3,3a,4,5,9b-hexahydro-[1H]-benz[e]isoindol-1-yl)ethyl]-7-methyl-pyrazino[2',3':4,5]thieno[3,2-d]pyrimidine-2,4(1H,3H)-dione hydrochloride The compound resulting from Example 92B (0.275 g, 1.16 mmol) was treated with triphosgene (0.344 g, 1.16 mmol) as described in Example 85B. The resulting isocyanate was treated with triethylamine (0.23 g, 2.28 mmol) and the compound resulting from Example 9D (0.280 g, 1.14 mmol) as described. Column chromatography of the crude concentrate on silica gel eluting with 18:1:1 ethyl acetate:water:formic acid gave the title compound. Coversion to the HCl salt gave 0.281 g (49%) of tan solid. mp: 264°–265° C. $^1$H NMR (300 MHz, DMSO-$d_6$) δ1.61 (m, 1H), 1.80 (m, 1H), 2.37–2.83 (m, 3H), 2.73 (s, 3H), 3.03 (m, 1H), 3.44–3.63 (m, 4H), 3.77 (s, 3H), 4.02 (m, 1H), 4.13 (m, 1H), 4.28 (m, 2H), 6.74 (d, 1H), 6.84 (d, 1H), 7.17 (t, 1H), 8.88 (s, 1H), 12.95 (s, 1H). MS ($DCI/NH_3$) m/e 464 $(M+H)^+$. Analysis calc'd. for $C_{24}H_{25}N_5O_3S \cdot HCl \cdot 1.50H_2O$: C, 54.69; H, 5.55; N, 13.29; Found: C, 54.83; H, 5.24; N, 13.24.

EXAMPLE 93

3-[2-(cis-(3aR,9bR)-6-Methoxy-2,3,3a,4,5,9b-hexahydro-[1H]-benz[e]isoindol-1-yl)ethyl]-7,8-diethyl-pyrazino[2',3':4,5]thieno[3,2-d]pyrimidine-2,4(1H,3H)-dione hydrochloride

EXAMPLE 93A

3-Carboxamido-2-hydroxy-5,6-diethyl)pyrazine 3,4-hexadione (8.77 g, 76.85 mmol) and aminomalonamide (7.50 g, 64.04 mmol) were dissolved in 50 ml $H_2O$ and heated on a steam bath for 3 h. After cooling overnight, the resulting crystals were collected, crushed and dried in vacuo to give 1.97 g (16%) of the title compound as a buff solid. mp: 95°–97° C. $^1$H NMR (300 MHz, DMSO-$d_6$) δ1.20 (m, 6H), 2.78 (m, 4H), 8.33 (br s, 1H), 8.44 (br s, 1H), 13.03 (s, 1H). MS ($DCI/NH_3$) m/e 196 $(M+H)^+$, 213 $(M+NH_4)^+$.

EXAMPLE 93B

3-Cyano-2-chloro-5,6-diethylpyrazine

The compound resulting from Example 93A (1.77 g, 9.07 mmol) was treated as described in Example 91A with triethylamine (2.75 g, 27.20 mmol) and 50 ml $POCl_3$ to yield the title compound (1.24 g, 70%) as a brown oil. $^1$H NMR (300 MHz, CDCl3) δ1.33 (t, 3H), 1.35 (t, 3H), 2.88 (q, 2H), 2.91 (q, 2H). MS ($DCI/NH_3$) m/e 196 $(M+H)^+$, 213 $(M+NH_4)^+$.

EXAMPLE 93C

Ethyl-3-amino-5,6-diethyl-thieno[2,3-b]pyrazine-2-carboxylate

The compound resulting from Example 93B (1.21 g, 6.18 mmol) was combined with ethyl thioglycolate (0.743 g, 6.18 mmol) and $Na_2CO_3$ (0.66 g, 6.18 mmol) in 30 ml EtOH and refluxed for 16h. The reaction mixture was cooled, partitioned between $CHCl_3$ and saturated $NH_4Cl$ and the layers separated. The organic phase was washed with water then brine and dried over $MgSO_4$. Concentration gave a brown oil that was purified by column chromatography on silica gel eluting first with 10:1 then 5:1 hexanes:ethyl acetate to give the title compound (1.24 g, 72%) as a yellow solid. mp: 96°–99° C. $^1$H NMR (300 MHz, $CDCl_3$) δ1.36 (t, 3H), 1.39 (t, 3H), 1.41 (t, 3H), 2.95 (q, 2H), 2.98 (q, 2H), 4.39 (q, 2H), 6.14 (br s, 2H). MS ($DCI/NH_3$) m/e 280 $(M+H)^+$, 297 $(M+NH_4)^+$. Analysis calc'd. for $C_{13}H_{17}N_3O_2S$: C, 55.89; H, 6.13; N, 15.04; Found: C, 55.81; H, 6.05; N, 14.79.

EXAMPLE 93D

3-[2-(cis-(3aR,9bR)-6-Methoxy-2,3,3a,4,5,9b-hexahydro-[1H]-benz[e]isoindol-1-yl)ethyl]-7,8-diethyl-pyrazino[2',3':4,5]thieno[3,2-d]pyrimidine-2,4(1H,3H)-dione hydrochloride The compound resulting from Example 93C (0.500 g, 1.79 mmol) was treated with triphosgene (0.530 g, 1.79 mmol) as described in Example 85B. The resulting isocyanate was treated with triethylamine (0.36 g, 3.58 mmol) and the compound resulting from Example 9D (0.418 g, 1.70 mmol) as described. Column chromatography of the crude concentrate on silica gel eluting with 18:1:1 ethyl acetate:water:formic acid gave the title compound. Conversion to the HCl salt and recrystallization from EtOH/Et2O gave the title compound (0.316 g, 35%) as a white solid. mp: 183°–186° C. $^1$H NMR (300 MHz, DMSO-$d_6$) δ1.32 (t, 3H), 1.37 (t, 3H), 1.60 (m, 1H), 1.78 (m, 1H), 2.43 (m, 1H), 2.57–2.85 (m, 2H), 2.95 (m, 1H), 3.03 (q, 2H), 3.05 (q, 2H), 3.40–3.60 (m, 4H), 3.78 (s, 3H), 3.80–4.20 (m, 2H), 4.27 (m, 2H), 6.76 (br d, 1H), 6.84 (d, 1H), 7.12 (t, 1H). MS ($DCI/NH_3$) m/e 506, $(M+H)^+$. Analysis calc'd. for $C_{27}H_{31}N_5O_3S \cdot HCl \cdot 1.0H_2O$: C, 57.90; H, 6.12; N, 12.50; Found: C, 57.79; H, 5.95; N, 12.44.

EXAMPLE 94

3-[2-(cis-(3aR,9bR)-6-Methoxy-2,3,3.a.,4,5,9b-hexahydro-[1H]-benz[e]isoindol-1-yl)ethyl]-1-(2-methoxyethyl)-7-methyl-pyrazino[2',3':45]thieno[3,2-d]pyrimidine-2,4(1H,3H)-dione hydrochloride

EXAMPLE 94A

Ethyl-3-(N-(2-methoxyethyl)amino)-6-methyl-thieno[2,3-b]pyrazine-2-carboxylate

The compound resulting from Example 92B (0.630 g, 2.66 mmol) was treated according to Example 90A with 6.37 ml 0.5M KHMDS in toluene (3.19 mmol) and 2-bromoethyl methyl ether (1.10 g, 7.96 mmol in 40 ml THF. Column chromatography of the crude concentrate on silica gel eluting first with 5:1 then 4:1 hexanes:ethyl acetate gave the title compound (0.360 g, 48%)-followed by starting material (0.160 g, 25%). $^1$H NMR (300 MHz, $CDCl_3$) δ1.40 (t, 3H), 2.68 (s, 3H), 3.42 (s, 3H), 3.63 (t, 2H), 4.31 (q, 2H), 4.37 (q, 2H), 7.70 (br t, 1H), 8.42 (s, 1H). MS ($DCI/NH_3$) m/e 296 $(M+H)^+$.

EXAMPLE 94B

Ethyl 3-(N-(2-methoxyethyl)-N-chlorocarbamoyl) aminothieno[2,3-b]pyrazine-2-carboxylate The compound resulting from Example 94A (0.340 g, 1.20 mmol) was treated with triethylamine (0.36 g, 3.60 mmol) and phosgene (0.37 ml of 20% solution in toluene, 3.60 mmol) as described in Example 90B. Purification by column chromatography on silica gel eluting with a solvent gradient from 3:1 to 1:1 hexanes:ethyl acetate gave the title compound (0.39 g, 91%) as a colorless oil. $^1$H NMR (300 MHz, CDCl$_3$) δ1.46 (t, 3H), 2.78 (s, 3H), 3.12 (s, 3H), 3.54–3.72 (m, 2H), 3.94–4.18 (m, 2H), 4.29–4.56 (m, 2H), 4.47 (q, 2H), 8.68 (s, 1H (DCI/NH$_3$) m/e 358 (M+H)$^+$, 375 (M+NH$_4$)$^+$.

EXAMPLE 94C

3-[2-(cis-(3aR,9bR)-6-Methoxy-2,3,3a,4,5,9b-hexahydro-[1H]-benz[e]isoindol-1-yl)ethyl]-1-(2-methoxyethyl)-7-methyl-pyrazino[2',3':4,5]thieno[3,2-d]pyrimidine-2,4(1H,3H)-dione hydrochloride The compound resulting from Example 94B (0.380 g, 1.06 mmol) was treated with triethylamine (0.107 g, 1.06 mmol) and the compound resulting from Example 9D (0.254 g, 1.03 mmol) as described in Example 85B. Recrystallization of the HCl salt from EtOH gave the title compound (0.263 g, 46%) as a white solid. mp: 222°–224° C. $^1$H NMR (300 MHz, DMSO-d$_6$) δ1.6 1 (m, 1H), 1.79 (m, 1H), 2.56–2.87 (m, 2H), 2.73 (s, 3H), 3.03 (m, 2H), 3.35 (s, 3H), 3.53 (m, 4H), 3.68 (m, 2H), 3.78 (s, 3H), 4.00 (m, 1H), 4.13 (m, 1H), 4.34 (m, 2H), 4.96 (m, 2H), 6.75 (br d, 1H), 6.83 (m, 1H), 7.17 (t, 1H), 8.92 (s, 1H). MS (DCI/NH$_3$) m/e 522 (M+H)$^+$. Analysis calc'd-for C$_{27}$H$_{31}$N$_5$O$_4$S-HCl.0.5 H$_2$O: C, 57.29; H, 5.70; N, 12.37; Found: C, 56.98; H, 5.72; N, 12.21.

EXAMPLE 95

3-[2-(cis-(3aR,9bR)-6-Methoxy-2 3 3a,4,5,9b-hexahydro-[1H]-benz[e]isoindol-1-yl)ethyl]-1-methylpyrazino[2',3':4,5]thieno[3,2-d]pyrimidine-2,4(1H,3H)-dione hydrochloride

EXAMPLE 95A

Ethyl 3-(N-methylamino)thieno[2,3]pyrazine-2-carboxylate

To a stirred suspension of neat NaH (0.82 g, 3.40 mmol) in 10 ml THF at –78° C. was canulated a cold (–78° C.) 20 ml THF solution of ethyl 3-aminothieno[2,3-b]pyrazine-2-carboxylate (0.690 g, 3.09 mmol). The reaction mixture was allowed to warm to rt, stir for 2 h and was then treated with iodomethane (0.460 g, 3.24 mmol). After stirring for 12 h at rt, the mixture was diluted with 5 ml MeOH and concentrated. Purification by column chromatography on silica gel eluting first with 10:1 then 5:1 hexanes:ethyl acetate gave the title compound (0.610 g, 84%) as a yellow solid. $^1$H NMR (300 MHz, CDCl$_3$) δ1.40 (t, 3H), 3.60 (d, 3H), 4.36 (q, 2H), 7.48 (br s, 2H), 8.54 (d, 1H), 8.57 (d, 1H). MS (DCI/NH$_3$) m/e 238 (M+H)$^+$.

EXAMPLE 95B

Ethyl 3-(N-methyl-N-chlorocarbamoylamino)thieno[2,3-b]pyrazine-2-carboxylate

The compound resulting from Example 95A (0.500 g, 2.11 mmol) was treated with triethylamine (0.53 g, 5.27 mmol) and phosgene (3.29 ml of 20% solution in toluene, 6.32 mmol) as described in Example 90B. Purification by column chromatography on silica gel eluting with a solvent gradient from 5:1 to 1:1 hexanes:ethyl acetate gave the title compound (0.58 g, 92%) as a colorless oil. $^1$H NMR (300 MHz, CDCl3) δ5 1.46 (t, 3H), 3.46 (s, 3H), 4.51 (m, 2H), 8.72 (d, 1H), 8.82 (d, 1H). MS (DCI/NH$_3$) m/e 300 (M+H)$^+$, 317 (M+NH$_4$)$^+$.

EXAMPLE 95C

3-[2-(cis-(3aR,9bR)-6-Methoxy-2,3,3a,4,5,9b-hexahydro-[1H]-benz[e]isoindol-1-yl)ethyl]-1-methylpyrazino[2',3':4,5]thieno[3,2-d]pyrimidine-2,4(1H,3H)-dione hydrochloride The compound resulting from Example 95B (0.421 g, 1.40 mmol) was treated with triethylamine (0.170 g, 1.68 mmol) and the compound resulting from Example 9D (0.346 g, 1.40 mmol) as described in Example 85B. Column chromatography of the crude concentrate on silica gel eluting with 18:1:1 ethyl acetate:water:formic acid gave the title compound. Conversion to the HCl salt and recrystallization from EtOH/Et2O gave 0.132 g (20%) of tan solid. mp: 293°–295° C. $^1$H NMR (300 MHz, DMSO-d$_6$) δ1.62 (m, 1H), 1.79 (m, 1H), 2.25–2.90 (m, 3H), 3.02 (m, 2H), 3.27–3.90 (m, 3H), 3.78 (s, 3H), 3.92–4.20 (m, 2H), 4.08 (s, 3H), 4.35 (m, 2H), 6.74 (d, 1H), 6.83 (d, 1H), 7.18 (t, 1H), 8.93 (d, 1H), 9.01 (d, 1H). MS (DCI/NH$_3$) m/e 464 (M+H)$^+$. Analysis calc'd. for C$_{24}$H$_{25}$N$_5$O$_3$S-HCl-H$_2$O: C, 55.65; H, 5.45; N, 13.52; Found: C, 55.87; H, 5.22; N, 13.42.

EXAMPLE 96

3-[2-(cis-(3aR,9bR)-6-Methoxy-2,3,3a,4,5,9b-hexahydro-[1H]-benz[e]isoindol-1-yl)ethyl]-1-benzylpyrazino[2',3':4,5]thieno[3,2-d]pyrimidine-2,4(1H,3H)-dione hydrochloride

EXAMPLE 96A

Ethyl 3-(N-benzylamino)thieno[2,3-b]pyrazine-2-carboxylate

Ethyl 3-aminothieno[2,3-b]pyrazine-2-carboxylate (0.450 g, 2.02 mmol) was treated with neat NaH (0.058 g, 2.42 mmol) and benzyl bromide (0.380 g, 2.22 mmol) as described in Example 94A. Purification by column chromatography on silica gel eluting with a solvent gradient from 10:1 to 3:1 hexanes:ethyl acetate gave the title compound (0.39 g, 62%) as a yellow solid. $^1$H NMR (300 MHz, CDCl$_3$) δ1.39 (t, 3H), 4.37 (q, 2H), 5.38 (d, 2H), 7.19–7.42 (m, 5H), 7.88 (br t, 1H), 8.55 (m, 2H). MS (DCI/NH$_3$) m/e 3 14 (M+H)$^+$.

EXAMPLE 96B

Ethyl 3-(N-benzyl-N-chlorocarbamoylamino)thieno[2,3-b]pyrazine-2-carboxylate

The compound resulting from Example 96A (0.380 g, 1.22 mmol) was treated with triethylamine (0.37 g, 3.66 mmol) and phosgene (1.91 ml of 20% solution in toluene, 3.66 mmol) as described in Example 94B. Purification by column chromatography on silica gel eluting with 5:1 hexanes:ethyl acetate gave the title compound (0.36 g, 76%) as a colorless oil. $^1$H NMR (300 MHz, CDCl3) δ1.32 (t, 3H), 4.13 (m, 1H), 4.35 (m, 1H), 4.92 (d, 1H), 5.18 (d, 1H), 7.18 (m, 5H), 8.68 (d, 1H), 8.76 (d, 1H). MS (DCI/NH$_3$) m/e 376 (M+H)$^+$, 393 (M+NH$_4$)$^+$.

EXAMPLE 96C

3-[2-(cis-(3aR,9bR)-6-Methoxy-2,3,3a,4,5,9b-hexahydro-[1H]-benz[e]isoindol-1-yl)ethyl]-1-benzylpyrazino[2',3':4,5]thieno[3,2-d]pyrimidine-2,4(1H,3H)-dione hydrochloride The compound resulting from Example 96B (0.32 g, 0.825 mmol) was treated with triethylamine (0.084 g, 0.825 mmol) and the compound from Example 9D (0.203 g, 0.825 mmol) as described in Example 85B. Column chromatography of the crude concentrate on silica gel eluting with 18:1:1 ethyl acetate:water:formic acid gave the title compound. Conversion to the HCl salt followed by trituration in boiling EtOH gave 0.255 g (54%) of white solid. mp: 280°–282° C . $^1$H NMR (300 MHz, DMSO-d$_6$) δ1.61 (m, 1H), 1.78 (m, 1H), 2.30–2.88 (m, 3H), 3.03 (m, 1H), 3.53 (m, 4H), 3.78 (s, 3H), 4.00 (m, 1H), 4.11 (m, 1H), 4.35 (m, 2H), 6.00 (m, 2H), 6.73 (d, 1H), 6.83 (d, 1H), 7.16 (t, 1H), 7.25 (m, 3H), 7.38 (m, 2H), 8.89 (d, 1H), 8.92 (d, 1H). MS (DCI/NH$_3$) m/e 540 (M+H)$^+$. Analysis calc'd. for C$_{30}$H$_{29}$N$_5$O$_3$S·HCl: C, 62.55; H, 5.25; N, 12.16; Found: C, 62.31; H, 5.17; N, 11.93.

EXAMPLE 97

3-[2-(cis-(3aR,9bR)-6-Methoxy-2,3,3a,4,5,9b-hexahydro-[1H]-benz[e]isoindol-1-yl)ethyl]-pyrido[3',4':4,5]pyrrolo[3,2-d]pyrimidine-2,4(1H,3H)-dione hydrochloride

EXAMPLE 97A

Ethyl-(4-(3-cyanopyridyl))glycinate

Ethyl glycinate hydrochloride (30.23 g, 216 mmol) and NaHCO$_3$ (12.73 g, 152 mmol) were combined in 200 ml 95% EtOH and refluxed for 1 h. To this was added 4-chloro-3-cyano pyridine (3.00 g, 21.6 mmol) and the reulting mixture refluxed for 13h. The mix was partitioned between Et2O and water and the layers separated. After extracting the aqueous phase with CH$_2$Cl$_2$, the combined organics were washed water then brine and dried over MgSO$_4$. Concentration gave an orange solid that was purified by column chromatography on silica gel eluting with ether to give the title compound (2.25 g, 51%) as well as 1.07 g (36%) starting material. $^1$H NMR (300 MHz, CDCl3) δ1.33 (t, 3H), 4.02 (d, 2H), 4.30 (q, 2H), 5.62 (br t, 1H), 6.44 (d, 1H), 8.38 (d, 1H), 8.50 (s, 1H). MS (DCI/NH$_3$) m/e 206 (M+H)$^+$.

EXAMPLE 97B

Ethyl-3-amino-1H-pyrrolo[3,2-c]pyridine-2-carboxylate.

The compound resulting from Example 97A (2.00 g, 9.75 mmol) was dissolved in 50 ml absolute EtOH under nitrogen and treated with solid NaOEt (0.730 g, 10.72 mmol). The resulting mixture was refluxed for 1 h, diluted with water and extracted with CHCl$_3$. The organic phase was dried over MgSO$_4$, concentrated, and purified by column chromatography on silica gel. Elution with 5% then 10% MeOH in CH$_2$Cl$_2$ gave the title compound as a yellow solid. $^1$H NMR (300 MHz, DMSO-d$_6$) δ1.33 (t, 3H), 4.30 (q, 2H), 6.02 (s, 2H), 7.12 (dd, 1H), 8.17 (d, 1H), 9.02 (s, 1H), 10.88 (s, 1H). MS (DCI/NH$_3$) m/e 206 (M+H)$^+$.

EXAMPLE 97C

3-[2-(cis-(3aR,9bR)-6-Methoxy-2,3,3a,4,5,9b-hexahydro-[1H-benz[e]isoindol-1-yl)ethyl]-pyrido[3',4':4,5]pyrrolo[3,2-d]pyrimidine-2,4(1H,3H)-dione hydrochloride The compound resulting from Example 97B (0.399 g, 1.94 mmol) was treated with triphosgene (0.433 g, 1.45 mmol) as described in Example 39. The resulting isocyanate was treated with triethylamine (0.402 g, 3.97 mmol) and the compound resulting from Example 9D (0.465 g, 1.89 mmol) as described. Column chromatography of the crude concentrate on silica gel eluting with 18:1:1 ethyl acetate:water:formic acid gave the intermediate ester-urea as the formic acid salt (1.07 g, 99%). The formic acid salt was converted to its free base by dissolving in 2 M NH$_3$ in MeOH and evaporating. The residue was dissolved in 75 ml THF under nitrogen and was treated with 5.2 ml of a 1M KOt-Bu solution in THF (5.2 mmol). After 15 min, the reaction was quenched with 5 ml water, concentrated and applied directly to a column of silica gel. Elution with 18:1:1 then 9:1:1 ethyl s acetate:water:formic acid gave 0.96 g (97%) of the title compound as the formic acid salt. This was converted to the HCl salt by treatment with methanolic HCl. mp: >300° C. (dec.). $^1$H NMR (300 MHz, DMSO-d$_6$) δ1.52–1.90 (m, 2H), 2.26–2.88 (m, 3H), 3.02 (m, 1H), 3.21–3.90 (m, 4H), 3.78 (s, 3H), 4.01 (m, 1H), 4.13 (m, 1H), 4.30 (m, 2H), 6.72 (d, 1H), 6.85 (d, 1H), 7.17 (t, 1H), 7.93 (d, 1H), 8.56 (d, 1H), 9.80 (s, 1H), 12.88 (s, 1H,0, 13.85 (br s, 1H). MS (DCI/NH$_3$) m/e 432 (M+H)+. HRCI calc'd. for C$_{24}$H$_{26}$N$_5$O$_3$: 432.2036; Found: 432.2032.

EXAMPLE 98

3-[2-(cis-(3aR,9bR)-6-Methoxy-2,3,3a,4,5,9b-hexahydro-[1H]-benz[e]isoindol-1-yl)ethyl]-1-ethylpyrazino[2',3':4,5]thieno[3,2-d]pyrimidine-2,4(1H,3H)-dione hydrochloride

EXAMPLE 98A

Ethyl 3-(N-ethylamino)thieno[2,3-b]pyrazine-2-carboxylate

Ethyl 3-amino[2,3-b]pyrazine-2-carboxylate (0.500 g, 2.24 mmol) prepared by the method of Schneller and Clough, J. Het. Chem., 12:513 (1975), was treated with Potassium bis(trimethylsilyl)amide (0.5M in toluene, 2.46 mmol) in 30 ml THF at −70° C., and allowed to warm to room temperature. Iodoethane (2.35 mmol, 0.188 ml) was added, and the reaction was stirred under N$_2$ for 12 h. More iodoethane was added (1.12 mmol, 0.09 ml) and after 0.5 h, ammonium chloride was added and the mixture was evaporated to a yellow solid which was purified by column chromatography on silica gel eluting with 2:98 ethyl acetate: hexanes to yield 0.300 g (53%) of the title compound as a yellow solid mp 90°–92° C. $^1$H NMR (300 MHz, CDCl$_3$) δ1.32 (t, 3H), 1.4 (t, 3H), 4.13 (m, 2H), 4.38 (q, 2H), 8.53 (d, 1H), 8.57 (d, 1H). MS (DCI/NH$_3$) m/e 252 (M+H)$^+$.

EXAMPLE 98B

Ethyl 3-(N-ethyl-N-chlorocarbamoylamino)thieno[2,3-b]pyrazine-2-carboxylate

The product from Example 98A (0.290 g, 1.16 mmol) was combined with triethylamine (2.90 mmol) in 30 mL anhydrous CH$_2$Cl$_2$ and cooled to 0° C. The resulting solution was treated with phosgene (1.93M in toluene, 3.48 mmol) and allowed to warm to rt overnight while stirring under N$_2$. The mixture was evaporated to a yellow oil which was purified by column chromatography on silica gel eluting with 5:95 ethyl acetate:hexanes to yield 0.278 g (84%) of the title compound as a yellow oil. $^1$H NMR (300 MHz, CDCl3) δ1.24 (t, 3H), 1.47 (t, 3H), 3.87 (q, 1H), is 4.02(q, 1H), 4.5 (q, 2H), 8.72 (d, 1H), 8.82 (d, 1H).MS (DCI/NH$_3$) m/e 3 14 (M+H)$^+$.

EXAMPLE 98C

3-[2-(cis-(3aR,9bR)-6-Methoxy-2,3,3a,4,5,9b-hexahydro-[1H]-benz[e]isoindol-1-yl)ethyl]-1-ethylpyrazino[2',3':4,5]thieno[3,2-d]pyrimidine-2,4(1H,3H)-dione hydrochloride The product from Example 98B (0.278 g, 0.975 mmol) was combined with triethylamine (0.340 mL, 2.44 mmol) and 0.240 g (0.975 mmol) of the product from Example 9D in 12 ml of anhydrous toluene and heated to reflux for 4 h.

The reaction mixture was concentrated to a solid and purified by column chromatography on silica gel eluting with 3:3:94 water:formic acid:ethyl acetate to yield 0.336 g (72%) of the title compound. This was converted to the HCl salt by treatment with an excess of HCl in methanol to give a tan solid, mp 278°–280° C. (dec). $^1$H NMR (300 MHz, DMSO-$d_6$) δ1.32 (t, 3H), 1.60 (m, 1H), 1.79 (m, 1H), 2.6–2.8 (m, 2H), 3.05 (m, 1H), 3.52 (m, 3H), 3.78 (s, 3H), 4.01 (m, 1H), 4.12 (m, 1H), 4.32 (m, 1H), 4.73 (m, 2H), 6.72 (d, 1H), 6.81 (m, 1H), 6.78 (dd, 1H), 8.92 (d, 1H), 9.01 (d, 1H). HRMS cald for $C_{25}H_{28}N_5SO_3$: 478.1913, found 478.1918. Analysis calc'd for $C_{25}H_{27}N_5SO_3$-HCl-½$H_2O$: C, 57.41; H, 5.59; N, 13.39; Found: C, 57.84; H, 5.40; N, 13.29.

EXAMPLE 99

3-[2-(cis-(3aR,9bR)-6-Methoxy-2,3,3a,4,5.,9b-hexahydro-[1H]-benz[e]isoindol-1-yl)ethyl]-1-8-phenylpyrazino[2',3':4,5]thieno[3,2-d]pyrimidine-2,4(1H,3H)-dione hydrochloride

EXAMPLE 99A

2-Chloro-3-cyano-5-phenylpyrazine and 2-chloro-3-cyano-6-phenylpyrazine

A mixture of 5-and 6-phenyl regioisomers of 2-hydroxy-3-carboxamidopyrazines (7.2g, 33.5 mmol) prepared by the method of R. G. Jones, J. Am. Chem. Soc. 71:78 (1949) was combined with phosphorous oxychloride (56 ml, 586 mmol) and triethylamine (9.3 mL, 67 mmol) and heated to reflux for 2 h. The mixture was evaporated to give a black oil which was extracted with ether (3×100 ml); the combined extracts were washed with 300 ml of 10% $Na_2CO_3$, after which the aqueous layer was back-extracted with ether. The combined organic layers were decolorized with activated carbon and filtered through Celite, then evaporated to give a white solid as a 60:40 mixture of the 5 and 6-phenyl isomers; mp(mixture) 121°–125° C. $^1$H NMR (300 MHz CDCl3) δ7.52 (m, 5H major and minor), 8.02 (d, 2H (major), 8.11 (d, 2H (minor)), 9.0 (s, 1H (major)), 9.05 (s, 1H (minor)). MS (DCI/NH$_3$) m/e 215 (M)+.

EXAMPLE 99B

Ethyl 3-amino-5-phenylthieno[2,3-b]pyrazine-2-carboxylate

The product from Example 99A (1.55 g, 7.16 mmol) was treated sequentially with ethyl thioglycolate (0.863 ml, 7.88 mmol), and sodium carbonate (0.760g, 7.16 mmol) in anhydrous ethanol (20 ml) and heated to reflux overnight. The reaction mixture was concentrated to a solid and purified by column chromatography on silica gel eluting with 5:95 hexanes:ethyl acetate to give 1.0 g (47%) of the title compound as a yellow solid, mp 116°–118° C. $^1$H NMR (300 MHz, CDCl3) δ1.24 (t, 3H), 4.40 (q, 2H), 7.53 (m, 3H), 8.09 (d, 2H), 9.09 (s, 1H). MS (DCI/NH$_3$) m/e 300 (M+H)$^+$.

EXAMPLE 99C

3-[2-(cis-(3aR,9bR)-6-Methoxy-2,3,3a,4,5,9b-hexahydro-[1H]-benz[e]isoindol-1-yl)ethyl]-8-phenylpyrazino[2',3':4,5]thieno[3,2-d]pyrimidine-2,4(1H,3H)-dione hydrochloride The product from Example 99B (0.484 g, 1.62 mmol) was treated with 0.529 g (1.78 mmol) of triphosgene in 48 ml of refluxing 1:1 toluene:THF mixture for 14 hours. The solvent was removed and the resulting isocyanate treated with 0.400g (1.62 mmol) of the product from Example 9B and 0.048g (3.40 mmol) triethylamine in 48 ml of refluxing toluene for 6 hours. The cooled mixture was filtered and the white precipitate was discarded. The resulting solution was concentrated to give a yellow solid which was mixed with an excess of HCl in methanol and evaporated; the resulting solid was triturated with boiling ethanol to give 0.208g (24%) of the title compound as a green-yellow solid, mp 296°–298° C. $^1$H NMR (300 MHz, DMSO-$d_6$) d 1.6 (m, 1H), 1.8 (m, 1H), 2.65 (m, 2H), 3.02 (m, 1H), 3.52 (m, 3H), 3.78 (s, 3H), 4.02 (m, 2H), 4.3 (m, 2H), 6.72–6.86 (m, 2H), 7.27 (dd, 1H), 7.6 (m, 3H), 8.48 (d, 2H), 9.55 (s, 1H). MS (DCI/NH$_3$) m/e 526 (M+H)+.Analysis calc'd for C29H28N5SO3-HCl-½H2O: C, 60.99; H, 5.12; N, 12.26; Found: C, 60.66; H, 5.03; N, 12.06.

EXAMPLE 100

3-[2-(cis-(3aR,9bR)-6-Methoxy-2,3,3a,4,5,9b-hexahydro-[1H]-benz[e]isoindol-1-yl)ethyl]-7,8-diphenylpyrazino[2',3':4,5]thieno[3,2-d]pyrimidine-2,4(1H,3H)-dione hydrochloride

EXAMPLE 100A

2-Chloro-3-cyano-5,6-diphenylpyrazine 5,6-diphenyl-2-hydroxy-3-carboximidopyrazine (5.42 g, 18.7 mmol), prepared by the method of R. G. Jones, J. Am. Chem. Soc. 71:78 (1949), was combined with phosphorous oxychloride (80 g, 204 mmol) and triethylamine (3.8 g, 37 mmol) and heated to reflux for 2 hours. The mixture was cooled, evaporated to a brown solid and then extracted with diethyl ether, the combined organic extracts were stirred over 10% $Na_2CO_3$ during which a precipitate occurred. The mixture was extracted with chloroform, dried with $MgSO_4$, filtered and evaporated to give 1.1g (20%) of the title compound as yellow solid mp 201°–204° C. $^1$H NMR (300 MHz, DMSO-d6) δ7.41 (m, 10 H). MS (DCI/NH$_3$) m/e 292 (M+H)$^+$.

EXAMPLE 100B

Ethyl 3-amino-5,6-diphenylthieno[2,3-b]pyrazine-2-carboxylate

The product from Example 100A (1.32 g, 4.5 mmol) was combined with ethyl thioglycolate (0.593 g, 4.95 mmol) and $Na_2CO_3$ in 12 ml ethanol and heated to reflux overnight. The reaction mixture was purified by column chromatography on silica gel eluting with 10:90 hexanes:ethyl acetate to give 0.355 g (21%) of the title compound as a yellow solid. $^1$H NMR (300 MHz, DMSO-$d_6$) δ1.33 (t, 3H), 4.33 (q, 2H), 7.12 (br s, 1H), 7.31–7.52 (sev m, 10H). MS (DCI/NH$_3$) m/e375.

EXAMPLE 100C

3-[2-(cis-(3aR,9bR)-6-Methoxy-23.,3a,4,5,9b-hexahydro-[1H]-benz[e]isoindol-1-yl)ethyl]-7,8-diphenylpyrazino[2',3':4,5]thieno[3,2-d]pyrimidine-2,4(1H,3H)-dione hydrochloride The product from Example 100B (0.355 g) was treated with triphosgene is (0.310 g, 1.04 mmol) as described in Example 99C . The resulting isocyanate was further treated with triethylamine (0.194 ml, 1.39 mmol) and 0.163 g (0.672 mmol) of the product from Example 9D and refluxed for 2 hours. The mixture was allowed to cool, filtered and evaporated, then mixed with ethanol and heated over steam; ether was added and the precipitate was collected. This was mixed with an excess of HCl methanol, then evaporated, then triturated with ethanol, filtered to give 0.140 g (35%) of the title compound mp 208°–211° C. $^1$H NMR (300 MHz DMSO-d6) δ1.62 (m, 1H), 1.80 (m, 1H), 2.52–2.81 (sev m, 3H), 3.0–3.08 (m, 2H), 3.5–3.59 (m, 2H), 3.78 (s, 3H), 3.9–4.31 (sev m, 5H), 6.78 (t, 1H), 6.82 (dd, 1H), 7.18 (t, 1H), 7.38–7.56 (sev m, 10H), 13.1 (s, 1H). MS (DCI/NH$_3$) m/e 602 (M+H)$^+$. Analysis calc'd for C35H31N5SO3·HCl·3/2 H$_2$O: C, 63.20; H, 5.30; N, 10.53; Found: C, 62.98; H, 5.08; N, 10.16.

EXAMPLE 101

3,2-(cis-(3aR,9bR)-6-Methoxy-2,3,3a,4,5,9b-hexahydro-: [1H-benz[e]isoindol-1-yl)ethyl]-1-butylpyrazino[2',3':4,5]thieno[3,2-d]pyrimidine-2,4(1H,3H)-dione hydrochloride

EXAMPLE 101A

Ethyl 3-(N-butylamino)thieno[2,3,-b]pyrazine-2-carboxylate

Ethyl 3-amino[2,3-b]pyrazine-2-carboxylate (0.500 g, 2.24 mmol) prepared by the method of Schneller and Clough, J. Het. Chem., 12:513 (1975), was treated with Potassium bis(trimethylsilyl)amide (0.5M in toluene, 3.70 mmol) in 50 ml THF at –70° C., and allowed to warm to room temperature. Iodobutane (0.401 ml, 3.53 mmol) was added and the mixture was heated to 60° C. overnight. NH$_4$Cl was added and the mixture was evaporated, then purified by column chromatography on silica gel eluting with 5:95 hexanes:ethyl acetate to give 0.606 g (64%) of the title compound as a yellow solid. $^1$H NMR (300 MHz DMSO-d$_6$) δ0.96 (t, 3H), 1.4 (t, 3H), 1.47 (m, 2H), 1.65 (m, 2H), 4.1 (q, 2H), 4.38 (q, 2H), 7.56 (br t, 1H), 8.53 (d, 1H), 8.56 (d, 1H). MS (DCI/NH$_3$) 280 (M+H)$^+$.

EXAMPLE 101B

Ethyl 3-(N-butyl-N-chlorocarbamoylamino)thieno[2,3-b]pyrazine-2-carboxylate

The product from Example 101A (0.590 g, 2.1 mmol), triethylamine (0.731 ml, 5.25 mmol), and phosgene (1.93M in toluene, 3.26 ml, 6.3 mmol) were reacted as in Example 98B in 50 ml anhydrous CH$_2$Cl$_2$. Purified by column chromatography on silica gel eluting with 1:1 ethyl acetate: hexanes to yield 0.718 g (100%) of the title compound as a yellow oil. $^1$H NMR (300 MHz DMSO-d$_6$) δ0.87 (t, 3H), 1.19–1.28 (m, 2H), 1.46 (t, 3H), 1.6 (m, 2H), 3.76 (m, 1H), 3.95 (m, 1H), 4.5 (m, 2H), 8.72 (d, 1H), 8.82 (d, 1H). MS (DCI/NH$_3$) 372 (M+H)$^+$.

EXAMPLE 101C

3-[2-(cis-(3aR,9bR)-6-Methoxy-2,3,3a,4,5,9b-hexahydro-[1H]-benz[e]isoindol-1-yl)ethyl]-1-butylpyrazino[2',3':4,5]thieno[3,2-d]pyrimidine-2,4(1H,3H)-dione hydrochloride The product from Example 101B (0.718 g, 2.10 mmol), triethylamine (0.731 ml, 5.25 mmol), and 0.517 g (2.10 mmol) of the product from Example 9D were combined in 25 ml anhydrous toluene and heated to reflux for 4 hours. The mixture was allowed to cool, was filtered, and the filtrate was mixed then evaporated in an excess of 1M HCl in methanol and then crystallized in isopropanol to give 0.392 g (37%) of the title compound as a yellow solid mp 240°–244° C. $^1$H NMR (300 MHz DMSO-d$_6$) δ0.94 (t, 3H), 1.42 (m, 2H), 1.6–1.82 (sev m, 4H), 2.42 (m, 1H), 2.60–2.82 (m, 3H), 3.05 (m, 1H), 3.40 (m,-2H), 3.52 (m, 3H), 3.78 (s, 3H), 3.82 (m, 1H), 4.02 (m, 1H), 4.12 (m, 1H), 4.32 (m, 2H), 4.71 (m, 2H), 6.72 (m, 2H), 7.18 (t, 1H), 8.91 (d, 1H), 9.02 (d, 1H). MS (DCI/NH$_3$) 506 (M+H)$^+$. Analysis calc'd for C$_{27}$H$_{31}$N$_5$SO$_3$·HCl: C, 59.82; H, 5.95; N, 12.92 Found: C, 59.69; H, 5.85; N, 12.74.

EXAMPLE 102

3-[2-(cis-(3aR,9bR)-6-Methoxy-2,3,3a,4,5,9b-hexahydro-[1H]-benz[e]isoindol-1-yl)ethyl]-1-(2-(2-methoxyethoxy)ethyl)pyrazino[2',3':4,5]thieno[3,2-d]pyrimidine-2,4(1H, 3H)-dione hydrochloride

EXAMPLE 102A

Ethyl 3-(N-(2-(2-methoxyethoxy)ethyl)amino)thieno[2,3,b]pyrazine-2-carboxylate

Ethyl 3-amino[2,3-b]pyrazine-2-carboxylate (0.750 g, 3.36 mmol) prepared by the method of Schneller and Clough, J. Het. Chem., 12:513 (1975), was treated with potassium bis(trimethylsilyl)amide (0.5M in toluene, 3.70 mmol) in 50 ml THF at –70° C., and allowed to warm to room temperature. 1-Bromo-2-(2-methoxyethoxy)ethane (0.457 ml, 3.36 mmol) was added and the the mixture was stirred under N$_2$ first at room temperature and then at 60° C. for 3 hours. NH$_4$Cl was added and the mixture was evaporated, then purified by column chromatography on silica gel eluting with 1:4 hexanes:ethyl acetate to give 0.324 g (29%) of the title compound as a yellow oil. $^1$H NMR (300 MHz DMSO-d$_6$) δ1.40 (t, 3H), 3.58 (m, 2H), 3.68 (m, 2H), 3.73 (t, 2H), 4.32 (m, 4H), 7.71 (br t, 1H), 8.53 (s, 2H). MS (DCI/NH$_3$) 325 (M+H)$^+$.

EXAMPLE 102B

Ethyl 3-(N-(2-(2-methoxyethoxy)ethyl)-N-chlorocarbamoylamino)thieno[2,3-b]pyrazine-2-carboxylate The product from Example 102A (0.324g, 1.0 mmol), phosgene (1.93M, 3.0 mmol ), and triethylamine (0.348 ml, 2.50 mmol) were reacted as in Example 98B. After stirring overnight under N$_2$ at room temperature, the mixture was cooled to 0° C. and treated with phosgene (1.93M, 1.0 mmol) and triethylamine (0.139 ml, 1 mmol) and allowed to stir under N$_2$ at room temperature for 2 hours. The mixture was evaporated, then purified by column chromatography on silica gel eluting with 1:1 hexanes:ethyl acetate to give 0.247 g (66%) of the title compound as a yellow oil. 1H NMR (300 MHz DMSO-d$_6$) δ1.48 (t, 3H), 3.12 (m, 1H), 3.26–3.4 (sev m, 5H), 3.72 (m, 2H), 4.04 (m, 1H), 4.16 (m, 1H), 4.48 (m, 2H), 8.70 (d, 1H), 8.80 (d, 1H). MS (DCI/NH$_3$) 388 (M+H)$^+$.

EXAMPLE 102C

3-[2-(cis-(3aR,9bR)-6-Methoxy-2,3,3a,4,5,9b-hexahydro-[1H]-benz[e]isoindol-1-yl)ethyl]-1-(2-(2-methoxyethoxy)ethyl)pyrazino[2',3':4,5]thieno[3,2-d]pyrimidine-2,4(1H, 3H)-dione hydrochloride The product from Example 102B (0.247 g, 0.664 mmol), triethylamine (0.231 ml, 1.66 mmol), and and 0.163 g (0.664 mmol) of the product from Example 9D were combined in 8 ml anhydrous toluene and heated to reflux for 2.5 hours. The mixture was evaporated, then purified by column chromatography on silica gel eluting with 5:5:90 water:formic acid:ethyl acetate. The resulting homogeneous fractions were concentrated and then mixed with an excess of 1M HCl in methanol and evaporated, the residue was crystallized with ethanol/diethyl ether to give 0.115g (39%) of the title compound as a yellow-white granular solid mp 226°–228° C. $^1$H NMR (300 MHz DMSO-d$_6$) δ1.40 (m, 1H), 1.78 (m, 1H), 2.6–2.83 (m, 3H), 3.0–3.08 (m, 1H), 3.1 (s, 3H), 3.28 (m, 2H), 3.52 (m, 4H), 3.7–4.38 (sev m, 12H), 4.95 (m, 2H), 6.75–6.88 (m, 2H), 7.28 (t, 1H), 8.92 (d, 1H), 9.01 (d, 1H). HRMS cald for C$_{28}$H$_{34}$N$_5$SO$_5$: 552.2281, found 552.2281.Analysis calc'd for $C_{28}H_{33}N_5SO_5 \cdot HCl \cdot H_2O$: C, 55.71; H, 5.54; N, 11.41; Found: C, 55.48; H, 5.99; N, 11.55.

EXAMPLE 103

3-[2-(cis-(3aR,9bR)-6-Methoxy-2,3,3a,4,5,9b-hexahydro-[1H]-benz[e]isoindol-1-yl)ethyl]-7,8-dimethylpyrazino[2', 3':4,5]thieno[3,2-d]pyrimidine-2,4(1H,3H)-dione hydrochloride

EXAMPLE 103A

2-Chloro-3-cyano-5,6-dimethylpyrazine 5,6-dimethyl-2-hydroxy-3-carboximidopyrazine (4.4 g, 26.3 mmol), prepared by the method of R. G. Jones, J. Am. Chem. Soc. 71:78 (1949) was combined with phosphorous oxychloride (70 ml), and triethylamine (7.3 ml, 52.3 mmol) and heated to reflux for 3 hours. The compound was further treated according to the procedure described in Example 100A to give 3.3 g (75%) of the title compound as a yellow solid mp 83°–85° C. $^1$H NMR (300 MHz DMSO-$d_6$) δ2.54 (s, 3H), 2.59 (s, 3H). MS (DCI/NH$_3$) 185.

EXAMPLE 103B

Ethyl 3-amino-5,6-dimethylthieno[2,3-b]pyrazine-2-carboxylate

The compound from Example 103A (1.5g, 8.95 mmol), ethyl thioglycolate (1.08 ml, 9.85 mmol), and Na$_2$CO$_3$ (0.949 g, 8.95 mmol) were combined in 25 ml anhydrous ethanol and heated to reflux overnight. The mixture was cooled, filtered, and the solid was recrystallized in ethanol/ H$_2$O to afford 1.3 g (58%) of the title compound mp 136°–139° C. $^1$H NMR (300 MHz, CDCl3) δ1.4 (t, 3H), 2.64 (s, 3H), 2.68 (s, 3H), 4.39 (q, 2H), 6.12 (br s 2H).MS (DCI/NH$_3$) 252 (M+H)$^+$.

EXAMPLE 103C

3-[2-(cis-(3aR,9bR)-6-Methoxy-2,3,3a,4,5,9b-hexahydro-[1H]-benz[e]isoindol-1-yl)ethyl]-7,8-dimethylpyrazino[2', 3':4,5]thieno3,2-d]pyrimidine-2,4(1H,3H)-dione hydrochloride The compound from Example 103B (0.269 g, 1.07 mmol) was combined with triphosgene (0.349 g, 1.18 mmol) in 26 ml 1:1THF:toluene and heated to reflux overnight. The mixture was cooled and evaporated, then combined with 0.290 g (1.18 mmol) of the compound from Example 9D in 26 ml of 1:1 THF:toluene, and triethylamine (0.313 ml, 2.25 mmol) and heated to reflux overnight. The mixture was evaporated, then purified by column chromatography on silica gel eluting with of 5:5:90 water:formic acid:ethyl acetate to obtain 0.560 g (77%) of the title compound. This was evaporated with an excess of HCl-methanol, then crystallized with ethanol/ diethyl ether to produce 0.236 g of the title compound as a tan solid mp 308°–3 10° C. $^1$H NMR(300MHz DMSO-$d_6$) δ1.61 (s, 1H), 1.79 (m, 1H), 2.69 (s, 3H), 2.6–2.79 (sev m, 4H), 3.01 (m, 1H), 3.32 (s, 3H), 3.52 (m, 2H), 3.78 (s, 3H), 3.09–4.81 (sev m, 4H), 6.71–6.86 (m, 3H), 7.18 (m, 1H), 12.86 (m, 1H). HMRS calc'd for $C_{25}H_{28}N_5SO_3$ 478.1913, found 478.1913. Analysis calc'd for $C_{25}H_{27}N_5SO_3 \cdot HCl \cdot H_2O$: C, 56.44; H, 5.68; N, 13.10; Found: C, 56.61; H, 5.19; N, 13.13.

EXAMPLE 104

3-[2-(cis-(3aR,9bR)-6-Methoxy-2,3,3a,4,5,9b-hexahydro-[1H]-benz[e]isoindol-1-yl)ethyl]-1-(2-methoxyethyl)pyrazino[2',3':4,5]thieno[3,2-d]pyrimidine-2,4(1H,3H)-dione hydrochloride

EXAMPLE 104A

Ethyl 3-(N-(2-methoxyethyl)ethyl)amino)thieno[2,3-b]pyrazine-2-carboxylate

Ethyl 3-amino[2,3-b]pyrazine-2-carboxylate (1.0 g g, 4.48 mmol) prepared by the method of Schneller and Clough, J. Het. Chem., 12:513 (1975), was treated with potassium bis(trimethylsilyl)amide (0.5M in toluene, 8.96 ml) in 15 ml THF at −70° C., and allowed to warm to room temperature. 2-Bromoethyl methyl ether (0.454 ml, 4.70 mmol) was added, and the reaction was stirred under N$_2$ at 60° C. overnight. The mixture was cooled and evaporated, then purified by column chromatography on silica gel eluting with 1:9 ethyl acetate:hexanes to yield 0.640 g (51%) of the title compound as a yellow solid. $^1$H NMR (300 MHz, DMSO-$d_6$) δ1.32 (t, 3H), 3.3 (s, 3H), 3.56 (t, 2H), 4.25 (q, 2H), 4.32 (t, 2H), 7.70 (br t, 1H), 8.76 (s, 1H), 8.77 (s, 1H). MS (DCI/NH$_3$) m/e 282 (M+H)$^+$.

EXAMPLE 104B

Ethyl 3-(N-(2-methoxyethyl)-N-chlorocarbamoylamino)thieno[2 3-b]pyrazine-2-carboxylate The product from Example 104A (0.620 g, 2.20 mmol) was reacted with phosgene (1.93M in toluene, 3.41 ml, 6.6 mmol) and triethylamine (0.767 ml, 5.5 mmol) and purified according to the procedure described in Example 98B. The title compound was obtained as 0.582 g (81%) of a yellow oil. $^1$H NMR (300 MHz DMSO-$d_6$) d 1.31 (t, 3H), 3.3 (s, 3H), 3.56 (t, 2H), 4.23 (q, 2H), 4.3 (q, 2H), 8.78 (2 singlets, 2H). MS (DCI/NH$_3$) 344 (M+H)$^+$.

EXAMPLE 104C

3-[2-(cis-(3aR,9bR)-6-Methoxy-2,3,3a,4,5,9b-hexahydro-[1H]-benz[e]isoindol-1-yl)ethyl]-1-(2-methoxyethyl)pyrazino[2',3':4,5]thieno[3,2-d]pyrimidine-2,4(1H,3H)-dione hydrochloride The product from Example 104B (0.466 g, 1.42 mmol) was combined with triethylamine (0.238 mL, 1.70 mmol) and 0.350 g (1.42 mmol) of the compound from Example 9D in 15 ml of anhydrous toluene and heated to reflux for 4 h. The reaction mixture was concentrated to a solid and purified by column chromatography on silica gel eluting with 5:5:90 water:formic acid:ethyl acetate to yield 0.505 g (69%) of the title compound. This was converted to the HCl salt by treatment with an excess of HCl in methanol to give 0.362 g of a tan solid, mp 247°–251° C. $^1$H NMR (300 MHz, DMSO-$d_6$) δ1.61 (m, 1H), 1.80 (m, 1H), 2.62–2.83 (sev m, 3H), 2.9–3.1 (m, 1H), 3.25 (s, 3H), 3.49–3.60 (sev m 3H), 3.69 (m, 2H), 3.78 (s, 3H), 3.81– 4.48 (sev m, 5H), 4.95 (m, 2H), 6.78 (d, 1H), 6.81 (dd, 1H), 7.18 (t, 1H), 8.91 (d, 1H), 9.01 (d, 1H). MS (DCI/NH$_3$) m/e 507 (M+H)$^+$. Analysis calc'd for C26H30N5O$_4$SCl·HCl: C, 57.40; H, 5.56; 12.87; Found: C, 57.17; H, 5.43; N, 12.70.

EXAMPLE 105

3-[2-(cis-(3aR,9bR)-6-Methoxy-2,3,3a,4,5,9b-hexahydro-[1H]-benz[e]isoindol-1-yl)ethyl]-1-(2-methoxyethyl)pyrido[2',3':4,5]thieno[3,2-d]pyrimidine-2,4(1H,3H)-dione hydrochloride

EXAMPLE 105A

Ethyl 3-(N-(2-methoxyethyl)ethyl)amino)thieno[3,2-b]pyridine-2-carboxylate

To a solution of 3-Amino-2-carbomethoxythieno[3,2-b]pyridine (1.08 g, 5.2 mmol), prepared by the procedure described in *J. Heterocyclic Chem.*, 24: 85 (1987), in THF (18 ml) was added KHMDS (11.4 ml, 5.7 mmol 0.5M toluene) dropwise at −78° C. under nitrogen. The resulting purple reaction mixture was allowed to warm to rt, treated with 2-bromoethyl methyl ether (0.53 ml, 5.5 mmol) in THF (20 ml) and then brought to reflux for 24h. Column chromatography of the crude concentrate on silica gel eluting with 9:1 hexanes:ethyl acetate gave the title compound (0.360 g, 26%). $^1$H NMR (300 MHz, CDCl$_3$) δ3.44 (s, 3H), 3.65 (t, 2H), 3.88 (s, 3H), 4.43 (t, 2H), 7.3 (dd, 1H), 8.1 (dd, 1H), 8.60 (dd, 1H). MS (DCI/NH$_3$) m/e 267 (M+H)$^+$.

EXAMPLE 105B

Ethyl 3-(N-(2-methoxyethyl)-N-chlorocarbamoylamino)thieno[3,2-b]pyridine-2-carboxylate A solution of the compound from Example 105A (0.360 g, 1.40 mmol) in methylene chloride (35 ml) was treated with triethylamine (0.47 ml, 3.40 mmol) and phosgene (2.1 ml, 4.1 mmol of 20% solution in toluene) at 0° C. The reaction mixture was allowed to warm up to rt, stirred overnight and evaporated in vacuo to afford a solid residue. The crude solid was dissolved in 1:1 methylene chloride:ethyl acetate and filtered through a pad of silica gel. Evaporation of the solvents gave the title compound (0.44 g, 95%) as a soild. $^1$H NMR (300 MHz, CDCl$_3$) δ3.12 (s, 3H), 3.37–3.54(m, 2H), 4.02 (s, 3H), 4.07–4.14 (m, 2H), 4.29–4.56 (m, 2H), 7.46 (dd, 1H), 8. 23 (dd, 1H), 8. 85 (dd, 1H). MS (DCI/NH$_3$) m/e 329(M+H)$^+$.

EXAMPLE 105C

3-[2-(cis-(3aR,9bR)-6-Methoxy-2,3,3a,4,5,9b-hexahydro-[1H]-benz[e]isoindol-1-yl)ethyl]-1-(2-methoxyethyl)pyrido[2',3':4,5]thieno[3,2-d]pyrimidine-2,4(1H,3H)-dione hydrochloride The compound resulting from Example 105B (0.44 g, 1.3 mmol) was combined with triethylamine (0.28 ml, 2.0 mmol) and the compound resulting from Example 9D (0.33 g, 1.3 mmol) in 15 ml of anhydrous toluene and heated to reflux for 4 h. The reaction mixture was concentrated to a solid and purified by column chromatography on silica gel eluting with 18:1:1 (ethyl acetatewater:formic acid) to yield 0.435 g (62%) of the title compound. This was converted to the HCl salt by treatment with an excess of HCl in methanol to give a tan solid, mp 278°–280° C. (dec).$^1$H NMR (300 MHz, DMSO-d$_6$) δ1.32 (t, 3H), 1.60 (m, 1H), 1.79 (m, 1H), 2.6–2.8 (m, 2H), Recrystallization of the HCl salt from EtOH gave the title compound (0.411 g, 56%) as a white solid. mp: 252°–254° C. $^1$H NMR (300 MHz, DMSO-d$_6$) NMR (300 MHz, DMSO-d$_6$) δ1.54–1.68 (m, 1H), 1.72–1.88 (m, 1H), 2.6–2.8 (m, 3H), 2.94–3.1 (m, 1H), 3.28 (s, 3H), 3.49 o 3.60 (m 3H), 3.69 (m, 2H), 3.78 (s, 3H), 3.81–4.48 (m, 5H), 5–5.15 (m, 2H), 6.78 (d, 1H), 6.88 (d, 1H), 7.15 (t, 1H), 7.71 (dd, 1H), 8.88 (dd, 1H). 8.7 (dd, 1H). MS (DCI/NH$_3$) m/e 507 (M+H)$^+$. Analysis calc'd. for C$_{27}$H$_{31}$N$_5$O$_4$S-1HCl-1.3H$_2$O: C, 57.25; H, 5.98; N, 9.89; Found: C, 57.11; H, 5.63; N, 10.0.

EXAMPLE 106

3-[2-((3aR,9bR)-cis-6-Methoxy-2,3,3a,4,5,9b-hexahydro-[1H]-benz[e]isoindol-1-yl)ethyl]-[1]-8-methoxy-benzothieno[3,2-d]pyrimidine-2,4(1H,3H)-dione hydrochloride 5-Methoxy-3-amino-2-caroboethoxy benzothiophene was prepared from 3-methoxy-6-nitrobenzonitrile and methyl thioglycolate utilizing the method of Dunn, A. D.; Norrie, R. *J. Heterocyclic Chem.* 1987, 24, 85. 5-Methoxy-3-amino-2-caroboethoxy benzothiophene (540 mg, 2.28 mmol) was treated in the manner described in Example 9E and the resultant isocyanate was combined with the material from Example 9D (300 mg, 1.90 mmol) and treated as in Example 34B to yield the title compound (1 10 mg, 12%) as a white solid: mp 192°–194° C.; $^1$H NMR (300 MHz, DMSO-d$_6$) δ8.00 (m, 1H), 7.30 (m, 2H), 7.10 (t, J=9 Hz, 1H), 6.85 (t, J=9 Hz, 1H), 6.75 (t, J=9 Hz, 1H), 3.35 (m, 2H), 4.02 (m, 2H), 3.95 (s, 3H), 3.75 (s, 3H), 3.52 (m, 2H), 3.05 (m, 2H), 2.70 (m, 2H), 1.80 (m, 1H), 1.62 (m, 1H), 1.22 (m, 1H), 1.05 (m, 1H); MS (DCI/NH$_3$) m/z 478 (M+H)$^+$. Anal. calcd for C$_{26}$H$_{29}$Cl$_2$N$_3$O$_4$S.0.10HCl: C, 56.35; H, 5.29; N, 7.58. Found: C, 56.50; H, 5.38; N, 7.98.

EXAMPLE 107

3-[2-((3aR,9bR)-cis-6-Methoxy-2,3,3a,4,5,9b-hexahydro-[1H]-benz[e]isoindol-1-yl)ethyl]-8-hydroxypyrido[2',3':4,5]thieno[3,2-d]pyrimidine-2,4(1H,3H)-dione dihydrochloride A solution of the product from Example 64 (800mg, 1.7 mmol) and 4M HCl (20 mL) in 1,4-dioxane (50 mL) was refluxed for 18 h. The reaction was concentrated and partitioned between CH$_2$Cl$_2$ and NaHCO$_3$ solution. The CH$_2$Cl$_2$ layer was dried (MgSO$_4$), filtered, concentrated and chromatographed (18:1:1 EtOAc:HCOOH:H2O). 0.46 g (60%) of the free base was obtained after a NaHCO$_3$/CH$_2$Cl$_2$ workup, which was converted to its hydrochloride salt: m.p. >260°; $^1$H NMR (300 MHz, DMSO-d$_6$(free base) d 1.37–1.50 (m, 1H), 1.58–1.70 (m, 1H), 2.15–2.25 (m, 1H), 2.34–2.67 (m, 6H), 3.15–3.33 (m, 3H), 3.75 (s, 3H), 4.00 (t, 2H), 6.57 (d, 1H), 6.73 (d, 2H), 7.08 (t, 1H), 8.03 (d, 1H); MS (DCI/NH3) m/e 465 (M+H)+; Analysis calc'd for C$_{24}$H$_{24}$N$_4$O$_4$S.HCl.(H$_2$O)0.5: C, 56.52; H, 5.14; N, 10.99; found: C, 56.49; H, 4.92; N, 10.79.

EXAMPLE 108

3-[2-((3aR,9bR)-cis-6-Methoxy-2,3,3a,4,5,9b-hexahydro-[1H]-benz[e]isoindol-1-yl)ethyl]-8-cyanopyrido[2',3':4,5]thieno[3,2-d]pyrimidine-2,4(1H,3H)-dione dihydrochloride

EXAMPLE 108A

3-Amino-2-carbomethoxy-5-Cyanothieno[3,2-b]pyridine
3-Amino-2-carbomethoxythieno[3,2-b]pyridine-4-oxide (3.1 g, 13.8 mmol) is stirred mechanically under N$_2$ at 25° C. as dimethyl sulfate (1.3 mL, 14 mmol) is added dropwise. After stirring at 80° C. for 2 h, the reaction is cooled to 250C and the resulting solid is washed with acetone (50 mL) is added. The solid is dissolved in 10 mL H$_2$O and is added dropwise to a 0° C. solution of KCN (2.7 g, 41 mmol) in H$_2$O (10 mL). After stirring at 25° C. 18 h. The reaction was extracted with CH$_2$Cl$_2$. The organic layer was dried (MgSO$_4$), filtered, concentrated, and chromatographed (CH$_2$Cl$_2$). 1.5 g (47%) of the title compound was obtained: $^1$H NMR (300 MHz, CDCl3) δ3.94 (s, 3H), 6.25 (bs, 2H), 7.70 (d, 1H), 8.20 (d, 1H); MS (DCI/NH3) m/e 234 (M+H)$^+$.

EXAMPLE 108B

3-[2-((3aR,9bR)-cis-6-Methoxy-2,3,3a,4,5,9b-hexahydro-[1H]-benz[e]isoindol-1-yl)ethyl]-8-cyanopyrido[2',3':4,5]thieno[3,2-d]pyrimidine-2,4(1H,3H )-dione dihydrochloride To a solution of the product from Example 108A (0.50 g, 2.1 mmol) and triethylamine (0.66 mL, 4.7 mmol) in THF (50 mL) at 25° C. is added phosgene (3.3 mL of 1.93M solution in toluene). After stirring 18 h at 25° C., the reaction is concentrated to dryness and the residue is taken up in hot toluene. The triethylamine hydrochloride is removed by filtration and the toluene filtrate was concentrated to dryness to remove residual phosgene. This intermediate isocyanate and the product from Example 9D (43 g, 1.7 mmol) were refluxed in toluene for 18 h. The reaction was concentrated and chromatographed (10% EtOH in $CH_2Cl_2$ sat'd with $NH_3$) to yield 0.55 g (67%) of the title compound, which was convened to the HCl salt: $^1$H NMR (300 MHz, $CDCl_3$ (free base)) δ1.65–1.80 (m, 1H), 1.96–2.11 (m, 1H), 2.55–2.68 (m, 1H), 2.77–3.14 (m, 4H), 3.36–3.68 (m, 1H), 3.79–3.96 (m, 1H), 3.82 (s, 3H), 3.97–4.22 (m, 1H), 4.29–4.44 (m, 1H), 4.50–4.69 (m, 1H), 6.71 (d, 1H), 6.81 (bd, 1H), 7.13 (t, 1H), 7.68 (d, 1H), 8.07 (d, 1H); MS (DCI/$NH_3$) m/e $(M+H)^+$.

EXAMPLE 109

3-[2-((3aR,9bR)-cis-6-Ethoxy-2,3,3a,4,5,9b-hexahydro-[1H]-benz[e]isoindol-1-yl)ethyl]-pyrido[3',2':4,5]thieno[3,2-d]pyrimidine-2,4(1H,3H)-dione hydrochloride

EXAMPLE 109A (3aR,9bR)-6-Hydroxy-2,3,3a,4,5,9b-[1H]-hexahydrobenz[e]isoindole hydrobromide The product resulting from Example 9B (5g, 20.9 mmol) was dissolved in 150 ml of $CH_2Cl_2$ and the resulting solution was cooled to −78° C. 21 ml of 1M solution of boron tribromide in methylene chloride was added to the solution and the reaction was warmed to room temperature and stirred for 4 hours. It was cooled again to −78C and treated with methanol. Evaporation and trituration with ethyl acetatate afforded 4.9g (87%) of the title compound as white crystals.

EXAMPLE 109B (3aR,9bR)-6-Hydroxy-2-carbobenzyloxy-2,3,3a,4,5,9b-[1H]-hexahydrobenz[e]isoindole hydrobromide The product obtained from Example 109A (4.9g, 18.21mmol) was dissolved in 100 ml of trifluoroacetic acid. The resulting solution was cooled to 0° C. and acetyl chloride (2.58ml, 36.42 mmol) was added to the reaction mixture. It was stirred at room temperature for 2.5 hours. The reaction mixture was evaporated and partitioned between $NaHCO_3$ solution and $CH_2Cl_2$. CBZ chloride (3.8 ml, 1.5 equiv.) was added to this biphasic solution and it was vigorously stirred for 2 hours. Then the layers were separated, and the combined organic layers were dried with $MgSO_4$ and evaporated. The residue was dissolved in ethanol and $NH_4OH$ solution was added to it. It was stirred overnight, then solvents were evaporated and the residue obtained was dissolved in ethyl acetate, washed with water, dil. HCl, and brine. Combined organic layers were dried with $MgSO_4$ and evaporated to yield 6.9 g of the title compound as an oil.

EXAMPLE 109C (3aR,9bR)-6-Ethoxy-2-carbobenzyloxy-2,3,3a,4,5,9b-[1H]-hexahydrobenz[e]isoindole hydrobromide The product from Example 109B (3.5g, 10.83mmol) was dissolved in 300 ml of acetone; 3.0 g of $K_2CO_3$ (2 equiv.) and 1.03 ml (12.87 mmol) iodoethane were added to the solution and it was stirred at reflux for 48 hours. The reaction mixture was evaporated and the residue was partitioned between water and ethylacetate. The organic layer was separated, dried with $MgSO_4$ and evaporated. The residue obtained was chromatographed, eluting with 20% ethyl acetate/hexane to afford 23 g of the title compound.

EXAMPLE 109D (3aR,9bR)-6-Ethoxy-2,3,3a,4,5,9b-[1H]-hexahydrobenz[e]isoindole hydrochloride The product from Example 109C (2.3 g) was dissolved in 100 ml of methanol, 0.23 g of Pd/C was added to the solution and it was hydrogenated under 4 atm pressure for 18 hours. The catalyst was removed by filtration and the solvent was evaporated to yield the title compound: $^1$H NMR (300 MHz, $CDCl_3$) δ7.1 (t, 1H), 6.78 (d, 1H), 6.68 (d, 1H), 4.03 (m, 2H), 3.45 (m, 1H), 3.35 (m, 1H), 3.25 (m, 1H), 2.82 (m, 3H), 2.5 (m, 2H), 1.8 (m, 1H), 1.55 (m, 1H), 1.42 (t, 3H).

EXAMPLE 109E

3aR,9bR)-2-Aminoethyl-6-ethoxy-2,3,3a,4,5,9b-[1H]-hexahydrobenz[e]isoindole

The product from Example 109D (1.4 g, 6.45 mmol) was treated with 0.45 ml (1.1 equiv.) of chloroacetonitrile as outlined in Example 9C to yield 1.3 g of the intermediate nitrile. Reduction with 1.3 g of $LiAlH_4$ as described in Example 9D yielded 1.1 g of title compound.: $^1$H NMR (300 MHz, $CDCl_3$) δ7.09 (t, 1H), 6.73 (d, 1H), 6.68 (d, 1H), 4.02 (q, 2H), 3.42 (m, 1H), 3.28 (m, 2H), 2.8 (t, 2H), 2.48–2.78 (m, 5H), 2.18 (t, 2H), 1.71 (m, 1H), 1.55 (m, 1H).

EXAMPLE 109F

3-[2-((3aR,9bR)-cis-6-Ethoxy-2,3,3a,4,5,9b-hexahydro-[1H]-benz[e]isoindol-1-yl)ethyl]-pyrido[3',2':4,5]thieno[3,2-d]pyrimidine-2,4(1H,3H)-dione hydrochloride Amino-2-carbomethoxythieno[2,3-b]pyridine (3.2 g), prepared by the method of Dunn and Norrie, J. Heterocyclic Chem., 24:85(1987), was treated with 0.33 equivalents of triphosgene. The resulting isocyanate (0.34 g, 1.3 mmol) and the compound resulting from Example 109E (0.3 g, 1.15 mmol) were treated by the procedure described in Example 9D to yield the title compound (0.12 g, 22.6%) as a white solid: m.p. 220°–222°; $^1$H NMR (300 MHz, $CDCl_3$(free base)) δ8.7 (dd, 1H), 8.45 (dd, 1H), 7.18 (dd, 1H), 7.04 (t, 1H), 6.68 (dd, 2H), 4.38 (t, 2H), 4.0 (q, 2H), 3.5.m (3), 2.92 (t, 2H), 2.61 (m, 3H), 2.48 (m, 2H), 1.73 (m, 1H), 1.57 (m, 1H), 1.4 (t, 3H); MS (DCI($NH_3$)) m/e 463(M+H)+; Analysis calc'd for $C_{25}H_{24}N_4SO_3 \cdot HCl$: C, 60.42; H, 5.07; N, 11.27; found: C, 59.93; H, 5.37; N, 11.03.

EXAMPLE 110

3-[2-((3aR,9bR)-cis-6-Ethoxy-2,3,3a,4,5,9b-hexahydro-[1H]-benz[e]isoindol-1-yl)ethyl]-pyrido[2',3':4,5]thieno[3,2-d]pyrimidine-2,4(1H,3H)-dione dihydrochloride 3-amino-2-carbomethoxythieno[3,2-b]pyridine, prepared by the method described in J. Heterocyclic Chem., 24:85(1987), was treated with 0.33 equivalents of triphosgene in the presence of 2 equivalents of triethylamine. The resulting isocyanate (0.4 g, 1.7 mmol) and the compound resulting from Example 109E (0.35 g, 1.35 mmol) were treated by the procedure described in Example 9D to yield 0.22 g(35%) of the title compound: $^1$H NMR (300 MHz, $CDCl_3$(free base)) δ8.72 (dd, 1H), 8.08 (d, 1H), 7.44 (dd, 1H), 7.08 (t, 1H), 6.75 (d, 1H), 6.64 (d, 1H), 4.32 (m, 2H), 4.0 (q, 2H), 3.95 (m, 2H), 3.58 (m, 1H), 3.25 (m, 1H), 3.05

(m, 1H), 2.72 (m, 2H), 2.58 (m, 1H), 2.4 (m, 2H), 1.8 (m, 1H), 1.55 (m, 1H), 1.41 (t, 3H); MS (DCI(NH$_3$)) m/e 463(M+H)+; Analysis calc'd for C$_{25}$H$_{24}$N$_4$SO$_3$·2HCl: C, 56.29; H, 4.91; N, 10.50; found: C, 55.87; H, 4.65; N, 10.44.

EXAMPLE 111

3-[2-(cis-6,7-Methylenedioxy-2,3,3a,4,5,9b-hexahydro-[1H]-benz[e]isoindol-1-yl)ethyl]-pyrido[3',2':4,5]thieno[3,2-d]pyrimidine-2,4(1H,3H)-dione hydrochloride

EXAMPLE 111A

2-Aminoethyl-6,7-methylenedioxy-2,3,3a,4,5,9b-[1H]-hexahydrobenz[e]isoindole 6,7-methylenedioxy-2,3,3a,4,5,9b-[1H]-hexahydrobenz[e]isoindole (3.8 g, 17.5 mmol) was treated with 1.3 ml (1.1 equiv.) of chloroacetonitrile as described in Example 9B to yield 3 g (67%) of the intermediate nitrile, which was further subjected to reduction with 3 g of LiAlH$_4$ as described in Example 9C to yield 2.6 g (86.2%) of title compound.: $^1$H NMR (300 MHz, CDCl$_3$) δ6.62 (dd, 2H), 5.93 (s, 2H), 3.38 (q, 1H), 3.22 (m, 2H), 2.81 (t, 2H), 2.48–2.7 (m, 5H), 2.18 (m, 2H), 1.75 (m, 1H), 1.55 (m, 1H).

EXAMPLE 111B

3-[2-(cis-6,7-Methylenedioxy-2,3,3a,4,5,9b-hexahydro-[1H]-benz[e]isoindol-1-yl)ethyl]-pyrido[3',2':4,5]thieno[3,2-d]pyrimidine-2,4(1H,3H)-dione hydrochloride 3-Amino-2-carbomethoxythieno[2,3-b]pyridine, prepared by the method of Dunn and Norrie, J. Heterocyclic Chem., 24:85(1987), was treated with 0.33 equivalents of triphosgene. The resulting isocyanate (0.42 g, 1.8 mmol) and the compound resulting from Example 111A (0.4 g, 1.5 mmol) were treated by the s procedure described in Example 9D to yield the title compound (0.2 g, 28.8%) as a white solid: m.p. >250°; $^1$H NMR (300 MHz, CDCl$_3$(free base)) δ8.73 (s, 1H), 8.46 (d, 1H), 7.18 (m, 1H), 6.6 (m, 2H), 5.91 (s, 2H), 4.38 (t, 2H), 3.46 (m, 3H), 2.92 (m, 2H), 2.6 (m, 3H), 2.35 (m, 2H), 1.73 (m, 1H), 1.58 (m, 1H); MS (DCI(NH$_3$)) m/e 463(M+H)$^+$; Analysis calc'd for C$_{24}$H$_{22}$N$_4$O$_4$S·HCl·H$_2$O: C, 54.80; H, 4.98; N, 10.65; found: C, 54.57; H, 4.60; N, 10.48.

EXAMPLE 112

3-[2-(cis-6,7-Methylenedioxy-2,3,3a,4,5,9b-hexahydro-[1H]-benz[e]isoindol-1-yl)ethyl]-pyrido[2',3':4,5]thieno[3,2-d]pyrimidine-2,4(1H,3H)-dione dihydrochloride 3-Amino-2-carbomethoxythieno[2,3-b]pyridine, prepared by the method of Dunn and Norrie, J. Heterocyclic Chem., 24:85(1987), was treated with 0.33 equivalents of triphosgene. The resulting isocyanate (0.42 g, 1.8 mmol) and the compound resulting from Example 111A (0.4 g, 1.5 mmol) were treated by the procedure described in Example 9D to yield the title compound (0.12 g, 22.6%) as a white solid: $^1$H NMR (300 MHz, CDCl$_3$(free base)) δ8.71 (dd, 1H), 8.02 (d, 1H), 7.42 (m, 1H), 6.61 (s, 2H), 5 (91, J=s Hz, 2H), 4.45 (m, 1H), 4.3 (m, 1H), 4.12 (m, 1H), 4.05 (m, 1H), 3.58 (m, 1H), 3.45 (m, 1H), 3.08 (m, 1H), 2.62–2.82 (m, 2H), 2.56 (m, 1H), 2.4 (m, 2H), 1.82 (m, 1H), 1.6 (m, 1H); MS (CDI(NH$_3$)) m/e 463(M+H)$^+$; Analysis calc'd for C$_{24}$H$_{22}$N$_4$O$_4$S·2HCl·0.25H$_2$O: C, 53.39; H, 4.57; N, 10.38; found: C, 53.20; H, 3.98; N, 10.10.

EXAMPLE 113

3-[2-((3aR,9bR)-cis-6-Ethyl-2,3,3a,4,5,9b-hexahydro-[1H]-benz[e]isoindol-1-yl)ethyl]-pyrido[2',3':4,5]thieno[3,2-d]pyrimidine-2,4(1H,3H)-dione dihydrochloride

EXAMPLE 113A (3aR,9bR)-6-Hydroxy-2-carbobenzyloxy-2,3,3a,4,5,9b-[1H]-hexahydrobenz[e]isoindole trifluoromethanesulfonate ester To a stirred solution of the product from Example 109B, (0.385 g., 1.2 mMol., 1.0 equiv.) in 12 mL CH$_2$Cl$_2$ cooled to −78° was added triethylamine, (0.17 mL, 1.2 mMol., 1.0 equiv.) followed by trifluoromethansulfonic anhydride, (0.17 mL, 1.2 mMol., 1.0 equiv.). The reaction solution was left stirring at −78° for 1 h when it was warmed to room temperature, diluted with 50 mL CH$_2$Cl$_2$ and washed with H$_2$O, (15 mL), followed by sat. NaHCO$_3$. The resulting solution was then dried over MgSO4, filtered, and solvents evaporated to furnish the crude product as an oil. Purification of the crude product on silica gel furnished the title compound as a colorless oil, (0.39 g, 70%) $^1$H NMR (300 MHz, CDCl$_3$), δ(TMS): 1.60, (1H, m); 1.92, (1H, m); 2.50, (1H, m), 2.67, (1H, m); 3.00, (½H, t, J=3.0 Hz); 3.05, (½H, t, J=3.0 Hz); 3.23, (1H, q, J=9.0 Hz); 3.45, (2H, m); 3.73, (1H, dd, J=6.0 Hz); 3.98, (1H, m); 5.13, (2H, m); 7.15, 3H, m); 7.34, (5H, m).

EXAMPLE 113B (3aR,9bR)-6-Acetyl-2-carbobenzyloxy-2,3,3a,4,5,9b-[1H]-hexahydrobenz[e]isoindole To a stirred solution of the product from Example 113A (0.385 g, 0.85 mMol., 1.0 equiv.), in 3 mL of DMF was added triethylamine, (0.355 mL, 0.255 mMol., 3.0 equiv.), butylvinyl ether, (0.821 mL, 5.9 mMol., 7.0 equiv.), 1,3-bis(diphenylphosphino)propane, (0.05 g, 0.12 mMol., 0.15 equiv.) and palladium(II)acetate, (0.02 g, 0.12 mMol., 0.15 equiv.). The resulting dark reaction solution was heated to 80° C. for 2 h when it was cooled to room tyemperature and quenched with 5% (v/v) HCl, (2 mL), and let stir at room temperature for 2 h. The reaction was then extracted with CH$_2$Cl$_2$ (3×30 mL), and the rtesulting combined organics washed with H$_2$O, and brine, dried over MgSO$_4$, filtered and evaporated and separated (silica gel, 5:1 hexanes/ethyl acetate), to furnish the title compound as a colorless oil, (0.18 g, 61%). $^1$H NMR (300 MHz, CDCl$_3$), δ(TMS): 1.54, (1H, m); 1.86, (1H, m); 2.45, (1H, m), 2.55, (3H, s); 2.90, (1H, m); 3.07, (1H, m); 3.25, (1H, q, J=9.0 Hz); 3.45, (2H, m); 3.73, (1H, dd, J=6.0 Hz); 4.00, (1H, m); 5.13, (2H, m); 7.22, (2H, m); 7.34, (5H, m); 7.52, (1H,m).

EXAMPLE 113C (3aR,9bR)-6-Ethyl-2,3,3a,4,5,9b-[1H]-hexahydrobenz[e]isoindole hydrochloride The product from Example 113B (0.30 g, 0.085 mMol., 1.0 equiv.) was dissolved in 25 mL of dry methanol to which was added 1 mL of conc. HCl. To this solution was added dry 10% Pd/C, (0.045 g), the resulting suspension was then put under a hydrogen atmosphere at 4 atmospheres pressure for 17 h at room temperature. The reaction suspension was then filtered and evaporated to give a crude solid which was triturated with methanol/diethyl ether to furnish the title compound, (0.172 g, 78%). $^1$H NMR (300 MHz, CDCl$_3$), δ(TMS): 1.17, (3H, t, J=7.5 Hz); 1.63, (1H, m); 1.95, (1H, m), 2.63, (4H, m); 2.90, (1H, m); 3.07, (1H, t, J=12 Hz); 3.22, (1H, dd, J=9.0Hz, J=3Hz);3.77,(1H, dd, J=12.0Hz, J=3.0Hz);7.07,(3H, m).

EXAMPLE 113D (3aR,9bR)-2-Cyanomethyl -6-ethyl-2,3,3a,4,5,9b-[1H]-hexahydrobenz[e]isoindole The product from Example 113C (1.23 g, 5.2 mmol), chloroacetonitrile (0.22 mL, 5.7 mmol), potassium carbonate (2.4 g, 11.4 mmol), acetone (30 mL), and water (10 mL) were stirred at reflux for 6 h. The reaction was partitioned between ethyl acetate and brine. The ethyl acetate layer was dried (MgSO$_4$), filtered, concentrated and chromatographed (2:1 hex:ethyl acetate) to yield 1.0 g (80%) of the title compound $^1$H NMR (300 MHz, CDCl$_3$) δ1.20 (t, 3H), 1.61–1.71 (m, 1H), 1.76–1.87 (m, 1H), 2.50–2.79 (m, 7H), 3.20–3.28 (m, 2H), 3.50 (q, 1H), 3.65 (s, 2H), 6.97 (d, 1H), 7.03 (d, 1H), 7.11 (t, 1H); MS (DCI/NH$_3$) m/e 241 (M+H)$^+$.

EXAMPLE 113E (3aR,9bR)-2-Aminoethyl-6-ethyl-2,3,3a,4,5,9b-[1H]-hexahydrobenz[e]isoindole The product from Example 113D (1.0 g, 4.2 mmol) in 20 mL THF was added dropwise to a suspension of LiAlH$_4$ (0.93 g, 25 mmol) in THF (80 mL). After stirring for 1 h, the reaction was quenched by the portionwise addition of sodium sulfate decahydrate. After stirring for 30 min, the reaction was diluted with ethyl acetate (100 mL) and the solid was removed by filtration. Concentration of the filtrate yielded 0.97 g (95%) of the title compound: $^1$H NMR (300 MHz, CDCl$_3$) δ1.19 (t, 3H), 1.47–1.84 (m, 4H), 2.14–2.22 (m, 2H), 2.45–2.74 (m, 6H), 2.81 (t, 2H), 3.22–3.33 (m, 2H), 3.45 (q, 1H), 4.15–4.27 (m, 1H), 6.95–7.13 (m, 3H); MS (DCI/NH$_3$) m/e 245 (M+H)$^+$.

EXAMPLE 113F

3-[2-((3aR,9bR)-cis-6-Ethyl-2,3,3a,4,5,9b-hexahydro-[1H]-benz[e]isoindol-1-yl)ethyl]-pyrido[2',3':4,5]thieno[3,2-d]pyrimidine-2,4(1H,3H)-dione dihydrochloride Following the procedure described in Example 62, 3-amino-2-carbomethoxythieno[3,2-b]pyridine (47 g, 2.3 mmol), prepared as described in *J. Heterocyclic Chem.*, 85 (1987), triethylamine (0.71 mL, 5.1 mmol), phosgene (1.2 mL of 1.93M solution in toluene), and the product from Example 113E (50 g, 2.0 mmol) provided 0.78 g (85%) of the title compound which was converted to the di-HCl salt: m.p. 245°–247°; $^1$H NMR (300 MHz, CDCl$_3$(free base)) δ1.17 (t, 3H), 1.56–1.69 (m, 1H), 1.80–1.91 (m, 1H), 2.39–2.50 (m, 2H), 2.53–2.87 (m, 5H), 3.08–3.19 (m, 1H), 3.44–3.57 (m, 1H), 3.67 (q, 1H), 4.13–4.25 (m, 2H), 4.25–4.37 (m, 1H), 4.39–4.50 (m, 1H), 6.97–7.10 (m, 3H), 7.40 (dd, 1H), 7.98 (dd, m), 8.70 (dd, 1H); MS (DCI/NH$_3$) m/e 447 (M+H)$^+$; Analysis calc'd for C$_{25}$H$_{26}$N$_4$O$_2$S.(HCl)$_2$: C, 57.80; H, 5.43; N, 10.78; found: C, 58.55; H, 5.52; N, 10.84.

EXAMPLE 114

3-[2-((3aR,9bR)-cis-6-Ethyl,2,3,3a,4,5,9b-hexahydro-[1H]-benz[e]isoindol-1-yl)ethyl]-pyrido[3',2':4,5]thieno[3,2-d]pyrimidine-2,4(1H,3H)-dione hydrochloride Following the procedure described in Example 62, 3-amino-2-carbomethoxythieno[2,3-b]pyridine (0.24 g, 1.1 mmol), prepared as described in *J. Heterocyclic Chem.*, 85 (1987), triethylamine (0.36 mL, 2.6 mmol), phosgene (0.59 mL of 1.93M solution in toluene), and the product from Example 113E (25 g, 1.0 mmol) provided 0.27 g (60%) of the title compound which was converted to the HCl salt: m.p. 197°–203°; $^1$H NMR (300 MHz, CDCl$_3$(free base)) δ1.16 (s, 3H), 1.53–1.66 (m, 1H), 1.70–1.82 (m, 1H), 2.30–2.44 (m, 2H), 2.54–2.71 (m, 5H), 2.93 (t, 2H), 3.44–3.59 (m, 3H), 4.36 (t, 2H), 6.95 (dd, 1H), 6.99–7.09 (m, 2H), 7.15 (dd, 1H), 8.45 (dd, 1H), 8.69 (dd, 1H); MS (DCI/NH$_3$) m/e 447 (M+H)$^+$; Analysis calc'd for C$_{25}$H$_{26}$N$_4$O$_2$S.HCl.(H$_2$O)$_{0.25}$: C, 61.59; H, 5.69; N, 11.49; found: C, 62.16; H, 5.63; N, 11.60.

EXAMPLEs 116–143

The following compounds can be prepared by the procedures described in the preceding examples and schemes.

| Example | Name |
|---|---|
| 116 | 3-[2-(cis-6-Methoxy-2,3,3a,4,5,9b-hexahydro-[1H]-benz[e]isoindol-1-yl)ethyl]-1-methyl-pyrido[3',2':4,5]thieno[3,2-d]pyrimidine-2,4(1H,3H)-dione; |
| 117 | 3-[2-(cis-6-Methoxy-2,3,3a,4,5,9b-hexahydro-[1H]-benz[e]isoindol-1-yl)ethyl]-1-methyl-pyrido[3',2':4,5]pyrrolo[3,2-d]pyrimidine-2,4(1H,3H)-dione; |
| 118 | 3-[2-(cis-6-Methoxy-2,3,3a,4,5,9b-hexahydro-[1H]-benz[e]isoindol-1-yl)ethyl]-2H-[1]benzothieno[2,3-e]-1,3-oxazine-2,4(1H,3H)-dione; |
| 119 | 3-[2-(cis-6-Methoxy-2,3,3a,4,5,9b-hexahydro-[1H]-benz[e]isoindol-1-yl)ethyl]-2H-[1]benzothieno[2,3-e]-1,3-oxazine-4(3H)-one; |
| 120 | 3-[2-(cis-6-Methoxy-2,3,3a,4,5,9b-hexahydro-[1H]-benz[e]isoindol-1-yl)ethyl]-pyrido[3',4':4,5]thieno[3,2-d]pyrimidine-2,4(1H,3H)-dione; |
| 121 | 3-[2-(cis-6-Methoxy-2,3,3a,4,5,9b-hexahydro-[1H]-benz[e]isoindol-1-yl)ethyl]-8-chloro-[1]benzothieno[3,2-d]pyrimidine-2,4(1H,3H)-dione; |
| 122 | 3-[2-(cis-6-Methoxy-2,3,3a,4,5,9b-hexahydro-[1H]-benz[e]isoindol-1-yl)ethyl]-pyrido[4',3':4,5]pyrrolo[3,2-d]pyrimidine-2,4(1H,3H)-dione; |
| 123 | 3-[2-(cis-6-Methoxy-2,3,3a,4,5,9b-hexahydro-[1H]-benz[e]isoindol-1-yl)ethyl]-pyrido[3',4':4,5]pyrrolo[3,2-d]pyrimidine-2,4(1H,3H)-dione; |
| 124 | 3-[2-(cis-6-Methoxy-2,3,3a,4,5,9b-hexahydro-[1H]-benz[e]isoindol-1-yl)ethyl]-pylido[2',3':4,5]pyrrolo[3,2-d]pyrimidine-2,4(1H,3H)-dione; |
| 125 | 3-[2-(cis-6-Methoxy-2,3,3a,4,5,9b-hexahydro-[1H]-benz[e]isoindol-1-yl)ethyl]-pyrimido[4',5':4,5]thieno[2,3-c]pyridazine-6,8(5H,7H)-dione; |
| 126 | 3-[2-(cis-6-Methoxy-2,3,3a,4,5,9b-hexahydro-[1H]-benz[e]isoindol-1-yl)ethyl]-oxazolo[4,5-g]quinazoline-6,8(5H,7H)-dione; |
| 127 | 3-[2-(cis-6-Methoxy-2,-3,3a,4,5,9b-hexahydro-[1H]-benz[e]isoindol-1-yl)ethyl]-thiazolo[4,5-g]quinazoline-6,8(5H,7H)-dione; |
| 128 | 3-[2-(cis-6-Methoxy-2,3,3a,4,5,9b-hexahydro-[1H]-benz[e]isoindol-1-yl)ethyl]-1H-imidazo[4,5-g]quinazoline-6,8(5H,7H)-dione; |
| 129 | 3-[2-((3aR,9aS)-trans-6-Methoxy-2,3,3a,4,5,9b-hexahydro-[1H]-benz[e]isoindol-1-yl)ethyl]-[1]benzothieno[3,2-d]pyrimidine-2,4(1H,3H)-dione; |

-continued

| Example | Name |
|---|---|
| 130 | 3-[2-((3aS,9aR)-trans-6-Methoxy-2,3,3a,4,5,9b-hexahydro-[1H]-benz[e]isoindol-1-yl)ethyl]-[1]benzothieno[3,2-d]pyrimidine-2,4(1H,3H)-dione; |
| 131 | 3-[2-(cis-6-Ethoxy-2,3,3a,4,5,9b-hexahydro-[1H]-benz[e]isoindol-1-yl)ethyl]-[1]benzothieno[3,2-d]pyrimidine-2,4(1H,3H)-dione; |
| 132 | 3-[2-(cis-6-Ethyl-2,3,3a,4,5,9b-hexahydro-[1H]-benz[e]isoindol-1-yl)ethyl]-[1]benzothieno[3,2-d]pyrimidine-2,4(1H,3H)-dione; |
| 133 | 3-[2-(cis-6-Bromo-2,3,3a,4,5,9b-hexahydro-[1H]-benz[e]isoindol-1-yl)ethyl]-[1]benzothieno[3,2-d]pyrimidine-2,4(1H,3H)-dione; |
| 134 | 3-[2-(cis-6-Methoxycarbonyl-2,3,3a,4,5,9b-hexahydro-[1H]-benz[e]isoindol-1-yl)ethyl]-[1]benzothieno[3,2-d]pyrimidine-2,4(1H,3H)-dione; |
| 135 | 3-[2-(cis-6-Methoxy-2,3,3a,4,5,9b-hexahydro-[1H]-benz[e]isoindol-1-yl)ethyl]-1H-pyrimido[5,4-b]indole-4(3H)-one; |
| 136 | 3-[2-(trans-6-Methoxy-2,3,3a,4,5,9b-hexahydro-[1H]-benz[e]isoindol-1-yl)ethyl]-1-methyl-[1]benzothieno[3,2-d]pyrimidine-2,4(1H,3H)-dione; |
| 137 | 3-[4-(trans-9-Methoxy-2,3,3a,4,5,9b-hexahydro-[1H]-benz[e]isoindol-1-yl)butyl]-[1]benzothieno[3,2-d]pyrimidine-2,4(1H,3H)-dione; |
| 138 | 3-[2-(trans-6-Methoxy-2,3,3a,4,5,9b-hexahydro-[1H]-benz[e]isoindol-1-yl)ethyl]-pyrido[3[40 ,2[40 :4,5]thieno[3,2-d]pyrimidine-2,4(1H,3H)-dione; |
| 139 | 3-[2-(trans-6-Methoxy-2,3,3a,4,5,9b-hexahydro-[1H]-benz[e]isoindol-1-yl)ethyl]-benzo[h]quinazoline-2,4(1H,3H)-dione; |
| 140 | 3-[2-(trans-6-Methoxy-2,3,3a,4,5,9b-hexahydro-[1H]-benz[e]isoindol-1-yl)ethyl]-pyrido[3',2':4,5]thieno[3,2-d]pyrimidine-2,4(1H,3H)-dione; |
| 141 | 3-[2-(tnuis-6-Methoxy-2,3,3a,4,5,9b-hexahydro-[1H]-benz[e]isoindol-1-yl)ethyl]-benzothieno[2,3-d]pyrimidin-4(3H)-one; |
| 142 | 3-[2-(trans-6-Methoxy-2,3,3a,4,5,9b-hexahydro-[1H]-benz[e]isoindol-1-yl)ethyl]-pyrido[4',3':4,5]thieno[3,2-d]pyrimidine-2,4(1H,3H)-dione; |
| 143 | 3-[2-(trans-6-Methoxy-2,3,3a,4,5,9b-hexahydro-[1H]-benz[e]isoindol-1-yl)ethyl]-pyrido[2',3':4,5]thieno[3,2-d]pyrimidine-2,4(1H,3H)-dione; |

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

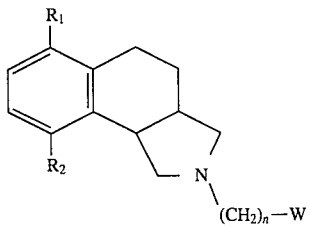

(I)

or a pharmaceutically acceptable salt thereof; wherein n is an integer from 2 to 6, inclusive;

$R_1$ and $R_2$ are independently selected from the group consisting of hydrogen, alkoxy, hydroxy, alkyl, halo, carboxy, and alkoxycarbonyl;

W is selected from the group consisting of

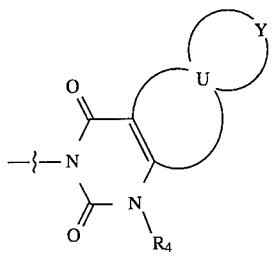

wherein $R_4$ is hydrogen or lower alkyl, and

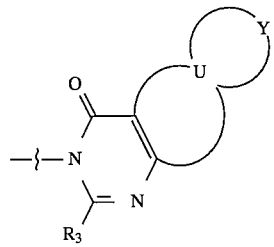

wherein $R_3$ is selected from the group consisting of hydrogen, lower alkyl, unsubstituted phenyl, and phenyl substituted with lower alkyl;

U, taken together with the carbon atoms to which it is attached toms a fused ring selected from the group consisting of (a) an unsubstituted or substituted five membered ring having four carbon atoms, two double bonds and one heteroatom selected from the group consisting of —N($R_5$)—, —O— and —S— wherein $R_5$ is hydrogen or lower alkyl and the ring substituent is selected from the group consisting of lower alkyl, phenyl, halo, cyano, nitro, carboxy, alkoxycarbonyl and alkoxy, and (b) a six-membered carbocyclic aromatic ring which is unsubstituted or substituted with a substitutent selected from the group consisting of lower alkyl, halo, cyano, nitro, carboxy, alkoxycarbonyl and alkoxy;

Y, is attached to two adjacent atoms of the ring U and, taken together with the two atoms of ring U to which it is attached, forms a fused ring selected from the group consisting of (a) a five membered ring having four carbon atoms, two double bonds and one heteroatom selected from the group consisting of —N($R_5$)—, —O— and —S— wherein $R_5$ is hydrogen or lower alkyl and the ring is unsubstituted or substituted with 1, 2, or 3 substituents independently selected from the group consisting of lower alkyl, phenyl, halo, cyano, nitro, carboxy, alkoxycarbonyl and alkoxy, (b) a six-membered carbocyclic aromatic ring which is unsubstituted or substituted with 1, 2, or 3 substituents selected from the group consisting of lower alkyl, halo, cyano, nitro, carboxy, alkoxycarbonyl, and alkoxy; and (c) a six membered aromatic ring having one or two nitrogen atoms, wherein the ring is unsubstituted or substituted with 1 or 2 substituents selected from the group consisting of lower alkyl, phenyl, halo, cyano, nitro, carboxy, alkoxycarbonyl and alkoxy.

2. A compound according to claim 1 of the formula:

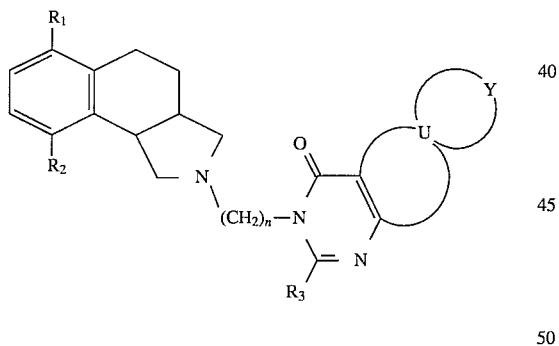

or a pharmaceutically acceptable salt thereof.

3. A compound according to claim 1 of the formula:

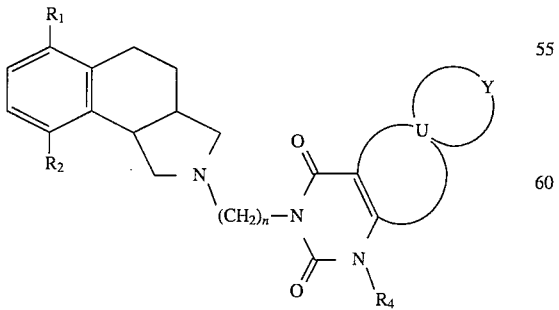

or a pharmaceutically acceptable salt thereof.

4. A compound according to claim 1 wherein W is selected from the group consisting of

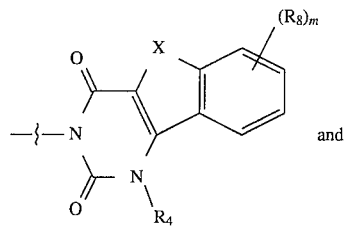

and

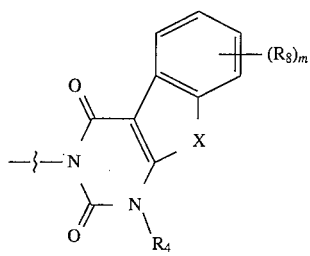

wherein X is selected from the group consisting of —N($R_5$)—, —O— and —S— wherein $R_5$ is hydrogen or lower alkyl, m is selected from 0, 1, 2 and 3, and $R_8$ at each occurence is independently selected from the group consisting of lower alkyl, halo, cyano, nitro, carboxy, alkoxycarbonyl, and alkoxy.

5. A compound according to claim 1 wherein W is selected from the group consisting of

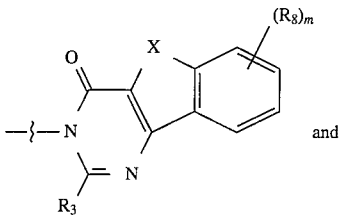

and

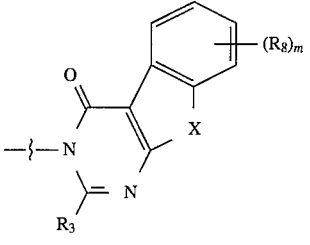

wherein X is selected from the group consisting of —N($R_5$)—, —O— and —S— wherein $R_5$ is hydrogen or lower alkyl, m is selected from 0, 1, 2 and 3, and $R_8$ at each occurence is independently selected from the group consisting of lower alkyl, halo, cyano, nitro, carboxy, alkoxycarbonyl, and alkoxy.

6. A compound according to claim 1 wherein W is selected from the group consisting of

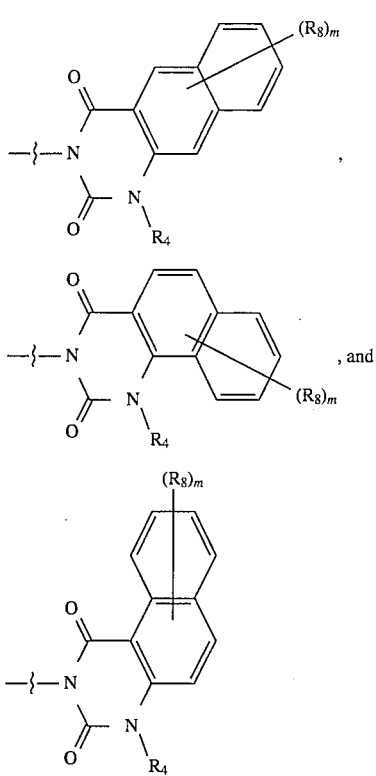

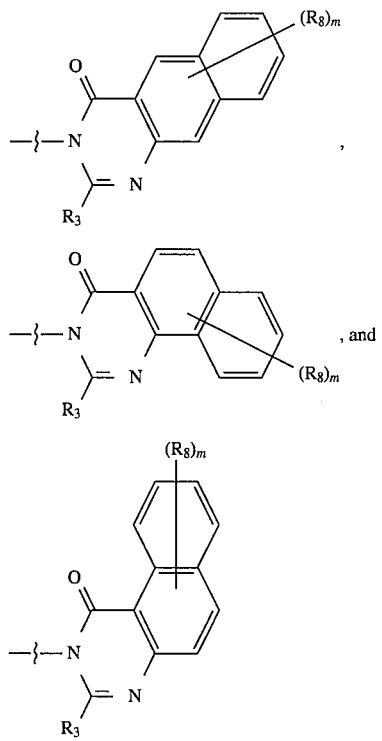

wherein m is selected from 0, 1, 2 and 3, and $R_8$ at each occurence is independently selected from the group consisting of lower alkyl, halo, cyano, nitro, carboxy, alkoxycarbonyl, and alkoxy.

7. A compound according to claim 1 wherein W is selected from the group consisting of wherein m is selected from 0, 1, 2 and 3, and $R_8$ at each occurence is independently selected from the group consisting of, lower alkyl, halo, cyano, nitro, carboxy, alkoxycarbonyl, and alkoxy.

8. A compound according to claim 1 wherein W is selected from the group consisting of

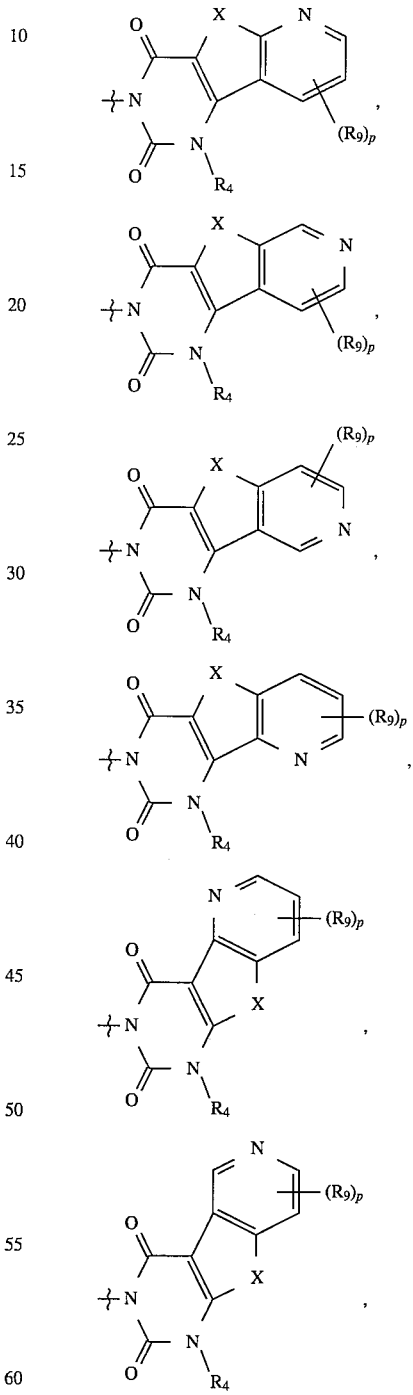

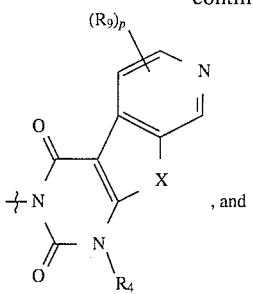

, and

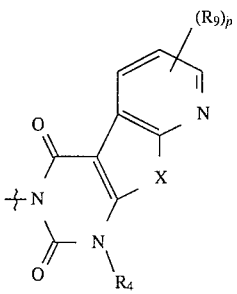

wherein X is selected from the group consisting of —N(R$_5$)—, —O— and —S— wherein R$_5$ is hydrogen or lower alkyl, p is selected from 0, 1 and 2, and R$_9$ at each occurence is independently selected from the group consisting of lower alkyl, phenyl, halo, cyano, nitro, carboxy, alkoxy, alkoxycarbonyl.

9. A compound according to claim 1 wherein W is selected from the group consisting of

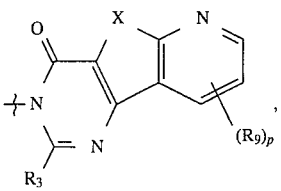

,

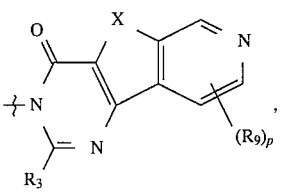

,

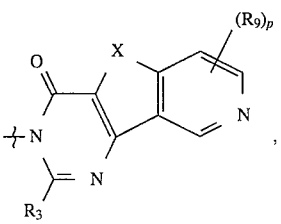

,

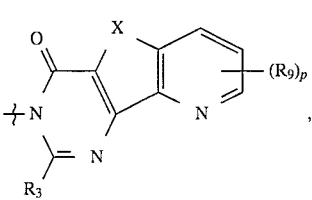

,

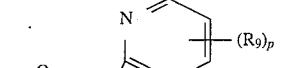

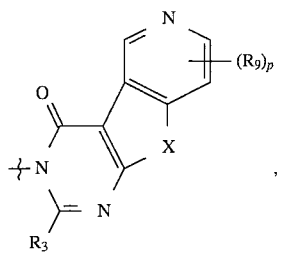

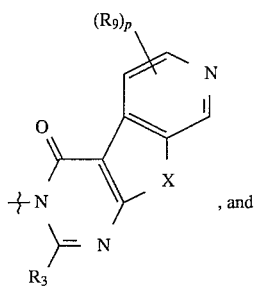

, and

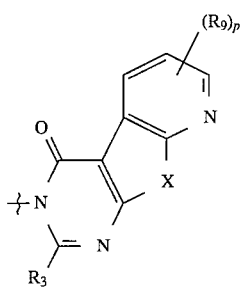

wherein X is selected from the group consisting of —N(R$_5$)—, —O— and —S— wherein R$_5$ is hydrogen or lower alkyl, p is selected from 0, 1 and 2, and R$_9$ at each occurence is independently selected from the group consisting of lower alkyl, phenyl, halo, cyano, nitro, carboxy, alkoxycarbonyl and alkoxy.

10. A compound according to claim 1 wherein W is selected from the group consisting of

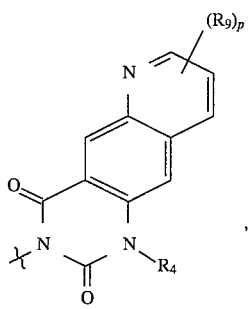

,

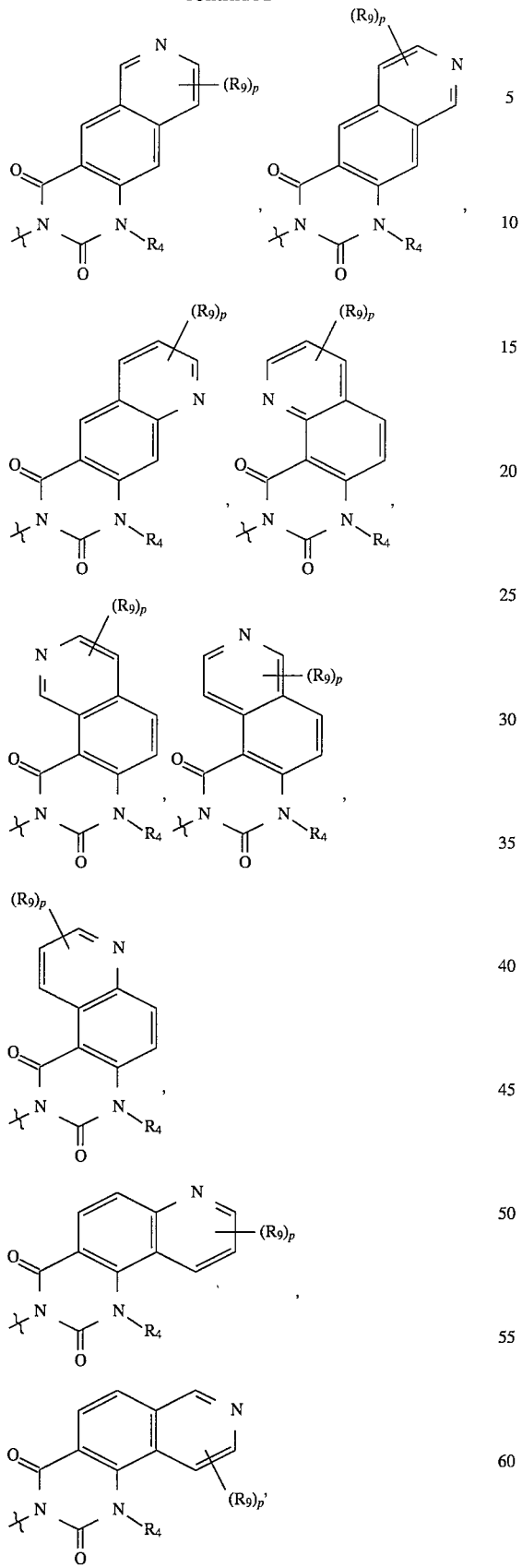
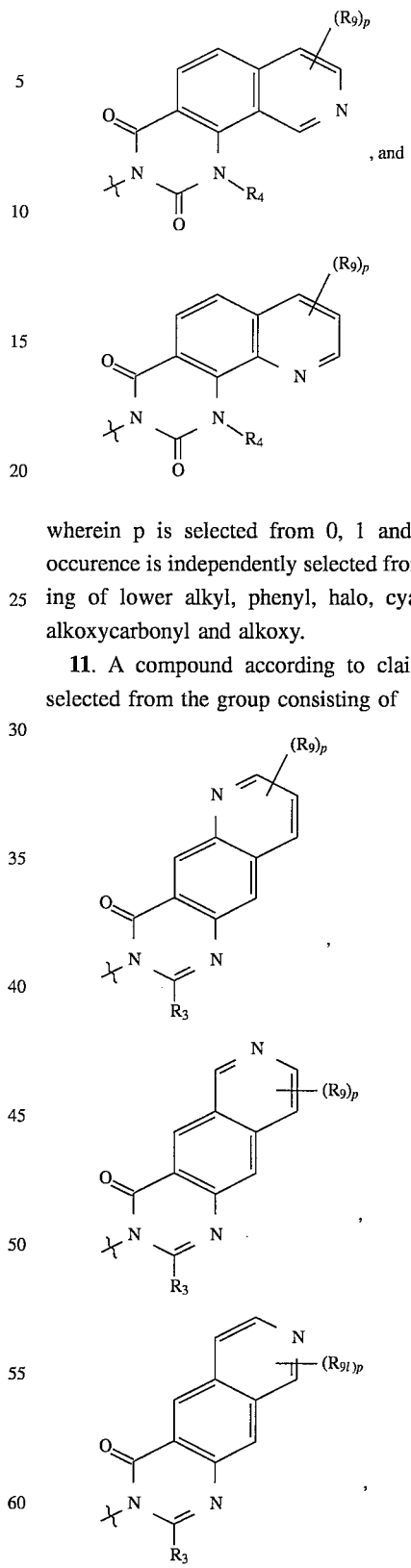
wherein p is selected from 0, 1 and 2 and $R_9$ at each occurence is independently selected from the group consisting of lower alkyl, phenyl, halo, cyano, nitro, carboxy, alkoxycarbonyl and alkoxy.
11. A compound according to claim 1 wherein W is selected from the group consisting of
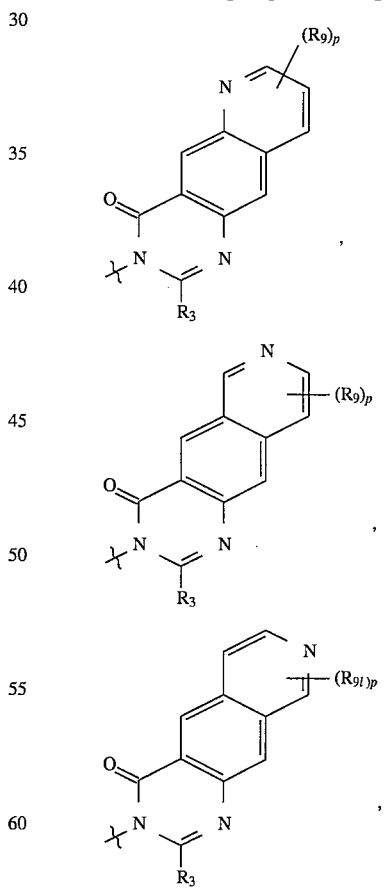

139
-continued

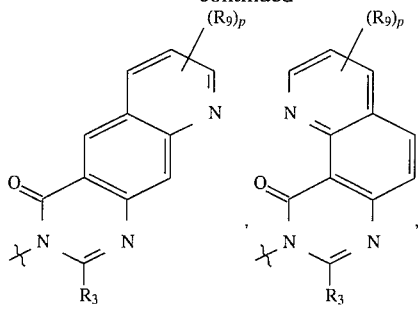

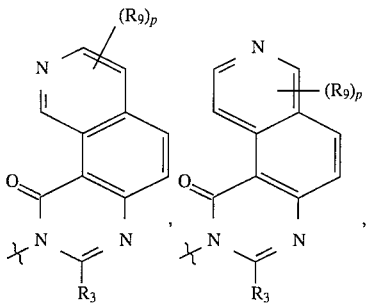

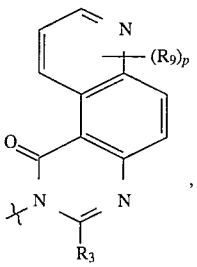

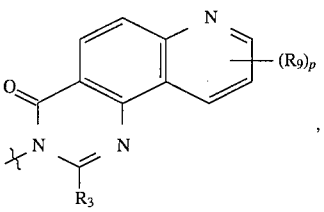

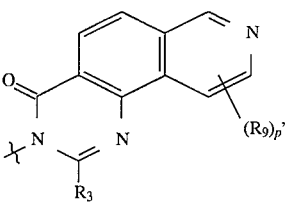

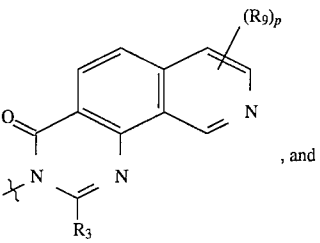, and

140
-continued

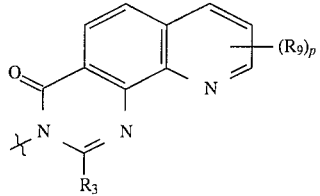

wherein p is selected from 0, 1 and 2 and $R_9$ at each occurence is independently selected from the group consisting of lower alkyl, phenyl, halo, cyano, nitro, carboxy, alkoxycarbonyl and alkoxy.

12. A compound according to claim 1 wherein U, taken together with the carbon atoms to which it is attached forms a fused ring selected from the group consisting of a fused benzene, fused thiophene, fused furan, and fused pyrrole ring and Y, taken together with the two carbon atoms of U to which it is attached forms a fused ring selected from the group consisting of a fused benzene and a fused pyridine ring.

13. A compound according to claim 1 wherein one of $R_1$ and $R_2$ is alkoxy and the other one is hydrogen, n is selected from an integer from 2 to 4 and W is selected from the group consisting of

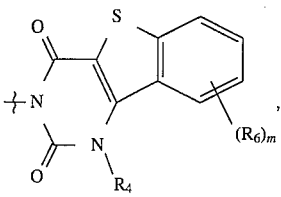

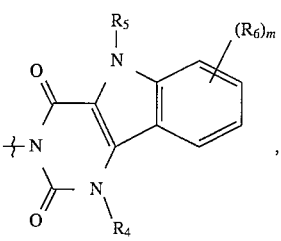

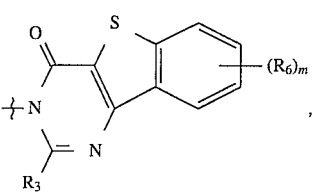

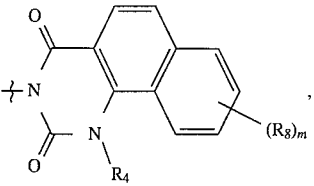

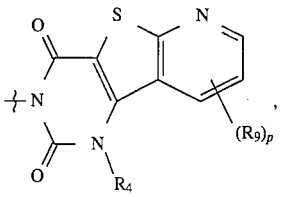

-continued

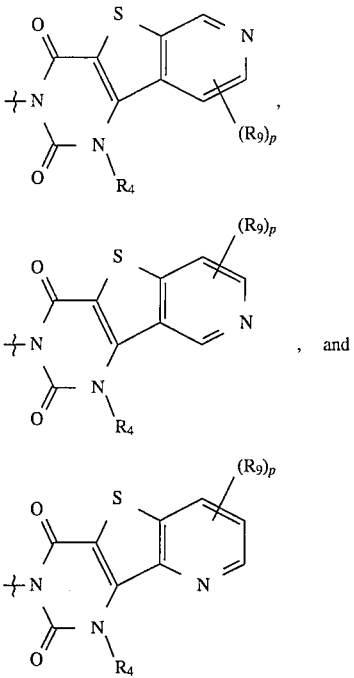

wherein m is selected from 0, 1, 2, and 3, p is selected from 0, 1 and 2, $R_8$ at each occurence is independently selected from the group consisting of lower alkyl, halo, cyano, nitro, carboxy, alkoxycarbonyl, and alkoxy, and $R_9$ at each occurence is independently selected from the group consisting of lower alkyl, phenyl, halo, cyano, nitro, carboxy, alkoxycarbonyl and alkoxy, or a pharmaceutically acceptable salt thereof.

14. A compound according to claim 1 wherein W is selected from the group consisting of

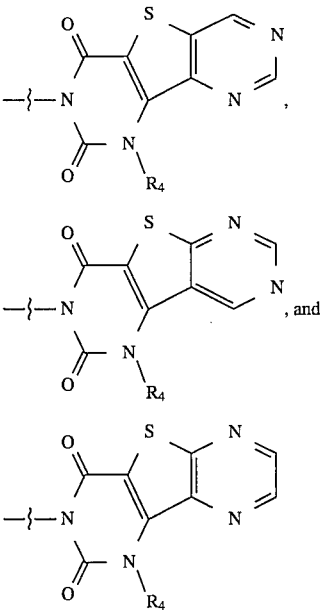

or a pharmaceutically acceptable salt thereof.

15. A compound according to claim 1 selected from the group consisting of
3-[2-((3aR,9bR)-cis-6-methoxy-2,3,3a,4,5,9b-hexahydro-[1H]-benz[e]isoindol-1-yl)ethyl]-[1]-benzothieno[3,2-d]pyrimidine-2,4(1H,3H)-dione;
3-[2-(trans-6-methoxy-2,3,3a,4,5,9b-hexahydro-[1H]-benz[e]isoindol-1-yl)ethyl]-[1]-benzothieno[3,2-d]pyrimidine-2,4(1H,3H)-dione;
3-[2-(cis-6-methoxy-2,3,3a,4,5,9b-hexahydro-[1H]-benz[e]isoindol-1-yl)ethyl]-1-methyl-[1]-benzothieno[3,2-d]pyrimidine-2,4(1H,3H)-dione;
3-[4-(cis-9-methoxy-2,3,3a,4,5,9b-hexahydro-[1H]-benz[e]isoindol-1-yl)butyl]-[1]-benzothieno[3,2-d]pyrimidine-2,4(1H,3H)-dione;
3-[2-(cis-6-methoxy-2,3,3a,4,5,9b-hexahydro-[1H]-benz[e]isoindol-1-yl)ethyl]-benzo[h]quinazoline-2,4(1H,3H)-dione;
3-[2-((3aR,9bR)-cis-6-methoxy-2,3,3a,4,5,9b-hexahydro-[1H]-benz[e]isoindol-1-yl)ethyl]-1H-pyrimido[5,4-b]indole-2,4(1H,3H)-dione;
3-[2-((3aR,9bR)-cis-6-methoxy-2,3,3a,4,5,9b-hexahydro-[1H]-benz[e]isoindol-1-yl)ethyl]pyrido[3',2':4,5]thieno[3,2-d]pyrimidine-2,4(1H,3H)-dione;
3-[2-((3aR,9bR)-cis-6-methoxy-2,3,3a,4,5,9b-hexahydro-[1H]-benz[e]isoindol-1-yl)ethyl]pyrido[3',2':4,5]thieno-[3,2-d]pyrimidine-4(3H)-one;
3-[2-((3aR,9bR)-cis-6-methoxy-2,3,3a,4,5,9b-hexahydro-[1H]-benz[e]isoindol-1-yl)ethyl]-9-methyl[1]benzothieno-[3,2-d]pyrimidine-2,4(1H,3H)-dione;
3-[2-((3aR,9bR)-cis-6-methoxy-2,3,3a,4,5,9b-hexahydro-[1H]-benz[e]isoindol-1-yl)ethyl]pyrido[4',3':4,5]thieno-[3,2-d]pyrimidine-2,4(1H,3H)-dione;
3-[2-((3aR,9bR)-cis-6-methoxy-2,3,3a,4,5,9b-hexahydro-[1H]-benz[e]isoindol-1-yl)ethyl]-1-methyl-[1]benzothieno[3,2-d]pyrimidine-2,4(1H,3H)-dione;
3-[2-((3aR,9bR)-cis-6-methoxy-2,3,3a,4,5,9b-hexahydro-[1H]-benz[e]isoindol-1-yl)ethyl]-[1]-7-cyano-benzothieno[3,2-d]pyrimidine-2,4(1H,3H)-dione;
3-[2-((3aR,9bR)-cis-6-methoxy-2,3,3a,4,5,9b-hexahydro-[1H]-benz[e]isoindol-1-yl)ethyl]-[1]-8cyano-benzothieno[3,2-d]pyrimidine-2,4(1H,3H)-dione;
3-[2-((3aR,9bR)-cis-6-methoxy-2,3,3a,4,5,9b-hexahydro-[1H]-benz[e]isoindol-1-yl)ethyl]-[1]-8-carboxamido-benzothieno[3,2-d]pyrimidine-2,4(1H,3H)-dione;
3-[2-((3aR,9bR)-cis-6-methoxy-2,3,3a,4,5,9b-hexahydro-[1H]-benz[e]isoindol-1-yl)ethyl]-[1]-7-nitro-benzothieno[3,2-d]pyrimidine-2,4(1H,3H)-dione;
3-[2-((3aR,9bR)-cis-6-methoxy-2,3,3a,4,5,9b-hexahydro-[1H]-benz[e]isoindol-1-yl)ethyl]-[1]-8-nitro-benzothieno[3,2-d]pyrimidine-2,4(1H,3H)-dione;
3-[2-((3aR,9bR)-cis-6-methoxy-2,3,3a,4,5,9b-hexahydro-[1H]-benz[e]isoindol-1-yl)ethyl]-[1]-8acetamido-benzothieno[3,2-d]pyrimidine-2,4(1H,3H)-dione;
3-[2-((3aR,9bR)-cis-6-methoxy-2,3,3a,4,5,9b-hexahydro-[1H]-benz[e]isoindol-1-yl)ethyl]-[1]-7-carboxamido-benzothieno[3,2-d]pyrimidine-2,4(1H,3H)-dione;
3-[2-((3aR,9bR)-cis-6-methoxy-2,3,3a,4,5,9b-hexahydro-[1H]-benz[e]isoindol-1-yl)ethyl]-[1]-8(N-methylcarboxamido)-benzothieno[3,2-d]pyrimidine-2,4(1H,3H)-dione;
3-[2-((3aR,9bR)-cis-6-methoxy-2,3,3a,4,5,9b-hexahydro-[1H]-benz[e]isoindol-1-yl)ethyl]-[1]-7-chloro-benzothieno[3,2-d]pyrimidine-2,4(1H,3H)-dione;
3-[2-((3aR,9bR)-cis-6-methoxy-2,3,3a,4,5,9b-hexahydro-[1H]-benz[e]isoindol-1-yl)ethyl]-1-methyl-pyrido[2',3':4,5]thieno[3,2-d]pyrimidine-2,4(1H,3H)-dione;
3-[2-((3aR,9bR)-cis-6-methoxy-2,3,3a,4,5,9b-hexahydro-[1H]-benz[e]isoindol-1-yl)ethyl]-8chloro-pyrido[2',3':4,5]thieno[3,2-d]pyrimidine-2,4(1H,3H)-dione;
3-[2-((3aR,9bR)-cis-6-methoxy-2,3,3a,4,5,9b-hexahydro-[1H]-benz[e]isoindol-1-yl)ethyl]-6-chloro-pyrido[2',3':4,5]thieno[3,2-d]pyrimidine-2,4(1H,3H) -dione;

3-[2-((3aR,9bR)-cis-6-methoxy-2,3,3a,4,5,9b-hexahydro-[1H]-benz[e]isoindol-1-yl)ethyl]-8-methoxy-pyrido[2',3':4,5]thieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-6-methoxy-pyrido[2'3':4,5]thieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-[1]-8chloro-benzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-[1]-7,8-dimethoxy-benzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-[1]-9-methyl-benzothieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-pyrazino[2'3':4,5]thieno[3,2-d]pyrimidine-4(1H,3H)-one;

3-[2-((3aR,9bR)-cis-6-methoxy-2,3,3a,4,5,9b-hexahydro-[1H]-benz[e]isoindol-1-yl)ethyl]-[1]-9-chloro-benzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-[1]-9-methoxy-benzothieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-pyrido[3',2':4,5]furo[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-pyrido[2',3':4,5]furo[3,2-d]pyrimidine-2,4(1H,3H)-dione;

3-[2-((3aR,9bR)-cis-9-methoxy-2,3,3a,4,5,9b-hexahydro-[1H]-benz[e]isoindol-1-yl)butyl]-pyrido[2',3':4,5]thieno[3,2 d]pyrimidine-2,4(1H,3H)-dione;

3-[2-((3aR,9bR)-cis-9-methoxy-2,3,3a,4,5,9b-hexahydro-[1H]-benz[e]isoindol-1-yl)butyl]-pyrazino[2',3':4,5]thieno[3,2-d]pyrimidine-2,4(1H,3H)-dione;

3-[2-((3aR,9bR)-cis-9-methoxy-2,3,3a,4,5,9b-hexahydro-[1H]-benz[e]isoindol-1-yl)butyl]-pyrido[3',2':4,5]thieno[3,2-d]pyrimidine-2,4(1H,3H)-dione;

3-[2-((3aR,9bR)cis-6-methoxy-2,3,3a,4,5,9b-hexahydro-[1H]-benz[e]isoindol-1-yl)ethyl]-pyrido[2,3-h]quinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-pyrido[3,2-h]quinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-pyrido[3,4-h]quinazoline-2,4(1H,3H)-dione;

3-[2-(cis-(3aR,9bR)-6-methoxy-2,3,3a,4,5,9b-hexahydro-[1H]-benz[e]isoindol-1-yl)ethyl]-pyrido[3',2':4,5]pyrrolo[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-7-chloro-pyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-7-methoxy-pyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-5-isopropyl-pyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-7-methyl-pyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-1-(2-methoxyethyl)-7-methyl-pyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-1-methylpyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-pyrido[3',4':4,5]pyrrolo[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-1-ethylpyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-1-(2-(2-methoxyethoxy)ethyl)pyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-7,8-dimethylpyrazino[2',3':4,5]thieno[3,2-d]pyrimidine-2,4(1H,3H)-dione;

3-[2-(cis-(3aR,9bR)-6-methoxy-2,3,3a,4,5,9b-hexahydro-[1H]-benz[e]isoindol-1-yl)ethyl]-1-(2-methoxyethyl)pyrazino[2',3':4,5]thieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-8-hydroxypyrido[2',3':4,5]thieno[3,2-d]pyrimidine-2,4(1H,3H)-dione; and 3-[2-((3aR,9bR)-cis-6-methoxy-2,3,3a,4,5,9b-hexahydro-[1H]-benz[e]isoindol-1-yl)ethyl]-8-cyanopyrido[2',3':4,5]thieno[3,2-d]pyrimidine-2,4(1H,3H)-dione;

or a pharmaceutically acceptable salt thereof.

16. A pharmaceutical composition comprising a therapeutically effective amount of a compound of claim 1 in combination with a pharmaceutically acceptable carrier.

17. A method of treating benign prostatic hyperplasia (BPH) in a host mammal in need of such treatment comprising administering a therapeutically effective amount of a compound of claim 1.

\* \* \* \* \*